US012799108B2

(12) United States Patent
Petrilli et al.

(10) Patent No.: US 12,799,108 B2
(45) Date of Patent: Nov. 17, 2026

(54) SUBSTITUTED 2-(2,6-DIOXOPIPERIDIN-3-YL)-5-(1-PIPERIDIN-4-YL)ISOINDOLINE-1,3-DIONE DERIVATIVES AND USES THEREOF

(71) Applicants: Neomorph, Inc., San Diego, CA (US); Dana-Farber Cancer Institute, Inc., Boston, MA (US)

(72) Inventors: Whitney L. Petrilli, San Diego, CA (US); Lyn Howard Jones, Winchester, MA (US); Hu Liu, Newton, MA (US)

(73) Assignees: DANA-FARBER CANCER INSTITUTE, INC., Boston, MA (US); NEOMORPH, INC., San Diego, CA (US)

( * ) Notice: Subject to any disclaimer, the term of this patent is extended or adjusted under 35 U.S.C. 154(b) by 391 days.

(21) Appl. No.: 18/287,972

(22) PCT Filed: Apr. 29, 2022

(86) PCT No.: PCT/US2022/026977
§ 371 (c)(1),
(2) Date: Oct. 23, 2023

(87) PCT Pub. No.: WO2022/232536
PCT Pub. Date: Nov. 3, 2022

(65) Prior Publication Data

US 2024/0239785 A1 Jul. 18, 2024

Related U.S. Application Data

(60) Provisional application No. 63/181,834, filed on Apr. 29, 2021.

(51) Int. Cl.

| | |
|---|---|
| ***C07D 417/14*** | (2006.01) |
| ***A61K 31/4545*** | (2006.01) |
| ***A61K 31/497*** | (2006.01) |
| ***A61K 31/498*** | (2006.01) |
| ***A61K 31/501*** | (2006.01) |
| ***A61K 31/506*** | (2006.01) |
| ***A61K 31/517*** | (2006.01) |
| ***A61K 31/519*** | (2006.01) |
| ***A61K 31/5377*** | (2006.01) |
| ***A61K 31/5415*** | (2006.01) |
| ***C07D 401/14*** | (2006.01) |
| ***C07D 405/14*** | (2006.01) |
| ***C07D 413/14*** | (2006.01) |
| ***C07D 471/04*** | (2006.01) |
| ***C07D 491/048*** | (2006.01) |
| ***C07D 495/04*** | (2006.01) |

(52) U.S. Cl.
CPC ........ *C07D 417/14* (2013.01); *A61K 31/4545* (2013.01); *A61K 31/497* (2013.01); *A61K 31/498* (2013.01); *A61K 31/501* (2013.01); *A61K 31/506* (2013.01); *A61K 31/517* (2013.01); *A61K 31/519* (2013.01); *A61K 31/5377* (2013.01); *A61K 31/5415* (2013.01); *C07D 401/14* (2013.01); *C07D 405/14* (2013.01); *C07D 413/14* (2013.01); *C07D 471/04* (2013.01); *C07D 491/048* (2013.01); *C07D 495/04* (2013.01)

(58) Field of Classification Search
CPC C07D 417/14; C07D 401/14; A61K 31/4545; A61K 31/497; A61K 31/498; A61K 31/501; A61K 31/506; A61K 31/517
See application file for complete search history.

(56) References Cited

U.S. PATENT DOCUMENTS

2019/0062309 A1 2/2019 Beckwith et al.

FOREIGN PATENT DOCUMENTS

| | | | |
|---|---|---|---|
| WO | WO-2019038717 | A1 | 2/2019 |
| WO | 2020/012337 | A1 | 1/2020 |
| WO | WO-2020128972 | A1 | 6/2020 |
| WO | WO-2020165833 | A1 | 8/2020 |
| WO | WO-2020165834 | A1 | 8/2020 |
| WO | WO-2021/087093 | A1 | 5/2021 |
| WO | WO-2022/081976 | A1 | 4/2022 |
| WO | 2022/221673 | A1 | 10/2022 |
| WO | WO-2022/232391 | A1 | 11/2022 |
| WO | WO-2022/232536 | A1 | 11/2022 |
| WO | 2023/278325 | A1 | 1/2023 |

OTHER PUBLICATIONS

International Search Report and Written Opinion for Application No. PCT/US22/26977 dated Sep. 14, 2022.
Invitation to Pay Additional Fees for International Application No. PCT/US22/26977 dated Jul. 8, 2022.
Ruchelman et al., "Isosteric analogs of lenalidomide and pomalidomide: Synthesis and biological activity" Bioorganic & Medicinal Chemistry Letters: 23, 360-365 (2013).

*Primary Examiner* — San Ming R Hui
(74) *Attorney, Agent, or Firm* — Lando & Anastasi, LLP

(57) ABSTRACT

Disclosed are compounds according to Formula (I), and related pharmaceutical compositions. Also disclosed are therapeutic methods for reducing IKZF2 and methods of treating cancer using the compounds of Formula (I).

(I)

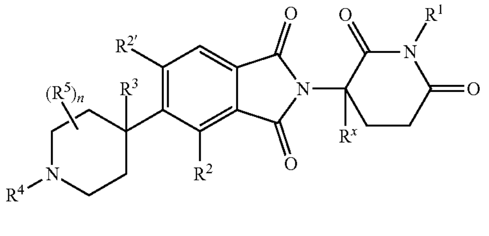

27 Claims, No Drawings

SUBSTITUTED 2-(2,6-DIOXOPIPERIDIN-3-YL)-5-(1-PIPERIDIN-4-YL)ISOINDOLINE-1,3-DIONE DERIVATIVES AND USES THEREOF

RELATED APPLICATIONS

This application is a U.S. national phase of International Patent Application No. PCT/US22/26977, filed 29 Apr. 2022; which claims the benefit of U.S. Provisional Application No. 63/181,834, filed 29 Apr. 2021.

BACKGROUND

IKAROS Family Zinc Finger 2 (IKZF2) (also known as Helios) is one of the five members of the Ikaros family of transcription factors found in mammals. IKZF2 contains four zinc finger domains near the N-terminus, which are involved in DNA binding, and two zinc finger domains at the C-terminus, which are involved in protein dimerization. IKZF2 is about 50% identical with Ikaros family members, Ikaros (IKZF1), Aiolos (IKZF3), and Eos (IKZF4) with highest homology in the zinc finger regions (80%+ identity). These four Ikaros family transcription factors bind to the same DNA consensus site and can heterodimerize with each other when co-expressed in cells. The fifth Ikaros family protein, Pegasus (IKZF5), is only 25% identical to IKZF2, binds a different DNA site than other Ikaros family members and does not readily heterodimerize with the other Ikaros family proteins. IKZF2, IKZF1 and IKZF3 are expressed mainly in hematopoietic cells while IKZF4 and IKZF5 are expressed in a wide variety of tissues. (John, L. B., et al., (2011), Mol. Immunol. 48: 1272-1278; Perdomo, J., et al., (2000), J. Biol. Chem. 275:38347-38354)

IKZF2 is believed to have an important role in the function and stability of regulatory T cells (Tregs). IKZF2 is highly expressed at the mRNA and protein level by regulatory T-cell populations. Knockdown of IKZF2 by siRNA has been shown to result in downregulation of FoxP3 and to impair the ability of isolated human CD4+ CD25+ Tregs to block T-cell activation in vitro. Moreover, overexpression of IKZF2 in isolated murine Tregs has been shown to increase expression of Treg related markers such as CD103 and GITR and the IKZF2 overexpressing cells showed increased suppression of responder T-cells. IKZF2 has also been found to bind the promoter of FoxP3, the defining transcription factor of the regulatory T-cell lineage, and to affect FoxP3 expression.

Knockout of IKZF2 within FoxP3-expressing Tregs in mice has been shown to cause activated Tregs to lose their inhibitory properties, to express T-effector cytokines, and to take on T-effector functions. IKZF2 knockout mutant mice develop autoimmune disease by 6-8 months of age, with increased numbers of activated CD4 and CD8 T cells, follicular helper T cells and germinal center B cells. This observed effect is believed to be cell intrinsic, as Rag2−/− mice given bone marrow from IKZF2 knockout mice, but not bone marrow from IKZF2+/+ develop autoimmune disease. Direct evidence that IKZF2 affects regulatory T-cell function has been shown in the analysis of mice in which IKZF2 was deleted only in FoxP3 expressing cells (FoxP3-YFP-Cre Heliosfl/fl). The results showed that the mice also develop autoimmune disease with similar features as observed in the whole animal IKZF2 knockout. Moreover, pathway analysis of a CHIP-SEQ experiment has also suggested that IKZF2 is affecting expression of genes in the STAT5/IL-2Ra pathway in regulatory T-cells. This effect of IKZF2 loss was shown to be more apparent after an immune challenge (viral infection or injection with sheep's blood), and it was noted that after immune stimulation, the IKZF2 negative regulatory T cells began to take on features of effector T cells. (Getnet, D., et al., Mol. Immunol. (2010), 47:1595-1600; Bin, Dhuban, K., et al., (2015), J. Immunol. 194:3687-96; Kim, H-J., et al., (2015), Science 350:334-339; Nakawaga, H., et al., (2016) PNAS, 113: 6248-6253)

Overexpression of Ikaros isoforms which lack the DNA binding regions have been shown to be associated with multiple human haematological malignancies. Recently, mutations in the IKZF2 gene, which lead to abnormal splicing variants, have been identified in adult T-cell leukemias and low hypodiploid acute lymphoblastic leukemia. It has been proposed that these isoforms, which are capable of dimerization, have a dominant negative effect on Ikaros family transcription factors which primes the development of lymphomas. IKZF2 knockout mutants that survive into adulthood do not develop lymphomas, supporting this hypothesis. (Asanuma, S., et al., (2013), Cancer Sci. 104: 1097-1106; Zhang, Z., et al., (2007), Blood 109:2190-2197; Kataoka, D., et al., (2015), Nature Genetics 47:1304-1315) Currently, anti-CTLA4 antibodies are used in the clinic to target Tregs in tumors. However, targeting CTLA4 often causes systemic activation of T-effector cells, resulting in excessive toxicity and limiting therapeutic utility. Up to ¾ of patients treated with a combination of anti-PD1 and anti-CTLA4 have reported grade 3 or higher adverse events. Thus, a strong need exists to provide compounds that target Tregs in tumors without causing systemic activation of T-effector cells. An IKZF2-specific degrader has the potential to focus the enhanced immune response to areas within or near tumors providing a potentially more tolerable and less toxic therapeutic agent for the treatment of cancer.

SUMMARY

One aspect of the disclosure provides phthaloyl-containing compounds having IKZF2 degrader activity. In another aspect, the compounds of the disclosure have degrader activity for IKZF2 that is selective over one or more of IKZF1, IKZF3, IKZF4, and/or IKZF5. The compounds are useful in treating cancer and other diseases for which such degrader activity would be beneficial for the patient. For example, while not intending to be bound by any theory, the inventors believe that reducing levels of IKZF2 in Tregs in a tumor may allow the patient immune system to more effectively attack the disease. In summary, the present disclosure provides novel IKZF2 degraders useful for the treatment of cancer and other diseases.

In some embodiments, the compound of the invention is a compound of Formula (I):

(I)

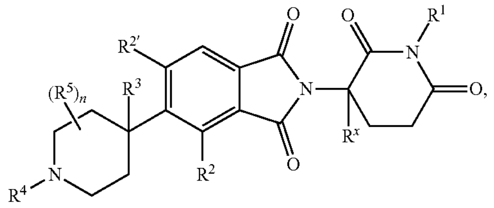

wherein:

$R^1$ is H or $-CH_2OC(O)R^{16}$, $-CH_2OC(O)NHR^{16}$, $-CH_2OC(O)OR^{16}$, $-CH_2OP(O)(OR^{16})_2$, $-CH_2OP(O)(OH)OR^{16}$, or $-CH_2OP(O)(R^{16})_2$;

$R^2$ and $R^{2'}$ are independently selected from H, $(C_1$-$C_6)$alkyl, $(C_1$-$C_6)$alkoxy, $(C_1$-$C_6)$hydroxyalkyl, $(C_1$-$C_6)$haloalkyl, halogen, —OH, and —CN;

$R^3$ is $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$(CH_2)_{0-2}NH(C_1$-$C_6)$alkyl, —$(CH_2)_{0-2}N((C_1$-$C_6)$alkyl$)_2$, —$C(O)NH_2$, —C(O)OH, —$C(O)OR^{15}$, —CN, —$OC(O)R^{16}$, —$OCH_2OC(O)R^{16}$, —$OCH_2OC(O)NHR^{16}$, —$OCH_2OC(O)OR^{16}$, —$OP(O)(OR^{16})_2$, —$OCH_2OP(O)(OH)OR^{16}$, or —$OCH_2OP(O)(R^{16})_2$;

$R^4$ is $(C_1$-$C_6)$alkyl, $(C_6$-$C_{10})$aryl, 5- or 6-membered heteroaryl comprising 1 to 3 heteroatoms selected from O, N, and S, $(C_3$-$C_8)$cycloalkyl, or 4- to 7-membered heterocycloalkyl comprising 1 to 3 heteroatoms selected from O, N, and S, wherein the alkyl is optionally substituted with one or more $R^6$, and the aryl, heteroaryl, cycloalkyl, and heterocycloalkyl are optionally substituted with one or more $R^7$;

each $R^5$ is independently H, $(C_1$-$C_6)$alkyl, $(C_1$-$C_6)$haloalkyl, $(C_1$-$C_6)$hydroxyalkyl, $(C_6$-$C_{10})$aryl, 5- or 6-membered heteroaryl ring comprising 1 to 3 heteroatoms selected from O, N, and S, —CN, or halogen, or two instances of $R^5$ together with the carbon atom or atoms to which they are attached form $(C_3$-$C_7)$cycloalkyl or a 4- to 7-membered heterocycloalkyl ring comprising 1 to 3 heteroatoms selected from O, N, and S, wherein the cycloalkyl and heterocycloalkyl are optionally substituted with one or more $(C_1$-$C_6)$alkyl, $(C_1$-$C_6)$alkoxy, $(C_1$-$C_6)$hydroxyalkyl, $(C_1$-$C_6)$haloalkyl, halogen, —OH, or —CN, or two adjacent instances of $R^5$ together with the carbon atoms to which they are attached form a fused $(C_6)$ aryl or 5- to 6-membered heteroaryl, wherein the aryl or heteroaryl are optionally substituted with one or more $(C_1$-$C_6)$alkyl, $(C_1$-$C_6)$alkoxy, $(C_1$-$C_6)$hydroxyalkyl, $(C_1$-$C_6)$haloalkyl, halogen, —OH, or —CN;

each $R^6$ is independently selected from —$C(O)OR^8$, —$C(O)NR^8R^{8'}$, —$NR^8C(O)R^{8'}$, halogen, —OH, —$NH_2$, —CN, $(C_6$-$C_{10})$aryl, monocyclic or bicyclic 5- to 10-membered heteroaryl comprising 1 to 3 heteroatoms selected from O, N, and S, $(C_3$-$C_8)$cycloalkyl, and 5- to 7-membered heterocycloalkyl ring comprising 1 to 3 heteroatoms selected from O, N, and S, wherein the aryl, heteroaryl, cycloalkyl, and heterocycloalkyl groups are optionally substituted with one or more $R^9$;

each $R^7$ is independently selected from $(C_1$-$C_6)$alkyl, $(C_2$-$C_6)$alkenyl, $(C_2$-$C_6)$alkynyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —$NH_2$, —CN, $(C_3$-$C_7)$cycloalkyl, 5- to 7-membered heterocycloalkyl comprising 1 to 3 heteroatoms selected from O, N, and S, $(C_6$-$C_{10})$aryl, and 5- or 6-membered heteroaryl comprising 1 to 3 heteroatoms selected from O, N, and S, or two instances of $R^7$, when on adjacent atoms, together with the atoms to which they are attached form a $(C_6$-$C_{10})$aryl ring or a 5- or 6-membered heteroaryl ring comprising 1 to 3 heteroatoms selected from O, N, and S, optionally substituted with one or more $R^{12}$, or two instances of $R^7$ together with the atoms to which they are attached form a $(C_3$-$C_7)$cycloalkyl ring or a 4- to 7-membered heterocycloalkyl ring comprising 1 to 3 heteroatoms selected from O, N, and S optionally substituted with one or more $R^{12}$, $R^8$ and $R^{8'}$ are each independently H, $(C_1$-$C_6)$alkyl, or $(C_6$-$C_{10})$aryl, or $R^8$ and $R^{8'}$, together with the nitrogen to which they are attached, form a 5- to 7-membered heterocycloalkyl ring comprising 1 to 3 heteroatoms selected from O, N, and S, optionally substituted with one or more $R^{12}$;

each $R^9$ is independently selected from $(C_1$-$C_6)$alkyl, $(C_2$-$C_6)$alkenyl, $(C_2$-$C_6)$alkynyl, $(C_1$-$C_6)$alkoxy, $(C_1$-$C_6)$haloalkyl, $(C_1$-$C_6)$haloalkoxy, —$C(O)R^{10}$, —$(CH_2)_{0-3}C(O)OR^{10}$, —$C(O)NR^{10}R^{11}$, —$NR^{10}C(O)R^{11}$, —$NR^{10}C(O)OR^{11}$, —$S(O)_pNR^{10}R^{11}$, —$S(O)_pR^{14}$, $(C_1$-$C_6)$hydroxyalkyl, halogen, —OH, —$O(CH_2)_{1-3}CN$, —$NH_2$, —CN, —$O(CH_2)_{0-3}(C_6$-$C_{10})$aryl, adamantyl, —$O(CH_2)_{0-3}$-5- or 6-membered heteroaryl comprising 1 to 3 heteroatoms selected from O, N, and S, $(C_6$-$C_{10})$aryl, monocyclic or bicyclic 5- to 10-membered heteroaryl comprising 1 to 3 heteroatoms selected from O, N, and S, $(C_3$-$C_7)$cycloalkyl, and 5- to 7-membered heterocycloalkyl comprising 1 to 3 heteroatoms selected from O, N, and S, wherein the alkyl is optionally substituted with one or more $R^{13}$, and the aryl, heteroaryl, and heterocycloalkyl are optionally substituted with one or more substituents each independently selected from halogen, $(C_1$-$C_6)$alkyl, $(C_1$-$C_6)$haloalkyl, and $(C_1$-$C_6)$alkoxy, or two instances of $R^9$ together with the carbon atom to which they are attached form C═(O), or two instances of $R^9$, when on adjacent atoms, together with the atoms to which they are attached form a $(C_6$-$C_{10})$aryl ring or a 5- or 6-membered heteroaryl ring comprising 1 to 3 heteroatoms selected from O, N, and S, optionally substituted with one or more $R^{12}$, or two instances of $R^9$ together with the atom or atoms to which they are attached form a $(C_5$-$C_7)$ cycloalkyl ring or a 5- to 7-membered heterocycloalkyl ring comprising 1 to 3 heteroatoms selected from O, N, and S, optionally substituted with one or more $R^{12}$;

$R^{10}$ and $R^{11}$ are each independently H or $(C_1$-$C_6)$alkyl, or $R^{10}$ and $R^{11}$, together with the nitrogen to which they are attached, form a 5- to 7-membered heterocycloalkyl ring comprising 1 to 3 heteroatoms selected from O, N, and S, optionally substituted with one or more $R^{12}$;

each $R^{12}$ is independently selected from $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, $(C_6$-$C_{10})$aryl, 5- to 6-membered heteroaryl, 4- to 7-membered cycloalkyl, 5- to 7-membered heterocyloalkyl, halogen, —OH, —$NH_2$, and —CN, wherein the aryl, heteroaryl, cycloalkyl and hetercycloalkyl are optionally substituted with one or more $(C_1$-$C_6)$alkyl, $(C_1$-$C_6)$alkoxy, $(C_1$-$C_6)$hydroxyalkyl, $(C_1$-$C_6)$haloalkyl, halogen, —OH, or —CN, or two instances of $R^{12}$ together with the carbon atom to which they are attached form C═(O);

each $R^{13}$ is independently selected from —CN, $(C_1$-$C_6)$alkoxy, $(C_6$-$C_{10})$aryl, and 5- to 7-membered heterocycloalkyl comprising 1 to 3 heteroatoms selected from O, N, and S, wherein the aryl and heterocycloalkyl are optionally substituted with one or more substituents each independently selected $(C_1$-$C_6)$alkyl, $(C_1$-$C_6)$alkoxy, $(C_1$-$C_6)$haloalkyl, $(C_1$-$C_6)$haloalkoxy, $(C_1$-$C_6)$hydroxyalkyl, halogen, —OH, —$NH_2$, and —CN;

$R^{14}$ is $(C_1$-$C_6)$alkyl, $(C_1$-$C_6)$haloalkyl, $(C_6$-$C_{10})$aryl, $(C_3$-$C_7)$cycloalkyl, or 5- to 7-membered heterocycloalkyl comprising 1 to 3 heteroatoms selected from O, N, and S;

$R^{15}$ and $R^{16}$ are independently selected for each occurrence H, ($C_1$-$C_6$)alkyl optionally substituted with one or more substituents independently selected from ($C_6$-$C_{10}$)aryl, ($C_1$-$C_6$)alkoxy, ($C_1$-$C_6$)hydroxyalkyl, ($C_1$-$C_6$) haloalkyl, halogen, —OH, —$NH_2$, and —CN, or ($C_6$-$C_{10}$)aryl optionally substituted with one or more substituents independently selected from ($C_1$-$C_6$)alkyl, ($C_1$-$C_6$)alkoxy, ($C_1$-$C_6$)hydroxyalkyl, ($C_1$-$C_6$)haloalkyl, halogen, —OH, —$NH_2$, and —CN;

$R^x$ is H or D;

n is 0, 1, 2, 3, or 4; and p is 1 or 2; or a pharmaceutically acceptable salt, hydrate, solvate, prodrug, stereoisomer, or tautomer thereof;

provided that the compound of Formula (I) is not selected from the group consisting of:

,

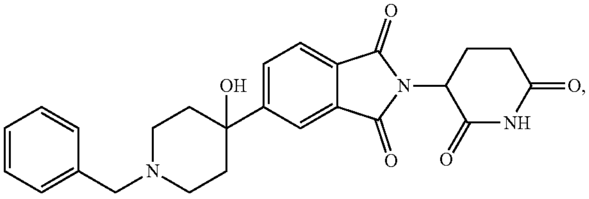

,

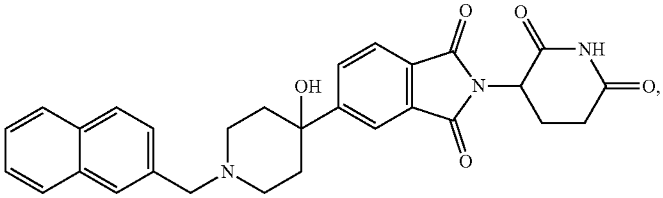

,

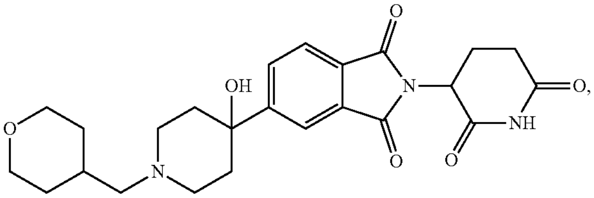

,

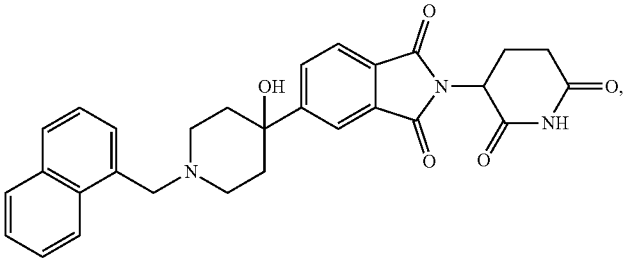

,

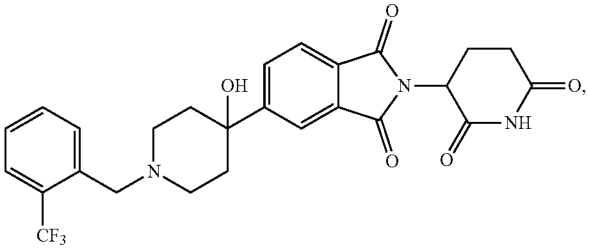

,

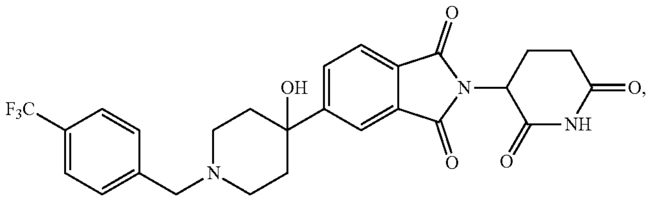

,

-continued
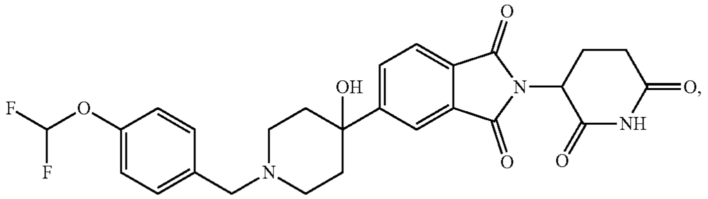
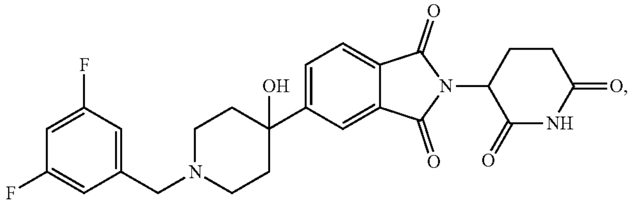
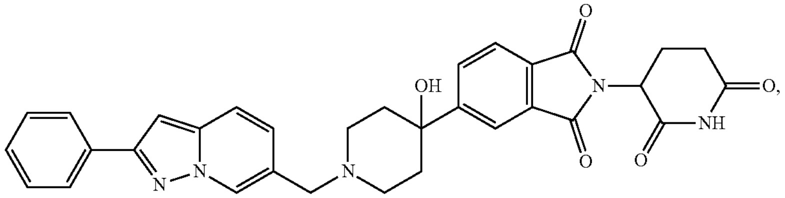
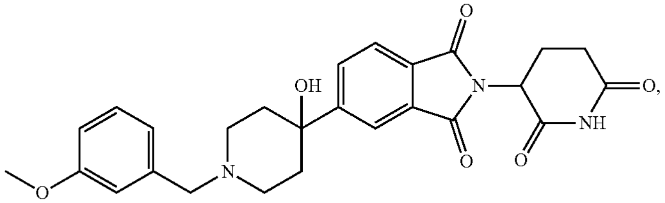
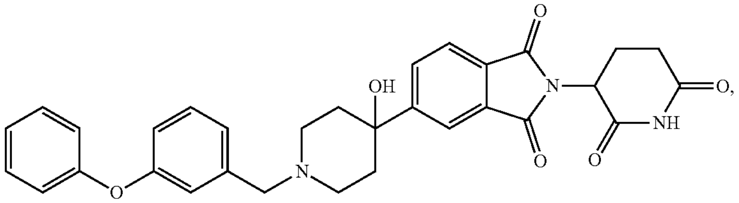
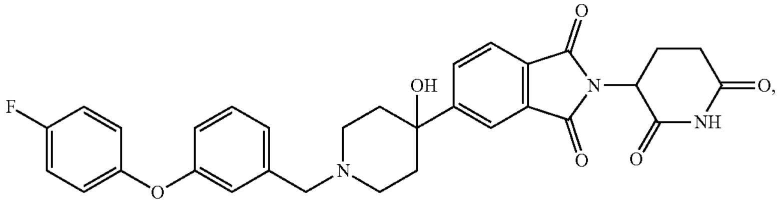
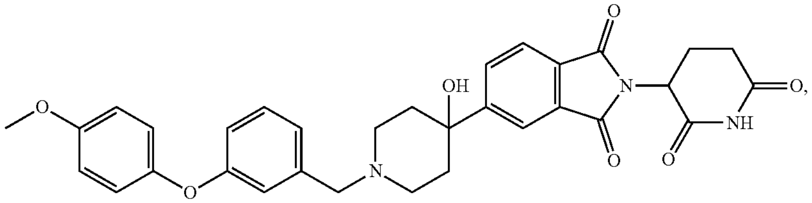
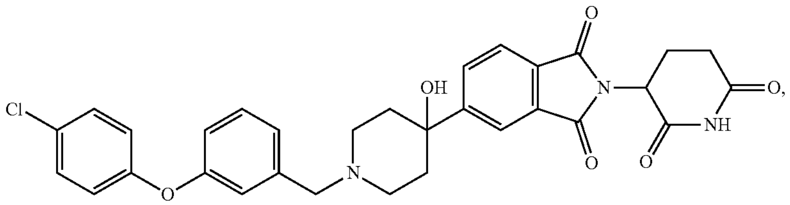
and -continued

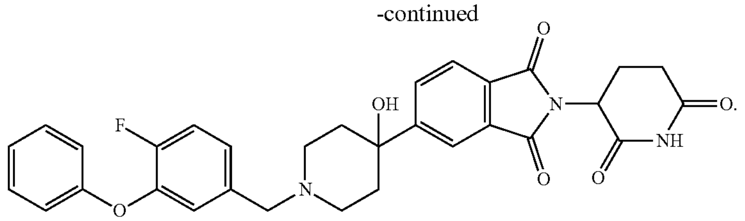

Another aspect of the present disclosure relates to a pharmaceutical composition comprising a therapeutically effective amount of a compound of Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment of IKZF2-dependent diseases or disorders. The pharmaceutical composition may further comprise at least one additional pharmaceutical agent.

In another aspect, the present disclosure relates to a pharmaceutical composition comprising a therapeutically effective amount of a compound of Formula (I), or a pharmaceutically acceptable salt, hydrate, solvate, prodrug, stereoisomer, or tautomer thereof, and a pharmaceutically acceptable carrier or excipient for use in the treatment of an IKZF2-dependent disease or disorder by reducing IKZF2 protein levels wherein reduction of IKZF2 protein levels treats the IKZF2-dependent disease or disorder. The pharmaceutical composition is useful in the treatment of IKZF2-dependent diseases or disorders. The pharmaceutical composition may further comprise at least one additional pharmaceutical agent.

Another aspect of the present disclosure relates to a pharmaceutical composition comprising a therapeutically effective amount of a compound of Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment of diseases or disorders affected by the reduction of IKZF2 protein levels. The pharmaceutical composition may further comprise at least one additional pharmaceutical agent.

In another aspect, the present disclosure relates to a pharmaceutical composition comprising a therapeutically effective amount of a compound of Formula (I), or a pharmaceutically acceptable salt, hydrate, solvate, prodrug, stereoisomer, or tautomer thereof, and a pharmaceutically acceptable carrier or excipient for use in the treatment of a disease or disorder affected by the reduction of IKZF2 protein levels wherein reduction of IKZF2 protein levels treats the disease or disorder. The pharmaceutical composition may further comprise at least one additional pharmaceutical agent.

Another aspect of the present disclosure relates to a method of degrading IKZF2 comprising administering to the patient in need thereof a compound of Formula (I), or a pharmaceutically acceptable salt, hydrate, solvate, prodrug, stereoisomer, or tautomer thereof.

In another aspect, the present disclosure relates to a method of treating a disease or disorder that is affected by the modulation of IKZF2 protein levels comprising administering to the patient in need thereof a compound of Formula (I), or a pharmaceutically acceptable salt, hydrate, solvate, prodrug, stereoisomer, or tautomer thereof.

Another aspect of the present disclosure relates to a method of modulating IKZF2 protein levels comprising administering to the patient in need thereof a compound of Formula (I), or a pharmaceutically acceptable salt, hydrate, solvate, prodrug, stereoisomer, or tautomer thereof.

In another aspect, the present disclosure relates to a method of reducing the proliferation of a cell, the method comprising, contacting the cell with a compound of Formula (I), or a pharmaceutically acceptable salt, hydrate, solvate, prodrug, stereoisomer, or tautomer thereof, and reducing IKZF2 protein levels.

Another aspect of the present disclosure relates to a method of treating cancer comprising administering to the patient in need thereof a compound of Formula (I), or a pharmaceutically acceptable salt, hydrate, solvate, prodrug, stereoisomer, or tautomer thereof. In one embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the cancer is a cancer for which the immune response is deficient or an immunogenic cancer.

In another aspect, the present disclosure relates to a method for reducing IKZF2 protein levels in a subject comprising the step of administering to a subject in need thereof a therapeutically effective amount of a compound of Formula (I), or a pharmaceutically acceptable salt. Another aspect of the present disclosure relates to a compound of Formula (I), or a pharmaceutically acceptable salt, hydrate, solvate, prodrug, stereoisomer, or tautomer thereof, for use in the treatment of a disease or disorder that is affected by the reduction of IKZF2 protein levels.

In another aspect, the present disclosure relates to the use of a compound of Formula (I), or a pharmaceutically acceptable salt, hydrate, solvate, prodrug, stereoisomer, or tautomer thereof, in the manufacture of a medicament for treating a disease or disorder that is affected by the reduction of IKZF2 protein levels.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease or disorder associated with the reduction of IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In another aspect, the present disclosure relates to the use of a compound of Formula (I), or a pharmaceutically acceptable salt, hydrate, solvate, prodrug, stereoisomer, or tautomer thereof, in the treatment of a disease or disorder associated with the reduction of IKZF2 protein levels. In one embodiment, the disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

In another aspect of the disclosure, the compounds according to the disclosure are formulated into pharmaceutical compositions comprising an effective amount, preferably a pharmaceutically effective amount, of a compound according to the disclosure or salt, hydrate, solvate, prodrug, stereoisomer, or tautomer thereof, and a pharmaceutically acceptable excipient or carrier.

In some embodiments of the methods disclosed herein, the administration of the compound of Formula (I), or a pharmaceutically acceptable salt, hydrate, solvate, prodrug, stereoisomer, or tautomer thereof, is performed orally, parentally, subcutaneously, by injection, or by infusion.

The present disclosure provides degraders of IKZF2 that are therapeutic agents in the treatment of diseases such as cancer and metastasis, in the treatment of diseases affected by the modulation of IKZF2 protein levels, and in the treatment IKZF2-dependent diseases or disorders.

In one embodiment, the disease or disorder that can be treated by the compounds of the present disclosure is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, gastrointestinal stromal tumor (GIST), prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, and Ewing's sarcoma. In another embodiment, the IKZF2-dependent disease or disorder is a cancer for which the immune response is deficient or an immunogenic cancer.

The present disclosure provides agents with novel mechanisms of action toward IKZF2 proteins in the treatment of various types of diseases including cancer and metastasis, in the treatment of diseases affected by the modulation of IKZF2 protein levels, and in the treatment IKZF2-dependent diseases or disorders. Ultimately the present disclosure provides the medical community with a novel pharmacological strategy for the treatment of diseases and disorders associated with IKZF2 proteins.

The present disclosure provides agents with novel mechanisms of action toward IKZF2 proteins in the treatment of various types of diseases including cancer and metastasis, in the treatment of diseases affected by the modulation of IKZF2 protein levels, and in the treatment IKZF2-dependent diseases or disorders. Ultimately, the present disclosure provides the medical community with a novel pharmacological strategy for the treatment of diseases and disorders associated with IKZF2 proteins.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

DETAILED DESCRIPTION

Definitions

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

Chemical Nomenclature, Terms, and Conventions

In the groups, radicals, or moieties defined below, the number of carbon atoms is often specified preceding the group, for example, $(C_1\text{-}C_{10})$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "optionally substituted" means that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2$CN, —O—$(C_1\text{-}C_6)$alkyl, $(C_1\text{-}C_6)$alkyl, $(C_1\text{-}C_6)$alkoxy, $(C_1\text{-}C_6)$haloalkyl, $(C_1\text{-}C_6)$haloalkoxy, —O—$(C_2\text{-}C_6)$alkenyl, —O—$(C_2\text{-}C_6)$alkynyl, $(C_2\text{-}C_6)$alkenyl, $(C_2\text{-}C_6)$alkynyl, —OH, —OP(O)$(OH)_2$, —OC(O)$(C_1\text{-}C_6)$alkyl, —C(O)$(C_1\text{-}C_6)$alkyl, —OC(O)O$(C_1\text{-}C_6)$alkyl, —$NH_2$, —NH($(C_1\text{-}C_6)$alkyl), N($(C_1\text{-}C_6)$alkyl$)_2$, —NHC(O)$(C_1\text{-}C_6)$alkyl, —C(O)NH$(C_1\text{-}C_6)$alkyl, —S$(O)_2(C_1\text{-}C_6)$alkyl, —S(O)NH$(C_1\text{-}C_6)$alkyl, and S(O)N($(C_1\text{-}C_6)$alkyl$)_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, —H, -halogen, —CN, —O—($C_1$-$C_6$)alkyl, ($C_1$-$C_6$)alkyl, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)$(OH)_2$, —OC(O)($C_1$-$C_6$)alkyl, —C(O)($C_1$-$C_6$)alkyl, —OC(O)O($C_1$-$C_6$)alkyl, $NH_2$, NH(($C_1$-$C_6$)alkyl), N(($C_1$-$C_6$)alkyl$)_2$, —$S(O)_2$—($C_1$-$C_6$)alkyl, —S(O)NH($C_1$-$C_6$)alkyl, and S(O)N(($C_1$-$C_6$)alkyl$)_2$. The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1D2-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4 d]thiazolyl, imidazo[2,1-b][1,3,4]thiadiazolyl, thieno[2,3-b]pyrrolyl, 3H-indolyl, and derivatives thereof. Furthermore, when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" mean fluorine, chlorine, bromine, or iodine.

"Alkyl" means a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

"Alkylene" or "alkylenyl" means a divalent alkyl radical. Any of the above mentioned monovalent alkyl groups may be an alkylene by abstraction of a second hydrogen atom from the alkyl. As herein defined, alkylene may also be a ($C_1$-$C_6$)alkylene. An alkylene may further be a ($C_1$-$C_4$)alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH$—, and the like.

"Cycloalkyl" or "carbocyclyl" means a monocyclic or polycyclic saturated or partially unsaturated non-aromatic carbon ring containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A ($C_3$-$C_8$)cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" means a saturated or partially saturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Hydroxyalkyl" means an alkyl group substituted with one or more —OH groups. Examples of hydroxyalkyl groups include $HO—CH_2—$, $HO—CH_2CH_2—$, and $CH_2—CH(OH)—$.

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

"Cyano" means a substituent having a carbon atom joined to a nitrogen atom by a triple bond.

"Amino" means a substituent containing at least one nitrogen atom (e.g., $NH_2$).

Salt, Prodrug, Derivative, and Solvate Terms and Conventions

"Prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

"Pharmaceutically acceptable prodrug" as used herein means a prodrug of a compound of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent compound or the product of the reaction between the parent compound with a suitable acid or base to make the acid salt or base salt of the parent compound. Salts of the compounds of the present disclosure can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents. "Pharmaceutically acceptable salt" means a salt of a compound of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present disclosure are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Solvate" means a complex of variable stoichiometry formed by a solute, for example, a compound of Formula (I)) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule(s) is/are water.

The compounds of the present disclosure as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

Isomer Terms and Conventions

"Isomers" means compounds having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure, which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers. "Non-racemic mixture" means a mixture containing unequal parts of individual enantiomers. "Geometrical isomer" means a stable isomer, which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C═N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^{1}H$ NMR, and $^{13}C$ NMR.

Some of the compounds of the disclosure can exist in more than one tautomeric form. As mentioned above, the compounds of the disclosure include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

An "effective amount" or "therapeutically effective amount" when used in connection with a compound means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "pharmaceutically effective amount" or "therapeutically effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, prodrug, stereoisomer, or tautomer thereof, together with at least one pharmaceutically acceptable carrier, in a form suitable for oral or parenteral administration. "Carrier" encompasses carriers, excipients, and diluents and means a material, composition, or vehicle, such as a liquid or solid filler, diluent, excipient, solvent or encapsulating material, involved in carrying or transporting a pharmaceutical agent from one organ, or portion of the body, to another organ, or portion of the body of a subject.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Prodrug" means a compound which is convertible in vivo by metabolic means (e.g., by hydrolysis) to a disclosed compound.

"Compounds of the present disclosure", "compounds of the disclosure", and equivalent expressions (unless specifically identified otherwise) refer to compounds of Formula (I), and other specific compounds described herein including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits. "Stable compound" or "stable structure" means a compound that is sufficiently robust to survive isolation to a useful degree of purity from a reaction mixture, and formulation into an efficacious therapeutic or diagnostic agent. For example, a compound, which would have a "dangling valency" or is a carbanion is not a compound contemplated by the disclosure.

In a specific embodiment, the term "about" or "approximately" means within 20%, preferably within 10%, and more preferably within 5% of a given value or range.

The yield of each of the reactions described herein is expressed as a percentage of the theoretical yield. "Cancer" means any cancer caused by the proliferation of malignant neoplastic cells, such as tumors, neoplasms, carcinomas, sarcomas, leukemias, lymphomas, and the like. For example, cancers include, but are not limited to, mesothelioma, leukemias, and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, and nasopharyngeal), esophageal cancer, genitourinary cancers (e.g., prostate, bladder, renal, uterine, ovarian, testicular), lung cancer (e.g., small-cell and non-small cell), breast cancer, pancreatic cancer, melanoma, and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating, and studying are, for example, colon carcinoma, familiary adenomatous polyposis carcinoma, and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing's sarcoma, and plasmocytoma.

"Simultaneously" or "simultaneous" when referring to a method of treating or a therapeutic use means with a combination of a compound of Formula (I), or a pharmaceutically acceptable salt, hydrate, solvate, prodrug, stereoisomer, or tautomer thereof, and one or more second agent(s) means administration of the compound and the one or more second agent(s) by the same route and at the same time.

"Separately" or "separate" when referring to a method of treating or a therapeutic use means with a combination of a compound of Formula (I), or a pharmaceutically acceptable salt, hydrate, solvate, prodrug, stereoisomer, or tautomer thereof, and one or more second agent(s) means administration of the compound and the one or more second agent(s) by different routes and at approximately the same time.

By therapeutic administration "over a period of time" means, when referring to a method of treating or a therapeutic use with a combination of a compound of Formula (I), or a pharmaceutically acceptable salt, hydrate, solvate, prodrug, stereoisomer, or tautomer thereof, and one or more second agent(s), administration of the compound and the one or more second agent(s) by the same or different routes and at different times. In some embodiments, the administration of the compound or the one or more second agent(s) occurs before the administration of the other begins. In this way, it is possible to administer a one of the active ingredients (i.e., a compound of Formula (I), or a pharmaceutically acceptable salt, hydrate, solvate, prodrug, stereoisomer, or tautomer thereof, or one or more second agent(s)) for several months before administering the other active ingredient or ingredients. In this case, no simultaneous administration occurs. Another therapeutic administration over a period of time consists of the administration over time of the two or more active ingredients of the combination using different frequencies of administration for each of the active ingredients, whereby at certain time points in time simultaneous administration of all of the active ingredients takes place whereas at other time points in time only a part of the active ingredients of the combination may be administered (e.g., for example. a compound of Formula (I), or a pharmaceutically acceptable salt, hydrate, solvate, prodrug, stereoisomer, or tautomer thereof, and the one or more second agents the therapeutic administration over a period of time could be such that a compound of Formula (I), or a pharmaceutically acceptable salt, hydrate, solvate, prodrug, stereoisomer, or tautomer thereof, is administered once a day and the one or more second agent(s) is administered once every four weeks.)

"IKZF2-dependent disease or disorder" means any disease or disorder which is directly or indirectly affected by the modulation of IKZF2 protein levels.

The present disclosure relates to compounds and compositions that are capable of modulating IKZF2 protein levels. The disclosure features methods of treating, preventing, or ameliorating a disease or disorder in which IKZF2 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of IKZF2-dependent diseases and disorders by modulating IKZF2 protein levels. Modulation of IKZF2 protein levels through degradation provides a novel approach to the treatment, prevention, or amelioration of diseases including, but not limited to, cancer and metathesis, and other IKZF2-dependent diseases or disorders.

In one aspect, the compounds of the disclosure have use as therapeutic agents, particularly for cancers and related diseases. In one aspect, the compounds of the disclosure have IKZF2 degradation activity, preferably having such activity at or below the 50 μM level, and more preferably having such activity at or below the 10 μM level. In another aspect, the compounds of the disclosure have degrader activity for IKZF2 that is selective over one or more of IKZF1, IKZF3, IKZF4, and/or IKZF5. The compounds of the disclosure have usefulness in treating cancer and other diseases for which such degradation activity would be beneficial for the patient. For example, while not intending to be bound by any theory, the inventors believe that reducing levels of IKZF2 in Tregs in a tumor may allow the patient immune system to more effectively attack the disease. In summary, the present disclosure provides novel IKZF2 degraders useful for the treatment of cancer and other diseases.

In some embodiments, the compound of the invention is a compound of Formula (I):

(I)

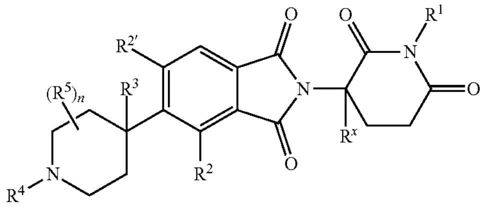

wherein:

$R^1$ is H or $—CH_2OC(O)R^{16}$, $—CH_2OC(O)NHR^{16}$, $—CH_2OC(O)OR^{16}$, $—CH_2OP(O)(OR^{16})_2$, $—CH_2OP(O)(OH)OR^{16}$, or $—CH_2OP(O)(R^{16})_2$;

$R^2$ and $R^{2'}$ are independently selected from H, $(C_1-C_6)$alkyl, $(C_1-C_6)$alkoxy, $(C_1-C_6)$hydroxyalkyl, $(C_1-C_6)$haloalkyl, halogen, —OH, and —CN;

$R^3$ is $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, halogen, —OH, $—NH_2$, $—NHR^{10}$, $—NR^{10}R^{11}$, $—NHC(O)R^{10}$, $—NR^{11}C(O)R^{10}$, $—(CH_2)_{0-2}NH_2$, $—(CH_2)_{0-2}NH(C_1-C_6)$alkyl, $—(CH_2)_{0-2}N((C_1-C_6)alkyl)_2$, $—C(O)NH_2$, —C(O)OH, $—C(O)OR^{15}$, —CN, $—OC(O)R^{16}$, $—OCH_2OC(O)R^{16}$, $—OCH_2OC(O)NHR^{16}$, $—OCH_2OC(O)OR^{16}$, $—OP(O)(OR^{16})_2$, $—OCH_2OP(O)(OH)OR^{16}$, or $—OCH_2OP(O)(R^{16})_2$;

$R^4$ is $(C_1-C_6)$alkyl, $(C_6-C_{10})$aryl, 5- or 6-membered heteroaryl comprising 1 to 3 heteroatoms selected from O, N, and S, $(C_3-C_8)$cycloalkyl, or 4- to 7-membered heterocycloalkyl comprising 1 to 3 heteroatoms selected from O, N, and S, wherein the alkyl is optionally substituted with one or more $R^6$; and the aryl, heteroaryl, cycloalkyl, and heterocycloalkyl are optionally substituted with one or more $R^7$;

each $R^5$ is independently H, $(C_1-C_6)$alkyl, $(C_1-C_6)$haloalkyl, $(C_1-C_6)$hydroxyalkyl, $(C_6-C_{10})$aryl, 5- or 6-membered heteroaryl ring comprising 1 to 3 heteroatoms selected from O, N, and S, —CN, or halogen, or two instances of $R^5$ together with the carbon atom or atoms to which they are attached form $(C_3-C_7)$cycloalkyl or a 4- to 7-membered heterocycloalkyl ring comprising 1 to 3 heteroatoms selected from O, N, and S, wherein the cycloalkyl and heterocycloalkyl are optionally substituted with one or more $(C_1-C_6)$alkyl, $(C_1-C_6)$alkoxy, $(C_1-C_6)$hydroxyalkyl, $(C_1-C_6)$haloalkyl, halogen, —OH, or —CN, or two adjacent instances of $R^5$ together with the carbon atoms to which they are attached form a fused $(C_6)$ aryl or 5- to 6-membered heteroaryl, wherein the aryl or heteroaryl are optionally substituted with one or more $(C_1-C_6)$alkyl, $(C_1-C_6)$alkoxy, $(C_1-C_6)$hydroxyalkyl, $(C_1-C_6)$haloalkyl, halogen, —OH, or —CN;

each $R^6$ is independently selected from $—C(O)OR^8$, $—C(O)NR^8R^{8'}$, $—NR^8C(O)R^{8'}$, halogen, —OH, $—NH_2$, —CN, $(C_6-C_{10})$aryl, monocyclic or bicyclic 5- to 10-membered heteroaryl comprising 1 to 3 heteroatoms selected from O, N, and S, $(C_3-C_8)$cycloalkyl, and 5- to 7-membered heterocycloalkyl ring comprising 1 to 3 heteroatoms selected from O, N, and S; wherein the aryl, heteroaryl, cycloalkyl, and heterocycloalkyl groups are optionally substituted with one or more $R^9$;

each $R^7$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, $(C_1-C_6)$hydroxyalkyl, halogen, —OH, $—NH_2$, —CN, $(C_3-C_7)$cycloalkyl, 5- to 7-membered heterocycloalkyl comprising 1 to 3 heteroatoms selected from O, N, and S, $(C_6-C_{10})$aryl, and 5- or 6-membered heteroaryl comprising 1 to 3 heteroatoms selected from O, N, and S, or two instances of $R^7$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one or more $R^{12}$, or two instances of $R^7$ together with the atoms to which they are attached form a $(C_3-C_7)$cycloalkyl ring or a 4- to 7-membered heterocycloalkyl ring comprising 1 to 3 heteroatoms selected from O, N, and S optionally substituted with one or more $R^{12}$;

$R^8$ and $R^{8'}$ are each independently H, $(C_1-C_6)$alkyl, or $(C_6-C_{10})$aryl, or $R^8$ and $R^{8'}$, together with the nitrogen to which they are attached, form a 5- to 7-membered heterocycloalkyl ring comprising 1 to 3 heteroatoms selected from O, N, and S, optionally substituted with one or more $R^{12}$;

each $R^9$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, $—C(O)R^{10}$, $—(CH_2)_{0-3}C(O)OR^{10}$, $—C(O)NR^{10}R^{11}$, $—NR^{10}C(O)R^{11}$, $—NR^{10}C(O)OR^{11}$, $—S(O)_pNR^{10}R^{11}$, $—S(O)_pR^{14}$, $(C_1-C_6)$hydroxyalkyl, halogen, —OH, $—O(CH_2)_{1-3}CN$, $—NH_2$, —CN, $—O(CH_2)_{0-3}(C_6-C_{10})$aryl, adamantyl, $—O(CH_2)_{0-3}$-5- or 6-membered heteroaryl comprising 1 to 3 heteroatoms selected from O, N, and S, $(C_6-C_{10})$aryl, monocyclic or bicyclic 5- to 10-membered heteroaryl comprising 1 to 3 heteroatoms selected from O, N, and S, $(C_3-C_7)$cycloalkyl, and 5- to 7-membered heterocycloalkyl comprising 1 to 3 heteroatoms selected from O, N, and S, wherein the alkyl is optionally substituted with one or more $R^{13}$, and the aryl, heteroaryl, and heterocycloalkyl are optionally substituted with one or more substituents each independently selected from halogen, $(C_1\text{-}C_6)$alkyl, $(C_1\text{-}C_6)$haloalkyl, and $(C_1\text{-}C_6)$alkoxy, or two instances of $R^9$ together with the carbon atom to which they are attached form C═(O), or two instances of $R^9$, when on adjacent atoms, together with the atoms to which they are attached form a $(C_6\text{-}C_{10})$aryl ring or a 5- or 6-membered heteroaryl ring comprising 1 to 3 heteroatoms selected from O, N, and S, optionally substituted with one or more $R^{12}$, or two instances of $R^9$ together with the atom or atoms to which they are attached form a $(C_5\text{-}C_7)$ cycloalkyl ring or a 5- to 7-membered heterocycloalkyl ring comprising 1 to 3 heteroatoms selected from O, N, and S, optionally substituted with one or more $R^{12}$;

$R^{10}$ and $R^{11}$ are each independently H or $(C_1\text{-}C_6)$alkyl, or $R^{10}$ and $R^{11}$, together with the nitrogen to which they are attached, form a 5- to 7-membered heterocycloalkyl ring comprising 1 to 3 heteroatoms selected from O, N, and S, optionally substituted with one or more $R^{12}$, each $R^{12}$ is independently selected from $(C_1\text{-}C_6)$alkyl, $(C_1\text{-}C_6)$alkoxy, $(C_1\text{-}C_6)$haloalkyl, $(C_1\text{-}C_6)$haloalkoxy, $(C_1\text{-}C_6)$hydroxyalkyl, $(C_6\text{-}C_{10})$aryl, 5- to 6-membered heteroaryl, 4- to 7-membered cycloalkyl, 5- to 7-membered heterocyloalkyl, halogen, —OH, —$NH_2$, and —CN, wherein the aryl, heteroaryl, cycloalkyl and hetercycloalkyl are optionally substituted with one or more $(C_1\text{-}C_6)$alkyl, $(C_1\text{-}C_6)$alkoxy, $(C_1\text{-}C_6)$hydroxyalkyl, $(C_1\text{-}C_6)$haloalkyl, halogen, —OH, or —CN, or two instances of $R^{12}$ together with the carbon atom to which they are attached form C═(O);

each $R^{13}$ is independently selected from —CN, $(C_1\text{-}C_6)$alkoxy, $(C_6\text{-}C_{10})$aryl, and 5- to 7-membered heterocycloalkyl comprising 1 to 3 heteroatoms selected from O, N, and S, wherein the aryl and heterocycloalkyl are optionally substituted with one or more substituents each independently selected from $(C_1\text{-}C_6)$alkyl, $(C_1\text{-}C_6)$alkoxy, $(C_1\text{-}C_6)$haloalkyl, $(C_1\text{-}C_6)$haloalkoxy, $(C_1\text{-}C_6)$hydroxyalkyl, halogen, —OH, —$NH_2$, and —CN;

$R^{14}$ is $(C_1\text{-}C_6)$alkyl, $(C_1\text{-}C_6)$haloalkyl, $(C_6\text{-}C_{10})$aryl, $(C_3\text{-}C_7)$cycloalkyl, or 5- to 7-membered heterocycloalkyl comprising 1 to 3 heteroatoms selected from O, N, and S;

$R^{15}$ and $R^{16}$ are independently selected for each occurrence H, $(C_1\text{-}C_6)$alkyl optionally substituted with one or more substituents independently selected from $(C_6\text{-}C_{10})$aryl, $(C_1\text{-}C_6)$alkoxy, $(C_1\text{-}C_6)$hydroxyalkyl, $(C_1\text{-}C_6)$haloalkyl, halogen, —OH, —$NH_2$, and —CN, or $(C_6\text{-}C_{10})$aryl optionally substituted with one or more substituents independently selected from $(C_1\text{-}C_6)$alkyl, $(C_1\text{-}C_6)$alkoxy, $(C_1\text{-}C_6)$hydroxyalkyl, $(C_1\text{-}C_6)$haloalkyl, halogen, —OH, —$NH_2$, and —CN;

$R^x$ is H or D;

n is 0, 1, 2, 3, or 4; and p is 1 or 2; or a pharmaceutically acceptable salt, hydrate, solvate, prodrug, stereoisomer, or tautomer thereof;

provided that the compound of Formula (I) is not selected from the group consisting of:

,

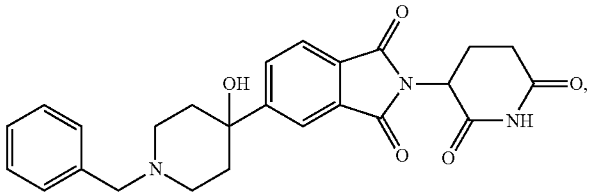

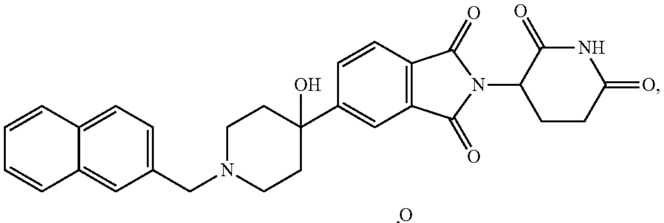

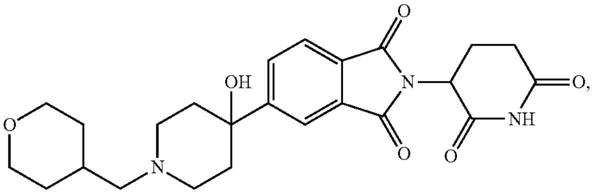

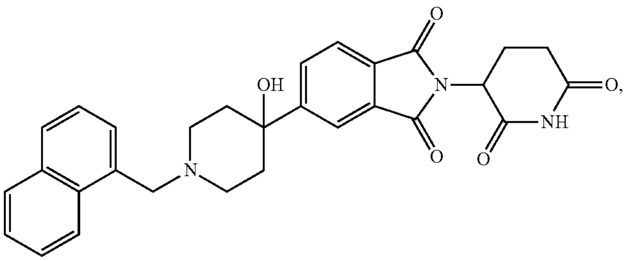

-continued
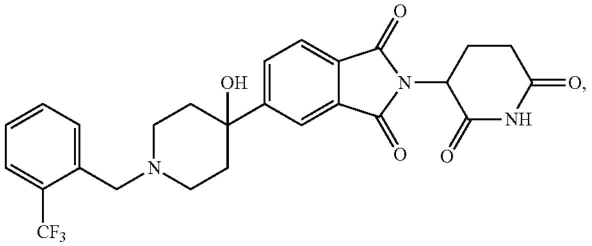
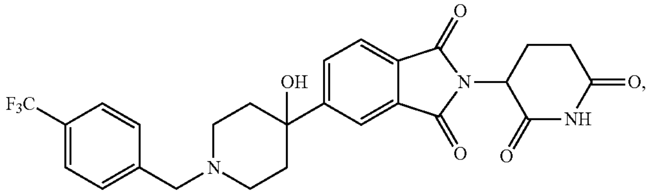
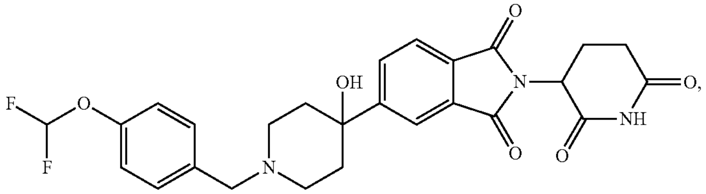
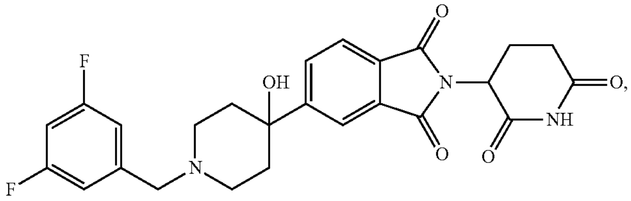
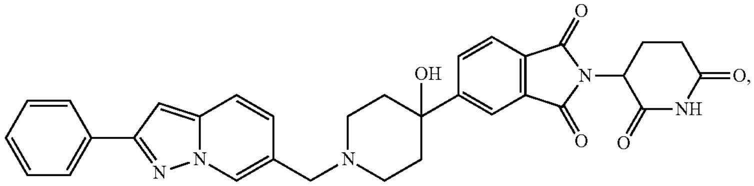
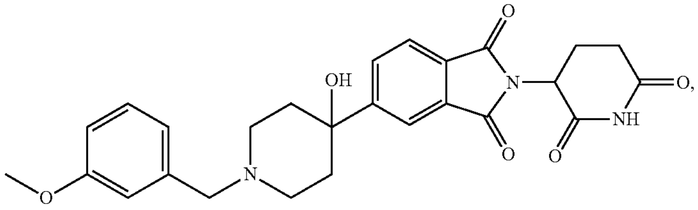
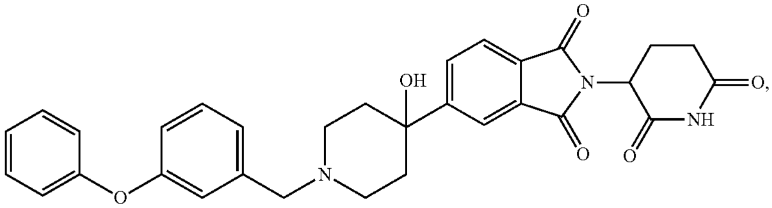
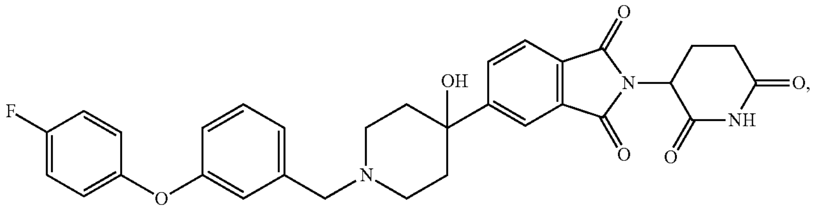

-continued

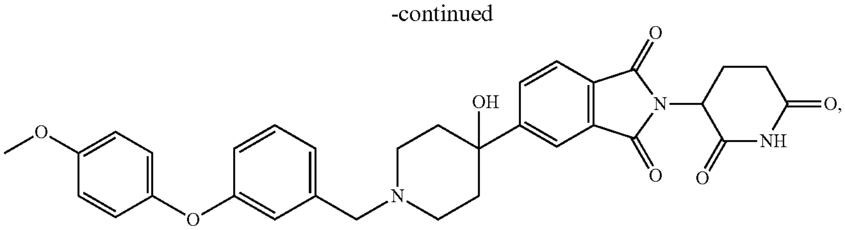

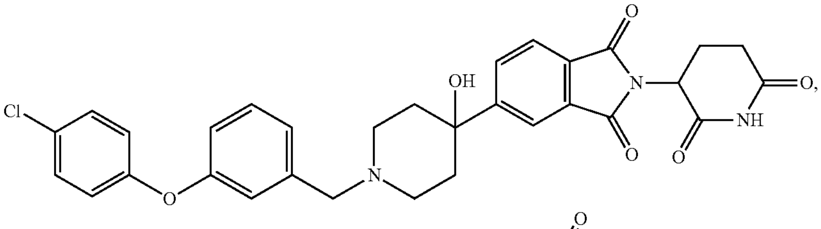

and

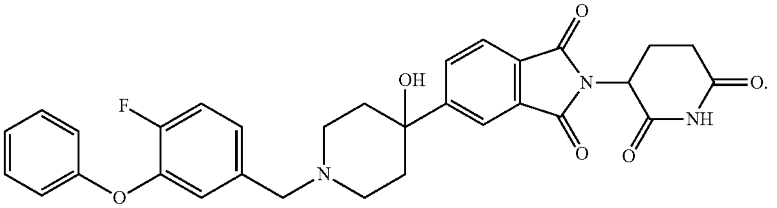

In some embodiments of the Formula (I), $R^1$ is H or —$CH_2OC(O)R^{16}$, —$CH_2OC(O)NHR^{16}$, —$CH_2OC(O)OR^{16}$, —$CH_2OP(O)(OR^{16})_2$, —$CH_2OP(O)(OH)OR^{16}$, or —$CH_2OP(O)(R^{16})_2$;

$R^2$ and $R^{2'}$ are independently selected from H, ($C_1$-$C_6$)alkyl, ($C_1$-$C_6$)alkoxy, ($C_1$-$C_6$)hydroxyalkyl, ($C_1$-$C_6$)haloalkyl, halogen, —OH, and —CN;

$R^3$ is ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$(CH_2)_{0-2}NH$($C_1$-$C_6$)alkyl, —$(CH_2)_{0-2}N$(($C_1$-$C_6$)alkyl$)_2$, —$C(O)NH_2$, —C(O)OH, —$C(O)OR^{15}$, —CN, —$OC(O)R^{16}$, —$OCH_2OC(O)R^{16}$, —$OCH_2OC(O)NHR^{16}$, —$OCH_2OC(O)OR^{16}$, —$OP(O)(OR^{16})_2$, —$OCH_2OP(O)(OH)OR^{16}$, or —$OCH_2OP(O)(R^{16})_2$;

$R^4$ is ($C_1$-$C_6$)alkyl, ($C_6$-$C_{10}$)aryl, 5- or 6-membered heteroaryl comprising 1 to 3 heteroatoms selected from O, N, and S, ($C_3$-$C_8$)cycloalkyl, or 4- to 7-membered heterocycloalkyl comprising 1 to 3 heteroatoms selected from O, N, and S, wherein the alkyl is optionally substituted with one to four $R^6$; and the aryl, heteroaryl, cycloalkyl, and heterocycloalkyl are optionally substituted with one to four $R^7$;

each $R^5$ is independently H, ($C_1$-$C_6$)alkyl, ($C_1$-$C_6$)haloalkyl, ($C_1$-$C_6$)hydroxyalkyl, ($C_6$-$C_{10}$)aryl, 5- or 6-membered heteroaryl ring comprising 1 to 3 heteroatoms selected from O, N, and S, —CN, or halogen, or two instances of $R^5$ together with the carbon atom or atoms to which they are attached form ($C_3$-$C_7$)cycloalkyl or a 4- to 7-membered heterocycloalkyl ring comprising 1 to 3 heteroatoms selected from O, N, and S, wherein the cycloalkyl and heterocycloalkyl are optionally substituted with one to four ($C_1$-$C_6$)alkyl, ($C_1$-$C_6$)alkoxy, ($C_1$-$C_6$)hydroxyalkyl, ($C_1$-$C_6$)haloalkyl, halogen, —OH, or —CN, or two adjacent instances of $R^5$ together with the carbon atoms to which they are attached form a fused ($C_6$) aryl or 5- to 6-membered heteroaryl, wherein the aryl or heteroaryl are optionally substituted with one to four ($C_1$-$C_6$)alkyl, ($C_1$-$C_6$)alkoxy, ($C_1$-$C_6$)hydroxyalkyl, ($C_1$-$C_6$)haloalkyl, halogen, —OH, or —CN;

each $R^6$ is independently selected from —$C(O)OR^8$, —$C(O)NR^8R^{8'}$, —$NR^8C(O)R^{8'}$, halogen, —OH, —$NH_2$, —CN, ($C_6$-$C_{10}$)aryl, monocyclic or bicyclic 5- to 10-membered heteroaryl comprising 1 to 3 heteroatoms selected from O, N, and S, ($C_3$-$C_8$)cycloalkyl, and 5- to 7-membered heterocycloalkyl ring comprising 1 to 3 heteroatoms selected from O, N, and S; wherein the aryl, heteroaryl, cycloalkyl, and heterocycloalkyl groups are optionally substituted with one to four $R^9$;

each $R^7$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —$NH_2$, —CN, ($C_3$-$C_7$)cycloalkyl, 5- to 7-membered heterocycloalkyl comprising 1 to 3 heteroatoms selected from O, N, and S, ($C_6$-$C_{10}$)aryl, and 5- or 6-membered heteroaryl comprising 1 to 3 heteroatoms selected from O, N, and S, or two instances of $R^7$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R^{12}$, or two instances of $R^7$ together with the atoms to which they are attached form a ($C_3$-$C_7$)cycloalkyl ring or a 4- to 7-membered heterocycloalkyl ring comprising 1 to 3 heteroatoms selected from O, N, and S optionally substituted with one to four $R^{12}$;

$R^8$ and $R^{8'}$ are each independently H, ($C_1$-$C_6$)alkyl, or ($C_6$-$C_{10}$)aryl, or $R^8$ and $R^{8'}$, together with the nitrogen to which they are attached, form a 5- to 7-membered heterocycloalkyl ring comprising 1 to 3 heteroatoms selected from O, N, and S, optionally substituted with one to four $R^{12}$;

each $R^9$ is independently selected from ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, —$C(O)R^{10}$, —$(CH_2)_{0-3}C(O)OR^{10}$, —$C(O)NR^{10}R^{11}$, —$NR^{10}C(O)R^{11}$, —$NR^{10}C(O)OR^{11}$, —$S(O)_pNR^{10}R^{11}$, —$S(O)_pR^{14}$, ($C_1$-$C_6$)hydroxyalkyl, halogen, —OH, —$O(CH_2)_{1-3}CN$, —$NH_2$, —CN, —$O(CH_2)_{0-3}$($C_6$-$C_{10}$)aryl, adamantyl, —$O(CH_2)_{0-3}$-5- or 6-membered heteroaryl comprising 1 to 3 heteroatoms selected from O, N, and S, ($C_6$-$C_{10}$)aryl, monocyclic or bicyclic 5- to 10-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S, wherein the alkyl is optionally substituted with one to four $R^{13}$, and the aryl, heteroaryl, and heterocycloalkyl are optionally substituted with one to four substituents each independently selected from halogen, ($C_1$-$C_6$)alkyl, ($C_1$-$C_6$)haloalkyl, and ($C_1$-$C_6$)alkoxy, or two instances of $R^9$ together with the carbon atom to which they are attached form C═(O), or two instances of $R^9$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R^{12}$, or two instances of $R^9$ together with the atom or atoms to which they are attached form a ($C_5$-$C_7$) cycloalkyl ring or a 5- to 7-membered heterocycloalkyl ring comprising 1 to 3 heteroatoms selected from O, N, and S, optionally substituted with one to four $R^{12}$;

$R^{10}$ and $R^{11}$ are each independently H or ($C_1$-$C_6$)alkyl, or $R^{10}$ and $R^{11}$, together with the nitrogen to which they are attached, form a 5- to 7-membered heterocycloalkyl ring comprising 1 to 3 heteroatoms selected from O, N, and S, optionally substituted with one to four $R^{12}$;

each $R^{12}$ is independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, ($C_6$-$C_{10}$)aryl, 5- to 6-membered heteroaryl, 4- to 7-membered cycloalkyl, 5- to 7-membered heterocycloalkyl, halogen, —OH, —$NH_2$, and —CN, wherein the aryl, heteroaryl, cycloalkyl and hetercycloalkyl are optionally substituted with one to four ($C_1$-$C_6$)alkyl, ($C_1$-$C_6$)alkoxy, ($C_1$-$C_6$)hydroxyalkyl, ($C_1$-$C_6$)haloalkyl, halogen, —OH, or —CN, or two instances of $R^{12}$ together with the carbon atom to which they are attached form C═(O);

each $R^{13}$ is independently selected from —CN, ($C_1$-$C_6$)alkoxy, ($C_6$-$C_{10}$)aryl, and 5- to 7-membered heterocycloalkyl comprising 1 to 3 heteroatoms selected from O, N, and S, wherein the aryl and heterocycloalkyl are optionally substituted with one to four substituents each independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, —$NH_2$, and —CN;

$R^{14}$ is ($C_1$-$C_6$)alkyl, ($C_1$-$C_6$)haloalkyl, ($C_6$-$C_{10}$)aryl, ($C_3$-$C_7$)cycloalkyl, or 5- to 7-membered heterocycloalkyl comprising 1 to 3 heteroatoms selected from O, N, and S;

$R^{15}$ and $R^{16}$ are independently selected for each occurrence H, ($C_1$-$C_6$)alkyl optionally substituted with one to four substituents independently selected from ($C_6$-$C_{10}$)aryl, ($C_1$-$C_6$)alkoxy, ($C_1$-$C_6$)hydroxyalkyl, ($C_1$-$C_6$)haloalkyl, halogen, —OH, —$NH_2$, and —CN, or ($C_6$-$C_{10}$)aryl optionally substituted with one to four substituents independently selected from ($C_1$-$C_6$)alkyl, ($C_1$-$C_6$)alkoxy, ($C_1$-$C_6$)hydroxyalkyl, ($C_1$-$C_6$)haloalkyl, halogen, —OH, —$NH_2$, and —CN;

$R^x$ is H or D;

n is 0, 1, 2, 3, or 4; and p is 1 or 2; or a pharmaceutically acceptable salt, hydrate, solvate, prodrug, stereoisomer, or tautomer thereof;

provided that the compound of Formula (I) is not selected from the group consisting of:

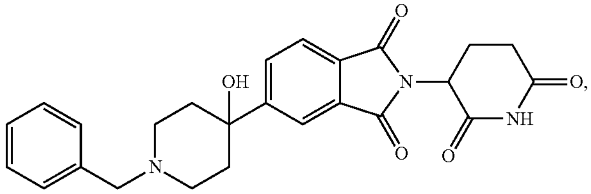

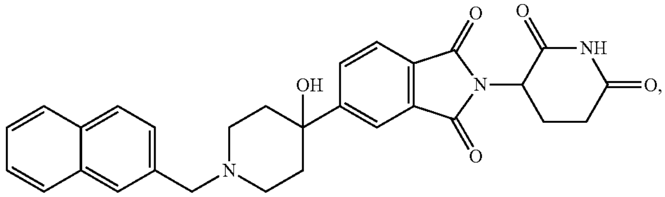

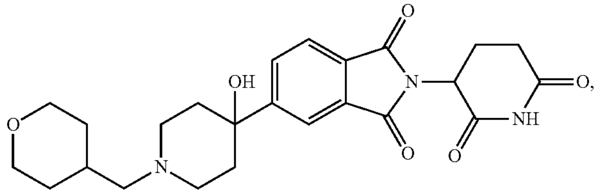

-continued
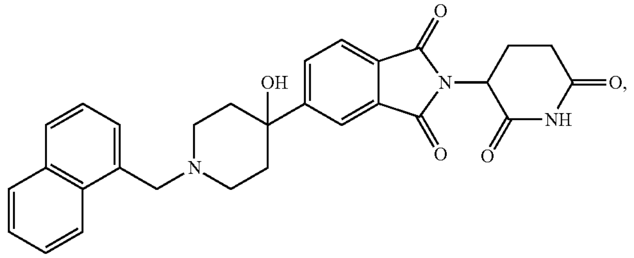
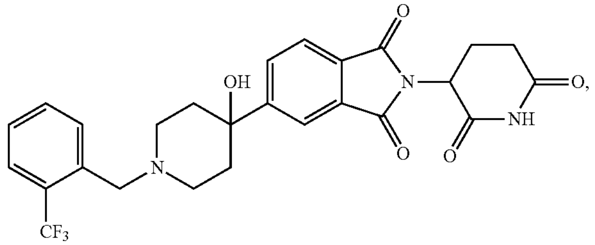
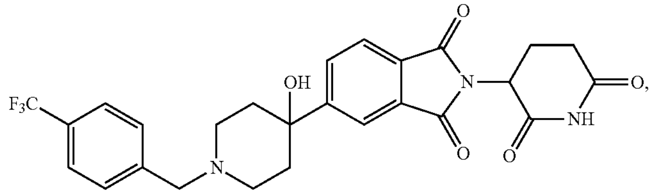
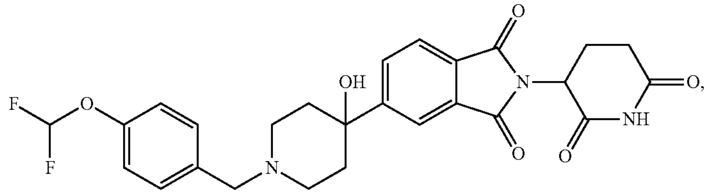
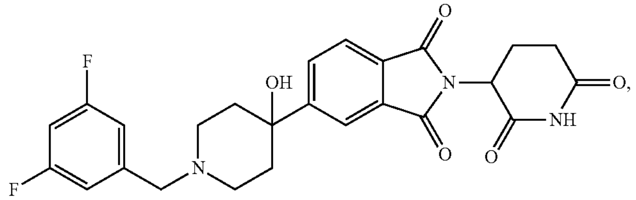
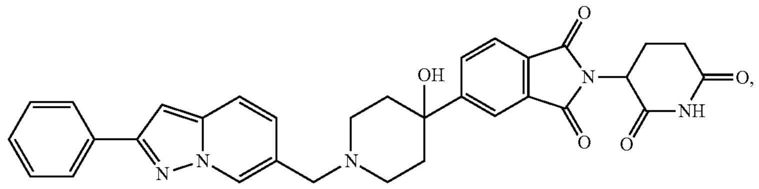
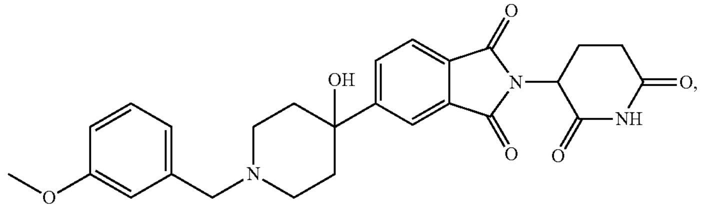
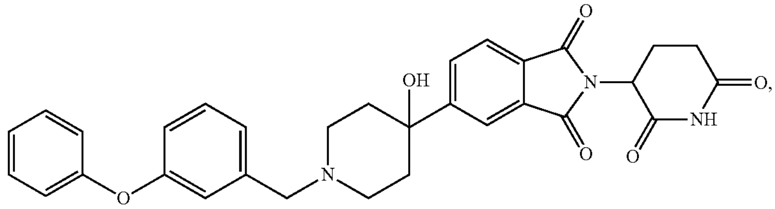

-continued

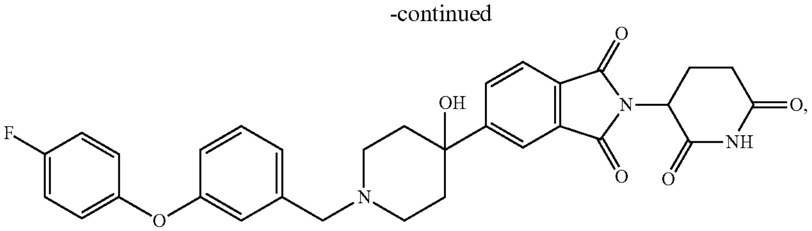

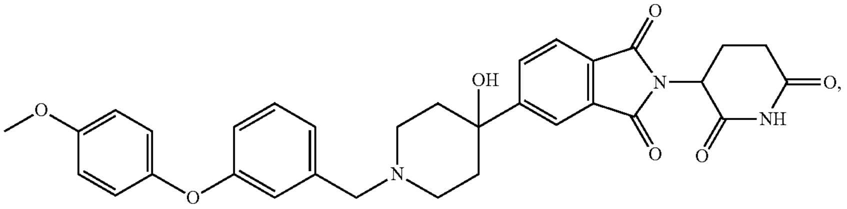

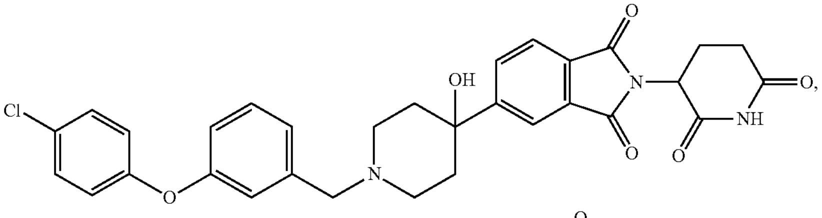

and

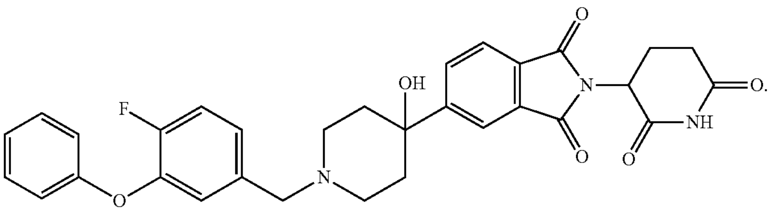

In some embodiments of the Formula (I), $R^4$ is $(C_1\text{-}C_6)$alkyl, $(C_6\text{-}C_{10})$aryl, 5- or 6-membered heteroaryl comprising 1 to 3 heteroatoms selected from O, N, and S, $(C_3\text{-}C_8)$cycloalkyl, or 4- to 7-membered heterocycloalkyl comprising 1 to 3 heteroatoms selected from O, N, and S, wherein the alkyl is optionally substituted with one to four $R^6$; and the aryl, heteroaryl, cycloalkyl, and heterocycloalkyl are optionally substituted with one to four $R^7$;

each $R^5$ is independently H, $(C_1\text{-}C_6)$alkyl, $(C_1\text{-}C_6)$haloalkyl, $(C_1\text{-}C_6)$hydroxyalkyl, $(C_6\text{-}C_{10})$aryl, 5- or 6-membered heteroaryl ring comprising 1 to 3 heteroatoms selected from O, N, and S, —CN, or halogen, or two instances of $R^5$ together with the carbon atom or atoms to which they are attached form $(C_3\text{-}C_7)$cycloalkyl or a 4- to 7-membered heterocycloalkyl ring comprising 1 to 3 heteroatoms selected from O, N, and S, wherein the cycloalkyl and heterocycloalkyl are optionally substituted with one to four $(C_1\text{-}C_6)$alkyl, $(C_1\text{-}C_6)$alkoxy, $(C_1\text{-}C_6)$hydroxyalkyl, $(C_1\text{-}C_6)$haloalkyl, halogen, —OH, or —CN, or two adjacent instances of $R^5$ together with the carbon atoms to which they are attached form a fused $(C_6)$ aryl or 5- to 6-membered heteroaryl, wherein the aryl or heteroaryl are optionally substituted with one to four $(C_1\text{-}C_6)$alkyl, $(C_1\text{-}C_6)$alkoxy, $(C_1\text{-}C_6)$hydroxyalkyl, $(C_1\text{-}C_6)$haloalkyl, halogen, —OH, or —CN;

each $R^6$ is independently selected from —C(O)OR$^8$, —C(O)NR$^8$R$^{8'}$, —NR$^8$C(O)R$^8$, halogen, —OH, —$NH_2$, —CN, $(C_6\text{-}C_{10})$aryl, monocyclic or bicyclic 5- to 10-membered heteroaryl comprising 1 to 3 heteroatoms selected from O, N, and S, $(C_3\text{-}C_8)$cycloalkyl, and 5- to 7-membered heterocycloalkyl ring comprising 1 to 3 heteroatoms selected from O, N, and S; wherein the aryl, heteroaryl, cycloalkyl, and heterocycloalkyl groups are optionally substituted with one to four $R^9$;

each $R^7$ is independently selected from $(C_1\text{-}C_6)$alkyl, $(C_2\text{-}C_6)$alkenyl, $(C_2\text{-}C_6)$alkynyl, $(C_1\text{-}C_6)$alkoxy, $(C_1\text{-}C_6)$haloalkyl, $(C_1\text{-}C_6)$haloalkoxy, $(C_1\text{-}C_6)$hydroxyalkyl, halogen, —OH, —$NH_2$, —CN, $(C_3\text{-}C_7)$cycloalkyl, 5- to 7-membered heterocycloalkyl comprising 1 to 3 heteroatoms selected from O, N, and S, $(C_6\text{-}C_{10})$aryl, and 5- or 6-membered heteroaryl comprising 1 to 3 heteroatoms selected from O, N, and S, or two instances of $R^7$, when on adjacent atoms, together with the atoms to which they are attached form a $(C_6\text{-}C_{10})$aryl ring or a 5- or 6-membered heteroaryl ring comprising 1 to 3 heteroatoms selected from O, N, and S, optionally substituted with one to four $R^{12}$, or two instances of $R^7$ together with the atoms to which they are attached form a $(C_3\text{-}C_7)$cycloalkyl ring or a 4- to 7-membered heterocycloalkyl ring comprising 1 to 3 heteroatoms selected from O, N, and S optionally substituted with one to four $R^{12}$;

$R^8$ and $R^{8'}$ are each independently H, $(C_1\text{-}C_6)$alkyl, or $(C_6\text{-}C_{10})$aryl, or $R^8$ and $R^{8'}$, together with the nitrogen to which they are attached, form a 5- to 7-membered heterocycloalkyl ring comprising 1 to 3 heteroatoms selected from O, N, and S, optionally substituted with one to four $R^{12}$;

each $R^9$ is independently selected from $(C_1\text{-}C_6)$alkyl, $(C_2\text{-}C_6)$alkenyl, $(C_2\text{-}C_6)$alkynyl, $(C_1\text{-}C_6)$alkoxy, $(C_1\text{-}C_6)$haloalkyl, $(C_1\text{-}C_6)$haloalkoxy, —C(O)R$^{10}$, —$(CH_2)_{0\text{-}3}$C(O)OR$^{10}$, —C(O)NR$^{10}$R$^{11}$, —NR$^{10}$C(O)

$R^{11}$, $—NR^{10}C(O)OR^{11}$, $—S(O)_pNR^{10}R^{11}$, $—S(O)_pR^{14}$, ($C_1$-$C_6$)hydroxyalkyl, halogen, —OH, $—O(CH_2)_{1-3}CN$, $—NH_2$, —CN, $—O(CH_2)_{0-3}(C_6$-$C_{10})$aryl, adamantyl, $—O(CH_2)_{0-3}$-5- or 6-membered heteroaryl comprising 1 to 3 heteroatoms selected from O, N, and S, ($C_6$-$C_{10}$)aryl, monocyclic or bicyclic 5- to 10-membered heteroaryl comprising 1 to 3 heteroatoms selected from O, N, and S, ($C_3$-$C_7$)cycloalkyl, and 5- to 7-membered heterocycloalkyl comprising 1 to 3 heteroatoms selected from O, N, and S, wherein the alkyl is optionally substituted with one to four $R^{13}$, and the aryl, heteroaryl, and heterocycloalkyl are optionally substituted with one to four substituents each independently selected from halogen, ($C_1$-$C_6$)alkyl, ($C_1$-$C_6$) haloalkyl, and ($C_1$-$C_6$)alkoxy, or two instances of $R^9$ together with the carbon atom to which they are attached form C═(O), or two instances of $R^9$, when on adjacent atoms, together with the atoms to which they are attached form a ($C_6$-$C_{10}$)aryl ring or a 5- or 6-membered heteroaryl ring comprising 1 to 3 heteroatoms selected from O, N, and S, optionally substituted with one to four $R^{12}$, or two instances of $R^9$ together with the atom or atoms to which they are attached form a ($C_5$-$C_7$) cycloalkyl ring or a 5- to 7-membered heterocycloalkyl ring comprising 1 to 3 heteroatoms selected from O, N, and S, optionally substituted with one to four $R^{12}$;

$R^{10}$ and $R^{11}$ are each independently H or ($C_1$-$C_6$)alkyl, or $R^{10}$ and $R^{11}$, together with the nitrogen to which they are attached, form a 5- to 7-membered heterocycloalkyl ring comprising 1 to 3 heteroatoms selected from O, N, and S, optionally substituted with one to four $R^{12}$;

each $R^{12}$ is independently selected from ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, ($C_6$-$C_{10}$)aryl, 5- to 6-membered heteroaryl, 4- to 7-membered cycloalkyl, 5- to 7-membered heterocyloalkyl, halogen, —OH, $—NH_2$, and —CN, wherein the aryl, heteroaryl, cycloalkyl and hetercycloalkyl are optionally substituted with one to four ($C_1$-$C_6$)alkyl, ($C_1$-$C_6$)alkoxy, ($C_1$-$C_6$)hydroxyalkyl, ($C_1$-$C_6$)haloalkyl, halogen, —OH, or —CN, or two instances of $R^{12}$ together with the carbon atom to which they are attached form C═(O);

each $R^{13}$ is independently selected from —CN, ($C_1$-$C_6$) alkoxy, ($C_6$-$C_{10}$)aryl, and 5- to 7-membered heterocycloalkyl comprising 1 to 3 heteroatoms selected from O, N, and S, wherein the aryl and heterocycloalkyl are optionally substituted with one to four substituents each independently ($C_1$-$C_6$)alkyl, ($C_1$-$C_6$)alkoxy, ($C_1$-$C_6$)haloalkyl, ($C_1$-$C_6$)haloalkoxy, ($C_1$-$C_6$)hydroxyalkyl, halogen, —OH, $—NH_2$, and —CN;

$R^{15}$ and $R^{16}$ are independently selected for each occurrence H, ($C_1$-$C_6$)alkyl optionally substituted with one to four substituents independently selected from ($C_6$-$C_{10}$)aryl, ($C_1$-$C_6$)alkoxy, ($C_1$-$C_6$)hydroxyalkyl, ($C_1$-$C_6$) haloalkyl, halogen, —OH, $—NH_2$, and —CN, or ($C_6$-$C_{10}$)aryl optionally substituted with one to four substituents independently selected from ($C_1$-$C_6$)alkyl, ($C_1$-$C_6$)alkoxy, ($C_1$-$C_6$)hydroxyalkyl, ($C_1$-$C_6$)haloalkyl, halogen, —OH, $—NH_2$, and —CN;

In some embodiments of Formula (I), $R^x$ is H.

In some embodiments of Formula (I), $R^1$ is H.

In some embodiments of Formula (I), $R^2$ is H, ($C_1$-$C_6$) alkyl, ($C_1$-$C_6$)alkoxy, or halogen.

In other embodiments of Formula (I), $R^2$ is H, $—CH_3$, F, Cl or $—OCH_3$.

In some embodiments of Formula (I), $R^{2'}$ is H.

In some embodiments of Formula (I), $R^2$ is H.

In some embodiments of Formula (I), $R^3$ is ($C_1$-$C_6$)alkyl, ($C_1$-$C_6$)alkoxy, —CN, ($C_1$-$C_6$)hydroxyalkyl, halogen, —OH, $—NH_2$, $—NHR^{10}$, $—NR^{10}R^{11}$, $—NHC(O)R^{10}$, $—NR^{11}C(O)R^{10}$, $—(CH_2)_{0-2}NH_2$, $—C(O)NH_2$, $—C(O)OR^{15}$ or —CN.

In some embodiments of Formula (I), $R^3$ is ($C_1$-$C_6$)alkyl, halogen, or —OH.

In some embodiments of Formula (I), $R^3$ is -Me, —F, —OH. In other embodiments of Formula (I), $R^3$ is —F.

In other embodiments of Formula (I), $R^3$ is -Me.

In other embodiments of Formula (I), $R^3$ is —OH.

In some embodiments of Formula (I), $R^4$ is ($C_1$-$C_6$)alkyl optionally substituted with one to three instances of $R^6$.

In some embodiments of Formula (I), $R^4$ is ($C_1$-$C_6$)alkyl substituted with one to three instances of $R^6$.

In some embodiments of Formula (I), $R^4$ is ($C_1$) alkyl, substituted with one or more instances of $R^6$.

In some embodiments of Formula (I), $R^5$ is ($C_1$-$C_6$)alkyl.

In some embodiments of Formula (I), $R^6$ is selected from ($C_6$-$C_{10}$)aryl and 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^6$ is phenyl optionally substituted with one to three instances of $R^8$ In some embodiments of Formula (I), $R^6$ is 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^6$ is cycloalkyl.

In some embodiments of Formula (I), n is 0.

In some embodiments, n is 0, 1, 2, or 3. In another embodiment, n is 1, 2, 3, or 4. In yet another embodiment, n is 0 or 1. In another embodiment, n is 1 or 2. In yet another embodiment, n is 3 or 4. In another embodiment, n is 1. In yet another embodiment, n is 2. In another embodiment, n is 3. In yet another embodiment, n is 4.

In some embodiments of Formula (I), $R^x$ is H and $R^1$ is H.

In some embodiments of Formula (I), $R^x$ is H, $R^1$ is H, and $R^2$ is H, ($C_1$-$C_6$)alkyl, ($C_1$-$C_6$)alkoxy, or halogen.

In some embodiments of Formula (I), $R^x$ is H, $R^1$ is H, and $R^2$ is H, $—CH_3$, F, Cl or $—OCH_3$.

In some embodiments of Formula (I), $R^x$ is H, $R^1$ is H, $R^2$ is H, ($C_1$-$C_6$)alkyl, ($C_1$-$C_6$)alkoxy, or halogen and $R^{2'}$ is H.

In some embodiments of Formula (I), $R^x$ is H, $R^1$ is H, $R^2$ is H, $—CH_3$, F, Cl or $—OCH_3$ and $R^{2'}$ is H. In some embodiments of Formula (I), wherein $R^x$ is H, $R^1$ is H, $R^2$ is H, ($C_1$-$C_6$)alkyl, ($C_1$-$C_6$)alkoxy, or halogen, $R^2$ is H and $R^3$ is ($C_1$-$C_6$)alkyl, ($C_1$-$C_6$)alkoxy, —CN, ($C_1$-$C_6$)hydroxyalkyl, halogen, —OH, $—NH_2$, $—NHR^{10}$, $—NR^{10}R^{11}$, $—NHC(O)R^{10}$, $—NR^{11}C(O)R^{10}$, $—(CH_2)_{0-2}NH_2$, $—C(O)NH_2$, $—C(O)OR^{15}$ or —CN.

In some embodiments of Formula (I), $R^x$ is H, $R^1$ is H, $R^2$ is H, $—CH_3$, F, Cl or $—OCH_3$, $R^{2'}$ is H and $R^3$ is ($C_1$-$C_6$) alkyl, ($C_1$-$C_6$)alkoxy, —CN, ($C_1$-$C_6$)hydroxyalkyl, halogen, —OH, $—NH_2$, $—NHR^{10}$, $—NR^{10}R^{11}$, $—NHC(O)R^{10}$, $—NR^{11}C(O)R^{10}$, $—(CH_2)_{0-2}NH_2$, $—C(O)NH_2$, $—C(O)OR^{15}$ or —CN.

In some embodiments of Formula (I), $R^x$ is H, $R^1$ is H, $R^2$ is H, ($C_1$-$C_6$)alkyl, ($C_1$-$C_6$)alkoxy, or halogen, $R^{2'}$ is H and $R^3$ is —F.

In some embodiments of Formula (I), $R^x$ is H, $R^1$ is H, $R^2$ is H, $—CH_3$, F, Cl or $—OCH_3$, $R^{2'}$ is H and $R^3$ is —F.

In some embodiments of Formula (I), $R^x$ is H, $R^1$ is H, $R^2$ is H, ($C_1$-$C_6$)alkyl, ($C_1$-$C_6$)alkoxy, or halogen, $R^2$ is H and $R^3$ is -Me.

In some embodiments of Formula (I), RY is H, $R^1$ is H, $R^2$ is H, —$CH_3$, F, Cl or —$OCH_3$, $R^2$ is H and $R^3$ is -Me.

In some embodiments of Formula (I), $R^x$ is H, $R^1$ is H, $R^2$ is H, ($C_1$-$C_6$)alkyl, ($C_1$-$C_6$)alkoxy, or halogen, $R^2$ is H and $R^3$ is —OH.

In some embodiments of Formula (I), $R^x$ is H, $R^1$ is H, $R^2$ is H, —$CH_3$, F, Cl or —$OCH_3$, $R^{2'}$ is H and $R^3$ is —OH.

In some embodiments of Formula (I), $R^x$ is H, $R^1$ is H, $R^2$ is H, ($C_1$-$C_6$)alkyl, ($C_1$-$C_6$)alkoxy, or halogen, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN and $R^4$ is ($C_1$-$C_6$)alkyl substituted with one to three instances of $R^6$.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN and $R^4$ is ($C_1$-$C_6$)alkyl substituted with one to three instances of $R^6$.

In some embodiments of Formula (I), $R^x$ is H, $R^1$ is H, $R^2$ is H, ($C_1$-$C_6$)alkyl, ($C_1$-$C_6$)alkoxy, or halogen, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and n is 0.

In some embodiments of Formula (I), $R^x$ is H, $R^1$ is H, $R^2$ is H, —$CH_3$, F, Cl or —$OCH_3$, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and n is 0.

In some embodiments of Formula (I), $R^x$ is H, $R^1$ is H, $R^2$ is H, ($C_1$-$C_6$)alkyl, ($C_1$-$C_6$)alkoxy, or halogen, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and $R^6$ is selected from ($C_6$-$C_{10}$)aryl and 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, —$CH_3$, F, Cl or —$OCH_3$, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and $R^6$ is selected from ($C_6$-$C_{10}$)aryl and 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, ($C_1$-$C_6$)alkyl, ($C_1$-$C_6$)alkoxy, or halogen, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and $R^6$ is 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and $R^6$ is 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, ($C_1$-$C_6$)alkyl, ($C_1$-$C_6$)alkoxy, or halogen, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and $R^6$ is cycloalkyl.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$-$C_6$)alkyl substituted with one to three instances of $R^6$ and $R^6$ is cycloalkyl.

In some embodiments of Formula (I), R is H, $R^1$ is H, $R^2$ is H, ($C_1$-$C_6$)alkyl, ($C_1$-$C_6$)alkoxy, or halogen, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN and $R^4$ is ($C_1$) alkyl, substituted with one or more instances of $R^6$.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN and $R^4$ is ($C_1$) alkyl, substituted with one or more instances of $R^6$.

In some embodiments of Formula (I), $R^x$ is H, $R^1$ is H, $R^2$ is H, ($C_1$-$C_6$)alkyl, ($C_1$-$C_6$)alkoxy, or halogen, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$) alkyl, substituted with one or more instances of $R^6$ and n is 0.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$) alkyl, substituted with one or more instances of $R^6$, and n=0

In some embodiments of Formula (I), $R^x$ is H, $R^1$ is H, $R^2$ is H, ($C_1$-$C_6$)alkyl, ($C_1$-$C_6$)alkoxy, or halogen, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —C(O)$NH_2$, —C(O)$OR^{15}$ or —CN, $R^4$ is ($C_1$) alkyl, substituted with one or more instances of $R^6$ and $R^6$ is selected from ($C_6$-$C_{10}$)aryl and 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —NHC(O)$R^{10}$, —$NR^{11}C(O)R^{10}$, —$(CH_2)_{0-2}NH_2$, —$C(O)NH_2$, —$C(O)OR^{15}$ or —CN, $R^4$ is ($C_1$) alkyl, substituted with one or more instances of $R^6$ and $R^6$ is selected from ($C_6$-$C_{10}$)aryl and 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, ($C_1$-$C_6$)alkyl, ($C_1$-$C_6$)alkoxy, or halogen, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$C(O)NH_2$, —$C(O)OR^{15}$ or —CN, $R^4$ is ($C_1$) alkyl, substituted with one or more instances of $R^6$ and $R^6$ is 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, —$CH_3$, F, Cl or —$OCH_3$, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$C(O)NH_2$, —$C(O)OR^{15}$ or —CN, $R^4$ is ($C_1$) alkyl, substituted with one or more instances of $R^6$ and $R^6$ is 5- or 6-membered heteroaryl comprising 1 to 4 heteroatoms selected from O, N, and S, wherein the aryl and heteroaryl are optionally substituted with one to three instances of $R^8$.

In some embodiments of Formula (I), $R^x$ is H, $R^1$ is H, $R^2$ is H, ($C_1$-$C_6$)alkyl, ($C_1$-$C_6$)alkoxy, or halogen, $R^{2'}$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$C(O)NH_2$, —$C(O)OR^{15}$ or —CN, $R^4$ is ($C_1$) alkyl, substituted with one or more instances of $R^6$ and $R^6$ is cycloalkyl.

In some embodiments of Formula (I), $R^x$ is H, $R^1$ is H, $R^2$ is H, —$CH_3$, F, Cl or —$OCH_3$, $R^2$ is H, $R^3$ is ($C_1$-$C_6$)alkyl, ($C_1$-$C_6$)alkoxy, —CN, ($C_1$-$C_6$)hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$C(O)NH_2$, —$C(O)OR^{15}$ or —CN, $R^4$ is ($C_1$) alkyl, substituted with one or more instances of $R^6$ and $R^6$ is cycloalkyl.

In some embodiments of Formula (I), the compound of the invention is selected from any one of the following compounds:

| Compound number | Structure | Name |
|---|---|---|
| 1 | 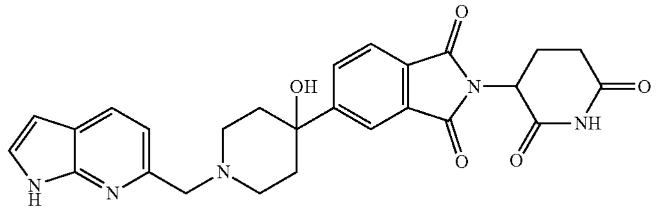 [SMILES: O=C1CCC(N2C(=O)c3ccc(C4(O)CCN(Cc5ccc6cc[nH]c6n5)CC4)cc3C2=O)C(=O)N1] | 5-(1-((1H-pyrrolo[2,3-b]pyridin-6-yl)methyl)-4-hydroxypiperidin-4-yl)-2-(2,6-dioxopiperidin-3-yl)isoindoline-1,3-dione |
| 2 | 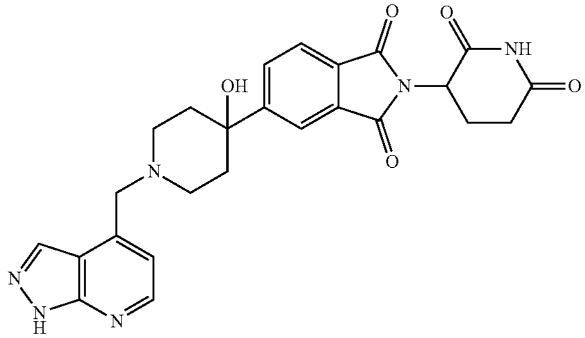 | 5-(1-((1H-indazol-4-yl)methyl)-4-hydroxypiperidin-4-yl)-2-(2,6-dioxopiperidin-3-yl)isoindoline-1,3-dione |
| 3 | 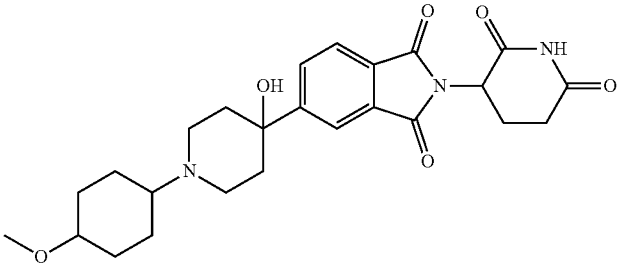 [SMILES: COC1CCC(N2CCC(O)(c3ccc4c(c3)C(=O)N(C3CCC(=O)NC3=O)C4=O)CC2)CC1] | 2-(2,6-dioxopiperidin-3-yl)-5-(4-hydroxy-1-(4-methoxycyclohexyl)piperidin-4-yl)isoindoline-1,3-dione |

-continued

| Compound number | Structure | Name |
|---|---|---|
| 4 | 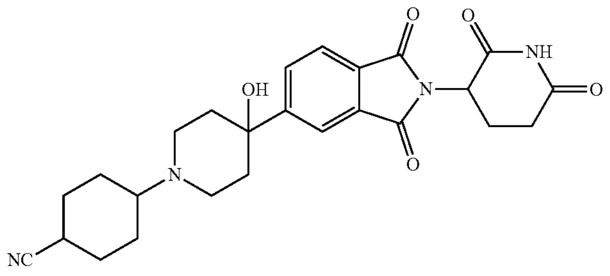 [SMILES: N#CC1CCC(N2CCC(O)(c3ccc4c(c3)C(=O)N(C3CCC(=O)NC3=O)C4=O)CC2)CC1] | 4-(4-(2-(2,6-dioxopiperidin-3-yl)-1,3-dioxoisoindolin-5-yl)-4-hydroxypiperidin-1-yl)cyclohexane-1-carbonitrile |
| 5 | 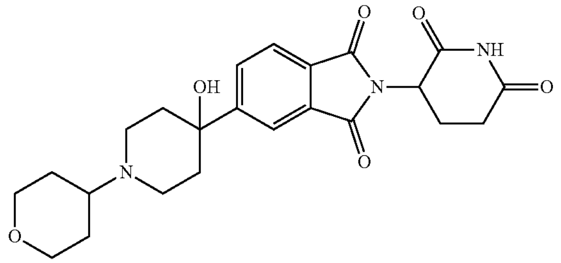 [SMILES: O=C1CCC(N2C(=O)c3ccc(C4(O)CCN(C5CCOCC5)CC4)cc3C2=O)C(=O)N1] | 2-(2,6-dioxopiperidin-3-yl)-5-(4-hydroxy-1-(tetrahydro-2H-pyran-4-yl)piperidin-4-yl)isoindoline-1,3-dione |
| 6 | 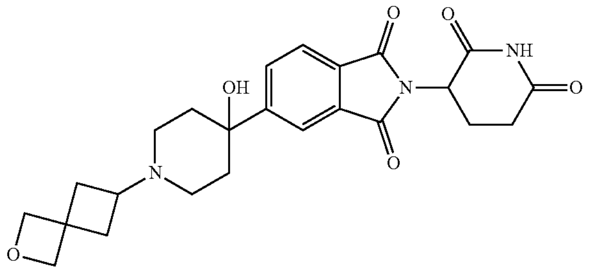 [SMILES: O=C1CCC(N2C(=O)c3ccc(C4(O)CCN(C5CC6(COC6)C5)CC4)cc3C2=O)C(=O)N1] | 2-(2,6-dioxopiperidin-3-yl)-5-(4-hydroxy-1-(2-oxaspiro[3.3]heptan-6-yl)piperidin-4-yl)isoindoline-1,3-dione |
| 7 | 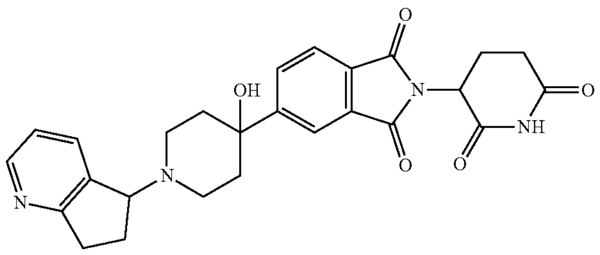 [SMILES: O=C1CCC(N2C(=O)c3ccc(C4(O)CCN(C5CCc6ncccc65)CC4)cc3C2=O)C(=O)N1] | 5-(1-(6.7-dihydro-5H-cyclopenta[b]pyridin-5-yl)-4-hydroxypiperidin-4-y])_2_(2'6_dioxopiperidin-3-yl)isoindoline-1,3-dione |
| 8 | 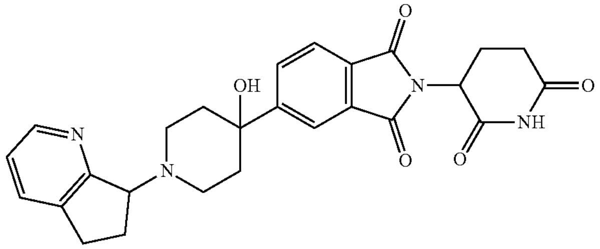 [SMILES: O=C1CCC(N2C(=O)c3ccc(C4(O)CCN(C5CCc6cccnc65)CC4)cc3C2=O)C(=O)N1] | 5-(1-(6,7-dihydro-5H-cyclopenta[b]pyridin-7-yl)-4-hydroxypiperidin-4-yl)-2-(2,6-dioxopiperidin-3-yl)isoindoline-1,3-dione |

-continued

| Compound number | Structure | Name |
|---|---|---|
| 9 | 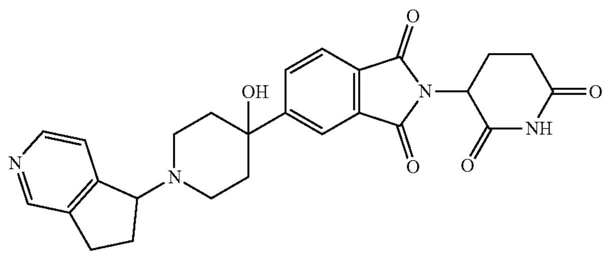 [SMILES: O=C1CCC(N2C(=O)c3ccc(C4(O)CCN(C5CCc6cnccc65)CC4)cc3C2=O)C(=O)N1] | 5-(1-(6,7-dihydro-5H-cyclopenta[c]pyridin-5-yl)-4-hydroxypiperidin-4-yl)-2-(2,6-dioxopiperidin-3-yl)isoindoline-1,3-dione |
| 10 | 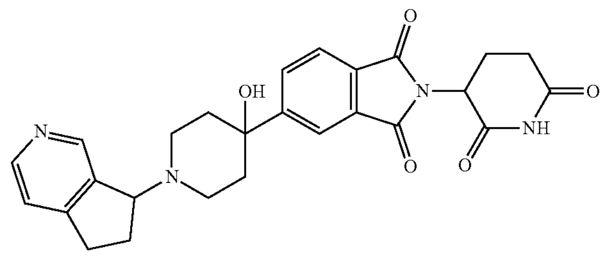 [SMILES: O=C1CCC(N2C(=O)c3ccc(C4(O)CCN(C5CCc6ccncc65)CC4)cc3C2=O)C(=O)N1] | 5-(1-(6,7-dihydro-5H-cyclopenta[c]pyridin-7-yl)-4-hydroxypiperidin-4-yl)-2-(2,6-dioxopiperidin-3-yl)isoindoline-1,3-dione |
| 11 | 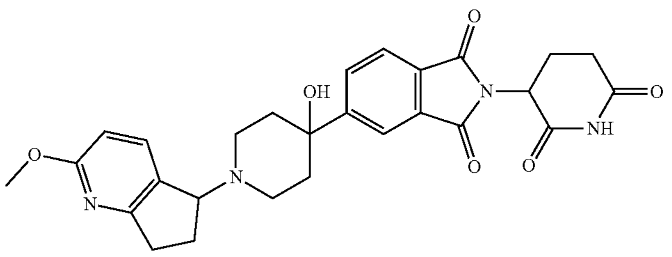 [SMILES: COc1ccc2c(n1)CCC2N1CCC(O)(c2ccc3c(c2)C(=O)N(C2CCC(=O)NC2=O)C3=O)CC1] | 2-(2,6-dioxopiperidin-3-yl)-5-(4-hydroxy-1-(2-methoxy-6,7-dihydro-5H-cyclopenta[b]pyridin-5-yl)piperidin-4-yl)isoindoline-1,3-dione |
| 12 | 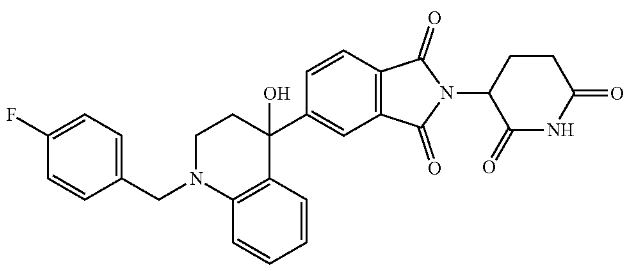 [SMILES: O=C1CCC(N2C(=O)c3ccc(C4(O)CCN(Cc5ccc(F)cc5)c5ccccc54)cc3C2=O)C(=O)N1] | 2-(2,6-dioxopiperidin-3-yl)-5-(1-(4-fluorobenzyl)-4-hydroxy-1,2,3,4-tetrahydroquinolin-4-yl)isoindoline-1,3-dione |
| 13 | 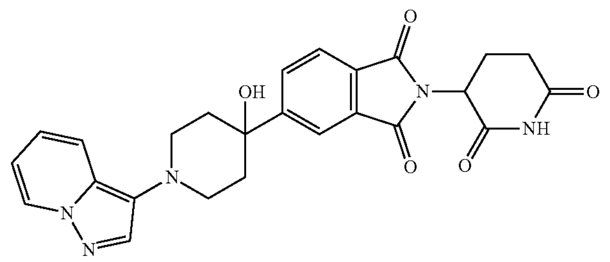 [SMILES: O=C1CCC(N2C(=O)c3ccc(C4(O)CCN(c5cnn6ccccc56)CC4)cc3C2=O)C(=O)N1] | 2-(2,6-dioxopiperidin-3-yl)-5-(4-hydroxy-1-(pyrazolo[1,5-a]pyridin-3-yl)piperidin-4-yl)isoindoline-1,3-dione |
| 14 | 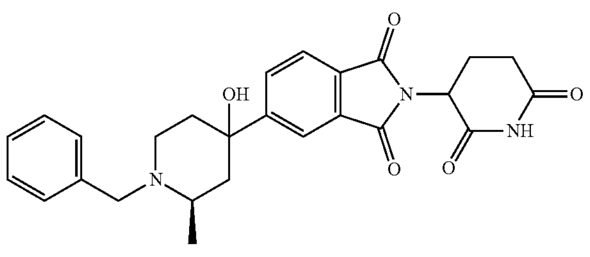 [SMILES: C[C@@H]1CC(O)(c2ccc3c(c2)C(=O)N(C2CCC(=O)NC2=O)C3=O)CCN1Cc1ccccc1] | 5-((2R)-1-benzyl-4-hydroxy-2-methylpiperidin-4-yl)-2-(2,6-dioxopiperidin-3-yl)isoindoline-1,3-dione |

-continued

| Compound number | Structure | Name |
|---|---|---|
| 15 | 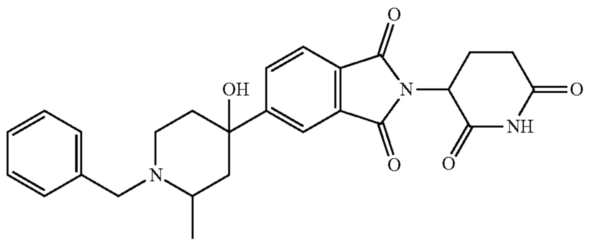 | 5-(1-benzyl-4-hydroxy-2-methylpiperidin-4-yl)-2-(2,6-dioxopiperidin-3-yl)isoindoline-1,3-dione |
| 16 | 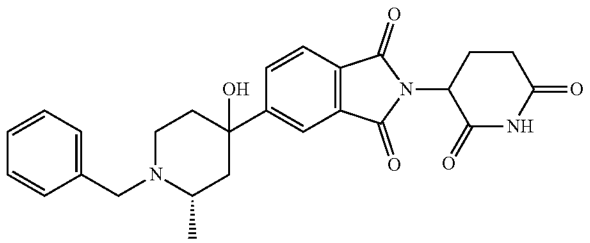 [SMILES: C[C@H]1CC(O)(c2ccc3c(c2)C(=O)N(C2CCC(=O)NC2=O)C3=O)CCN1Cc1ccccc1] | 5-((2S)-1-benzyl-4-hydroxy-2-methylpiperidin-4-yl)-2-(2,6-dioxopiperidin-3-yl)isoindoline-1,3-dione |
| 17 | 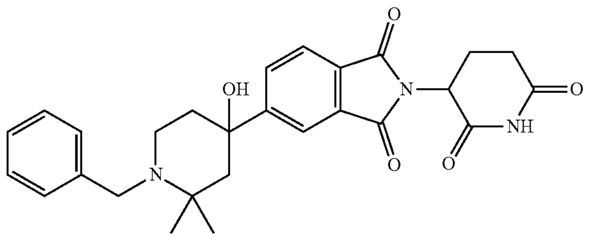 [SMILES: CC1(C)CC(O)(c2ccc3c(c2)C(=O)N(C2CCC(=O)NC2=O)C3=O)CCN1Cc1ccccc1] | 5-(1-benzyl-4-hydroxy-2,2-dimethylpiperidin-4-yl)-2-(2,6-dioxopiperidin-3-yl)isoindoline-1,3-dione |
| 18 | 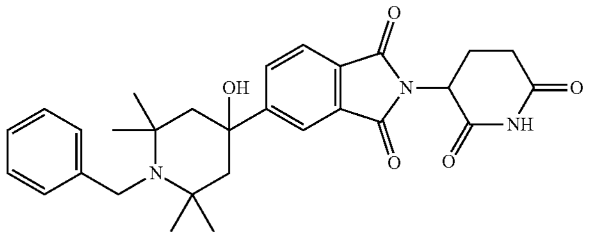 [SMILES: CC1(C)CC(O)(c2ccc3c(c2)C(=O)N(C2CCC(=O)NC2=O)C3=O)CC(C)(C)N1Cc1ccccc1] | 5-(1-benzyl-4-hydroxy-2,2,6,6-tetramethylpiperidin-4-yl)-2-(2,6-dioxopiperidin-3-yl)isoindoline-1,3-dione |
| 19 | 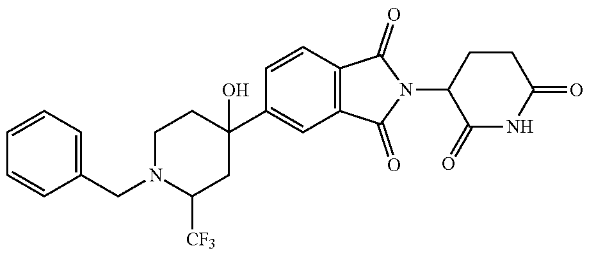 [SMILES: O=C1CCC(N2C(=O)c3ccc(C4(O)CCN(Cc5ccccc5)C(C(F)(F)F)C4)cc3C2=O)C(=O)N1] | 5-(1-benzyl-4-hydroxy-2-(trifluoromethyl)piperidin-4-yl)-2-(2,6-dioxopiperidin-3-yl)isoindoline-1,3-dione |
| 20 | 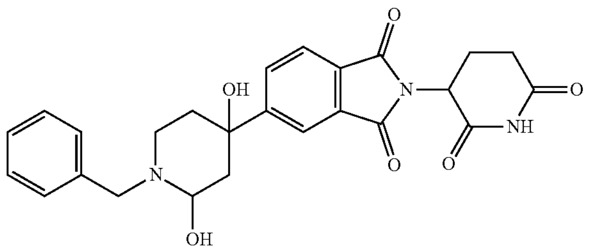 [SMILES: O=C1CCC(N2C(=O)c3ccc(C4(O)CCN(Cc5ccccc5)C(O)C4)cc3C2=O)C(=O)N1] | 1-benzyl-4-(2-(2,6-dioxopiperidin-3-yl)-1,3-dioxoisoindolin-5-yl)-4-hydroxypiperidine-2-carbonitrile |

-continued

| Compound number | Structure | Name |
| --- | --- | --- |
| 21 | 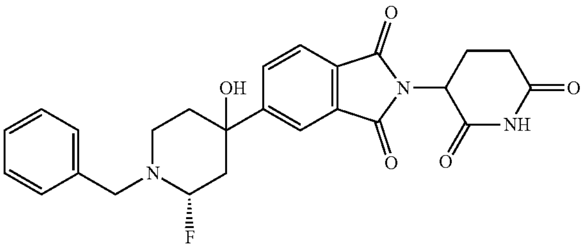 [SMILES: O=C1CCC(N2C(=O)c3ccc(C4(O)CCN(Cc5ccccc5)[C@@H](F)C4)cc3C2=O)C(=O)N1] | 5-((2S)-1-benzyl-2-fluoro-4-hydroxypiperidin-4-yl)-2-(2,6-dioxopiperidin-3-yl)isoindoline-1,3-dione |
| 22 | 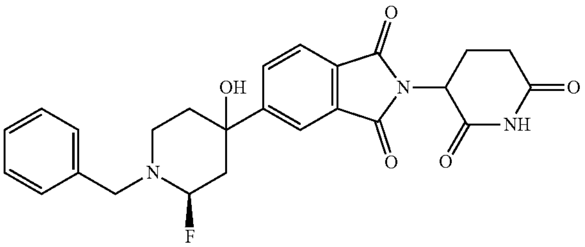 [SMILES: O=C1CCC(N2C(=O)c3ccc(C4(O)CCN(Cc5ccccc5)[C@H](F)C4)cc3C2=O)C(=O)N1] | 5-((2R)-1-benzyl-2-fluoro-4-hydroxypiperidin-4-yl)-2-(2,6-dioxopiperidin-3-yl)isoindoline-1,3-dione |
| 23 | 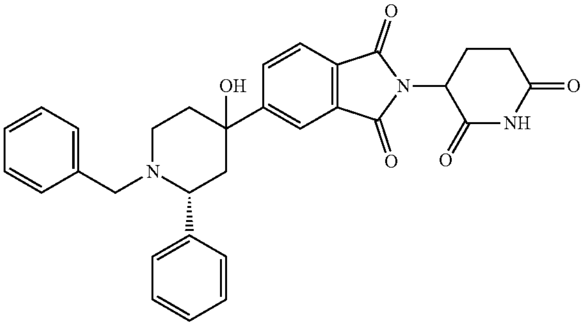 [SMILES: O=C1CCC(N2C(=O)c3ccc(C4(O)CCN(Cc5ccccc5)[C@@H](c5ccccc5)C4)cc3C2=O)C(=O)N1] | 5-((2R)-1-benzyl-4-hydroxy-2-phenylpiperidin-4-yl)-2-(2,6-dioxopiperidin-3-yl)isoindoline-1,3-dione |
| 24 | 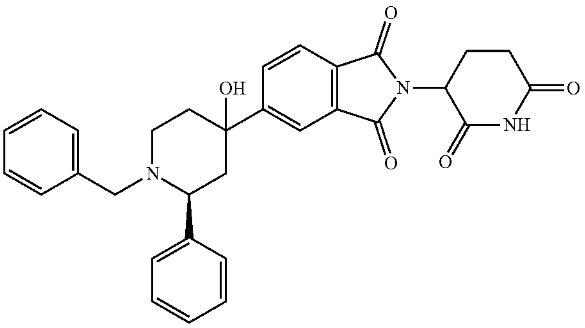 [SMILES: O=C1CCC(N2C(=O)c3ccc(C4(O)CCN(Cc5ccccc5)[C@H](c5ccccc5)C4)cc3C2=O)C(=O)N1] | 5-((2S)-1-benzyl-4-hydroxy-2-phenylpiperidin-4-yl)-2-(2,6-dioxopiperidin-3-yl)isoindoline-1,3-dione |
| 25 | 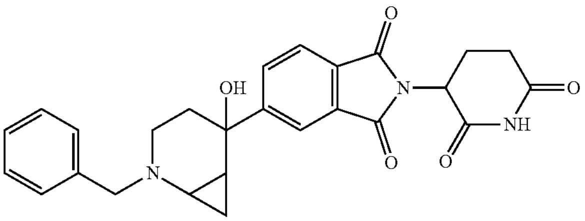 [SMILES: O=C1CCC(N2C(=O)c3ccc(C4(O)CCN(Cc5ccccc5)C5CC54)cc3C2=O)C(=O)N1] | 5-(2-benzyl-5-hydroxy-2-azabicyclo[4.1.0]heptan-5-yl)-2-(2,6-dioxopiperidin-3-yl)isoindoline-1,3-dione |

-continued

| Compound number | Structure | Name |
|---|---|---|
| 26 | 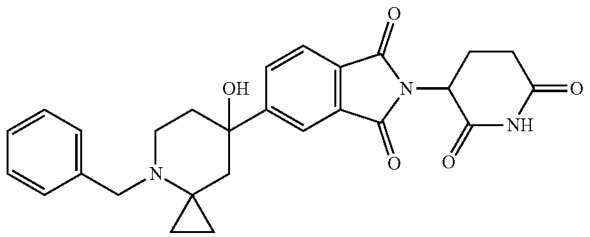 [SMILES: O=C1CCC(N2C(=O)c3ccc(C4(O)CCN(Cc5ccccc5)C5(CC5)C4)cc3C2=O)C(=O)N1] | 5-(4-benzyl-7-hydroxy-4-azaspiro[2.5]octan-7-yl)-2-(2,6-dioxopiperidin-3-yl)isoindoline-1,3-dione |
| 27 | 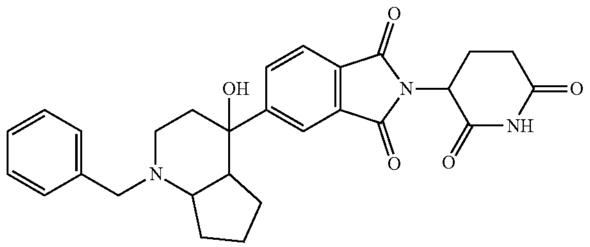 [SMILES: O=C1CCC(N2C(=O)c3ccc(C4(O)CCN(Cc5ccccc5)C5CCCC54)cc3C2=O)C(=O)N1] | 5-(1-benzyl-4-hydroxyoctahydro-1H-cyclopenta[b]pyridin-4-yl)-2-(2,6-dioxopiperidin-3-yl)isoindoline-1,3-dione |
| 28 | 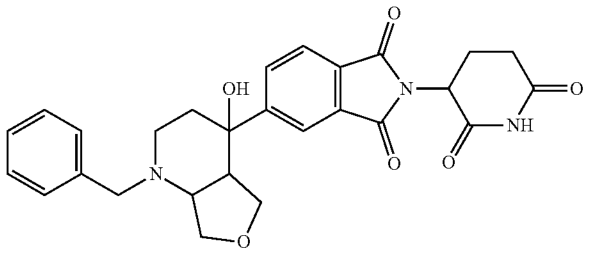 [SMILES: O=C1CCC(N2C(=O)c3ccc(C4(O)CCN(Cc5ccccc5)C5COCC54)cc3C2=O)C(=O)N1] | 5-(1-benzyl-4-hydroxyoctahydrofuro[3,4-b]pyridin-4-yl)-2-(2,6-dioxopiperidin-3-yl)isoindoline-1,3-dione |
| 29 | 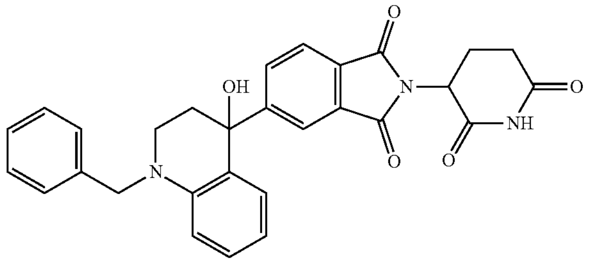 [SMILES: O=C1CCC(N2C(=O)c3ccc(C4(O)CCN(Cc5ccccc5)c5ccccc54)cc3C2=O)C(=O)N1] | 5-(1-benzyl-4-hydroxy-1,2,3,4-tetrahydroquinolin-4-yl)-2-(2,6-dioxopiperidin-3-yl)isoindoline-1,3-dione |
| 30 | 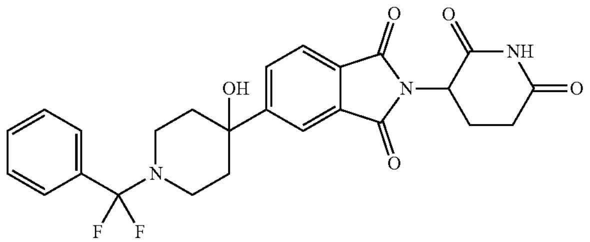 [SMILES: O=C1CCC(N2C(=O)c3ccc(C4(O)CCN(C(F)(F)c5ccccc5)CC4)cc3C2=O)C(=O)N1] | 5-(1-(difluoro(phenyl)methyl)-4-hydroxypiperidin-4-yl)-2-(2,6-dioxopiperidin-3-yl)isoindoline-1,3-dione |
| 31 | 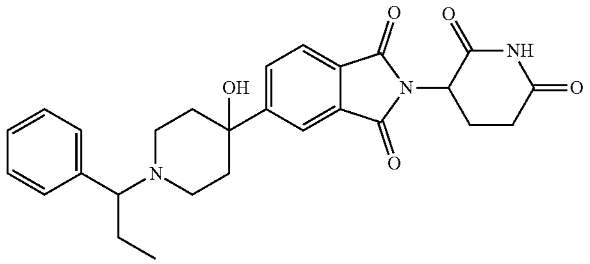 [SMILES: CCC(c1ccccc1)N1CCC(O)(c2ccc3c(c2)C(=O)N(C2CCC(=O)NC2=O)C3=O)CC1] | 2-(2,6-dioxopiperidin-3-yl)-5-(4-hydroxy-1-(1-phenylpropyl)piperidin-4-yl)isoindoline-1,3-dione |

-continued

| Compound number | Structure | Name |
|---|---|---|
| 32 | 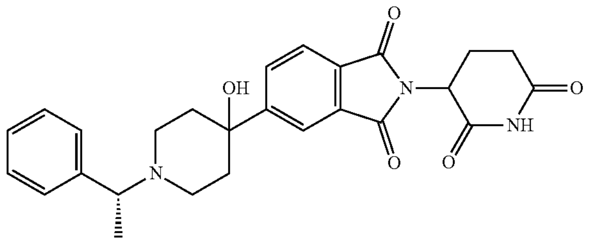 [SMILES: C[C@H](c1ccccc1)N1CCC(O)(c2ccc3c(c2)C(=O)N(C2CCC(=O)NC2=O)C3=O)CC1] | 2-(2,6-dioxopiperidin-3-yl)-5-(4-hydroxy-1-((R)-1-phenylethyl)piperidin-4-yl)isoindoline-1,3-dione |
| 33 | 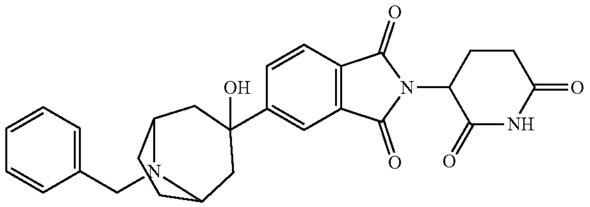 [SMILES: O=C1CCC(N2C(=O)c3ccc(C4(O)CC5CCC(C4)N5Cc4ccccc4)cc3C2=O)C(=O)N1] | 5-(8-benzyl-3-hydroxy-8-azabicyclo[3.2.1]octan-3-yl)-2-(2,6-dioxopiperidin-3-yl)isoindoline-1,3-dione |
| 34 | 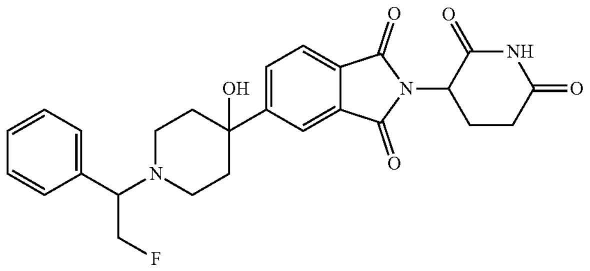 [SMILES: O=C1CCC(N2C(=O)c3ccc(C4(O)CCN(C(CF)c5ccccc5)CC4)cc3C2=O)C(=O)N1] | 2-(2,6-dioxopiperidin-3-yl)-5-(1-(2-fluoro-1-phenylethyl)-4-hydroxypiperidin-4-yl)isoindoline-1,3-dione |
| 35 | 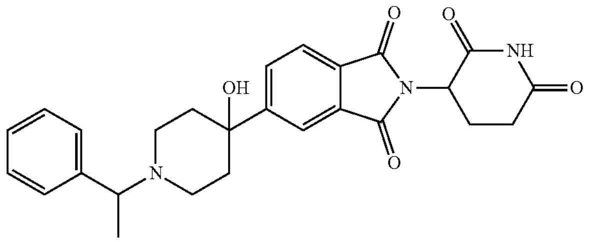 [SMILES: CC(c1ccccc1)N1CCC(O)(c2ccc3c(c2)C(=O)N(C2CCC(=O)NC2=O)C3=O)CC1] | 2-(2,6-dioxopiperidin-3-yl)-5-(4-hydroxy-1-(1-phenylethyl)piperidin-4-yl)isoindoline-1,3-dione |
| 36 | 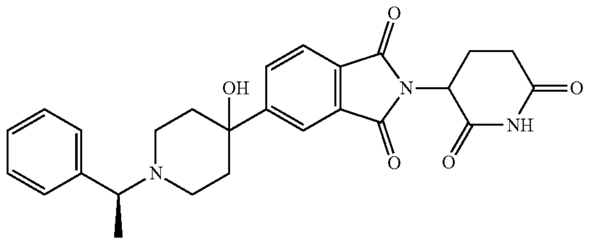 [SMILES: C[C@@H](c1ccccc1)N1CCC(O)(c2ccc3c(c2)C(=O)N(C2CCC(=O)NC2=O)C3=O)CC1] | 2-(2,6-dioxopiperidin-3-yl)-5-(4-hydroxy-1-((S)-1-phenylethyl)piperidin-4-yl)isoindoline-1,3-dione |
| 37 | 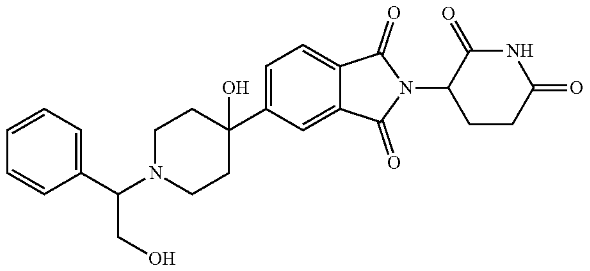 [SMILES: O=C1CCC(N2C(=O)c3ccc(C4(O)CCN(C(CO)c5ccccc5)CC4)cc3C2=O)C(=O)N1] | 2-(2,6-dioxopiperidin-3-yl)-5-(4-hydroxy-1-(2-hydroxy-1-phenylethyl)piperidin-4-yl)isoindoline-1,3-dione |

-continued

| Compound number | Structure | Name |
|---|---|---|
| 38 | 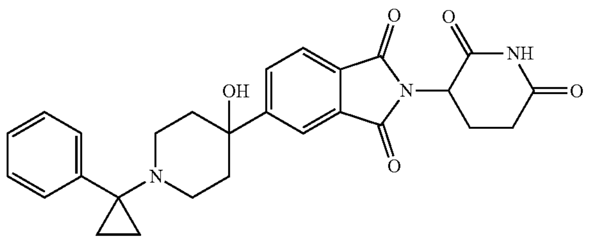 [SMILES: O=C1CCC(N2C(=O)c3ccc(C4(O)CCN(C5(c6ccccc6)CC5)CC4)cc3C2=O)C(=O)N1] | 2-(2,6-dioxopiperidin-3-yl)-5-(4-hydroxy-1-(1-phenyleyclopropyl) piperidin-4-yl)isoindoline-1,3-dione |
| 39 | 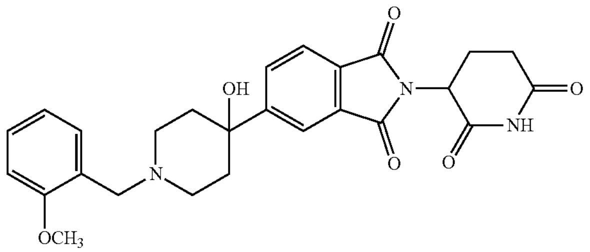 [SMILES: COc1ccccc1CN1CCC(O)(c2ccc3c(c2)C(=O)N(C2CCC(=O)NC2=O)C3=O)CC1] | 2-(2,6-dioxopiperidin-3-yl)-5-(4-hydroxy-1-(2-methoxybenzyl)piperidin-4-yl)isomdoline-1,3-dione |
| 40 | 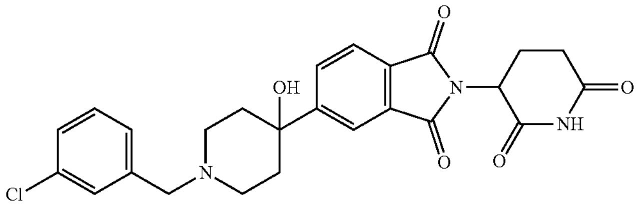 [SMILES: O=C1CCC(N2C(=O)c3ccc(C4(O)CCN(Cc5cccc(Cl)c5)CC4)cc3C2=O)C(=O)N1] | 5-(1-(3-chlorobenzyl)-4-hydroxypiperidin-4-yl)-2-(2,6-dioxopiperidin-3-yl)isoindoline-1,3-dione |
| 41 | 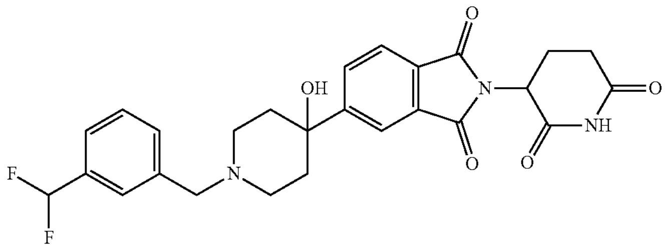 [SMILES: O=C1CCC(N2C(=O)c3ccc(C4(O)CCN(Cc5cccc(C(F)F)c5)CC4)cc3C2=O)C(=O)N1] | 5-(1-(3-(difluoromethyl)benzyl)-4-hydroxypiperidin-4-yl)-2-(2,6-dioxopiperidin-3-yl)isoindoline-1,3-dione |
| 42 | 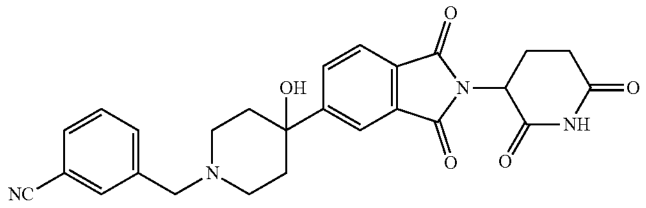 [SMILES: N#Cc1cccc(CN2CCC(O)(c3ccc4c(c3)C(=O)N(C3CCC(=O)NC3=O)C4=O)CC2)c1] | 3-((4-(2-(2,6-dioxopiperidin-3-yl)-1,3-dioxoisoindolin-5-yl)-4-hydroxypiperidin-1-yl)methyl)benzonitrile |
| 43 | 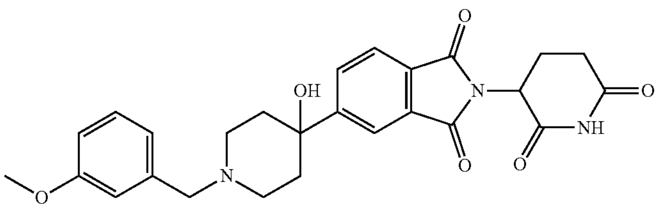 [SMILES: COc1cccc(CN2CCC(O)(c3ccc4c(c3)C(=O)N(C3CCC(=O)NC3=O)C4=O)CC2)c1] | 2-(2,6-dioxopiperidin-3-yl)-5-(4-hydroxy-1-(3-methoxybenzyl)piperidin-4-yl)isomdoline-1,3-dione |

-continued

| Compound number | Structure | Name |
| --- | --- | --- |
| 44 | 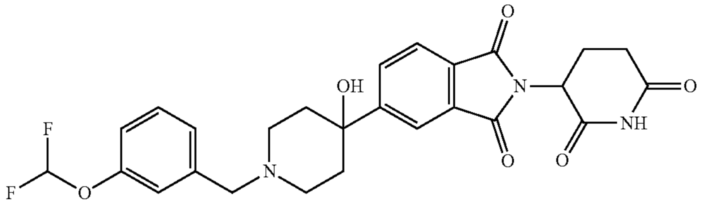 [SMILES: O=C1CCC(N2C(=O)c3ccc(C4(O)CCN(Cc5cccc(OC(F)F)c5)CC4)cc3C2=O)C(=O)N1] | 5-(1-(3-(difluoromethoxy)benzyl)-4-hydroxypiperidin-4-yl)-2-(2,6-dioxopiperidin-3-yl)isoindoline-1,3-dione |
| 45 | 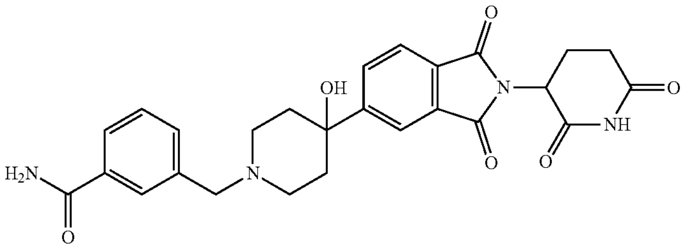 [SMILES: NC(=O)c1cccc(CN2CCC(O)(c3ccc4c(c3)C(=O)N(C3CCC(=O)NC3=O)C4=O)CC2)c1] | 3-((4-(2-(2,6-dioxopiperidin-3-yl)-1,3-dioxoisoindolin-5-yl)-4-hydroxypiperidin-1-yl)methyl)benzamide |
| 46 | 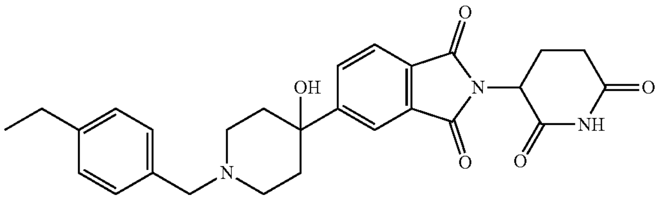 [SMILES: CCc1ccc(CN2CCC(O)(c3ccc4c(c3)C(=O)N(C3CCC(=O)NC3=O)C4=O)CC2)cc1] | 2-(2,6-dioxopiperidin-3-yl)-5-(1-(4-ethylbenzyl)-4-hydroxypiperidin-4-yl)isoindoline-1,3-dione |
| 47 | 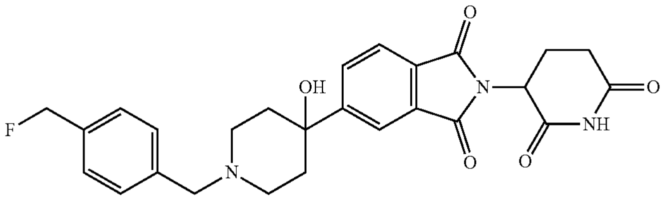 [SMILES: O=C1CCC(N2C(=O)c3ccc(C4(O)CCN(Cc5ccc(CF)cc5)CC4)cc3C2=O)C(=O)N1] | 2-(2,6-dioxopiperidin-3-yl)-5-(1-(4-(fluoromethyl)benzyl)-4-hydroxypiperidin-4-yl)isoindoline-1,3-dione |
| 48 | 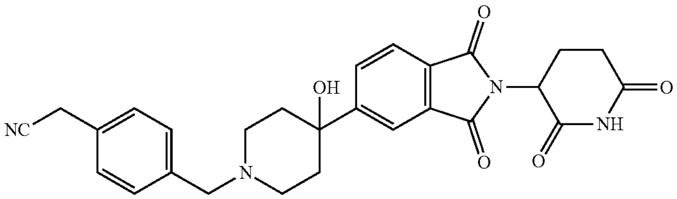 [SMILES: N#CCc1ccc(CN2CCC(O)(c3ccc4c(c3)C(=O)N(C3CCC(=O)NC3=O)C4=O)CC2)cc1] | 2-(4-((4-(2-(2,6-dioxopiperidin-3-yl)-1,3-dioxoisoindolin-5-yl)-4-hydroxypiperidin-1-yl)methyl)phenyl) acetonitrile |
| 49 | 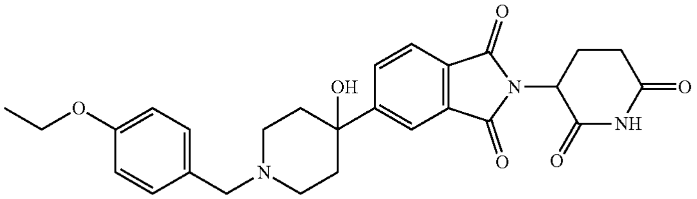 [SMILES: CCOc1ccc(CN2CCC(O)(c3ccc4c(c3)C(=O)N(C3CCC(=O)NC3=O)C4=O)CC2)cc1] | 2-(2,6-dioxopiperidin-3-yl)-5-(1-(4-ethoxybenzyl)-4-hydroxypiperidin-4-yl)isoindoline-1,3-dione |
| 50 | 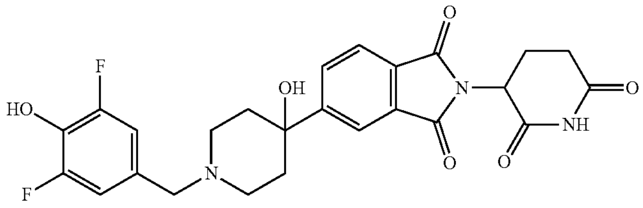 [SMILES: O=C1CCC(N2C(=O)c3ccc(C4(O)CCN(Cc5cc(F)c(O)c(F)c5)CC4)cc3C2=O)C(=O)N1] | 5-(1-(3,5-difluoro-4-hydroxybenzyl)-4-hydroxypiperidin-4-yl)-2-(2,6-dioxopiperidin-3-yl)isoindoline-1,3-dione |

-continued

| Compound number | Structure | Name |
|---|---|---|
| 51 | 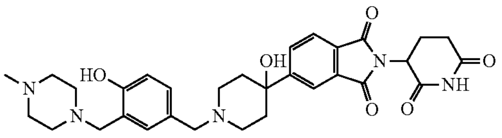 [SMILES: CN1CCN(Cc2cc(CN3CCC(O)(c4ccc5c(c4)C(=O)N(C4CCC(=O)NC4=O)C5=O)CC3)ccc2O)CC1] | 2-(2,6-dioxopiperidin-3-yl)-5-(4-hydroxy-1-(4-hydroxy-3-((4-methylpiperazin-1-yl)methyl)benzyl)piperidin-4-yl)isoindoline-1,3-dione |
| 52 | 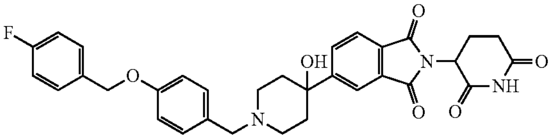 [SMILES: O=C1CCC(N2C(=O)c3ccc(C4(O)CCN(Cc5ccc(OCc6ccc(F)cc6)cc5)CC4)cc3C2=O)C(=O)N1] | 2-(2,6-dioxopiperidin-3-yl)-5-(1-(4-((4-fluorobenzyl)oxy)benzyl)-4-hydroxypiperidin-4-yl)isoindoline-1,3-dione |
| 53 | 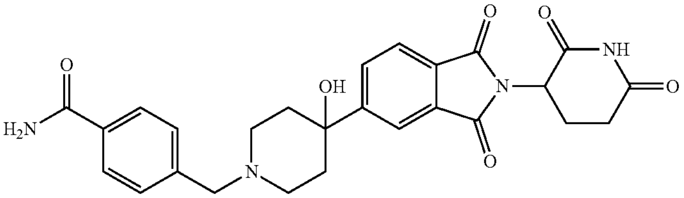 [SMILES: NC(=O)c1ccc(CN2CCC(O)(c3ccc4c(c3)C(=O)N(C3CCC(=O)NC3=O)C4=O)CC2)cc1] | 4-((4-(2-(2,6-dioxopiperidin-3-yl)-1,3-dioxoisoindolin-5-yl)-4-hydroxypiperidin-1-yl)methyl)benzamide |
| 54 | 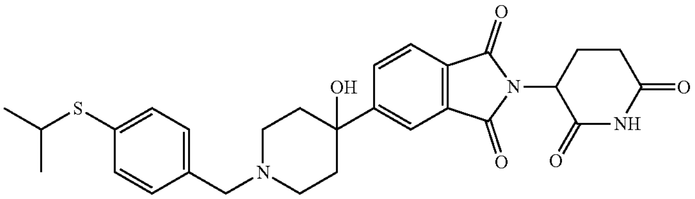 [SMILES: CC(C)Sc1ccc(CN2CCC(O)(c3ccc4c(c3)C(=O)N(C3CCC(=O)NC3=O)C4=O)CC2)cc1] | 2-(2,6-dioxopiperidin-3-yl)-5-(4-hydroxy-1-(4-(isopropylthi0)benzyl) piperidin-4-yl)isoindoline-1,3-dione |
| 55 | 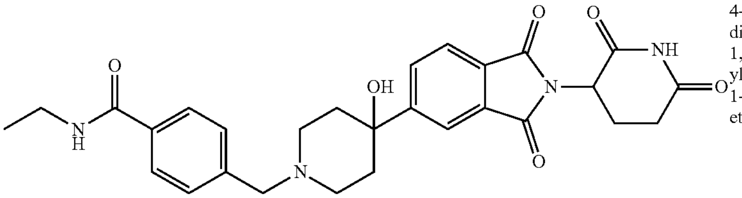 | 4-((4-(2-(2,6-dioxopiperidin-3-yl)-1,3-dioxoisoindolin-5-yl)-4-hydroxypiperidin-1-yl)methyl)-N-ethylbenzamide |
| 56 | 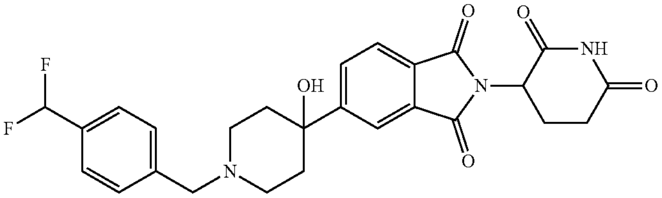 [SMILES: O=C1CCC(N2C(=O)c3ccc(C4(O)CCN(Cc5ccc(C(F)F)cc5)CC4)cc3C2=O)C(=O)N1] | 5-(1-(4-(difluoromethyl)benzyl)-4-hydroxypiperidin-4-yl)-2-(2,6-dioxopiperidin-3-yl)isoindoline-1,3-dione |
| 57 | 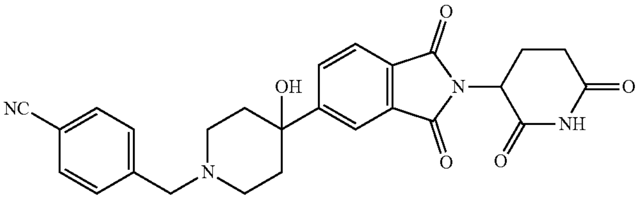 [SMILES: N#Cc1ccc(CN2CCC(O)(c3ccc4c(c3)C(=O)N(C3CCC(=O)NC3=O)C4=O)CC2)cc1] | 4-((4-(2-(2,6-dioxopiperidin-3-yl)-1,3-dioxoisoindolin-5-yl)-4-hydroxypiperidin-1-yl)methyl)benzonitrile |
| 58 | 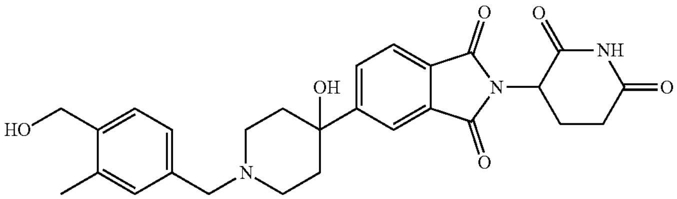 [SMILES: Cc1cc(CN2CCC(O)(c3ccc4c(c3)C(=O)N(C3CCC(=O)NC3=O)C4=O)CC2)ccc1CO] | 2-(2,6-dioxopiperidin-3-yl)-5-(4-hydroxy-1-(4-(hydroxymethyl)benzyl) piperidin-4-yl)isoindoline-1,3-dione |

-continued

| Compound number | Structure | Name |
|---|---|---|
| 59 | 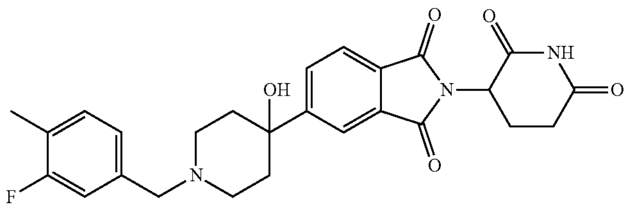 [SMILES: Cc1ccc(CN2CCC(O)(c3ccc4c(c3)C(=O)N(C3CCC(=O)NC3=O)C4=O)CC2)cc1F] | 2-(2,6-dioxopiperidin-3-yl)-5-(1-(3-fluoro-4-methylbenzyl)-4-hydroxypiperidin-4-yl)isoindoline-1,3-dione |
| 60 | 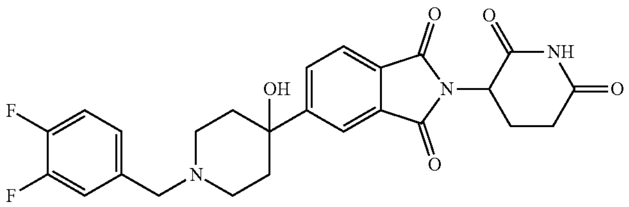 [SMILES: O=C1CCC(N2C(=O)c3ccc(C4(O)CCN(Cc5ccc(F)c(F)c5)CC4)cc3C2=O)C(=O)N1] | 5-(1-(3,4-difluorobenzyl)-4-hydroxypiperidin-4-yl)-2-(2,6-dioxopiperidin-3-yl)isoindoline-1,3-dione |
| 61 | 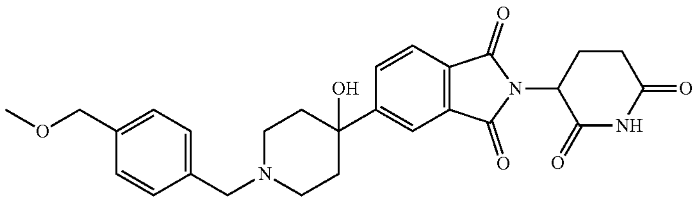 [SMILES: COCc1ccc(CN2CCC(O)(c3ccc4c(c3)C(=O)N(C3CCC(=O)NC3=O)C4=O)CC2)cc1] | 2-(2,6-dioxopiperidin-3-yl)-5-(4-hydroxy-1-(4-(methoxymethyl)benzyl)piperidin-4-yl)isoindoline-1,3-dione |
| 62 | 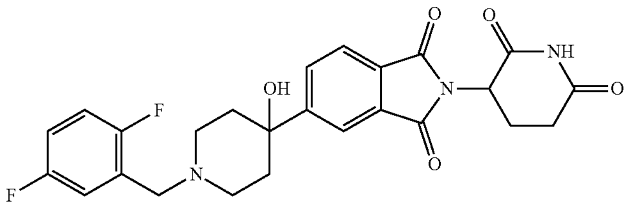 [SMILES: O=C1CCC(N2C(=O)c3ccc(C4(O)CCN(Cc5cc(F)ccc5F)CC4)cc3C2=O)C(=O)N1] | 5-(1-(2,5-difluorobenzyl)-4-hydroxypiperidin-4-yl)-2-(2,6-dioxopiperidin-3-yl)isoindoline-1,3-dione |
| 63 | 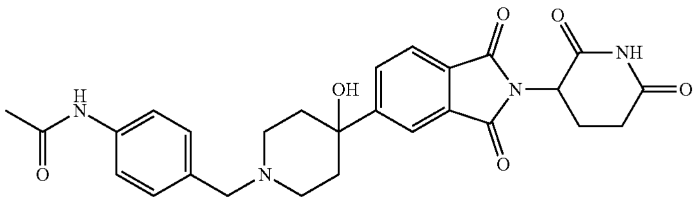 [SMILES: CC(=O)Nc1ccc(CN2CCC(O)(c3ccc4c(c3)C(=O)N(C3CCC(=O)NC3=O)C4=O)CC2)cc1] | N-(4-((4-(2-(2,6-dioxopiperidin-3-yl)-1,3-dioxoisoindolin-5-yl)-4-hydroxypiperidin-1-yl)methyl)phenyl)acetamide |
| 64 | 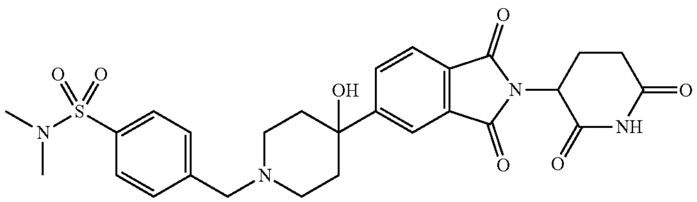 [SMILES: CN(C)S(=O)(=O)c1ccc(CN2CCC(O)(c3ccc4c(c3)C(=O)N(C3CCC(=O)NC3=O)C4=O)CC2)cc1] | 4-((4-(2-(2,6-dioxopiperidin-3-yl)-1,3-dioxoisoindolin-5-yl)-4-hydroxypiperidin-1-yl)methyl)-N,N-dimethylbenzenesulfonamide |
| 65 | 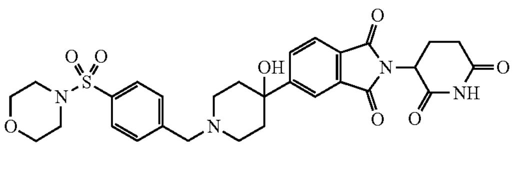 [SMILES: O=C1CCC(N2C(=O)c3ccc(C4(O)CCN(Cc5ccc(S(=O)(=O)N6CCOCC6)cc5)CC4)cc3C2=O)C(=O)N1] | 2-(2,6-dioxopiperidin-3-yl)-5-(4-hydroxy-1-(4-(morpholinosulfonyl)benzyl)piperidin-4-yl)isoindoline-1,3-dione |

-continued

| Compound number | Structure | Name |
|---|---|---|
| 66 | 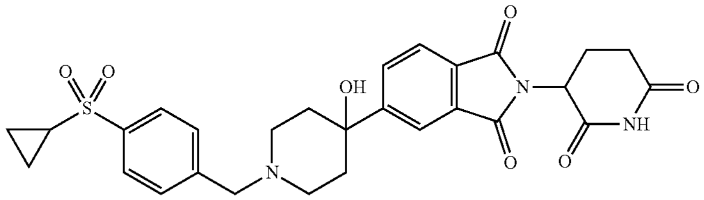 [SMILES: O=C1CCC(N2C(=O)c3ccc(C4(O)CCN(Cc5ccc(S(=O)(=O)C6CC6)cc5)CC4)cc3C2=O)C(=O)N1] | 5-(1-(4-(cyclopropylsulfonyl)benzyl)-4-hydroxypiperidin-4-yl)-2-(2,6-dioxopiperidin-3-yl)isoindoline-1,3-dione |
| 67 | 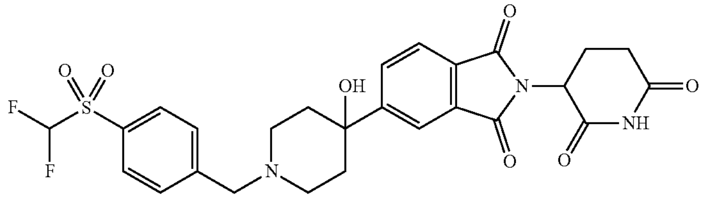 [SMILES: O=C1CCC(N2C(=O)c3ccc(C4(O)CCN(Cc5ccc(S(=O)(=O)C(F)F)cc5)CC4)cc3C2=O)C(=O)N1] | 5-(1-(4-((difluoromethyl)sulfonyl)benzyl)-4-hydroxypiperidin-4-yl)-2-(2,6-dioxopiperidin-3-yl)isoindoline-1,3-dione |
| 68 | 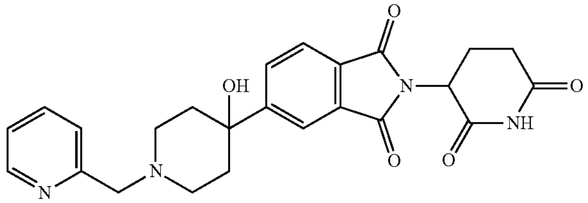 [SMILES: O=C1CCC(N2C(=O)c3ccc(C4(O)CCN(Cc5ccccn5)CC4)cc3C2=O)C(=O)N1] | 2-(2,6-dioxopiperidin-3-yl)-5-(4-hydroxy-1-(pyridin-2-ylmethyl)piperidin-4-yl)isoindoline-1,3-dione |
| 69 | 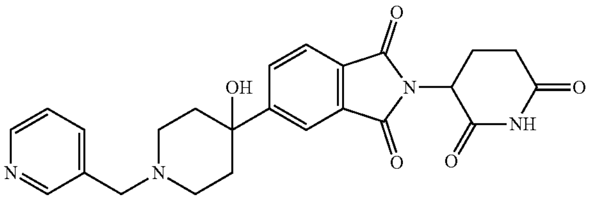 [SMILES: O=C1CCC(N2C(=O)c3ccc(C4(O)CCN(Cc5cccnc5)CC4)cc3C2=O)C(=O)N1] | 2-(2,6-dioxopiperidin-3-yl)-5-(4-hydroxy-1-(pyridin-3-ylmethyl)piperidin-4-yl)isoindoline-1,3-dione |
| 70 | 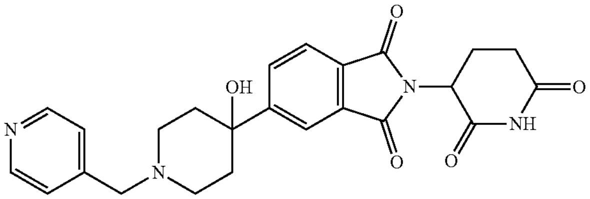 [SMILES: O=C1CCC(N2C(=O)c3ccc(C4(O)CCN(Cc5ccncc5)CC4)cc3C2=O)C(=O)N1] | 2-(2,6-dioxopiperidin-3-yl)-5-(4-hydroxy-1-(pyridin-4-ylmethyl)piperidin-4-yl)isoindoline-1,3-dione |
| 71 | 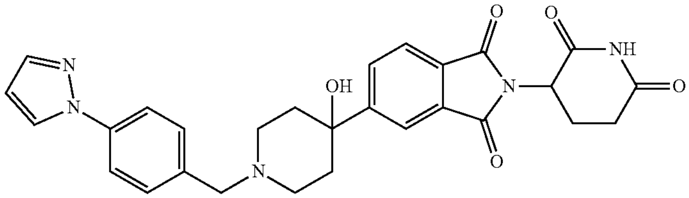 [SMILES: O=C1CCC(N2C(=O)c3ccc(C4(O)CCN(Cc5ccc(-n6cccn6)cc5)CC4)cc3C2=O)C(=O)N1] | 5-(1-(4-(1H-pyrazol-1-yl)benzyl)-4-hydroxypiperidin-4-yl)-2-(2,6-dioxopiperidin-3-yl)isoindoline-1,3-dione |
| 72 | 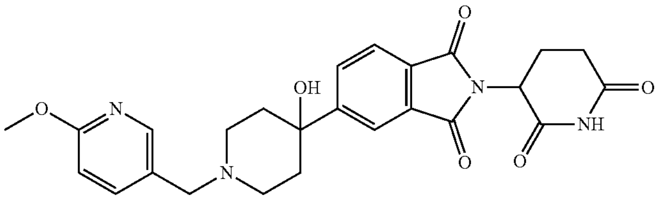 [SMILES: COc1ccc(CN2CCC(O)(c3ccc4c(c3)C(=O)N(C3CCC(=O)NC3=O)C4=O)CC2)cn1] | 2-(2,6-dioxopiperidin-3-yl)-5-(4-hydroxy-1-((6-methoxypyridin-3-yl)methyl)piperidin-4-yl)isoindoline-1,3-dione |

-continued

| Compound number | Structure | Name |
|---|---|---|
| 73 | 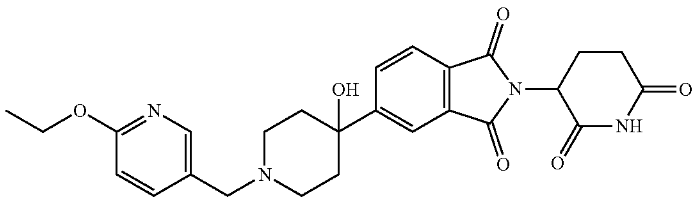 | 2-(2,6-dioxopiperidin-3-yl)-5-(1-((6-ethoxypyridin-3-yl)methyl)-4-hydroxypiperidin-4-yl)isoindoline-1,3-dione |
| 74 | 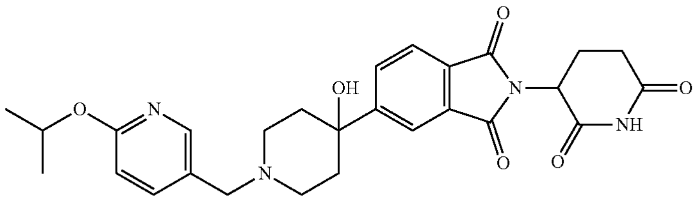 [SMILES: CC(C)Oc1ccc(CN2CCC(O)(c3ccc4c(c3)C(=O)N(C3CCC(=O)NC3=O)C4=O)CC2)cn1] | 2-(2,6-dioxopiperidin-3-yl)-5-(4-hydroxy-1-((6-Isopropoxypyridin-3-yl)methyl)piperidin-4-yl)isoindoline-1,3-dione |
| 75 | 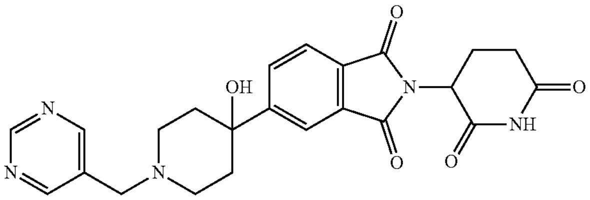 | 2-(2,6-dioxopiperidin-3-yl)-5-(4-hydroxy-1-(pyrimidin-5-ylmethyl)piperidin-4-yl)isoindoline-1,3-dione |
| 76 | 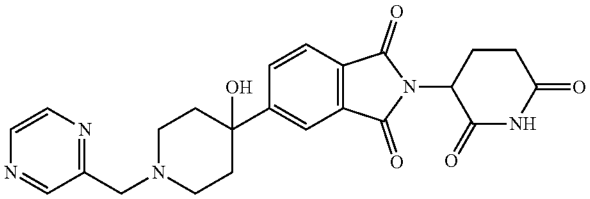 [SMILES: O=C1CCC(N2C(=O)c3ccc(C4(O)CCN(Cc5cnccn5)CC4)cc3C2=O)C(=O)N1] | 2-(2,6-dioxopiperidin-3-yl)-5-(4-hydroxy-1-(pyrazin-2-ylmethyl)piperidin-4-yl)isoindoline-1,3-dione |
| 77 | 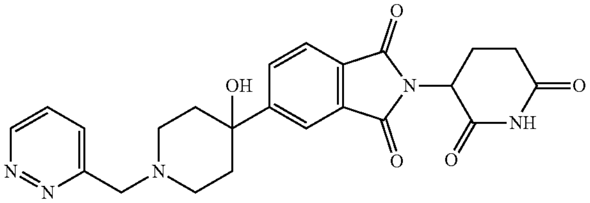 [SMILES: O=C1CCC(N2C(=O)c3ccc(C4(O)CCN(Cc5cccnn5)CC4)cc3C2=O)C(=O)N1] | 2-(2,6-dioxopiperidin-3-yl)-5-(4-hydroxy-1-(pyridazin-3-ylmethyl)piperidin-4-yl)isoindoline-1,3-dione |
| 78 | 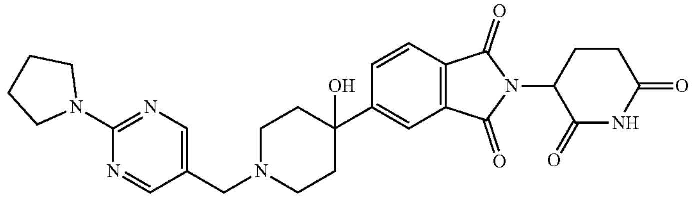 [SMILES: O=C1CCC(N2C(=O)c3ccc(C4(O)CCN(Cc5cnc(N6CCCC6)nc5)CC4)cc3C2=O)C(=O)N1] | 2-(2,6-dioxopiperidin-3-yl)-5-(4-hydroxy-1-((2-(pyrrolidin-1-yl)pyrimidin-5-yl)methyl)piperidin-4-yl)isoindoline-1,3-dione |
| 79 | 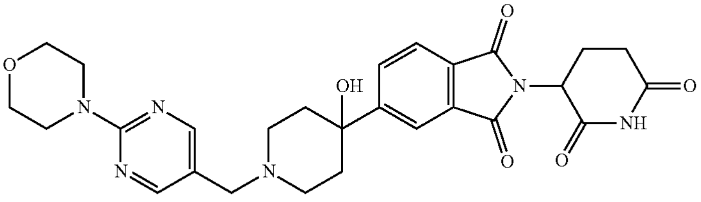 [SMILES: O=C1CCC(N2C(=O)c3ccc(C4(O)CCN(Cc5cnc(N6CCOCC6)nc5)CC4)cc3C2=O)C(=O)N1] | 2-(2,6-dioxopiperidin-3-yl)-5-(4-hydroxy-1-((2-morpholinopyrimidin-5-yl)methyl)piperidin-4-yl)isoindoline-1,3-dione |

-continued

| Compound number | Structure | Name |
| --- | --- | --- |
| 80 | 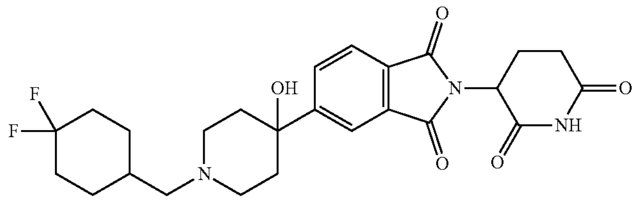 [SMILES: O=C1CCC(N2C(=O)c3ccc(C4(O)CCN(CC5CCC(F)(F)CC5)CC4)cc3C2=O)C(=O)N1] | 5-(1-((4,4-difluorocyclohexyl)methyl)-4-hydroxypiperidin-4-yl)-2-(2,6-dioxopiperidin-3-yl)isoindoline-1,3-dione |
| 81 | 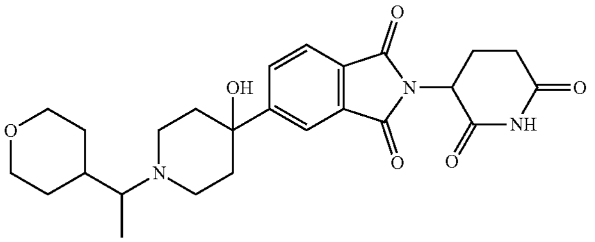 [SMILES: CC(C1CCOCC1)N1CCC(O)(c2ccc3c(c2)C(=O)N(C2CCC(=O)NC2=O)C3=O)CC1] | 2-(2,6-dioxopiperidin-3-yl)-5-(4-hydroxy-1-(1-(tetrahydro-2H-pyran-4-yl)ethyl)piperidin-4-yl)isoindoline-1,3-dione |
| 82 | 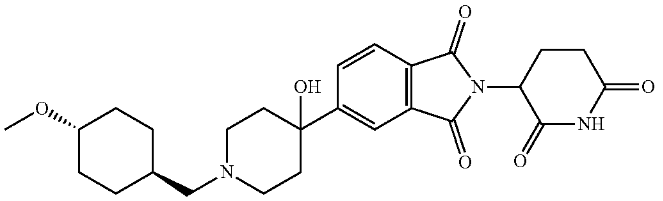 [SMILES: CO[C@H]1CC[C@H](CN2CCC(O)(c3ccc4c(c3)C(=O)N(C3CCC(=O)NC3=O)C4=O)CC2)CC1] | trans-2-(2,6-dioxopiperidin-3-yl)-5-(4-hydroxy-1-((-4-methoxycyclohexyl)methyl)piperidin-4-yl)isoindoline-1,3-dione |
| 83 | 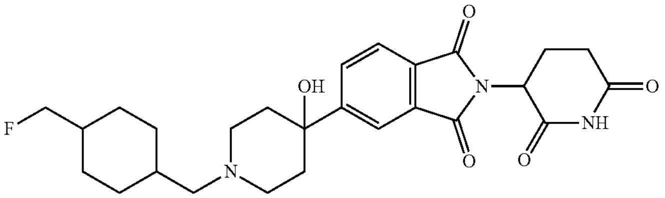 [SMILES: O=C1CCC(N2C(=O)c3ccc(C4(O)CCN(CC5CCC(CF)CC5)CC4)cc3C2=O)C(=O)N1] | 2-(2,6-dioxopiperidin-3-yl)-5-(1-((4-(fluoromethyl)cyclohexyl)methyl)-4-hydroxypiperidin-4-yl)isoindoline-1,3-dione |
| 84 | 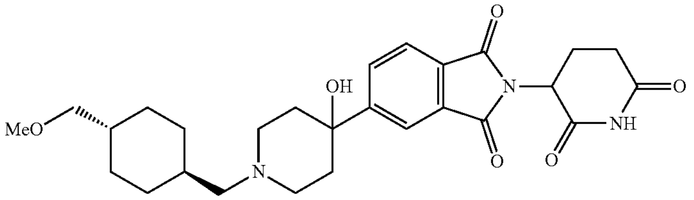 [SMILES: COC[C@H]1CC[C@H](CN2CCC(O)(c3ccc4c(c3)C(=O)N(C3CCC(=O)NC3=O)C4=O)CC2)CC1] | trans-2-(2,6-dioxopiperidin-3-yl)-5-(4-hydroxy-1-((-4-(methoxymethyl)cyclohexyl)methyl)piperidin-4-yl)isoindoline-1,3-dione |
| 85 | 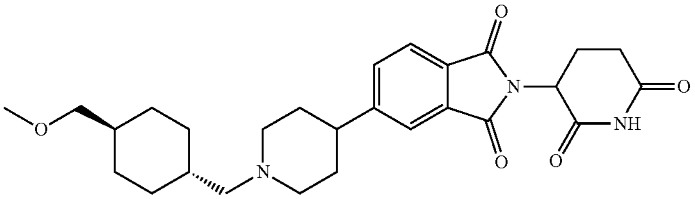 [SMILES: COC[C@H]1CC[C@H](CN2CCC(c3ccc4c(c3)C(=O)N(C3CCC(=O)NC3=O)C4=O)CC2)CC1] | Trans-2-(2,6-dioxopiperidin-3-yl)-5-(1-((4-(methoxymethyl)cyclohexyl)methyl)piperidin-4-yl)isoindoline-1,3-dione |
| 86 | 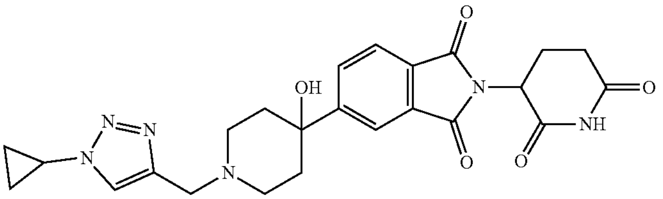 [SMILES: O=C1CCC(N2C(=O)c3ccc(C4(O)CCN(Cc5cn(C6CC6)nn5)CC4)cc3C2=O)C(=O)N1] | 5-(1-((1-cyclopropyl-1H-1,2,3-triazol-4-yl)methyl)-4-hydroxypiperidin-4-yl)-2-(2,6-dioxopiperidin-3-yl)isoindoline-1,3-dione |

-continued

| Compound number | Structure | Name |
|---|---|---|
| 87 | 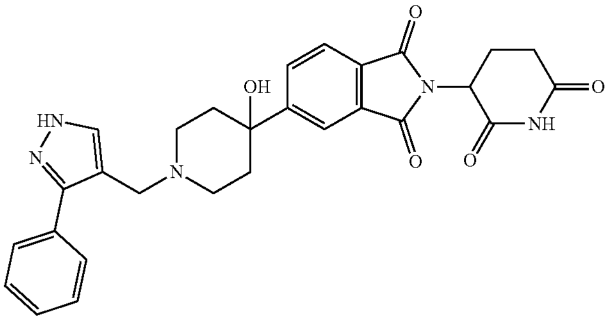 [SMILES: O=C1CCC(N2C(=O)c3ccc(C4(O)CCN(Cc5c[nH]nc5-c5ccccc5)CC4)cc3C2=O)C(=O)N1] | 2-(2,6-dioxopiperidin-3-yl)-5-(4-hydroxy-1-((3-phenyl-1H-pyrazol-4-yl)methyl)piperidin-4-yl)isoindoline-1,3-dione |
| 88 | 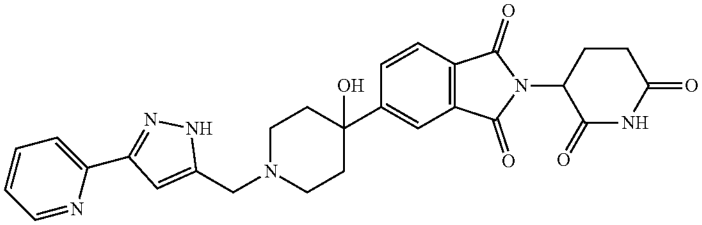 [SMILES: O=C1CCC(N2C(=O)c3ccc(C4(O)CCN(Cc5cc(-c6ccccn6)n[nH]5)CC4)cc3C2=O)C(=O)N1] | 2-(2,6-dioxopiperidin-3-yl)-5-(4-hydroxy-1-((3-(pyridin-2-yl)-1H-pyrazol-5-yl)methyl)piperidin-4-yl)isoindoline-1,3-dione |
| 89 | 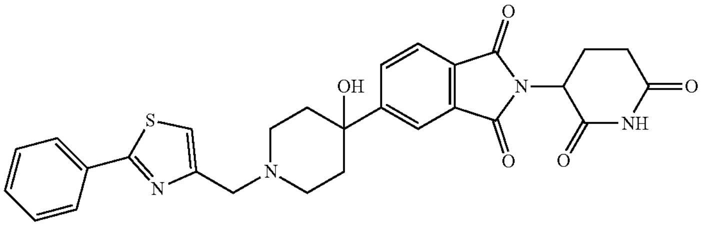 | 2-(2,6-dioxopiperidin-3-yl)-5-(4-hydroxy-1-((2-phenylthiazol-4-yl)methyl)piperidin-4-yl)isoindoline-1,3-dione |
| 90 | 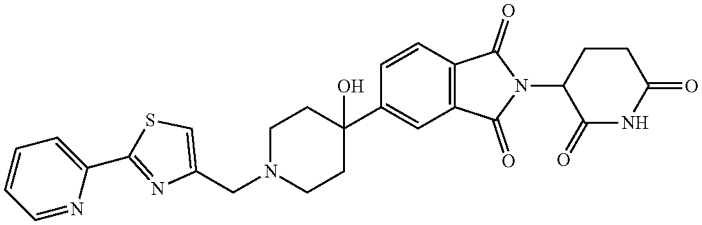 [SMILES: O=C1CCC(N2C(=O)c3ccc(C4(O)CCN(Cc5csc(-c6ccccn6)n5)CC4)cc3C2=O)C(=O)N1] | 2-(2,6-dioxopiperidin-3-yl)-5-(4-hydroxy-1-((2-(pyridin-2-yl)thiazol-4-yl)methyl)piperidin-4-yl)isoindoline-1,3-dione |
| 91 | 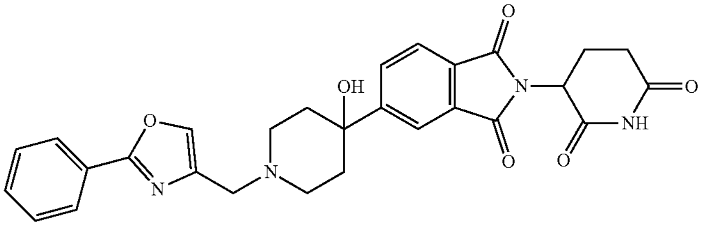 | 2-(2,6-dioxopiperidin-3-yl)-5-(4-hydroxy-1-((2-phenyloxazol-4-yl)methyl)piperidin-4-yl)isoindoline-1,3-dione |
| 92 | 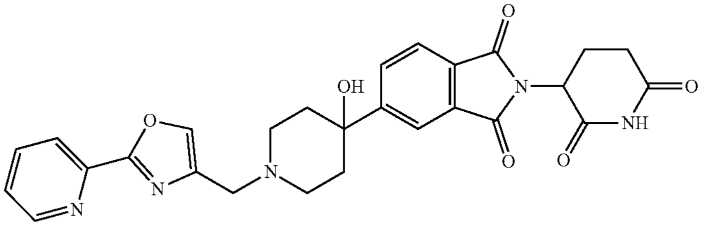 | 2-(2,6-dioxopiperidin-3-yl)-5-(4-hydroxy-1-((2-(pyridin-2-yl)oxazol-4-yl)methyl)piperidin-4-yl)isoindoline-1,3-dione |

-continued

| Compound number | Structure | Name |
|---|---|---|
| 93 | 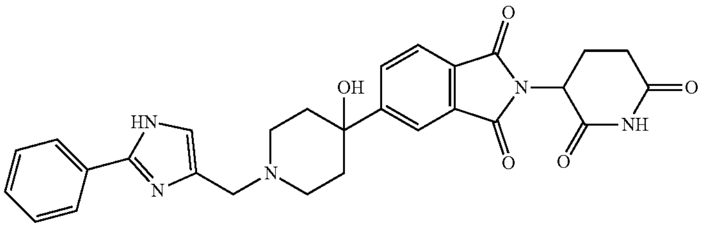 [SMILES: O=C1CCC(N2C(=O)c3ccc(C4(O)CCN(Cc5c[nH]c(-c6ccccc6)n5)CC4)cc3C2=O)C(=O)N1] | 2-(2,6-dioxopiperidin-3-yl)-5-(4-hydroxy-1-((2-phenyl-1H-imidazol-4-yl)methyl)piperidin-4-yl)isoindoline-1,3-dione |
| 94 | 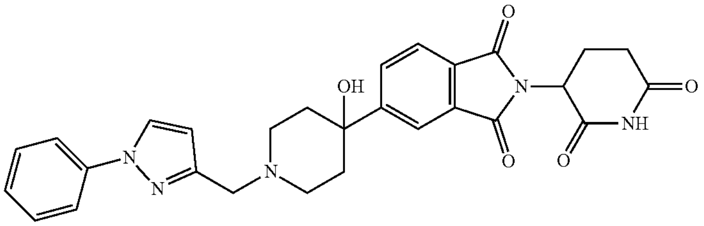 [SMILES: O=C1CCC(N2C(=O)c3ccc(C4(O)CCN(Cc5ccn(-c6ccccc6)n5)CC4)cc3C2=O)C(=O)N1] | 2-(2,6-dioxopiperidin-3-yl)-5-(4-hydroxy-1-((1-phenyl-1H-pyrazol 3-yl)methyl)piperidin-4-yl)isoindoline-1,3-dione |
| 95 | 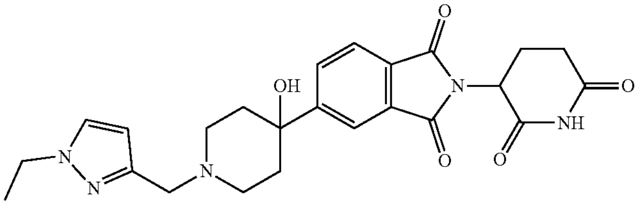 [SMILES: CCn1ccc(CN2CCC(O)(c3ccc4c(c3)C(=O)N(C3CCC(=O)NC3=O)C4=O)CC2)n1] | 2-(2,6-dioxopiperidin-3-yl)-5-(1-((1-ethyl-1H-pyrazol-3-yl)methyl)-4-hydroxypiperidin-4-yl)isoindoline-1,3-dione |
| 96 | 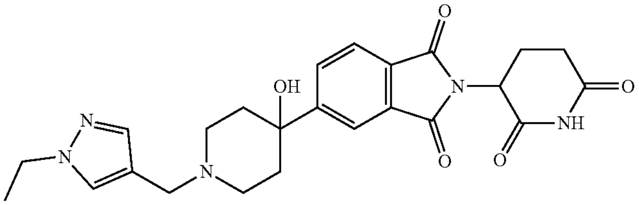 [SMILES: CCn1cc(CN2CCC(O)(c3ccc4c(c3)C(=O)N(C3CCC(=O)NC3=O)C4=O)CC2)cn1] | 2-(2,6-dioxopiperidin-3-yl)-5-(1-((1-ethyl-1H-pyrazol-4-yl)methyl)-4-hydroxypiperidin-4-yl)isoindoline-1,3-dione |
| 97 | 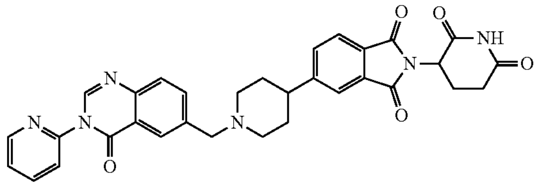 [SMILES: O=C1CCC(N2C(=O)c3ccc(C4CCN(Cc5ccc6ncn(-c7ccccn7)c(=O)c6c5)CC4)cc3C2=O)C(=O)N1] | 2-(2,6-dioxopiperidin-3-yl)-5-(1-((4-oxo-3-(pyridin-2-yl)-3,4-dihydroquinazolin-6-yl)methyl)piperidin-4-yl)isoindoline-1,3-dione |
| 98 | 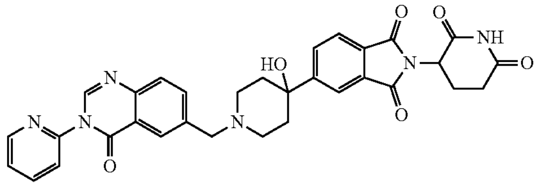 [SMILES: O=C1CCC(N2C(=O)c3ccc(C4(O)CCN(Cc5ccc6ncn(-c7ccccn7)c(=O)c6c5)CC4)cc3C2=O)C(=O)N1] | 2-(2,6-dioxopiperidin-3-yl)-5-(1-((4-oxo-3-(pyridin-2-yl)-3,4-dihydroquinazolin-6-yl)methyl)piperidin-4-yl)isoindoline-1,3-dione |
| 99 | 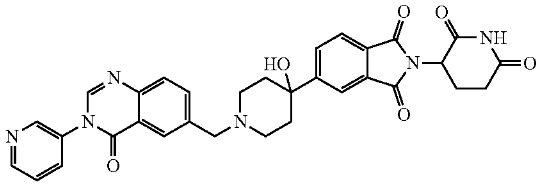 [SMILES: O=C1CCC(N2C(=O)c3ccc(C4(O)CCN(Cc5ccc6ncn(-c7cccnc7)c(=O)c6c5)CC4)cc3C2=O)C(=O)N1] | 2-(2,6-dioxopiperidin-3-yl)-5-(4-hydroxy-1-((4-oxo-3-(pyridin-3-yl)-3,4-dihydroquinazolin-6-yl)methyl)piperidin-4-yl)isoindoline-1,3-dione |

-continued

| Compound number | Structure | Name |
|---|---|---|
| 100 | 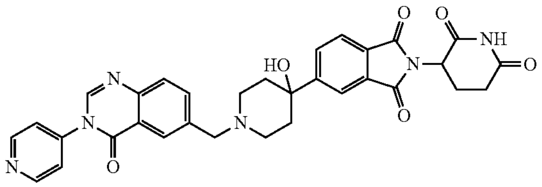 [SMILES: O=C1CCC(N2C(=O)c3ccc(C4(O)CCN(Cc5ccc6ncn(-c7ccncc7)c(=O)c6c5)CC4)cc3C2=O)C(=O)N1] | 2-(2,6-dioxopiperidin-3-yl)-5-(4-hydroxy-1-((4-oxo-3-(pyridin-4-yl)-3,4-dihydroquinazolin-6-yl)methyl)piperidin-4-yl)isoindoline-1,3-dione |
| 101 | 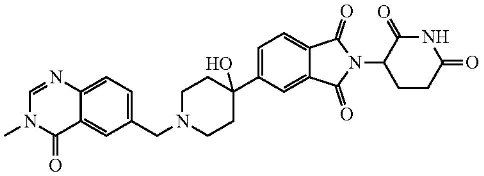 [SMILES: Cn1cnc2ccc(CN3CCC(O)(c4ccc5c(c4)C(=O)N(C4CCC(=O)NC4=O)C5=O)CC3)cc2c1=O] | 2-(2,6-dioxopiperidin-3-yl)-5-(4-hydroxy-1-((3-methyl-4-oxo-3,4-dihydroquinazolin-6-yl)methyl)piperidin-4-yl)isoindoline-1,3-dione |
| 102 | 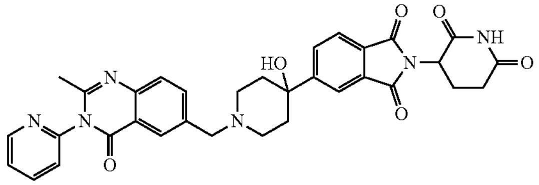 [SMILES: Cc1nc2ccc(CN3CCC(O)(c4ccc5c(c4)C(=O)N(C4CCC(=O)NC4=O)C5=O)CC3)cc2c(=O)n1-c1ccccn1] | 2-(2,6-dioxopiperidin-3-yl)-5-(4-hydroxy-1-((2-methyl-4-oxo-3-(pyridin-2-yl)-3,4-dihydroquinazolin-6-yl)methyl)piperidin-4-yl)isoindoline-1,3-dione |
| 103 | 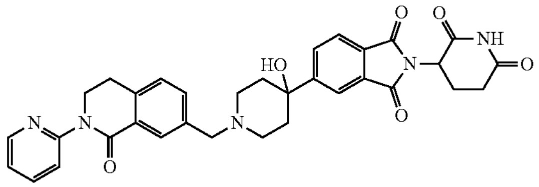 [SMILES: O=C1CCC(N2C(=O)c3ccc(C4(O)CCN(Cc5ccc6c(c5)C(=O)N(c5ccccn5)CC6)CC4)cc3C2=O)C(=O)N1] | 2-(2,6-dioxopiperidin-3-yl)-5-(4-hydroxy-1-((1-oxo-2-(pyridin-2-yl)-1,2,3,4-tetrahydroisoquinolin-7-y)methyl)piperidin-4-yl)isoindoline-1,3-dione |
| 104 | 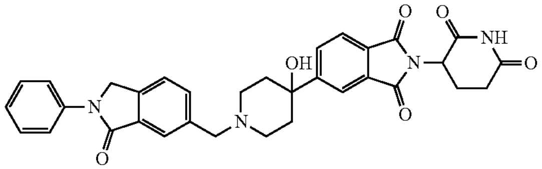 [SMILES: O=C1CCC(N2C(=O)c3ccc(C4(O)CCN(Cc5ccc6c(c5)C(=O)N(c5ccccc5)C6)CC4)cc3C2=O)C(=O)N1] | 2-(2,6-dioxopiperidin-3-yl)-5-(4-hydroxy-1-((3-oxo-2-phenylisoindolin-5-yl)methyl)piperidin-4-yl)isoindoline-1,3-dione |
| 105 | 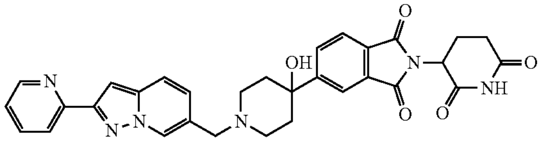 [SMILES: O=C1CCC(N2C(=O)c3ccc(C4(O)CCN(Cc5ccc6cc(-c7ccccn7)nn6c5)CC4)cc3C2=O)C(=O)N1] | 2-(2,6-dioxopiperidin-3-yl)-5-(4-hydroxy-1-((2-(pyridin-2-yl)pyrazolo[1,5-a]pyridin-6-yl)methyl)piperidin-4-yl)isoindoline-1,3-dione |
| 106 | 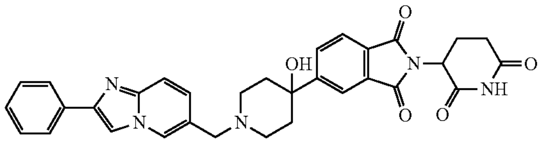 [SMILES: O=C1CCC(N2C(=O)c3ccc(C4(O)CCN(Cc5ccc6nc(-c7ccccc7)cn6c5)CC4)cc3C2=O)C(=O)N1] | 2-(2,6-dioxopiperidin-3-yl)-5-(4-hydroxy-1-((2-phenylimidazo[1,2-a]pyridin-6-yl)methyl)piperidin-4-yl)isoindoline-1,3-dione |
| 107 | 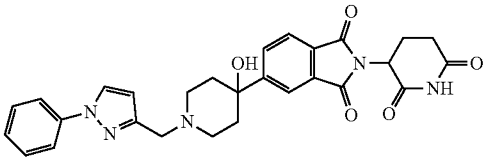 [SMILES: O=C1CCC(N2C(=O)c3ccc(C4(O)CCN(Cc5ccn(-c6ccccc6)n5)CC4)cc3C2=O)C(=O)N1] | 2-(2,6-dioxopiperidin-3-yl)-5-(4-hydroxy-1-((1-phenyl-1H-pyrazol-3-yl)methyl)piperidin-4-yl)isoindoline-1,3-dione |

-continued

| Compound number | Structure | Name |
|---|---|---|
| 108 | 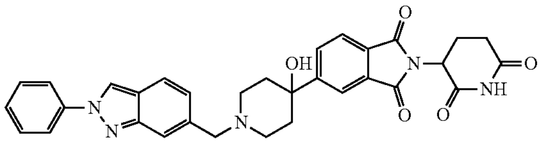 [SMILES: O=C1CCC(N2C(=O)c3ccc(C4(O)CCN(Cc5ccc6cn(-c7ccccc7)nc6c5)CC4)cc3C2=O)C(=O)N1] | 2-(2,6-dioxopiperidin-3-yl)-5-(4-hydroxy-1-((2-phenyl-2H-indazol-6-yl)methyl)piperidin-4-yl)isoindoline-1,3-dione |
| 109 | 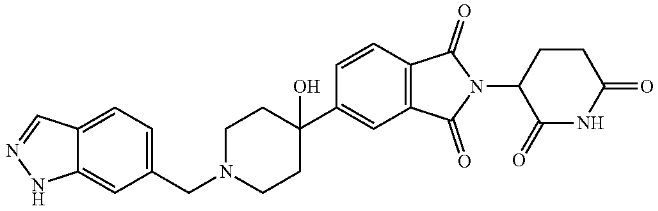 [SMILES: O=C1CCC(N2C(=O)c3ccc(C4(O)CCN(Cc5ccc6cn[nH]c6c5)CC4)cc3C2=O)C(=O)N1] | 5-(1-((1H-indazol-6-yl)methyl)-4-hydroxypiperidin-4-yl)-2-(2,6-dioxopiperidin-3-yl)isoindoline-1,3-dione |
| 110 | 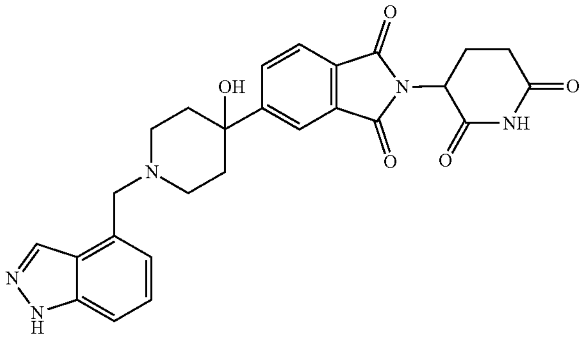 [SMILES: O=C1CCC(N2C(=O)c3ccc(C4(O)CCN(Cc5cccc6[nH]ncc56)CC4)cc3C2=O)C(=O)N1] | 5-(1-((1H-indazol-4-yl)methyl)-4-hydroxypiperidin-4-yl)-2-(2,6-dioxopiperidin-3-yl)isoindoline-1,3-dione |
| 111 | 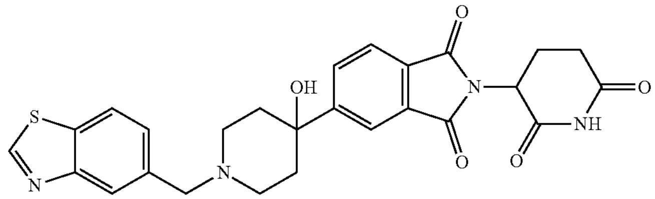 [SMILES: O=C1CCC(N2C(=O)c3ccc(C4(O)CCN(Cc5ccc6scnc6c5)CC4)cc3C2=O)C(=O)N1] | 5-(1-(benzo[d]thiazol-5-ylmethyl)-4-hydroxypiperidin-4-yl)-2-(2,6-dioxopiperidin-3-yl)isoindoline-1,3-dione |
| 112 | 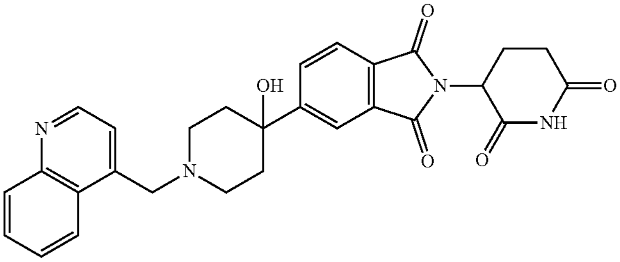 [SMILES: O=C1CCC(N2C(=O)c3ccc(C4(O)CCN(Cc5ccnc6ccccc56)CC4)cc3C2=O)C(=O)N1] | 2-(2,6-dioxopiperidin-3-yl)-5-(4-hydroxy-1-(quinolin-4-ylmethyl)piperidin-4-yl)isoindoline-1,3-dione |
| 113 | 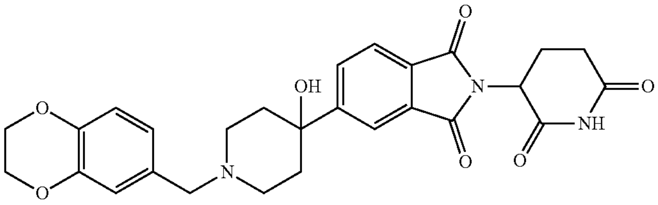 [SMILES: O=C1CCC(N2C(=O)c3ccc(C4(O)CCN(Cc5ccc6c(c5)OCCO6)CC4)cc3C2=O)C(=O)N1] | 5-(1-((2,3-dihydrobenzo[b][1,4]dioxin-6-yl)methyl)-4-hydroxypiperidin-4-yl)-2-(2,6-dioxopiperidin-3-yl)isoindoline-1,3-dione |

-continued

| Compound number | Structure | Name |
|---|---|---|
| 114 | 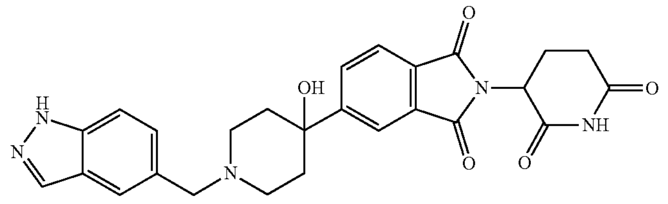 [SMILES: O=C1CCC(N2C(=O)c3ccc(C4(O)CCN(Cc5ccc6[nH]ncc6c5)CC4)cc3C2=O)C(=O)N1] | 5-(1-((1H-indazol-5-yl)methyl)-4-hydroxypiperidin-4-yl)-2-(2,6-dioxopiperidin-3-yl)isoindoline-1,3-dione |
| 115 | 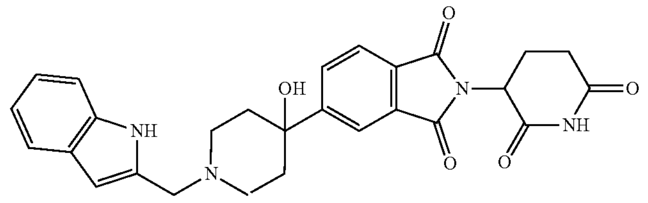 [SMILES: CCC(O)(CCN(C)Cc1cc2ccccc2[nH]1)c1ccc2c(c1)C(=O)N(C1CCC(=O)NC1=O)C2=O] | 5-(1-((1H-indol-2-yl)methyl)-4-hydroxypiperidin-4-yl)-2-(2,6-dioxopiperidin-3-yl)isoindoline-1,3-dione |
| 116 | 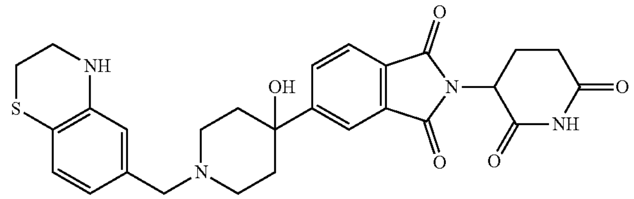 [SMILES: O=C1CCC(N2C(=O)c3ccc(C4(O)CCN(Cc5ccc6c(c5)NCCS6)CC4)cc3C2=O)C(=O)N1] | 5-(1-((3,4-dihydro-2H-benzol[b][1,4]thiazin-6-yl)methyl)-4-hydroxypiperidin-4-yl)-2-(2,6-dioxopiperidin-3-yl)isoindoline-1,3-dione |
| 117 | 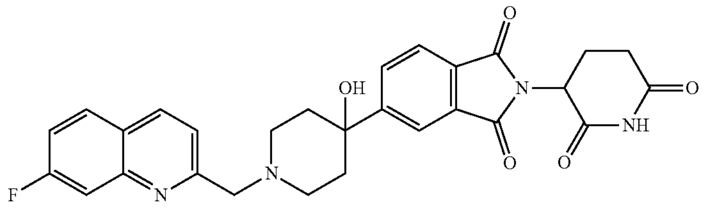 [SMILES: O=C1CCC(N2C(=O)c3ccc(C4(O)CCN(Cc5ccc6ccc(F)cc6n5)CC4)cc3C2=O)C(=O)N1] | 2-(2,6-dioxopiperidin-3-yl)-5-(1-((7-fluoroquinolin-2-yl)methyl)-4-hydroxypiperidin-4-yl)isoindoline-1,3-dione |
| 118 | 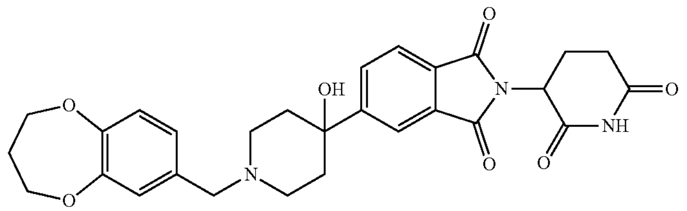 [SMILES: O=C1CCC(N2C(=O)c3ccc(C4(O)CCN(Cc5ccc6c(c5)OCCCO6)CC4)cc3C2=O)C(=O)N1] | 5-(1-((3,4-dihydro-2H-benzo[b][1,4]dioxepin-7-y)methyl)-4-hydroxypiperidin-4-yl)-2-(2,6-dioxopiperidin-3-yl)isoindoline-1,3-dione |
| 119 | 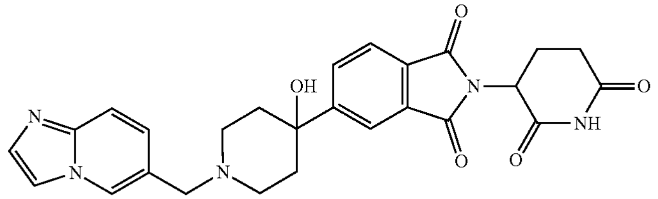 [SMILES: O=C1CCC(N2C(=O)c3ccc(C4(O)CCN(Cc5ccc6nccn6c5)CC4)cc3C2=O)C(=O)N1] | 2-(2,6-dioxopiperidin-3-yl)-5-(4-hydroxy-1-(imidazo[1,2-a]pyridin-6-ylmethyl)piperidin-4-yl)isoindoline-1,3-dione |
| 120 | 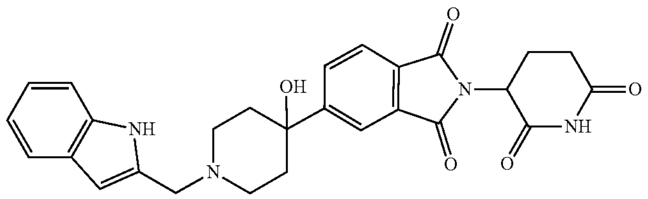 [SMILES: O=C1CCC(N2C(=O)c3ccc(C4(O)CCN(Cc5cc6ccccc6[nH]5)CC4)cc3C2=O)C(=O)N1] | 5-(1-((1H-indol-2-yl)methyl)-4-hydroxypiperidin-4-yl)-2-(2,6-dioxopiperidin-3-yl)isoindoline-1,3-dione |

-continued

| Compound number | Structure | Name |
| --- | --- | --- |
| 121 | 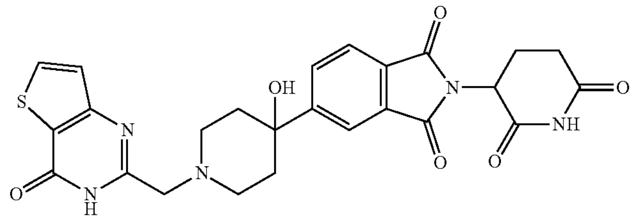 [SMILES: O=C1CCC(N2C(=O)c3ccc(C4(O)CCN(Cc5nc6ccsc6c(=O)[nH]5)CC4)cc3C2=O)C(=O)N1] | 2-(2,6-dioxopiperidin-3-yl)-5-(4-hydroxy-1-((4-oxo-3,4-dihydrothieno[3,2-d]pyrimidin-2-yl)methyl)piperidin-4-yl)isoindoline-1,3-dione |
| 122 | 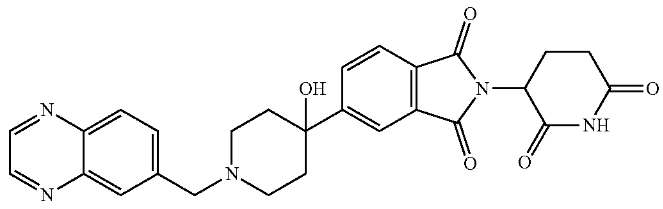 [SMILES: O=C1CCC(N2C(=O)c3ccc(C4(O)CCN(Cc5ccc6nccnc6c5)CC4)cc3C2=O)C(=O)N1] | 2-(2,6-dioxopiperidin-3-yl)-5-(4-hydroxy-1-(quinoxalin-6-ylmethyl)piperidin-4-yl)isoindoline-1,3-dione |
| 123 | 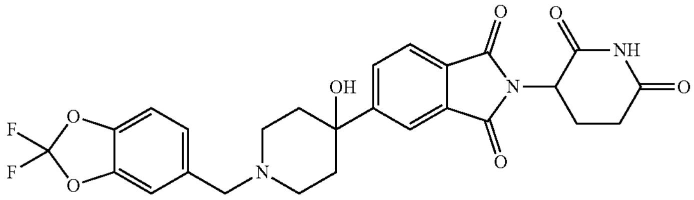 [SMILES: O=C1CCC(N2C(=O)c3ccc(C4(O)CCN(Cc5ccc6c(c5)OC(F)(F)O6)CC4)cc3C2=O)C(=O)N1] | 5-(1-((2,2-difluorobenzo[d][1,3]dioxol-5-yl)methyl)-4-hydroxypiperidin-4-yl)-2-(2,6-dioxopiperidin-3-yl)isoindoline-1,3-dione |
| 124 | 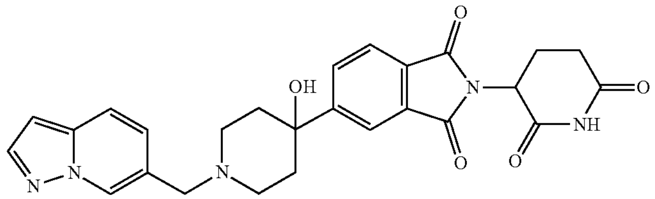 [SMILES: O=C1CCC(N2C(=O)c3ccc(C4(O)CCN(Cc5ccc6ccnn6c5)CC4)cc3C2=O)C(=O)N1] | 2-(2,6-dioxopiperidin-3-yl)-5-(4-hydroxy-1-(pyrazolo[1,5-a]pyridin-6-ylmethyl)piperidin-4-yl)isoindoline-1,3-dione |
| 125 | 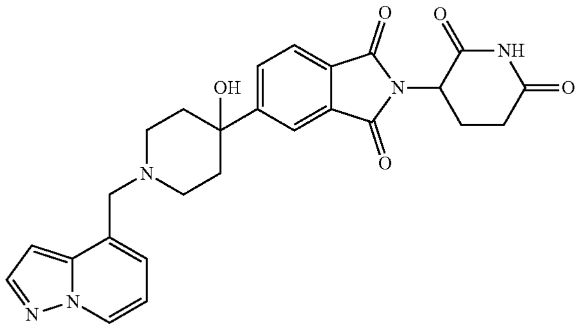 [SMILES: O=C1CCC(N2C(=O)c3ccc(C4(O)CCN(Cc5cccn6nccc56)CC4)cc3C2=O)C(=O)N1] | 2-(2,6-dioxopiperidin-3-yl)-5-(4-hydroxy-1-(pyrazolo[1,5-a]pyridin-4-ylmethyl)piperidin-4-yl)isoindoline-1,3-dione |
| 126 | 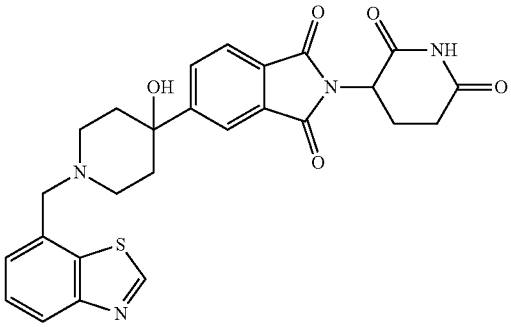 [SMILES: O=C1CCC(N2C(=O)c3ccc(C4(O)CCN(Cc5cccc6ncsc56)CC4)cc3C2=O)C(=O)N1] | 5-(1-(benzo[d]thiazol-7-ylmethyl)-4-hydroxypiperidin-4-yl)-2-(2,6-dioxopiperidin-3-yl)isoindoline-1,3-dione |

-continued

| Compound number | Structure | Name |
|---|---|---|
| 127 | 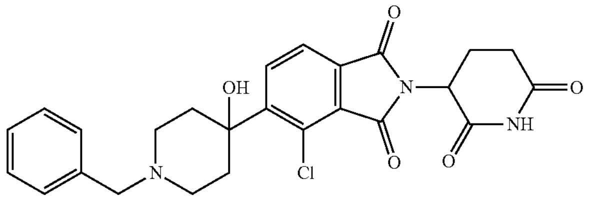 [SMILES: O=C1CCC(N2C(=O)c3ccc(C4(O)CCN(Cc5ccccc5)CC4)c(Cl)c3C2=O)C(=O)N1] | 5-(1-benzyl-4-hydroxypiperidin-4-yl)-4-chloro-2-(2,6-dioxopiperidin-3-yl)isoindoline-1,3-dione |
| 128 | 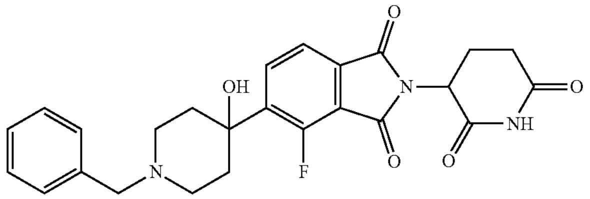 | 5-(1-benzyl-4-hydroxypiperidin-4-yl)-2-(2,6-dioxopiperidin-3-yl)-4-fluoroisoindoline-1,3-dione |
| 129 | 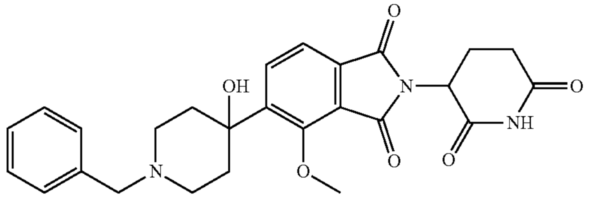 [SMILES: COc1c(C2(O)CCN(Cc3ccccc3)CC2)ccc2c1C(=O)N(C1CCC(=O)NC1=O)C2=O] | 5-(1-benzyl-4-hydroxypiperidin-4-yl)-2-(2,6-dioxopiperidin-3-yl)-4-methoxyisoindoline-1,3-dione |
| 130 | 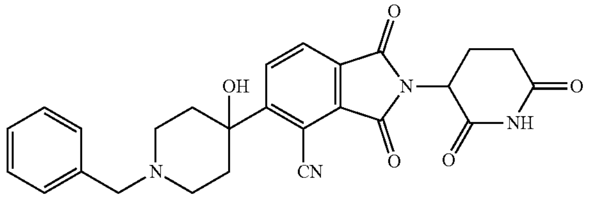 | 5-(1-benzyl-4-hydroxypiperidin-4-yl)-2-(2,6-dioxopiperidin-3-yl)-1,3-dioxoisoindoline-4-carbonitrile |
| 131 | 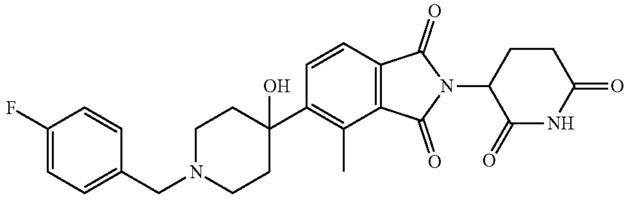 | 2-(2,6-dioxopiperidin-3-yl)-5-(1-(4-fluorobenzyl)-4-hydroxypiperidin-4-yl)-4-methylisoindoline-1,3-dione |
| 132 | 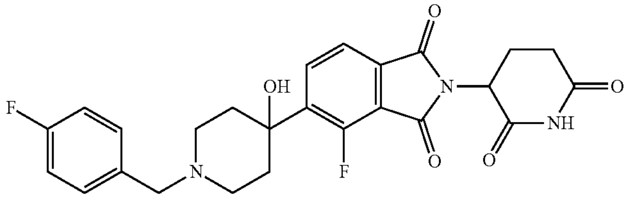 [SMILES: O=C1CCC(N2C(=O)c3ccc(C4(O)CCN(Cc5ccc(F)cc5)CC4)c(F)c3C2=O)C(=O)N1] | 2-(2,6-dioxopiperidin-3-yl)-4-fluoro-5-(1-(4-fluorobenzyl)-4-hydroxypiperidin-4-yl)-isoindoline-1,3-dione |
| 133 | 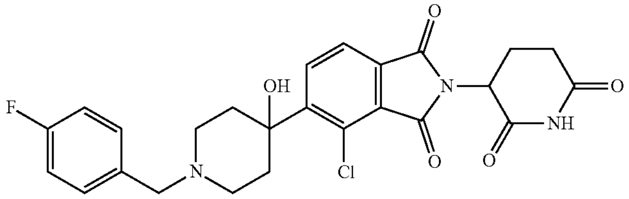 [SMILES: O=C1CCC(N2C(=O)c3ccc(C4(O)CCN(Cc5ccc(F)cc5)CC4)c(Cl)c3C2=O)C(=O)N1] | 4-chloro-2-(2,6-dioxopiperidin-3-yl)-5-(1-(4-fluorobenzyl)-4-hydroxypiperidin-4-yl)isoindoline-1,3-dione |

-continued

| Compound number | Structure | Name |
|---|---|---|
| 134 | 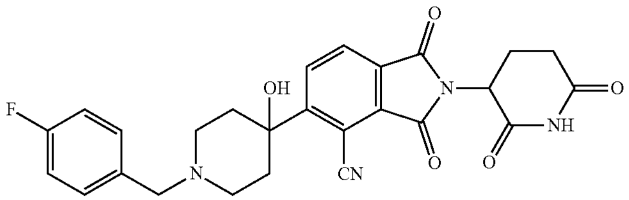 | 2-(2,6-dioxopiperidin-3-yl)-5-(1-(4-fluorobenzyl)-4-hydroxypiperidin-4-yl)-1,3-dioxoisoindoline-4-carbonitrile |
| 135 | 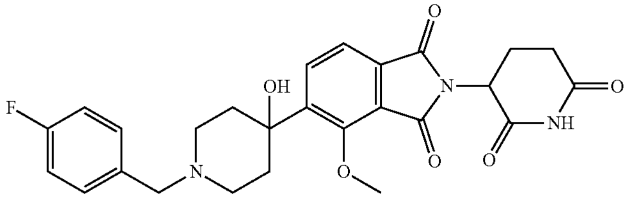 [SMILES: COc1c(C2(O)CCN(Cc3ccc(F)cc3)CC2)ccc2c1C(=O)N(C1CCC(=O)NC1=O)C2=O] | 2-(2,6-dioxopiperidin-3-yl)-5-(1-(4-fluorobenzyl)-4-hydroxypiperidin-4-yl)-4-methoxyisoindoline-1,3-dione |
| 136 | 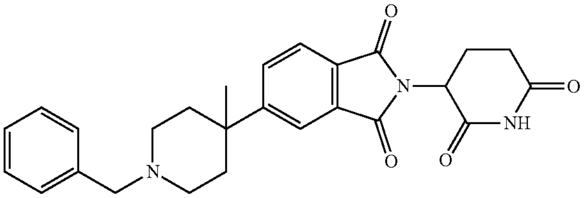 [SMILES: CC1(c2ccc3c(c2)C(=O)N(C2CCC(=O)NC2=O)C3=O)CCN(Cc2ccccc2)CC1] | 5-(1-benzyl-4-methylpiperidin-4-yl)-2-(2,6-dioxopiperidin-3-yl)isoindoline-1,3-dione |
| 137 | 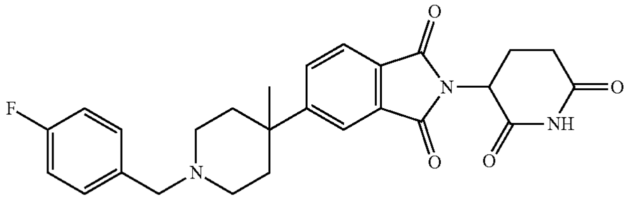 [SMILES: CC1(c2ccc3c(c2)C(=O)N(C2CCC(=O)NC2=O)C3=O)CCN(Cc2ccc(F)cc2)CC1] | 2-(2,6-dioxopiperidin-3-yl)-5-(1-(4-fluorobenzyl)-4-methylpiperidin-4-yl)isoindoline-1,3-dione |
| 138 | 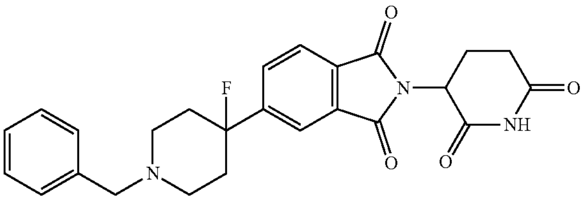 [SMILES: O=C1CCC(N2C(=O)c3ccc(C4(F)CCN(Cc5ccccc5)CC4)cc3C2=O)C(=O)N1] | 5-(1-benzyl-4-fluoropiperidin-4-yl)-2-(2,6-dioxopiperidin-3-yl)isoindoline-1,3-dione |
| 139 | 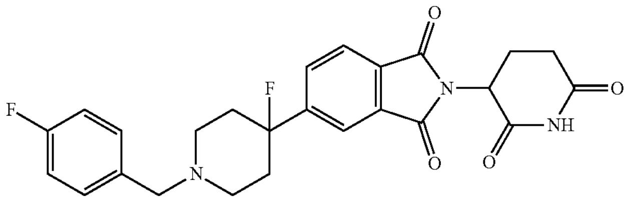 [SMILES: O=C1CCC(N2C(=O)c3ccc(C4(F)CCN(Cc5ccc(F)cc5)CC4)cc3C2=O)C(=O)N1] | 2-(2,6-dioxopiperidin-3-yl)-5-(4-fluoro-1-(4-fluorobenzyl)piperidin-4-yl)isoindoline-1,3-dione |
| 140 | 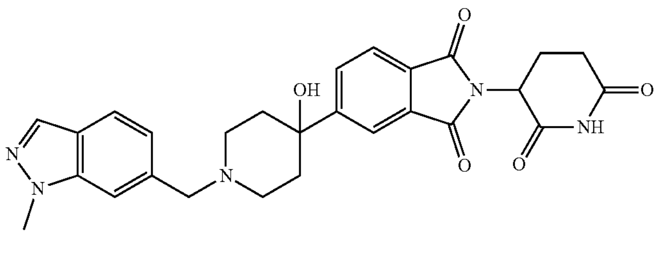 [SMILES: Cn1ncc2ccc(CN3CCC(O)(c4ccc5c(c4)C(=O)N(C4CCC(=O)NC4=O)C5=O)CC3)cc21] | 2-(2,6-dioxopiperidin-3-yl)-5-{4-hydroxy-1-[(1-methyl-1H-indazol-6-yl)methyl]piperidin-4-yl}-2,3-dihydro-1H-isoindole-1,3-dione |

-continued

| Compound number | Structure | Name |
| --- | --- | --- |
| 141 | 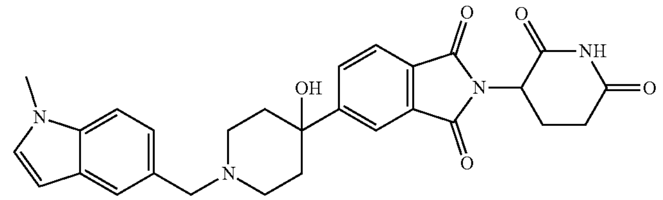 | 2-(2,6-dioxopiperidin-3-yl)-5-{4-hydroxy-1-[(1-methyl-1H-indol-5-yl)methyl]piperidin-4-yl}-2,3-dihydro-1H-isoindole-1,3-dione |
| 142 | 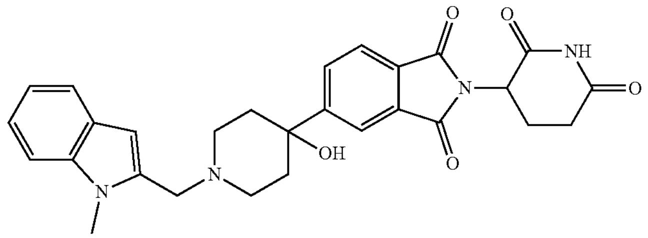 [SMILES: Cn1c(CN2CCC(O)(c3ccc4c(c3)C(=O)N(C3CCC(=O)NC3=O)C4=O)CC2)cc2ccccc21] | 2-(2,6-dioxopiperidin-3-yl)-5-{4-hydroxy-1-[(1-methyl-1H-indol-2-yl)methyl]piperidin-4-yl}-2,3-dihydro-1H-isoindole-1,3-dione |
| 143 | 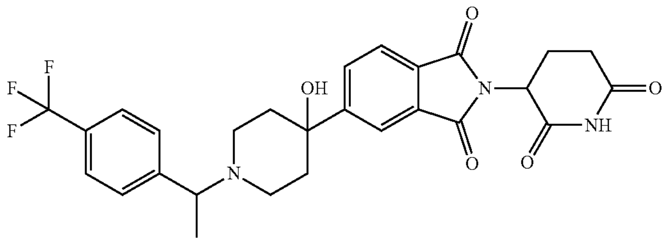 [SMILES: CC(c1ccc(C(F)(F)F)cc1)N1CCC(O)(c2ccc3c(c2)C(=O)N(C2CCC(=O)NC2=O)C3=O)CC1] | 2-(2,6-dioxopiperidin-3-yl)-5-(4-hydroxy-1-{1-[4-(trifluoromethyl)phenyl Jethyl}piperidin-4-yl)-2,3-dibhydro-1H-isoindole-1,3-dione |
| 144 | 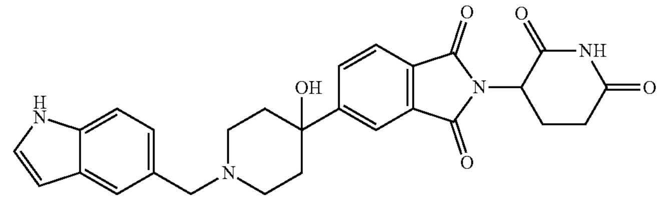 [SMILES: O=C1CCC(N2C(=O)c3ccc(C4(O)CCN(Cc5ccc6[nH]ccc6c5)CC4)cc3C2=O)C(=O)N1] | 2-(2,6-dioxopiperidin-3-yl)-5-{4-hydroxy-1-[(1H-indol-5-yl)methyl]piperidin-4-yl}-2,3-dihydro-1H-isoindole-1,3-dione |
| 145 | 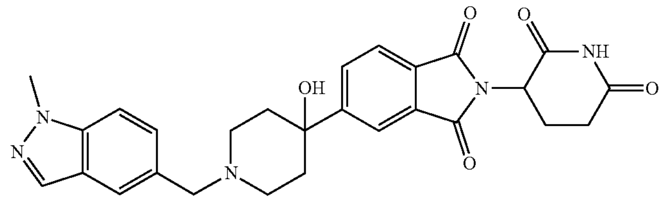 [SMILES: Cn1ncc2cc(CN3CCC(O)(c4ccc5c(c4)C(=O)N(C4CCC(=O)NC4=O)C5=O)CC3)ccc21] | 2-(2,6-dioxopiperidin-3-yl)-5-{4-hydroxy-1-[(1-methyl-1H-indazol-5-yl)methyl]piperidin-4-yl}-2,3-dihydro-1H-isoindole-1,3-dione |
| 146 | 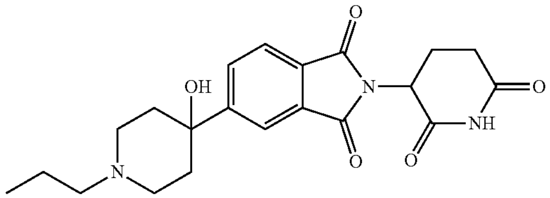 [SMILES: CCCN1CCC(O)(c2ccc3c(c2)C(=O)N(C2CCC(=O)NC2=O)C3=O)CC1] | 2-(2,6-dioxopiperidin-3-yl)-5-(4-hydroxy-1-propylpiperidin-4-yl)-2,3-dibhydro-1H-isoindole-1,3-dione |
| 147 | 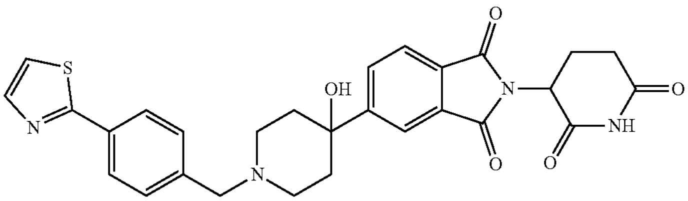 [SMILES: O=C1CCC(N2C(=O)c3ccc(C4(O)CCN(Cc5ccc(-c6nccs6)cc5)CC4)cc3C2=O)C(=O)N1] | 2-(2,6-dioxopiperidin-3-yl)-5-(4-hydroxy-1-{{[4-(1,3-thiazol-2-yl)phenylJmethyl} piperidin-4-yl)-2, 3-dihydro-1H-isoindole-1,3-dione |

-continued

| Compound number | Structure | Name |
|---|---|---|
| 148 | 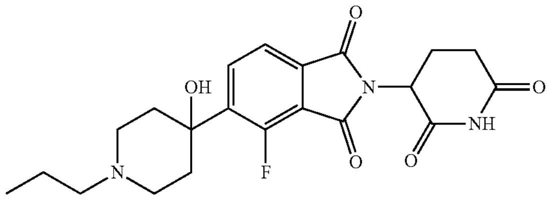 [SMILES: CCCN1CCC(O)(c2ccc3c(c2F)C(=O)N(C2CCC(=O)NC2=O)C3=O)CC1] | 2-(2,6-dioxopiperidin-3-yl)-4-fluoro-5-(4-hydroxy-1-propylpiperidin-4-yl)-2,3-dibhydro-1H-isoindole-1,3-dione |
| 149 | 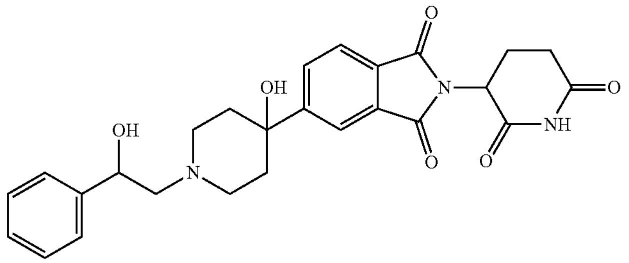 [SMILES: O=C1CCC(N2C(=O)c3ccc(C4(O)CCN(CC(O)c5ccccc5)CC4)cc3C2=O)C(=O)N1] | 2-(2,6-dioxopiperidin-3-yl)-5-[4-hydroxy-1-(2-hydroxy-2-phenylethyl)piperidin-4-yl]-2,3-dihydro-1H-isoindole-1,3-dione |

or a pharmaceutically acceptable salt, hydrate, solvate, prodrug, stereoisomer, or tautomer thereof.

In another embodiment of the disclosure, the compounds of the present disclosure are enantiomers. In some embodiments the compounds are the (S)-enantiomer. In other embodiments the compounds are the (R)-enantiomer. In yet other embodiments, the compounds of the present disclosure may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers, and prodrugs thereof may exist in their tautomeric form (for example, as an amide or imino ether). All such tautomeric forms are contemplated herein as part of the present disclosure.

The compounds of the disclosure may contain asymmetric or chiral centers and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure and chemical structures and names. Also, for example, all keto-enol and imine-enamine forms of the compounds are included in the disclosure.

All stereoisomers (for example, geometric isomers, optical isomers, and the like) of the present compounds (including those of the salts, solvates, esters, and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). Individual stereoisomers of the compounds of the disclosure may, for example, be substantially free of other isomers, or is admixed, for example, as racemates or with all other, or other selected, stereoisomers.

The chiral centers of the compounds of the disclosure can have the S or R configuration as defined by the IUPAC 1974 Recommendations. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

The use of the terms "salt", "solvate", "ester", "prodrug", and the like, is intended to equally apply to the salt, solvate, ester, and prodrug of enantiomers, stereoisomers, rotamers, tautomers, positional isomers, racemates, or prodrugs of the inventive compounds.

The compounds of the disclosure may form salts which are also within the scope of this disclosure. Reference to a compound of Formula (I) herein is generally understood to include reference to salts thereof, unless otherwise indicated.

The compounds and intermediates may be isolated and used as the compound per se. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and, such as $^{2}H$, $^{3}H$, $^{11}C$, $^{13}C$, $^{14}C$, $^{15}N$, $^{18}F$, $^{31}P$, $^{32}P$, respectively. The disclosure includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$, $^{11}C$ or labeled compound may be particularly desirable for PET or SPECT studies.

Further, substitution with heavier isotopes, particularly deuterium (i.e., $^{2}H$ or D) may afford certain therapeutic advantages resulting from greater metabolic stability, for example, increased in vivo half-life, reduced dosage requirements, reduced CYP450 inhibition (competitive or time dependent) or an improvement in therapeutic index. For example, substitution with deuterium may modulate undesirable side effects of the undeuterated compound, such as competitive CYP450 inhibition, time dependent CYP450 inactivation, etc. It is understood that deuterium in this context is regarded as a substituent in compounds of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present disclosure can generally be prepared by conventional techniques known to those skilled in the art or by carrying out the procedures disclosed in the schemes or in the examples and preparations described below using an appropriate isotopically-labeled reagent in place of the non-isotopically labeled reagent.

Pharmaceutically acceptable solvates in accordance with the disclosure include those wherein the solvent of crystallization may be isotopically substituted, e.g., $D_2O$, $d_6$-acetone, $d_6$-DMSO.

The present disclosure relates to compounds which are modulators of IKZF2 protein levels. In one embodiment, the compounds of the present disclosure decrease IKZF2 protein levels. In another embodiment, the compounds of the present disclosure reduce IKZF2 protein levels. In yet another embodiment, the compounds of the present disclosure are degraders of IKZF2.

In some embodiments, the compounds of the disclosure are selective over other proteins. As used herein "selective modulator", "selective degrader", or "selective compound" means, for example, a compound of the disclosure, that effectively modulates, decreases, or reduces the levels of a specific protein or degrades a specific protein to a greater extent than any other protein. A "selective modulator", "selective degrader", or "selective compound" can be identified, for example, by comparing the ability of a compound to modulate, decrease, or reduce the levels of or to degrade a specific protein to its ability to modulate, decrease, or reduce the levels of or to degrade other proteins. In some embodiments, the selectivity can be identified by measuring the $AC_{50}$, $EC_{50}$, or $IC_{50}$ of the compounds.

In some embodiments, the compounds of the present application are selective IKZF2 modulators. As used herein "selective IKZF2 modulator", "selective IKZF2 degrader", or "selective IKZF2 compound" refers to a compound of the application, for example, that effectively modulates, decrease, or reduces the levels of IKZF2 protein or degrades IKZF2 protein to a greater extent than any other protein, particularly any protein (transcription factor) from the Ikaros protein family (e.g., IKZF1, IKZF3, IKZF4, and IKZF5).

A "selective IKZF2 modulator", "selective IKZF2 degrader", or "selective IKZF2 compound" can be identified, for example, by comparing the ability of a compound to modulate IKZF2 protein levels to its ability to modulate levels of other members of the Ikaros protein family or other proteins. For example, a substance may be assayed for its ability to modulate IKZF2 protein levels, as well as IKZF1, IKZF3, IKZF4, IKZF5, and other proteins. In some embodiments, the selectivity can be identified by measuring the $EC_{50}$ of the compounds. In some embodiments, the selectivity can be identified by measuring the $AC_{50}$ of the compounds. In some embodiments, the selectivity can be identified by measuring the $DC_{50}$ of the compounds. In some embodiments, a selective IKZF2 degrader is identified by comparing the ability of a compound to degrade IKZF2 to its ability to degrade other members of the Ikaros protein family or other proteins.

In certain embodiments, the compounds of the application are IKZF2 degraders that exhibit at least 2-fold, 3-fold, 5-fold, 10-fold, 25-fold, 50-fold or 100-fold selectivity for the degradation of IKZF2 over other proteins (e.g., IKZF1, IKZF3, IKZF4, and IKZF5). In various embodiments, the compounds of the application exhibit up to 1000-fold selectivity for the degradation of IKZF2 over other proteins.

In certain embodiments, the compounds of the application exhibit at least 2-fold, 3-fold, 5-fold, 10-fold, 25-fold, 50-fold or 100-fold selectivity for the degradation of IKZF2 over the other members of the Ikaros protein family (e.g., IKZF1, IKZF3, IKZF4, and IKZF5). In various embodiments, the compounds of the application exhibit up to 1000-fold selectivity for the degradation of IKZF2 over the other members of the Ikaros protein family (e.g., IKZF1, IKZF3, IKZF4, and IKZF5).

In certain embodiments, the compounds of the application exhibit at least 2-fold, 3-fold, 5-fold, 10-fold, 25-fold, 50-fold or 100-fold selectivity for the degradation of IKZF2 over IKZF1. In various embodiments, the compounds of the application exhibit up to 1000-fold selectivity for the degradation of IKZF2 over IKZF1. In certain embodiments, the compounds of the application exhibit at least 2-fold, 3-fold, 5-fold, 10-fold, 25-fold, 50-fold or 100-fold selectivity for the degradation of IKZF2 over IKZF3. In various embodiments, the compounds of the application exhibit up to 1000-fold selectivity for the degradation of IKZF2 over IKZF3.

In certain embodiments, the compounds of the application exhibit at least 2-fold, 3-fold, 5-fold, 10-fold, 25-fold, 50-fold or 100-fold selectivity for the degradation of IKZF2 over IKZF4. In various embodiments, the compounds of the application exhibit up to 1000-fold selectivity for the degradation of IKZF2 over IKZF4.

In certain embodiments, the compounds of the application exhibit at least 2-fold, 3-fold, 5-fold, 10-fold, 25-fold, 50-fold or 100-fold selectivity for the degradation of IKZF2 over IKZF5. In various embodiments, the compounds of the application exhibit up to 1000-fold selectivity for the degradation of IKZF2 over IKZF5.

In some embodiments, the degradation of IKZF2 is measured by AC50. In another embodiment, the degradation of IKZF2 is measured by $DC_{50}$.

Potency of can be determined by $AC_{50}$ value. A compound with a lower $AC_{50}$ value, as determined under substantially similar degradation conditions, is a more potent degrader relative to a compound with a higher $AC_{50}$ value. In some embodiments, the substantially similar conditions comprise determining degradation of protein levels in cells expressing the specific protein, or a fragment of any thereof.

Potency of can be determined by $DC_{50}$ value. A compound with a lower $DC_{50}$ value, as determined under substantially similar degradation conditions, is a more potent degrader relative to a compound with a higher $DC_{50}$ value. In some embodiments, the substantially similar conditions comprise determining degradation of protein levels in cells expressing the specific protein, or a fragment of any thereof.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Methods of Synthesizing Compounds of Present Disclosure

The compounds of the present disclosure may be made by a variety of methods, including standard chemistry. Suitable synthetic routes are depicted in the Schemes 1-7 that follow.

Scheme 1

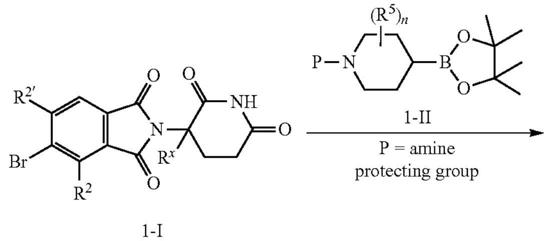

1-I

-continued

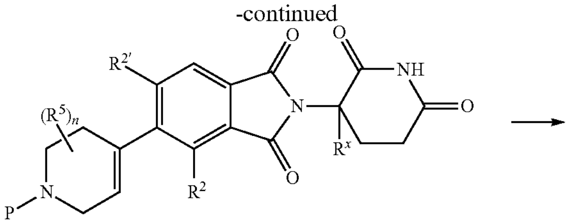

1-III

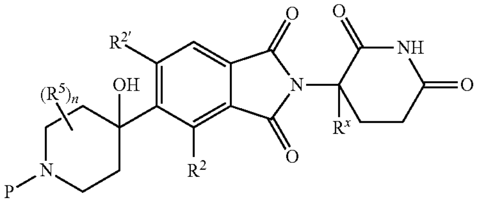

1-IV

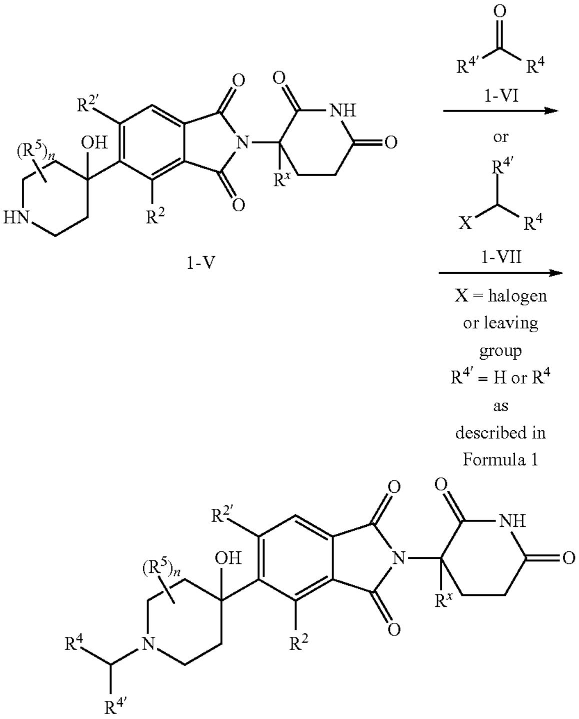

1-VIII wherein $R^x$, $R^2$, $R^{2'}$, $R^4$, $R^5$ and n are defined in Formula (I).

Scheme 1 depicts a general route for synthesizing compounds embodied in Formula (I) wherein $R^4$ is ($C_1$-$C_6$) alkyl. Suzuki cross-coupling of compound 1-I and boronic ester 1-II in the presence of a catalyst (e.g., $Pd(tBu_3P)_2$) and a base (e.g., N,N-Diisopropylethylamine (DIPEA)) in a mixture of solvents (e.g., 1,4-dioxane and water) optionally at elevated temperature yields 1-III. Hydration of 1-III in the presence of oxygen, an appropriate catalyst (e.g., $Mn(dpm)_3$) and stoichiometric silane (e.g., triphenylsilane) in a mixture of solvents (e.g., dichloromethane (DCM), isopropyl alcohol (IPA), N,N-dimethylformamide (DMF), etc.) at ambient temperature provides 1-IV. Deprotection of the nitrogen protecting group (e.g., a tert-butoxycarbonyl (Boc) protecting group) to give piperidine 1-V can be achieved under acidic conditions (e.g., trifluoroacetic acid (TFA) or hydrogen chloride (HCl)) in a solvent (e.g., DCM or 1,4-dioxane). Alkylation of 1-V can be accomplished through reductive amination with an aldehyde or ketone of the formula 1-VI in the presence of a reducing agent (e.g., $NaBH_4$ or $NaBH(OAc)_3$) in a solvent (e.g., tetrahydrofuran (THF)) optionally in the presence of a drying agent (e.g., $MgSO_4$ or $Na_2SO_4$). Alternatively, alkyl moieties bearing a halide or other leaving group as in 1-VII, can be treated with piperidine 1-V under basic conditions (e.g., DIPEA, triethylamine (TEA) or $Cs_2CO_3$, etc.) in an organic solvent (e.g., DCM, DMF, etc.) at ambient or elevated temperature to yield 1-VIII (e.g., compounds of Formula (I) wherein $R^4$ is $(C_1\text{-}C_6)$ alkyl).

Scheme 2

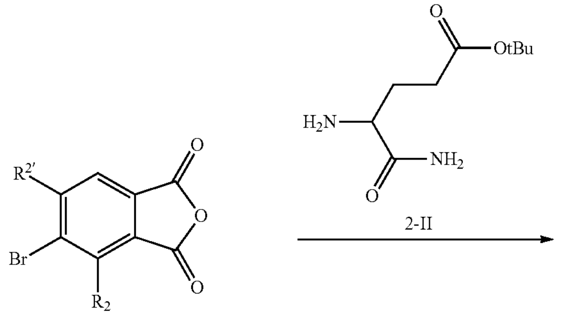

2-II

2-I

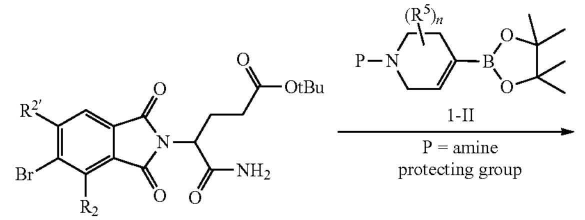

2-III

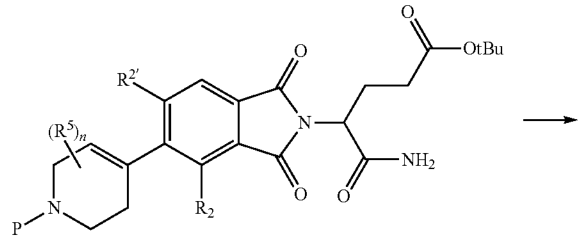

2-V

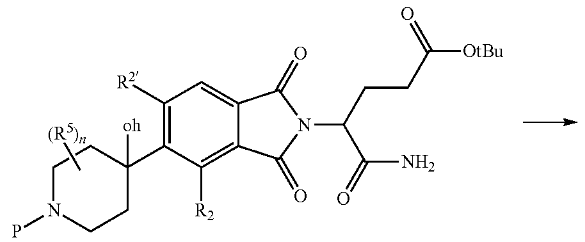

2-VI

-continued

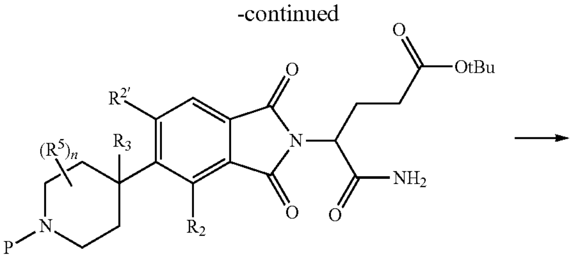

2-VII wherein $R^3$ = F, OMe

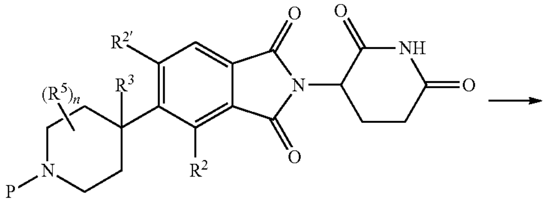

2-VIII

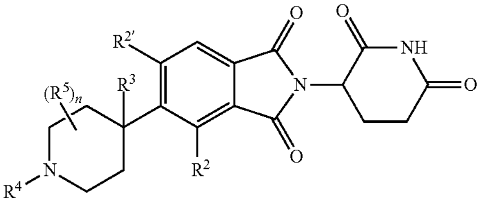

2-IX wherein $R^2$, $R^{2'}$, $R^4$, $R^5$ and n are defined in Formula (I).

Scheme 2 outlines the general way for preparing compounds of Formula (I) wherein $R^3$ is fluoro or methoxy. Bromo phthalic anhydride 2-I can be treated with glutamine 2-II in the presence of a base (e.g., triethylamine) and in a solvent (e.g., toluene) optionally at elevated temperature to afford 2-III. Suzuki cross-coupling of 2-III with boronic ester 1-II in the presence of a catalyst (e.g., $Pd(tBu_3P)_2$) and a base (e.g., DIPEA) in a mixture of solvents (e.g., 1,4-dioxane and water) optionally at elevated temperature yields 2-V. Hydration of 2-V in the presence of oxygen, an appropriate catalyst (e.g., tris(2,2,6,6-tetramethyl-3,5-heptanedionato)manganese(III) ($Mn(dpm)_3$)) and stoichiometric silane (e.g., triphenylsilane) in a mixture of solvents (e.g., DCM, IPA, DMF, etc.) at ambient temperature affords 2-VI which can then be either be fluorinated or methylated. Fluorination of 2-VI can be accomplished by treatment with a fluorinating reagent (e.g., diethylaminosulfur trifluoride (DAST)) in a solvent (e.g., DCM or tetrahydrofuran (THF)) optionally at reduced temperature to afford 2-VII wherein $R^3$ is F. Alternatively, methylation of 2-VI can be performed in the presence of a methylating agent (e.g., iodomethane) and a base (e.g., sodium hydride) in a solvent (e.g., THF) optionally at reduced temperature to afford 2-VII wherein $R^3$ is —OMe. The glutarimide ring can be then cyclized by heating 2-VII with a sulfonic acid (e.g., benzene sulfonic acid or p-toluene sulfonic acid) in a solvent (e.g., acetonitrile) to provide 2-VIII. Deprotection of 2-VIII under acidic conditions (e.g., HCl, TFA) in a solvent (e.g., 1,4-dioxane, DCM) when the amine protecting group is Boc and subsequent alkylation of the piperidine by either reductive amination with an aldehyde or ketone of the formula 1-VI in the presence of a reducing agent (e.g., $NaBH_4$ or $NaBH(OAc)_3$) in a solvent (e.g., tetrahydrofuran (THF)) optionally in the presence of a drying agent (e.g., $MgSO_4$ or $Na_2SO_4$) or treatment with alkyl moieties bearing a halide or other leaving group as in 1-VII under basic conditions (e.g., DIPEA, TEA or $Cs_2CO_3$, etc.) in an organic solvent (e.g., DCM, DMF, etc.) at ambient or elevated temperature yields 2-IX (compounds of Formula (I) wherein $R^3$ is fluoro or methoxy).

benzenesulfonic or p-toluene sulfonic acid) in a solvent (e.g., acetonitrile (ACN)) at elevated temperature to afford 3-IV. Further functionalization of 3-IV can be accomplished by deprotecting the benzyl group on the piperidine using catalytic hydrogenation conditions (e.g., using a hydrogenation catalyst (e.g., Pd/C or $PtO_2$), in a solvent (e.g., DCM), Scheme 3

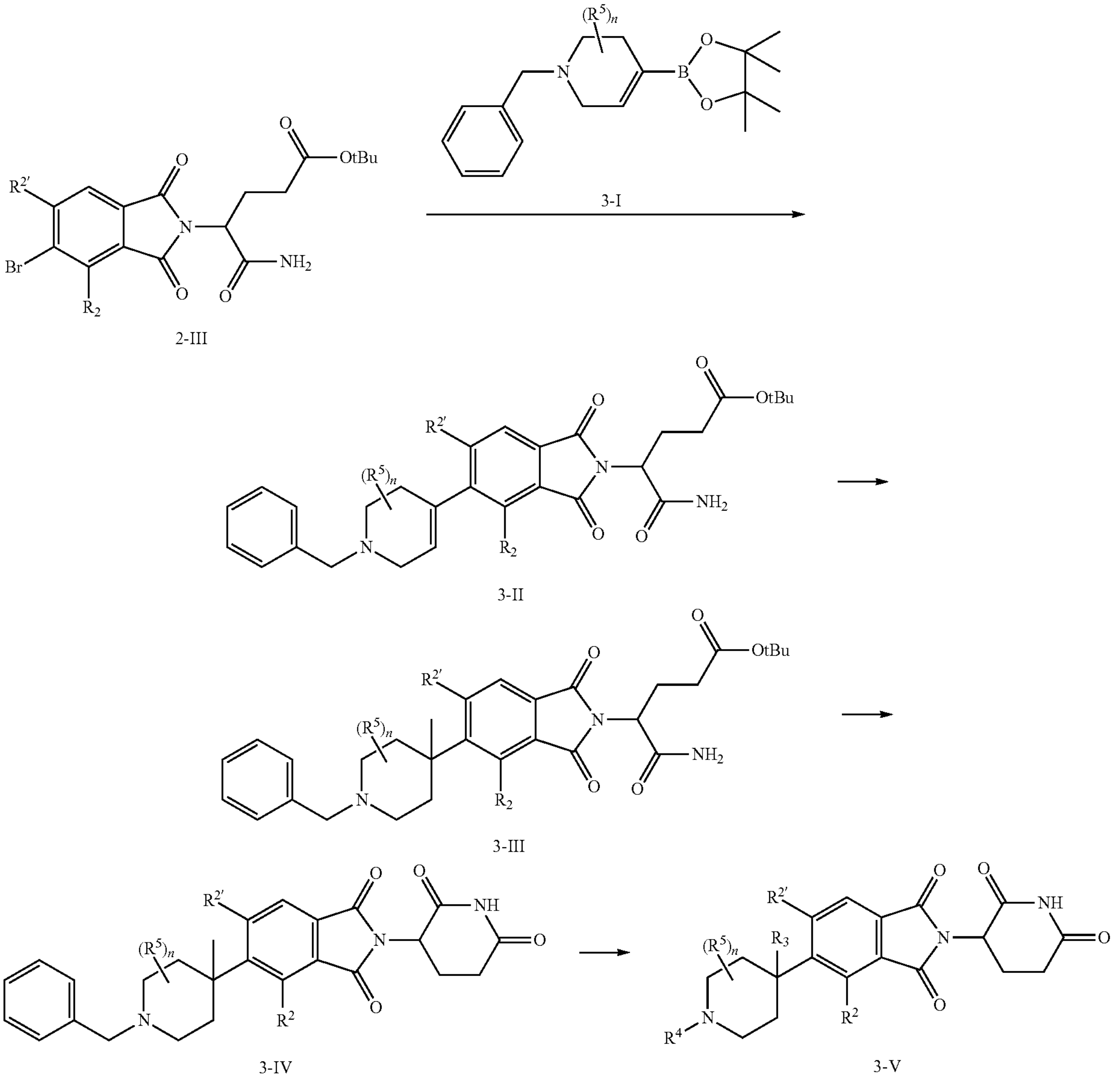

2-III 3-I 3-II 3-III 3-IV 3-V wherein $R^2$, $R^{2'}$, $R^4$, $R^5$ and n are defined in Formula (I).

Scheme 3 outlines the general way to make compounds of Formula (I) wherein $R^3$=Me. Suzuki cross-coupling of 2III with boronic ester 3-I can be carried out in the presence of a catalyst (e.g., $Pd(tBu_3P)_2$) and a base (e.g., DIPEA) in a mixture of solvents (e.g., 1,4-dioxane and water) optionally at elevated temperature to yield 3-II. Methylation of the olefin can be accomplished by treating 3-II with base (e.g., n-butyllithium) in a solvent (e.g., THF) at reduced temperature followed by addition of a methylating agent (e.g., dimethyl sulfate) to afford 3-III. Cyclization of the glutarimide ring can be accomplished using a sulfonic acid (e.g., under an atmosphere of hydrogen gas) to obtain 3-V wherein $R^4$ is H. Subsequent alkylation of the piperidine (3-V wherein $R^4$ is H) by either reductive amination with an aldehyde or ketone of the formula 1-VI in the presence of a reducing agent (e.g., $NaBH_4$ or $NaBH(OAc)_3$) in a solvent (e.g., tetrahydrofuran (THF)) optionally in the presence of a drying agent (e.g., $MgSO_4$ or $Na_2SO_4$) or by treatment with alkyl moieties bearing a halide or other leaving group as in formula 1-VII under basic conditions (e.g., DIPEA, TEA or $Cs_2CO_3$, etc.) in an organic solvent (e.g., DCM, DMF, etc.) at ambient or elevated temperature affords 3-V (compounds of Formula (I) wherein $R^3$=Me).

Scheme 4

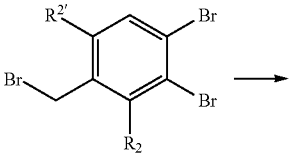

4-I

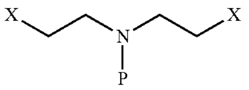

4-III

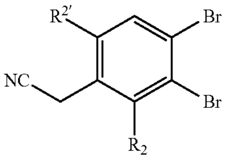

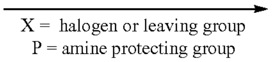

4-II

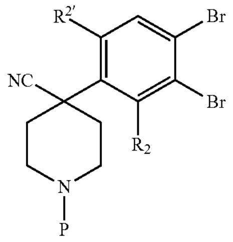

4-IV

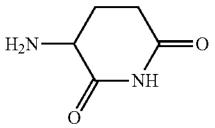

4-V

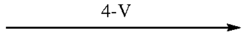

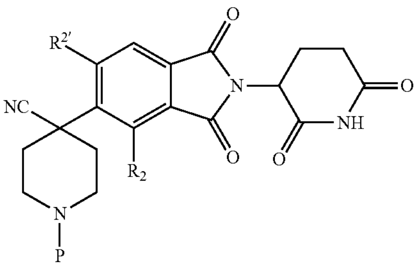

4-VI

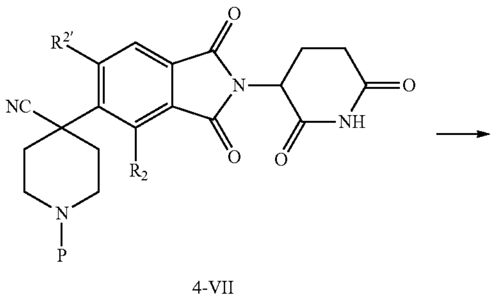

4-VII

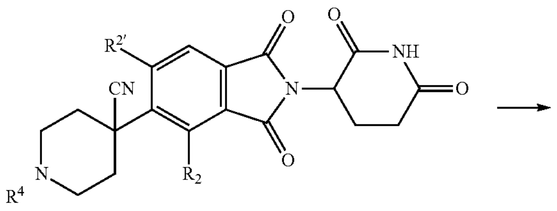

4-VIII

-continued

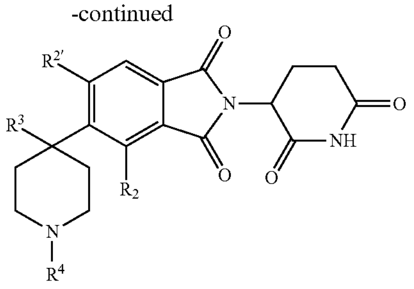

4-IX where in $R^3$ = —$CH_2NH_2$, —$CH_2NHR^{10}$, —$CH_2NR^{10}R^{11}$, wherein $R^2$, $R^{2'}$, and $R^4$ are defined in Formula (I).

Scheme 4 outlines the general way to make compounds of Formula (I) wherein $R^3$=—$CH_2NH_2$, —$CH_2NHR^{10}$ or —$CH_2NR^{10}R^{11}$. Treatment of alkyl bromide 4-I with sodium cyanide in a solvent (e.g., N,N-dimethylformamide) at elevated temperature yields 4-II. Formation of the piperidine ring can be accomplished by treating 4-II with 4-III in the presence of a base (e.g., sodium hydride) and a solvent (e.g., THF) optionally at elevated temperature. Carbonylation of 4-IV in the presence of 3-aminoglutarimide 4-V, a carbonylation reagent (e.g., molybdenum hexacarbonyl), a catalyst (e.g., palladium (II) acetate ($(Pd(OAc)_2)_3$)), a ligand (e.g., di(1-adamantyl)-n-butylphosphine (CataCXium A)) and a base (e.g., triethylamine) in a solvent (e.g., N,N-dimethylacetamide) at elevated temperature affords 4-VI. Removal of the piperidine protecting group (e.g., when the protecting group is Boc) can be accomplished under acidic conditions (e.g., HCl or TFA) in a solvent (e.g., 1,4-dioxane or DCM). Subsequent alkylation of the piperidine by either reductive amination with an aldehyde or ketone of the formula 1-VI or by treatment with alkyl moieties bearing a halide or other leaving group as in formula 1-VII under basic conditions (e.g., DIPEA, TEA or $Cs_2CO_3$, etc.) in an organic solvent (e.g., DCM, DMF, etc.) at ambient or elevated temperature yields 4-VIII. Reduction of the nitrile with hydrogen optionally at increased pressure in the presence of a catalyst (e.g., platinum hydroxide) in a solvent (e.g., ethanol) and an acid (e.g., HCl) provides the amino methyl analogs which can be further elaborated by either reductive amination with an aldehyde or ketone of formula 1-VI in the presence of a reducing agent (e.g., $NaBH_4$ or $NaBH(OAc)_3$) in a solvent (e.g., tetrahydrofuran (THF)) optionally in the presence of a drying agent (e.g., $MgSO_4$ or $Na_2SO_4$) or alkylation with 1-VII under basic conditions (e.g., DIPEA, TEA or $Cs_2CO_3$, etc.) in an organic solvent (e.g., DCM, DMF, etc.) at ambient or elevated temperature to provide 4-IX wherein $R^{10}$ and $R^{11}$ are described in Formula (I).

Scheme 5

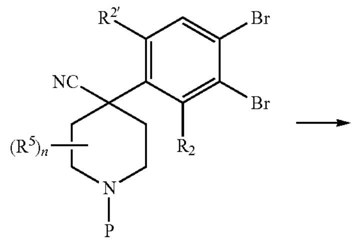

4-IV

-continued

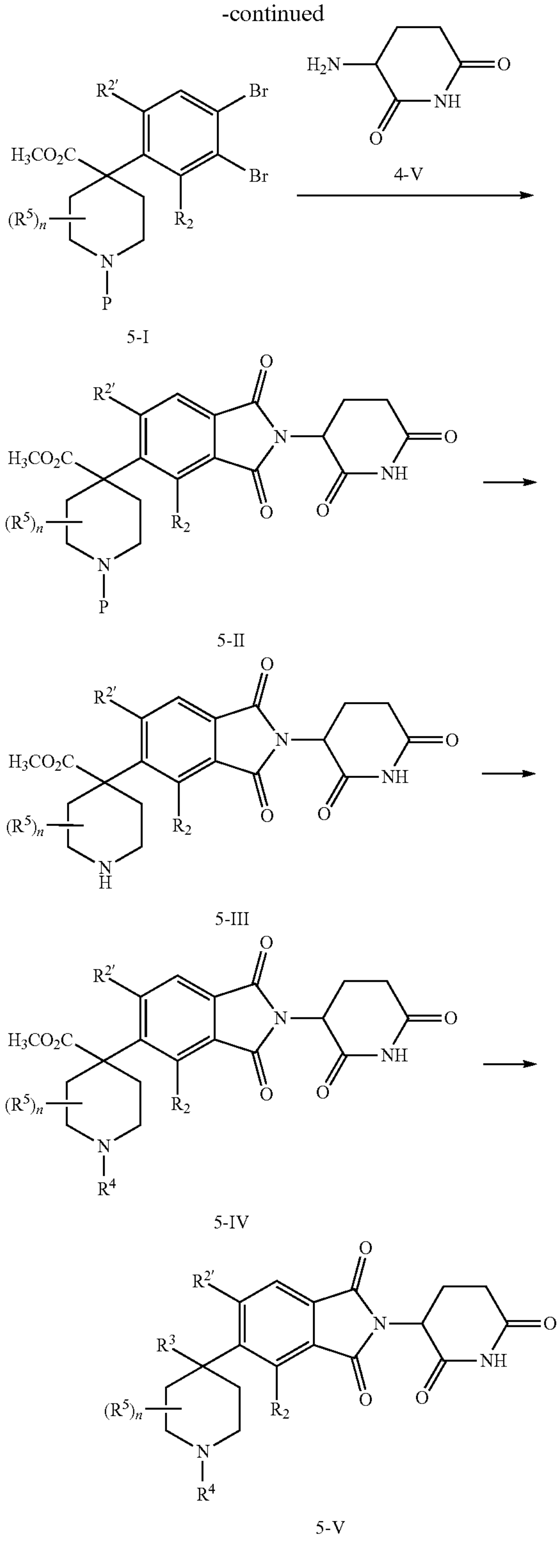

4-V

5-I

5-II

5-III

5-IV

5-V wherein $R^3$ = —C(O)OCH$_3$, —C(O)OH, —C(O)NR$^{10}$R$^{11}$ wherein $R^2$, $R^{2'}$, $R^4$, $R^5$ and n are defined in Formula (I)

The general way to prepare compounds of Formula (I) wherein $R^3$=—CO$_2$CH$_3$, —CH$_2$OH, —C(O)OH and —C(O)NR$^{10}$N$^{11}$ is shown in Scheme 5. Hydrolysis of 4-IV can be accomplished under acidic conditions (e.g., sulfuric acid) in a solvent (e.g., methanol) at elevated temperature to yield 5-I. Carbonylation of 5-I in the presence of 3-amino-glutaramide 4-V, a carbonylation reagent (e.g., molybdenum hexacarbonyl), a catalyst (e.g., palladium (II) acetate), a ligand (e.g., CataCXium A) and a base (e.g., triethylamine) in a solvent (e.g., N,N-dimethylacetamide) at elevated temperature affords 5-II. Deprotection or removal of the Boc protecting group can be completed by stirring 5-II with an acid (e.g., HCl or TFA) in a solvent (e.g., 1,4-dioxane or THF) to provide 5-III. Subsequent alkylation by either reductive amination with 1-VI in the presence of a reducing agent (e.g., NaBH$_4$ or NaBH(OAc)$_3$) in a solvent (e.g., tetrahydrofuran (THF)) optionally in the presence of a drying agent (e.g., MgSO$_4$ or Na$_2$SO$_4$) or alkylation with 1-VII under basic conditions (e.g., DIPEA, TEA or Cs$_2$CO$_3$, etc.) in an organic solvent (e.g., DCM, DMF, etc.) at ambient or elevated temperature yields 5-IV. Saponification of 5-IV under acidic conditions (e.g., sulfuric acid) provides the compound of Formula (I) wherein $R^3$=—C(O)OH. Treatment of 5-V where $R^3$=—C(O)OH with amines (e.g., NHR$^{10}$R$^{11}$), a coupling reagent (e.g., HATU, 1-ethyl-3-(3-dimethylaminopropyl)carbodiimide (EDCI)/HOBt) and a base (e.g., DIPEA, TEA) in a solvent (e.g., DCM, DMF) provides 5-V wherein $R^3$=—C(O)NR$^{10}$R$^{11}$ (compounds of Formula (I) wherein $R^3$=—C(O)NR$^{10}$R$^{11}$).

Scheme 6

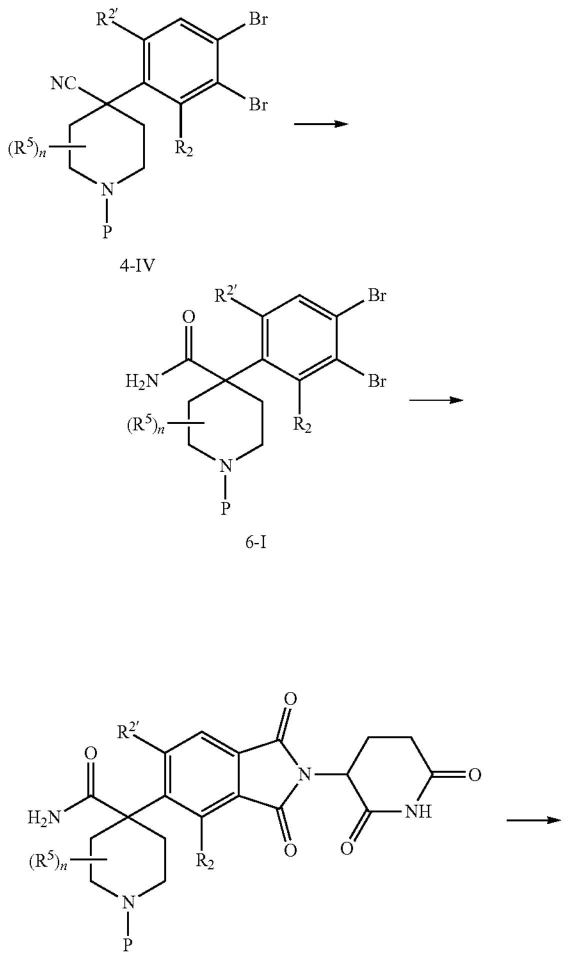

4-IV

6-I

6-II

-continued

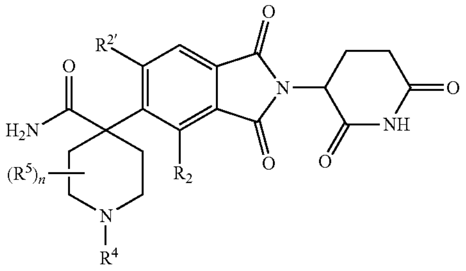

6-III wherein $R^2$, $R^{2'}$, $R^4$, $R^5$ and n are defined in Formula (I)

The general route for preparing compounds of Formula (I) wherein $R^3$=—C(O)$NH_2$ is shown in Scheme 6. Treatment of 4-IV with an acid (e.g., sulfuric acid) optionally at elevated temperatures hydrolyzes the nitrile to yield amide 6-I. Carbonylation of 6-I in the presence of 3-aminoglutarimide 4-V, a carbonylation reagent (e.g., molybdenum hexacarbonyl), a catalyst (e.g., palladium (II) acetate), a ligand (e.g., CataCXium A) and a base (e.g., triethylamine) in a solvent (e.g., N,N-dimethylacetamide) at elevated temperature affords 6-II. Deprotection can be completed by stirring 6-II, when P is Boc, with an acid (e.g., HCl or TFA) in solvent (e.g., 1,4-dioxane or THF) and subsequent alkylation by either reductive amination with 1-VI in the presence of a reducing agent (e.g., $NaBH_4$ or $NaBH(OAc)_3$) in a solvent (e.g., tetrahydrofuran (THF)) optionally in the presence of a drying agent (e.g., $MgSO_4$ or $Na_2SO_4$) or alkylation with 1-VII under basic conditions (e.g., DIPEA, TEA or $Cs_2CO_3$, etc.) in an organic solvent (e.g., DCM, DMF, etc.) at ambient or elevated temperature yields 6-III (compounds of Formula (I) wherein $R^3$=—C(O)$NH_2$).

Scheme 7

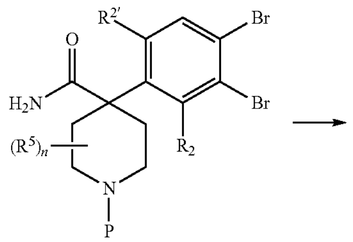

6-I

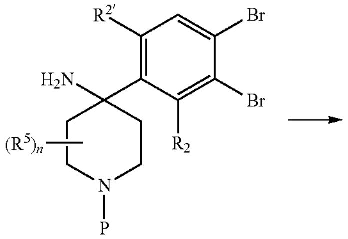

7-I

-continued

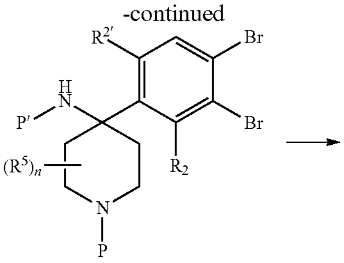

7-II

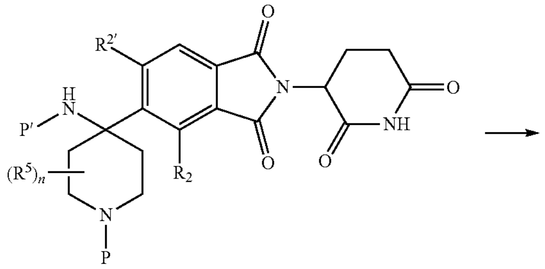

7-III

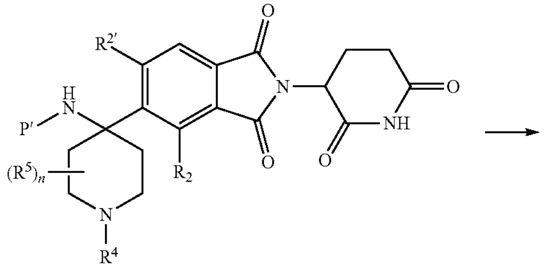

7-IV

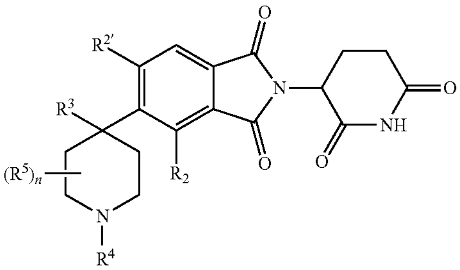

7-V $R^3$ = —$NH_2$ wherein $R^2$, $R^{2'}$, $R^4$, $R^5$ and n are defined in Formula (I).

Scheme 7 outlines the general route for preparing compounds of Formula (I) wherein $R^3$=—$NH_2$. Treatment of 6-I with the appropriate hypervalent iodine compound (e.g., bis(trifluoroacetoxy)iodobenzene, iodobenzene diacetate) in a solvent (e.g., acetonitrile) and water at ambient or optionally at elevated temperature provides 7-I. Protection of the primary amine with an orthogonal amine protecting group (e.g., benzyl, N-carboxybenzyl (Cbz), Fluorenylmethyloxycarbonyl (Fmoc)) provides 7-II. Carbonylation of 7-II in the presence of 3-aminoglutarimide 4-V, a carbonylation reagent (e.g., molybdenum hexacarbonyl), a catalyst (e.g., palladium (II) acetate), a ligand (e.g., ('ataCXium A) and a base (e.g., triethylamine) in a solvent (e.g., N,N-dimethylacetamide) at elevated temperature affords 7-III. Deprotection of 7-III, when P is Boc, can be accomplished by stirring 7-III in acid (e.g, HCl or TFA) in a solvent (e.g., 1,4-dioxane or THF). Alkylation by either reductive amination with 1-VI in the presence of a reducing agent (e.g., $NaBH_4$ or NaBH $(OAc)_3$) in a solvent (e.g., tetrahydrofuran (THF)) optionally in the presence of a drying agent (e.g., $MgSO_4$ or $Na_2SO_4$) or alkylation with alkyl moieties bearing a halide or other leaving group as in 1-VII under basic conditions (e.g., DIPEA, TEA or $Cs_2CO_3$, etc.) in an organic solvent (e.g., DCM, DMF, etc.) at ambient or elevated temperature yields 7-IV followed by deprotection of amine protecting group P' affords 7-V (compounds of Formula (I) wherein $R^3$=—$NH_2$).

The compounds of the present disclosure may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

Those skilled in the art will recognize if a stereocenter exists in the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes. The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art.

A mixture of enantiomers, diastereomers, and cis/trans isomers resulting from the process described above can be separated into their single components by chiral salt technique, chromatography using normal phase, reverse phase or chiral column, depending on the nature of the separation. Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid, or camphor-10-sulfonic acid. Racemic compounds of the present disclosure or racemic intermediates can also be resolved by chiral chromatography, e.g., high pressure liquid chromatography (HPLC) using a chiral adsorbent.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Methods of Using Compounds of the Present Disclosure

Another aspect of the disclosure relates to a method of treating, preventing, inhibiting, or eliminating a disease or disorder in a patient associated with or affected by modulation of IKZF2 protein levels. The method comprises administering to a patient in need of a treatment for diseases or disorders associated with modulation of IKZF2 protein levels an effective amount of a compound of Formula (I) or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the disclosure relates to a method of treating, preventing, inhibiting, or eliminating a disease or disorder that is affected by the reduction of or decrease in IKZF2 protein levels. The method comprises administering to a patient in need of a treatment for diseases or disorders affected by the reduction of IKZF2 protein levels an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

Another aspect of the disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is associated with or affected by the modulation of IKZF2 protein levels. In another aspect, the disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the manufacture of a medicament for the treatment, prevention, inhibition or elimination of a disease or disorder that is affected by the reduction of or a decrease in IKZF2 protein levels.

Another aspect of the disclosure relates to a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof, for use in the manufacture of a medicament for treating, preventing, inhibiting, or eliminating a disease or disorder that is associated with or affected by the modulation of, the reduction of, or a decrease in IKZF2 protein levels.

In another aspect, the present disclosure is directed to a method of modulating, reducing, or decreasing IKZF2 protein levels. The method involves administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof. In some embodiments, IKZF2 protein levels are modulated, reduced, or decreased through degradation of the IKZF2 protein. In other embodiments, IKZF2 protein levels are modulated, reduced, or decreased through degradation of the IKZF2 protein mediated by an E3 ligase.

Another aspect of the present disclosure relates to a method of treating, preventing, inhibiting, or eliminating a disease or disorder in a patient associated with the reduction of or decrease in IKZF2 protein levels, the method comprising administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

The present disclosure also relates to the use of a degrader of IKZF2 for the preparation of a medicament used in the treatment, prevention, inhibition or elimination of a IKZF2-dependent disease or disorder, wherein the medicament comprises a compound of Formula (I), or a pharmaceutically acceptable salt, hydrate, solvate, prodrug, stereoisomer, or tautomer thereof or a composition comprising a Compound of Formula (I), or a pharmaceutically acceptable salt, hydrate, solvate, prodrug, stereoisomer, or tautomer thereof.

In another aspect, the present disclosure relates to a method for treating, preventing, inhibiting, or eliminating a IKZF2-dependent disease or disorder, wherein the medicament comprises a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof.

In another aspect, the present disclosure relates to a method for the manufacture of a medicament for treating, preventing, inhibiting, or eliminating a IKZF2-dependent disease or disorder mediated, wherein the medicament comprises a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

Another aspect of the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for treating a disease or disorder associated with the modulation of, the reduction of, or a decrease in IKZF2 protein levels. In some embodiments, IKZF2 levels are modulated through degradation of the IKZF2 protein. In some embodiments, IKZF2 protein levels are modulated through degradation of the IKZF2 protein mediated by an E3 ligase.

Another aspect of the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in treating a disease associated with the modulation of, the reduction of, or a decrease in IKZF2 protein levels. In some embodiments, IKZF2 levels are modulated, reduced, or decreased through degradation of the IKZF2 protein. In some embodiments, IKZF2 protein levels are modulated, reduced, or decreased through degradation of the IKZF2 protein mediated by an E3 ligase.

In another aspect, the present disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the treatment of a disease associated with the modulation of, the reduction of, or a decrease in IKZF2 protein levels. In some embodiments, IKZF2 protein levels are modulated, reduced, or decreased through degradation of the IKZF2 protein. In some embodiments, IKZF2 protein levels are modulated, reduced, or decreased through degradation of the IKZF2 protein mediated by an E3 ligase.

In another aspect, the present disclosure relates to a method of inhibiting IKZF2 activity through degradation of IKZF2. In some embodiments, IKZF2 protein degradation is mediated by an E3 ligase.

Another aspect of the disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for inhibiting IKZF2 activity through degradation of IKZF2. In some embodiments, IKZF2 protein degradation is mediated by an E3 ligase.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the inhibition of IKZF2 activity through degradation of IKZF2. In some embodiments, IKZF2 protein degradation is mediated by an E3 ligase.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for inhibiting IKZF2 activity through degradation of IKZF2. In some embodiments, IKZF2 protein degradation is mediated by an E3 ligase.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the treatment of an IKZF2-dependent disease or disorder by reducing or decreasing IKZF2 protein levels, wherein reduction or decrease of IKZF2 protein levels treats the IKZF2-dependent disease or disorder. In another aspect, the present disclosure the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the treatment of an IKZF2-dependent disease or disorder by reducing or decreasing IKZF2 protein levels wherein reduction of or decrease in IKZF2 protein levels treats the IKZF2-dependent disease or disorder.

In another aspect, the present disclosure the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the manufacture of a medicament for treating an IKZF2-dependent disease or disorder by reducing or decreasing IKZF2 protein levels wherein reduction of or decrease in IKZF2 protein levels treats the IKZF2-dependent disease or disorder.

Another aspect of the disclosure relates to a method of treating cancer. The method comprises administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the present disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the treatment of treating cancer.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for treating cancer.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the treatment of cancer.

Another aspect of the disclosure relates to a method of treating an IKZF2-dependent cancer. The method comprises administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the present disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the treatment of treating an IKZF2-dependent cancer.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for treating an IKZF2-dependent cancer.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the treatment of an IKZF2-dependent cancer.

Another aspect of the disclosure relates to a method of treating a cancer affected by the modulation of, the reduction of, or a decrease in IKZF2 protein levels. The method comprises administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the present disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, in the treatment of treating a cancer affected by the modulation of, the reduction of, or a decrease in IKZF2 protein levels Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for treating a cancer affected by the modulation of, the reduction of, or a decrease in IKZF2 protein levels.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the treatment of a cancer affected by the modulation of, the reduction of, or a decrease in IKZF2 protein levels.

Another aspect of the disclosure relates to a method of degrading IKZF2. The method comprises administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof. In some embodiments, IKZF2 protein degradation is mediated by an E3 ligase.

In another aspect, the present disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for degrading IKZF2. In some embodiments, IKZF2 protein degradation is mediated by an E3 ligase.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the degradation IKZF2. In some embodiments, IKZF2 protein degradation is mediated by an E3 ligase.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for degrading IKZF2. In some embodiments, IKZF2 protein degradation is mediated by an E3 ligase.

In another aspect, the present disclosure relates to a method of modulating IKZF2 protein levels through degradation of IKZF2. The method comprises administering to a patient in need thereof an effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof. In some embodiments, IKZF2 protein degradation is mediated by an E3 ligase.

Another aspect of the disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for modulating IKZF2 protein levels through degradation of IKZF2. In some embodiments, IKZF2 protein degradation is mediated by an E3 ligase.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the modulation IKZF2 protein levels through degradation of IKZF2. In some embodiments, IKZF2 protein degradation is mediated by an E3 ligase.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for modulating IKZF2 protein levels through degradation of IKZF2. In some embodiments, IKZF2 protein degradation is mediated by an E3 ligase.

Another aspect of the disclosure relates to a method of treating an IKZF2-dependent disease or disorder in a patient in need thereof by modulating IKZF2 protein levels through the degradation of IKZF2. In some embodiments, IKZF2 protein degradation is mediated by an E3 ligase.

In another aspect, the present disclosure relates to the use of a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for treating an IKZF2-dependent disease or disorder in a patient in need thereof by modulating IKZF2 protein levels through the degradation of IKZF2. In some embodiments, IKZF2 protein degradation is mediated by an E3 ligase.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in treating an IKZF2-dependent disease or disorder in a patient in need thereof, by modulating IKZF2 protein levels through the degradation of IKZF2. In some embodiments, IKZF2 protein degradation is mediated by an E3 ligase.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for treating an IKZF2-dependent disease or disorder in a patient in need thereof by modulating IKZF2 protein levels through the degradation of IKZF2. In some embodiments, IKZF2 protein degradation is mediated by an E3 ligase.

Another aspect of the disclosure relates to a method of reducing the proliferation of a cell, the method comprising contacting the cell with a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, that reduces IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to the use a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for reducing the proliferation of a cell by reducing IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in reducing the proliferation of a cell by IKZF 2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for reducing the proliferation of a cell by reducing IKZF2 protein levels. In some embodiments, IKZF2 protein levels are reduced through degradation of the IKZF2 protein. In some embodiments, IKZF2 protein levels are reduced through degradation of the IKZF2 protein mediated by an E3 ligase.

In another aspect, the present disclosure relates to a method for treating an IKZF2-dependent disease or disorder. The method comprises the step of administering to a subject in need thereof a therapeutically effective amount of a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the treatment of an IKZF2-dependent disease or disorder.

In another aspect, the present disclosure relates to the use of a compound of Formula (I), or a pharmaceutically acceptable salt, hydrate, solvate, prodrug, stereoisomer, or tautomer thereof, in the manufacture of a medicament for treating an IKZF2-dependent disease or disorder.

Another aspect of the disclosure relates to a compound of Formula (I), or a pharmaceutically acceptable salt, hydrate, solvate, prodrug, stereoisomer, or tautomer thereof, or a composition comprising a compound of Formula (I), or a pharmaceutically acceptable salt, hydrate, solvate, prodrug, stereoisomer, or tautomer thereof, for use in the manufacture of a medicament for treating an IKZF2-dependent disease or disorder.

In another aspect, the present disclosure relates to a method of reducing IKZF2 protein levels. The method comprises administering to the patient in need thereof a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the present disclosure relates to a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof for use in the reduction of IKZF2 protein levels.

In another aspect, the present disclosure relates to the use of a compound of Formula (I), or a pharmaceutically acceptable salt, hydrate, solvate, prodrug, stereoisomer, or tautomer thereof or a composition, in the manufacture of a medicament for reducing IKZF2 protein levels.

In another aspect, the present disclosure relates to a method of reducing IKZF2 protein levels, wherein reduction of IKZF2 protein levels treats or ameliorates the disease or disorder. The method comprises administering to the patient in need thereof a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the present disclosure relates to a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof for use in the reduction of IKZF2 protein levels, wherein reduction of IKZF2 protein levels treats or ameliorates the disease or disorder.

In another aspect, the present disclosure relates to the use of a compound of Formula (I), or a pharmaceutically acceptable salt, hydrate, solvate, prodrug, stereoisomer, or tautomer thereof or a composition, in the manufacture of a medicament for reducing IKZF2 protein levels, wherein reduction of IKZF2 protein levels treats or ameliorates the disease or disorder.

In another aspect, the present disclosure relates to a method of treating a disease or disorder by reducing IKZF2 protein levels, wherein reduction of IKZF2 protein levels treats or ameliorates the disease or disorder. The method comprises administering to the patient in need thereof a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof.

In another aspect, the present disclosure relates to a compound of Formula (I), or a pharmaceutically acceptable salt, hydrate, solvate, prodrug, stereoisomer, or tautomer thereof or a composition comprising a compound of Formula (I), or a pharmaceutically acceptable salt, hydrate, solvate, prodrug, stereoisomer, or tautomer thereof for use in the treatment of a disease or disorder by reducing IKZF2 protein levels, wherein reduction of IKZF2 protein levels treats or ameliorates the disease or disorder.

In another aspect, the present disclosure relates to the use of a compound of Formula (I), or a pharmaceutically acceptable salt, hydrate, solvate, prodrug, stereoisomer, or tautomer thereof or a composition, in the manufacture of a medicament for treating a disease or disorder by reducing IKZF2 protein levels, wherein reduction of IKZF2 protein levels treats or ameliorates the disease or disorder.

The compounds of the present disclosure can be used for the treatment, of a disease or disorder selected from liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. the cancer is selected from prostate cancer, breast carcinoma, lymphomas, leukaemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, cancer for which the immune response is deficient, an immunogenic cancer, and Ewing's sarcoma. In one embodiment, the IKZF2-dependent disease or disorder is a disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the IKZF2-dependent disease or disorder is a disease or disorder is selected from non-small cell lung cancer (NSCLC), melanoma, triple-negative breast cancer (TNBC), nasopharyngeal cancer (NPC), and microsatellite stable colorectal cancer (mssCRC).

The disclosed compounds of the disclosure can be administered in effective amounts to treat or prevent a disorder and/or prevent the development thereof in subjects.

Administration, Pharmaceutical Compositions, and Dosing of Compounds of the Disclosure Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride, and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes, and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles, and multilamellar vesicles. Liposomes can be formed from a variety of phospholipids, containing cholesterol, stearylamine or phosphatidylcholines.

In some embodiments, a film of lipid components is hydrated with an aqueous solution of drug to a form lipid layer encapsulating the drug, as described in U.S. Pat. No. 5,262,564, which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I), and a pharmaceutically acceptable carrier. The pharmaceutical acceptable carrier may further include an excipient, diluent, or surfactant.

Another aspect of the disclosure is directed to pharmaceutical compositions comprising a compound of Formula (I), and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the disclosure provides a kit comprising two or more separate pharmaceutical compositions, at least one of which contains a compound of the present disclosure. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

The dosage regimen utilizing the disclosed compound is selected in accordance with a variety of factors including type, species, age, weight, sex, and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

The compounds of the disclosure can be administered in therapeutically effective amounts in a combinational therapy with one or more therapeutic agents (pharmaceutical combinations) or modalities, e.g., non-drug therapies. For example, synergistic effects can occur with other cancer agents. Where the compounds of the application are administered in conjunction with other therapies, dosages of the co-administered compounds will of course vary depending on the type of co-drug employed, on the specific drug employed, on the condition being treated and so forth.

The compounds can be administered simultaneously (as a single preparation or separate preparation), sequentially, separately, or over a period of time to the other drug therapy or treatment modality. In general, a combination therapy envisions administration of two or more drugs during a single cycle or course of therapy. A therapeutic agent is, for example, a chemical compound, peptide, antibody, antibody fragment or nucleic acid, which is therapeutically active or enhances the therapeutic activity when administered to a patient in combination with a compound of the present disclosure.

EXAMPLES

The invention is further described in the following examples, which do not limit the scope of the invention described in the claims.

Analytical Methods, Materials, and Instrumentation

Unless otherwise noted, reagents and solvents were used as received from commercial suppliers. Proton nuclear magnetic resonance (NMR) spectra were acquired in Bruker Avance Neo nano bay 400 MHz NMR Spectrometer unless otherwise noted. Spectra are given in ppm (δ) and coupling constants, J, are reported in Hertz. Tetramethylsilane (TMS) was used as an internal standard. Chemical Shifts are reported in ppm relative to dimethyl sulfoxide (δ 2.50), methanol (δ 3.31), chloroform (δ7.26), or other solvents as indicated in NMR spectral data. A small amount (e.g., 1-2 mg) of sample is dissolved in an appropriate deuterated solvent (e.g., 0.6 mL). The chemical names were generated using ChemBioDraw 19.0 from CambridgeSoft. Mass Spectra (ESI-APCI) were collected using the Shimadzu N-Series UPLC-MS system (LCMS-2020). All masses reported are the m/z of the protonated parent ions unless recorded otherwise. The sample was dissolved in a suitable solvent such as methanol, acetonitrile, or DMSO and was directly injected into the column using an automated sample handler. The analysis was performed on, Waters Acquity UPLC CSH C18 1.7 μm, 2.1×30 mm: flow rate: 1.0 mL/min; 40° C. (Column temperature) Solvent A: 0.1% formic acid in water, solvent B: 0.1% formic acid in Acetonitrile, gradient: Solvent A: 0.01 min-3.0%, 1.5-1.9 min-97.0%, 2.0 min-3.0%. Agilent Zorbax eclipse plus C18 2.1×50 mm 1.8 μm: flow rate: 0.8 mL/Min: 40° ° C. (Column temperature) Solvent A: 0.1% formic acid in water, solvent B: 0.1% formic acid in Acetonitrile, gradient: Solvent A: 0.01-0.25 min-5.0%, 2.5-3.0 min-100.0%, 3.1-4.0 min-5.0%. Waters X-Bridge C8 (50×4.6) mm, 3.5 μm: flow rate: 0.8 mL/min; 40° C. (Column temperature): Solvent A: 10 mM Ammonium bicarbonate in water, solvent B: Acetonitrile, gradient: Solvent A: 0.01 min-5.0%, 1.5-3.0 min-95.0%, 3.5-4.0 min-5.0%. Waters X-Bridge C8 (50×4.6) mm, 3.5 μm: flow rate: 0.8 mL/min; 40° C. (Column temperature): Solvent A: 10 mm Ammonium acetate in water, solvent B: Acetonitrile, gradient: Solvent A: 0.01 min-5.0%, 1.5-3.0 min-95.0%, 3.5-4.0 min-5.0%.

Abbreviations $AC_{50}$ half maximal active concentration
AcOH Acetic acid
ACN acetonitrile
AIBN azobisisobutyronitrile
APCI atmospheric pressure chemical ionization
aq. Aqueous
Bispin Bis(pinacolato)diboron
Boc tert-butoxycarbonyl
BuLi n-buty lithium
br broad
d doublet
dd doublet of doublets
ddd doublet of doublet of doublets
ddq doublet of doublet of quartets
ddt doublet of doublet of triplets
dq doublet of quartets
dt doublet of triplets
dtd doublet of triplet of doublets
CataCXium A di(1-adamantyl)-n-butylphosphine
CDI carbonyldiimidazole
$Cs_2CO_3$ cesium carbonate
$DC_{50}$ half maximal degradation concentration
DAST Diethylaminosulfur trifluoride
DCE 1,2-dichloroethane
DCM dichloromethane
DIBAL-H diisobutylaluminum hydride
DIPEA N,N-Diisopropylethylamine
DMA N,N-dimethylacetamide
DMAP 4-dimethylaminopyridine
DME 1,2-Dimethoxyethane
DMF N,N-dimethylformamide
DMP Dess-Martinperiodinane or 1,1,1-Tris(acetyloxy)-1,1-dihydro-1,2-benziodoxol-3-(1H)-one
DMSO dimethylsulfoxide
dpm dipivaloylmethanato
$EC_{50}$ half maximal effective concentration
EDCI 1-ethyl-3-(3-dimethylaminopropyl)carbodiimide
ESI electrospray ionization
EtOH ethanol
$Et_2O$ diethyl ether
EtOAc ethyl acetate
HCl hydrogen chloride
hept heptet
HOBT 1-hydroxybenzotriazole
HPLC high performance liquid chromatography
H or hr hour
HRMS high resolution mass spectrometry g gram
$IC_{50}$ half maximal inhibitory concentration
IPA isopropyl alcohol or 2-propanol
$K_2CO_3$ potassium carbonate
KI potassium iodide
$K_3PO_4$ tripotassium phosphate
LCMS liquid chromatography mass spectrometry
LDA lithium diisopropylamide
m multiplet
MeCN acetonitrile MeOH methanol
mg milligram
MHz megahertz
min minutes
mL milliliter
mmol millimole
$Mn(dpm)_3$ Tris(2,2,6,6-tetramethyl-3,5-heptanedionato) manganese(III)
M molar
MS mass spectrometry
MsCl methanesulfonyl chloride
m/z mass to charge ratio
MTBE methyl tert-butyl ether
$NaBH(OAc)_3$ sodium triacetoxyborohydride
$NaHCO_3$ sodium bicarbonate
$Na_2SO_4$ sodium sulfate
NBS N-bromo succinimide
$NiBr_2$DME nickel (II) bromide ethylene glycol dimethyl ether complex
NMI n-methyl imidazole
NMP N-Methyl-2-pyrrolidone
NMR Nuclear magnetic resonance
$PdCl_2$(dppf)*DCM [1,1'-Bis(diphenylphosphino)ferrocene]dichloropalladium(II), complex with dichloromethane
Pd/C palladium on carbon
Py pyridine
q quartet
qd quartet of doublets
quint quintet
quintd quintet of doublets
RT room temperature
Rt retention time
S singlet
sat. saturated
t triplet
TEA or $Et_2N$ triethylamine
Td triplet of doublet
Tdd triplet of doublet of doublets
TFA trifluoroacetic acid
THF tetrahydrofuran
TMP 2,2,6,6-tetramethylpiperidine
TMS tetramethylsilane
Ts tosyl
Tt triplet of triplets
Ttd triplet of triplet of doublets
TLC thin layer chromatography
UPLC ultra-performance liquid chromatography
XPhos Pd G2 chloro(2-dicyclohexylphosphino-2',4',6'-triisopropyl-1,1'-biphenyl) [2-(2'-amino-1,1'-biphenyl)]palladium(II)
v/v volume/volume (volume ratio)
wt weight
μW microwave

Biological Examples

MOLT4 IKZF2 HiBit Assay Protocol:

This protocol used MOLT4 cells that were engineered using CRISPR/Cas9-mediated genomic insertion of HiBit, tagged to the N terminus of the IKZF2 coding sequence. Day 1. A 10-point dose response was created starting from 30 μM down to InM using a Tecan D300e. Next was added 8,000 cells/well of the MOLT4 IKZF2 HiBit cells to the compound plate. The compounds plate was incubated for 6 hours. Day 2. Nano-Glo HiBit Lytic Buffer/Nano-Glo HiBit Lytic substrate/LgBit Protein mix was added to each well and the compound plate was incubated for 15 minutes. Finally, luminescence signal was read using a BMG Labtech PHERAstar FSX. Data was normalized to DMSO and graphed using GraphPad Prism to determine the concentration points at which 50% of HiBiT-Helios degradation was achieved by each compound. The extent of degradation (range of luminescence) from the highest to lowest concentration points was calculated to determine Dmax. Data for selected compounds is provided in Table 1.

TABLE 1

| Compound number | IKZF2 $DC_{50}$ (μM) | % reduction of IKZF2 @ 30 μM (6 hr) | GSPT1 $DC_{50}$ (μM) | hERG $IC_{50}$ (μM) |
|---|---|---|---|---|
| 1 | 0.160 | 78% | — | — |
| 7 | 0.009 | 90% | — | >30 |
| 15 | 0.012 | 66% | — | >30 |
| 34 | 0.031 | 76% | — | — |
| 35 | 0.004 | 84% | — | — |
| 42 | 0.009 | 80% | — | — |
| 57 | 0.006 | 81% | — | — |
| 60 | 0.006 | 80% | — | 23 |
| 61 | 0.005 | 83% | — | — |
| 68 | 0.021 | 71% | — | — |
| 69 | 0.039 | 72% | — | — |
| 70 | 0.020 | 78% | — | — |
| 72 | 0.001 | 80% | — | — |
| 84 | 0.0083 | 60% | — | — |
| 85 | | 25% @ 30 μM | — | — |
| 91 | 0.021 | 60% | — | — |
| 94 | 0.008 | 79% | — | — |
| 96 | 0.136 | 64% | — | — |
| 97 | | 36% @ 30 μM | — | — |
| 98 | 0.0015 | 72% | — | — |
| 99 | 0.001 | 89% | — | — |
| 111 | 0.005 | 83% | — | >30 |
| 128 | 0.002 | 81% | — | — |
| 132 | 0.007 | 79% | — | 30 |
| 140 | 0.003 | 87% | — | — |
| 141 | 0.011 | 86% | — | — |
| 142 | 0.013 | 82% | — | — |
| 143 | 0.006 | 84% | — | — |
| 144 | 0.016 | 88% | — | — |
| 145 | 0.004 | 83% | — | — |
| 146 | 0.043 | 69% | — | — |
| 147 | 0.008 | 88% | — | — |
| 148 | 0.030 | 73% | — | — |
| 149 | 0.022 | 76% | — | — |

Example 1: Synthesis of Intermediate A, 2-(2,6-dioxopiperidin-3-yl)-5-(4-hydroxypiperidin-4-yl)isoindoline-1,3-dione

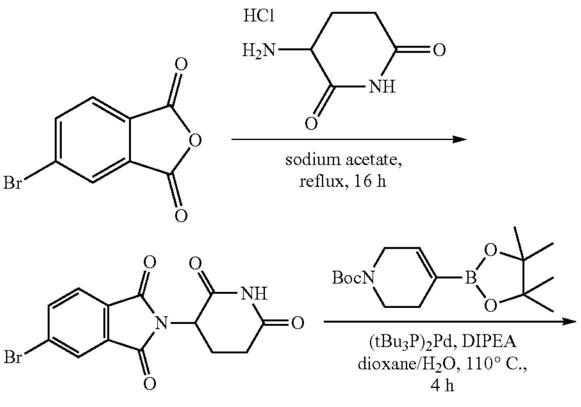

-continued

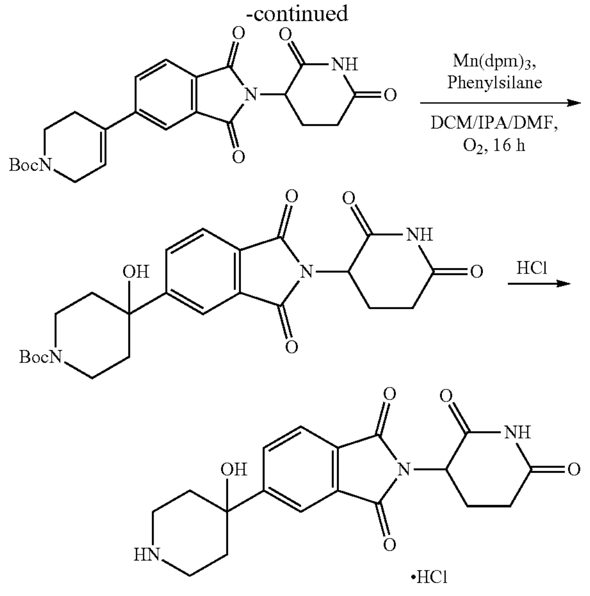

Intermediate A

Step 1: Preparation of 5-Bromo-2-(2,6-dioxopiperidin-3-yl)isoindoline-1,3-dione

To a stirred solution of 5-bromoisobenzofuran-1,3-dione (20.0 g, 88.0 mmol) and 3-aminopiperidine-2,6-dione hydrochloride (14.5 g, 88.0 mmol) in acetic acid (300 mL) was added sodium acetate (7.23 g, 88.0 mmol) at room temperature. The resulting mixture was heated to 120° C. and stirred for 16 h. After completion of the reaction, reaction mixture was cooled to room temperature and concentrated under vacuum. The obtained crude residue was stirred in water (300 mL) for 3 h and the resulting solid was filtered. The solid was washed with water (200 mL) and dried under vacuum to obtain a blue colored solid. The obtained solid was purified by silica gel column chromatography (15% MeOH in DCM as an eluent) to afford the desired product, 5-bromo-2-(2,6-dioxopiperidin-3-yl)isoindoline-1,3-dione (16.0 g, 47.5 mmol, 53.9% yield) as light blue solid; UPLC: m/z MM-ES+APCI, positive $[M+H]^+$=337; $^1$H NMR (400 MHZ, DMSO-$d_6$) δ (ppm)=11.15 (s, 1H), 8.19-8.06 (m, 2H), 7.87 (d, J=7.9 Hz, 1H), 5.17 (dd, J=5.4, 12.8 Hz, 1H), 2.98-2.80 (m, 1H), 2.68-2.53 (m, 2H), 2.13-2.00 (m, 1H).

Step 2: Preparation of tert-butyl 4-(2-(2,6-dioxopiperidin-3-yl)-1,3-dioxoisoindolin-5-yl)-3,6-dihydropyridine-1(2H)-carboxylate To a stirred solution of 5-bromo-2-(2,6-dioxopiperidin-3-yl)isoindoline-1,3-dione (1.00 g, 2.97 mmol) and tert-butyl 4-(4,4,5,5-tetramethyl-1,3,2-dioxaborolan-2-yl)-3,6-dihydropyridine-1(2H)-carboxylate (3.67 g, 11.9 mmol) in 1,4 dioxane (18.0 mL):water (2.00 mL) was added DIPEA (0.767 g, 5.93 mmol) followed by bis(tri-t-butylphosphine) palladium(0) (0.303 g, 0.593 mmol) at room temperature under continuous $N_2$ bubbling. The resulting mixture was heated to 110° C. and stirred for 4 h. The reaction mixture was then filtered through a pad of celite using 1,4-dioxane (100 mL) and the filtrate was concentrated under reduced pressure to afford the crude compound. The crude compound was purified by silica gel column chromatography (40% EtOAc in n-hexane as an eluent). The pure fractions were concentrated under reduced pressure to obtain tert-butyl 4-(2-(2,6-dioxopiperidin-3-yl)-1,3-dioxoisoindolin-5-yl)-3,6-dihydropyridine-1(2H)-carboxylate (0.75 g, 1.6 mmol, 55.8% yield) as an off white solid; LCMS: m/z MM-ES+APCI, Negative $[M-H]^+$=438.2; HPLC: Rt: 6.00, 98.1%; $^1$H NMR (400 MHz, DMSO-$d_6$) δ (ppm)=11.13 (s, 1H), 8.03-7.77 (m, 3H), 6.51 (br s, 1H), 5.21-5.05 (m, 1H), 4.06 (br s, 2H), 3.57 (br t, J=5.6 Hz, 2H), 3.00-2.78 (m, 1H), 2.71-2.53 (m, 4H), 2.14-1.96 (m, 1H), 1.44 (s, 9H).

Step 3: Tert-butyl 4-(2-(2,6-dioxopiperidin-3-yl)-1,3-dioxoisoindolin-5-yl)-4-hydroxypiperidine-1-carboxylate To a stirred solution of tert-butyl 4-(2-(2,6-dioxopiperidin-3-yl)-1,3-dioxoisoindolin-5-yl)-3,6-dihydropyridine-1(2H)-carboxylate (0.55 g, 1.25 mmol) in IPA (6.0 mL), DCM (6.0 mL) and DMF (1.8 mL) was added tris(2,2,6,6-tetramethyl-3,5-heptanedionato)manganese(III) (0.38 g, 0.63 mmol) and phenylsilane (0.27 g, 2.50 mmol) at 0° C. The resulting mixture was stirred at 0° C. under an atmosphere of $O_2$ for 16 h. The resulting mixture was stirred at 0° C. for 4 h, then slowly warmed to room temperature and stirred for 16 h. A saturated aqueous solution of $Na_2S_2O_3$ (70 mL) was then added and stirring was continued at room temperature for 2 h. Brine solution (100 mL) was added, and the reaction mixture was extracted with EtOAc (2×150 mL). The combined organic layers were dried ($Na_2SO_4$), filtered and concentrated. The crude compound was purified by silica gel column chromatography (50% EtOAc in n-hexane as an eluent) to obtain tert-butyl 4-(2-(2,6-dioxopiperidin-3-yl)-1,3-dioxoisoindolin-5-yl)-4-hydroxypiperidine-1-carboxylate (0.25 g, 0.54 mmol, 43.2% yield) as an off white solid; LCMS: m/z MM-ES+APCI, positive $[M+H]^+$=358.2; HPLC: 99.8%; $^1$H NMR (400 MHZ, DMSO-$d_6$) δ (ppm)=11.12 (s, 1H), 8.05-7.96 (m, 2H), 7.88 (d, J=7.9 Hz, 1H), 5.53 (s, 1H), 5.15 (dd, J=5.4, 12.9 Hz, 1H), 3.98-3.82 (m, 2H), 3.23-3.02 (m, 2H), 2.96-2.81 (m, 1H), 2.70-2.56 (m, 2H), 2.12-2.02 (m, 1H), 1.92 (dt, J=4.5, 12.9 Hz, 2H), 1.61 (br d, J=12.9 Hz, 2H), 1.43 (s, 9H).

Step 4: Preparation of 2-(2,6-dioxopiperidin-3-yl)-5-(4-hydroxypiperidin-4-yl)isoindoline-1,3-dione A solution of tert-butyl 4-(2-(2,6-dioxopiperidin-3-yl)-1,3-dioxoisoindolin-5-yl)-4-hydroxypiperidine-1-carboxylate (0.25 g, 0.54 mmol) in HCl (4.0M in 1,4-dioxane, 3.00 mL) was stirred at room temperature for 2 h. The reaction mixture was then concentrated under reduced pressure. The obtained crude product was triturated with MTBE (2×10 mL) and dried to afford 2-(2,6-dioxopiperidin-3-yl)-5-(4-hydroxypiperidin-4-yl)isoindoline-1,3-dione (0.18 g, 0.45 mmol, 83% yield) as an off white solid in the form of HCl salt; LCMS: m/z MM-ES+APCI, positive $[M+H]^+$=358.2; HPLC: 99.5%; $^1$H NMR (400 MHZ, DMSO-$d_6$) δ (ppm)=11.14 (s, 1H), 8.82 (br s, 2H), 7.97 (s, 3H), 5.90 (s, 1H), 5.16 (dd, J=5.4, 12.9 Hz, 1H), 3.31-3.17 (m, 4H), 2.98-2.83 (m, 1H), 2.69-2.55 (m, 2H), 2.39-2.25 (m, 2H), 2.12-2.01 (m, 1H), 1.80 (br d, J=13.6 Hz, 2H).

Example 1B: Synthesis of Intermediate A2, 2-(2,6-dioxopiperidin-3-yl)-4-fluoro-5-(4-hydroxypiperidin-4-yl)isoindoline-1,3-dione

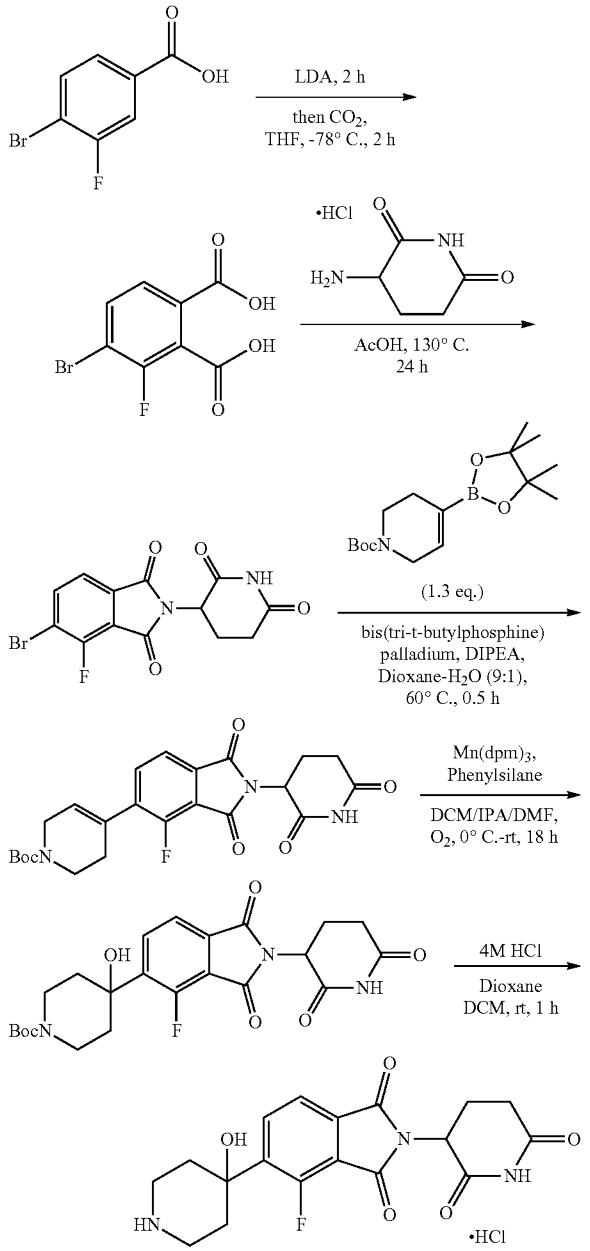

Intermediate A2

Step 1: Preparation of 4-bromo-3-fluorophthalic acid

To a stirred solution of 4-bromo-3-fluorobenzoic acid (10.0 g, 45.7 mmol) in THF (100 mL) was added lithium diisopropylamide (2 M in THF) (68.5 mL, 137 mmol) dropwise at −78° C. under an atmosphere of argon. The resulting mixture was stirred at −78° C. for 1.5 h before the reaction mixture was purged with $CO_2$ gas at −78° C. for 30 min. The reaction mixture was quenched with 4 M HCl in dioxane (30 mL) and then concentrated under reduced pressure to give a crude residue which was washed with ethyl acetate (2×100 mL). The solids were filtered off and the ethyl acetate layer was concentrated under reduced pressure to afford the crude compound as gummy solid. Cold water (100 mL) was added to the crude compound and the mixture was basified with $NaHCO_3$ solution (30 mL). The aqueous layer was washed with ethyl acetate (3×200 mL). The aqueous layer was acidified with 1N HCl solution (30 mL) and was extracted with n-butanol (3×100 mL). The combined organics were washed with brine solution (100 mL), dried over anhydrous $Na_2SO_4$ and concentrated under reduced pressure to afford 4-bromo-3-fluorophthalic acid (9.40 g, 69% yield) as an off-white solid which was carried onto the next step without further purification. LCMS: m/z MM−ES+APCI, negative $[M-2]^+$=261.0, 263.0; $^1H$ NMR (400 MHZ, DMSO-$d_6$) δ ppm 13.55 (br, 2H), 7.92-7.88 (m, 1H), 7.68-7.66 (m, 1H).

Step 2: Preparation of 5-bromo-2-(2,6-dioxopiperidin-3-yl)-4-fluoroisoindoline-1,3-dione To a stirred solution of 4-bromo-3-fluorophthalic acid (9.40 g, 35.7 mmol) in acetic acid (94 mL) was added 3-aminopiperidine-2,6-dione hydrochloride (5.88 g, 35.7 mmol) at room temperature. The resulting reaction mixture was stirred at 130° C. under an atmosphere of $N_2$ for 24 h. The reaction mixture was cooled to room temperature, diluted with water (500 mL), and stirred for 10 minutes. The solids were filtered, washed with chilled water, and dried to afford 5-bromo-2-(2,6-dioxopiperidin-3-yl)-4-fluoroisoindoline-1,3-dione (8.30 g, 63% yield) as an off-white solid which was carried onto the next step without further purification. LCMS: m/z MM−ES+APCI, $[M-2]^+$=398.9, 400.9: $^1H$ NMR (400 MHZ, DMSO-$d_6$) δ ppm 11.16 (s, 1H), 8.26-8.23 (m, 1H), 7.73-7.71 (d, J=7.9 Hz, 1H), 5.19-5.15 (q, J=6.1 Hz, 1H), 2.94-2.85 (m, 1H), 2.63-2.59 (m, 2H), 2.09-2.01 (m 1H).

Step 3: Preparation of tert-butyl 4-(2-(2,6-dioxopiperidin-3-yl)-4-fluoro-1,3-dioxoisoindolin-5-yl)-3,6-dihydropyridine-1(2H)-carboxylate To the stirred solution of 5-bromo-2-(2,6-dioxopiperidin-3-yl)-4-fluoroisoindoline-1,3-dione (3.00 g, 8.45 mmol) in 1,4-dioxane (60 mL) and water (7.5 mL) was added tert-butyl 4-(4,4,5,5-tetramethyl-1,3,2-dioxaborolan-2-yl)-3,6-dihydropyridine-1(2H)-carboxylate (3.13 g, 10.1 mmol) and DIPEA (4.43 mL, 25.3 mmol) before it was degassed with $N_2$ for 15 min. To this resulting mixture was added bis(tri-tert-butylphosphine)palladium(0) (0.432 g, 0.845 mmol) in one portion and the reaction mixture was stirred at 60° C. for 30 min. The mixture was then cooled to room temperature and water (30 mL) was added. The resulting mixture was extracted with ethyl acetate (4×50 mL) and the combined organic layers were dried over anhydrous $Na_2SO_4$, filtered, and concentrated under reduced pressure to give the crude compound. The crude compound was purified using silica gel column chromatography (100-200 mesh silica gel) using 10% MeOH in DCM as an eluent to afford tert-butyl 4-(2-(2,6-dioxopiperidin-3-yl)-4-fluoro-1,3-dioxoisoindolin-5-yl)-3,6-dihydropyridine-1(2H)-carboxylate (1.60 g, 30% yield) as light yellow solid. LCMS: m/z MM−ES+APCI, negative $[M-H]^+$=456.2; $^1H$ NMR (400 MHZ, DMSO-$d_6$) δ ppm 11.14 (s, 1H), 7.88-7.85 (m, 1H), 7.76-7.74 (d, J=7.7 Hz, 1H), 6.20 (s, 1H), 5.17-5.13 (m, 1H), 4.06-4.02 (m, 2H), 3.57-3.54 (t, J=5.5 Hz, 2H), 2.89-2.86 (m, 2H), 2.63-2.54 (m, 1H), 2.51-2.48 (m, 2H), 2.08-2.06 (m, 1H), 1.44 (s, 9H).

Step 4: Preparation of tert-butyl 4-(2-(2,6-dioxopiperidin-3-yl)-4-fluoro-1,3-dioxoisoindolin-5-yl)-4-hydroxypiperidine-1-carboxylate To a stirred solution of tert-butyl 4-(2-(2,6-dioxopiperidin-3-yl)-4-fluoro-1,3-dioxoisoindolin-5-yl)-3,6-dihydropyridine-1(2H)-carboxylate (1.40 g, 3.06 mmol) in DCM (28 mL), 2-propanol (28 mL) and DMF (14 mL) were added $Mn(dpm)_3$ (0.555 g, 0.918 mmol) and phenylsilane (0.75 mL, 6.1 mmol) at 0° C. The resulting mixture was stirred at 0° C. under an atmosphere of $O_2$ for 16 h. The reaction mixture was then concentrated under reduced pressure to give a crude compound as a light black solid. The crude compound was purified by reverse phase column chromatography by using C18 cartridge (150 g) using 50% acetonitrile in 0.1% formic acid in water as the eluent (flow rate: 15 mL/min). The pure fractions were collected and lyophilized to give tert-butyl 4-(2-(2,6-dioxopiperidin-3-yl)-4-fluoro-1,3-dioxoisoindolin-5-yl)-4-hydroxy-piperidine-1-carboxylate (1.0 g, 58%) as a white solid. LCMS: m/z MM-ES+APCI, positive $[M+H]^+$=474.3; $^1H$ NMR (400 MHZ, DMSO-$d_6$) δ ppm 11.14 (s, 1H), 8.16 (t, J=6.8 Hz, 1H), 7.80 (d, J=8.0 Hz, 1H), 5.77 (s, 1H), 5.13 (dd, J=5.6, 12.8 Hz, 1H), 3.95-3.80 (m, 2H), 3.25-3.05 (m, 2H), 2.95-2.80 (m, 1H), 2.65-2.45 (m, 2H), 2.13-2.00 (m, 3H), 1.65-1.55 (m, 2H), 1.42 (s, 9H).

Step 5: Preparation of 2-(2,6-dioxopiperidin-3-yl)-4-fluoro-5-(4-hydroxypiperidin-4-yl)isoindoline-1,3-dione To a stirred solution of tert-butyl 4-(2-(2,6-dioxopiperidin-3-yl)-4-fluoro-1,3-dioxoisoindolin-5-yl)-4-hydroxypiperidine-1-carboxylate (1.00 g, 2.10 mmol) in DCM (22 mL) under an atmosphere of nitrogen at 0° C. was added 4 M HCl in 1,4-dioxane (7.89 mL, 31.5 mmol). The resulting mixture was allowed to stir at room temperature for 2 h. The reaction mixture was then concentrated under reduced pressure to give a crude residue which was triturated with MTBE, filtered and dried to afford 2-(2,6-dioxopiperidin-3-yl)-4-fluoro-5-(4-hydroxypiperidin-4-yl)isoindoline-1,3-dione, HCl (800 mg, 90% yield) as a white solid. LCMS: m/z MM-ES+APCI, positive $[M+H]^+$=376.0; $^1H$ NMR (400 MHZ, DMSO-$d_6$) δ ppm 11.15 (s, 1H), 8.90-8.55 (m, 2H), 8.16 (t, J=7.2 Hz, 1H), 7.82 (d, J=7.6 Hz, 1H), 6.12 (s, 1H), 5.15 (dd, J=5.6, 12.8 Hz, 1H), 3.30-3.15 (m, 4H), 2.94-2.89 (m, 1H), 2.63-2.50 (m, 1H), 2.45-2.37 (m, 2H), 2.11-2.00 (m, 1H), 1.86-1.75 (m, 2H). $^{19}F$ NMR (200 MHZ, DMSO-$d_6$) δ (ppm)=−114.52.

Example 2: Synthesis of piperidine Intermediate B, 2-(2,6-dioxopiperidin-3-yl)-5-(4-hydroxypiperidin-4-yl)isoindoline-1,3-dione

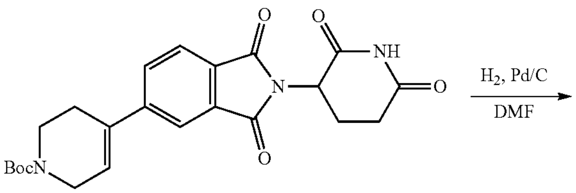

-continued

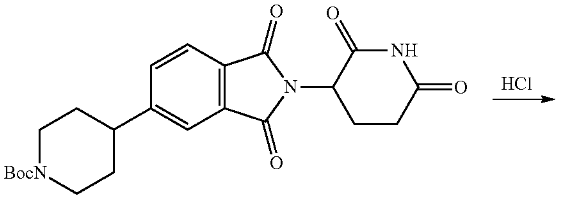

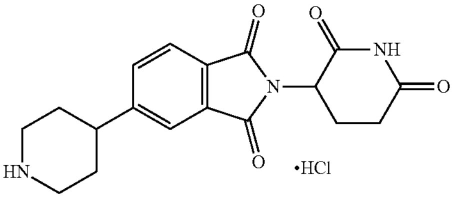

Intermediate B

Step 1: Preparation of tert-butyl 4-(2-(2,6-dioxopiperidin-3-yl)-1,3-dioxoisoindolin-5-yl)piperidine-1-carboxylate To a stirred solution of tert-butyl 4-(2-(2,6-dioxopiperidin-3-yl)-1,3-dioxoisoindolin-5-yl)-3,6-dihydropyridine-1(2H)-carboxylate (0.30 g, 0.68 mmol) in DMF (10.0 mL) was added 10% Pd—C(0.07 g, 0.68 mmol) at room temperature. The resulting mixture was stirred for 7 h under Hydrogen at room temperature. The reaction mixture was filtered through a pad of celite, and the filtrate was concentrated under reduced pressure to get the crude product. The crude compound was purified by silica gel column chromatography (40% EtOAc in n-hexane as an eluent) to obtain tert-butyl 4-(2-(2,6-dioxopiperidin-3-yl)-1,3-dioxoisoindolin-5-yl)piperidine-1-carboxylate (0.25 g, 0.56 mmol, 82% yield) as an off white solid; LCMS: m/z MM-ES+APCI, positive $[M+H]^+$=342.2; HPLC: Rt: 6.00, 99.9%; $^1H$ NMR (400 MHZ, DMSO-$d_6$) δ (ppm)=11.12 (s, 1H), 7.92-7.70 (m, 3H), 5.14 (dd, J=5.3, 12.9 Hz, 1H), 4.10 (br d, J=11.4 Hz, 2H), 3.07-2.73 (m, 4H), 2.68-2.54 (m, 2H), 2.15-1.93 (m, 1H), 1.81 (br d, J=12.4 Hz, 2H), 1.59 (dq, J=4.1, 12.5 Hz, 2H), 1.43 (s, 9H).

Step 2: Preparation of 2-(2,6-dioxopiperidin-3-yl)-5-(piperidin-4-yl)isoindoline-1,3-dione A solution of tert-butyl 4-(2-(2,6-dioxopiperidin-3-yl)-1,3-dioxoisoindolin-5-yl)piperidine-1-carboxylate (0.20 g, 0.45 mmol) in HCl (4.0M in 1,4-dioxane, 3.00 mL) was stirred at room temperature for 2 h. The reaction mixture was then concentrated under reduced pressure to get the crude product. The obtained crude was triturated with MTBE (2×10 mL) and dried to get 2-(2,6-dioxopiperidin-3-yl)-5-(piperidin-4-yl)isoindoline-1,3-dione (0.17 g, 0.45 mmol, 98% yield) as an off white solid in the form of the HCl salt; LCMS: m/z MM-ES+APCI, positive $[M+H]^+$=342.2; HPLC: Rt: 2.67, 99.9%; $^1H$ NMR (400 MHz, DMSO-$d_6$) δ (ppm)=11.13 (s, 1H), 8.77 (br s, 2H), 7.92 (d, J=7.6 Hz, 1H), 7.80-7.72 (m, 2H), 5.15 (dd, J=5.4, 12.9 Hz, 1H), 3.40 (br d, J=13.1 Hz, 2H), 3.16-2.85 (m, 4H), 2.70-2.54 (m, 2H), 2.11-1.85 (m, 5H).

Example 3: Synthesis of Intermediate C, trans-4-(hydroxymethyl)-N-methoxy-N-methylcyclohexane-1-carboxamide

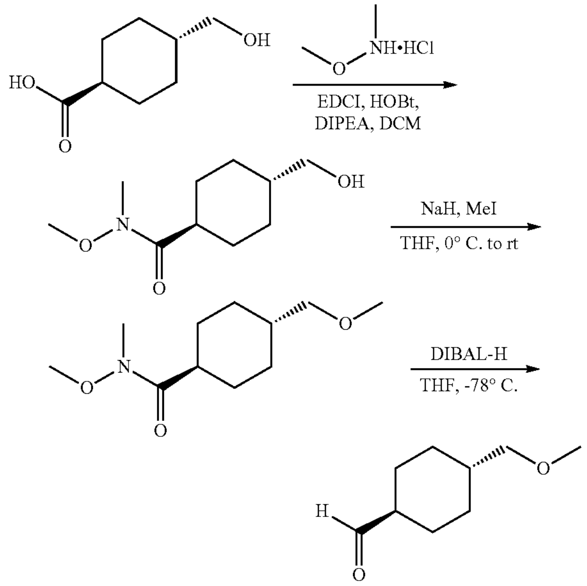

Intermediate C

Step 1: Synthesis of trans-4-(hydroxymethyl)-N-methoxy-N-methylcyclohexane-1-carboxamide To the stirred solution of trans-4-(hydroxymethyl)cyclohexane-1-carboxylic acid (3.00 g, 18.9 mmol) in DCM (30.0 mL) was added DIPEA (4.97 mL, 28.4 mmol) dropwise, followed by HOBt (0.668 g, 4.36 mmol) and 1-(3-dimethylaminopropyl)-3-ethylcarbodiimide hydrochloride (4.73 g, 24.6 mmol) at 0° C. After 10 minutes of stirring, N,O-dimethylhydroxylamine hydrochloride (2.77 g, 28.4 mmol) was added at 0° C. and the resulting mixture was allowed to stir at 27° C. for 16 h. After completion of reaction (complete consumption o the starting material), the mixture was diluted with DCM (30 mL) and washed with water (20 mL) and brine (15 L). The organic layer was separated, dried over anhydrous $Na_2SO_4$ and concentrated under reduced pressure. The crude product was purified by column chromatography on silica gel using 15-20% of EtOAc in n-hexane as an eluent. Fractions were concentrated to afford trans-4-(hydroxymethyl)-N-methoxy-N-methylcyclohexane-1-carboxamide (2.90 g, 12.1 mmol, 63.8% yield) as a colorless semisolid. LCMS: m/z MM-ES+APCI, positive $[M+H]^+$ =202.5; $^1H$ NMR (400 MHZ, CHLOROFORM-d) δ ppm, 3.72 (s, 3H), 3.47-3.52 (m, 2H), 3.20 (s, 3H), 2.62-2.72 (m, 1H), 1.81-1.94 (m, 4H), 1.50-1.65 (m, 4H), 0.99-1.12 (m, 2H).

Step 2: Synthesis of trans-N-methoxy-4-(methoxymethyl)-N-methylcyclohexane-1-carboxamide To the stirred solution of trans-4-(hydroxymethyl)-N-methoxy-N-methylcyclohexane-1-carboxamide (2.90 g, 14.4 mmol) in THF (30.0 L) was added sodium hydride (0.450 g, 18.7 mmol), followed by methyl iodide (1.17 mL, 18.7 mmol) dropwise at 0° C. The resulting mixture was stirred at 25° C. for 16 h. The reaction was not complete so it was left to stir at 25° C. for another 24 h. After completion (complete consumption of starting material), the reaction mixture was quenched with ice cold water (40 mL) and extracted with EtOAc (50 mL). The organic layer was washed with brine solution (20 mL), dried over anhydrous $Na_2SO_4$ and concentrated under reduced pressure to get the crude compound. The crude compound was purified by column chromatography on silica gel using 2-44% of EtOAc in n-Hexane as an eluent. Pure fractions were concentrated to afford trans-N-methoxy-4-(methoxymethyl)-N-methylcyclohexane-1-carboxamide (1.90 g, 8.65 mmol, 60.0% yield) as a colorless liquid. LCMS: m/z MM-ES+APCI, positive $[M+H]^+$=216.6; $^1H$ NMR (400 MHZ, CHLOROFORM-d) δ ppm 3.71 (s, 3H), 3.33-3.36 (m, 3H), 3.17-3.24 (m, 5H), 2.37-2.97 (m, 1H), 1.80-1.93 (m, 4H), 1.50-1.66 (m, 3H), 0.99-1.12 (m, 2H).

Step 3: Synthesis of trans-4-(methoxymethyl)cyclohexane-1-carbaldehyde

To the stirred solution of trans-N-methoxy-4-(methoxymethyl)-N-methylcyclohexane-1-carboxamide (1.9 g, 8.8 mmol) in THF (50 mL) was added DIBAL-H (11 mL, 13 mmol) dropwise at −78° C. and the resulting mixture was stirred at −78° C. for 1 h. The reaction progress was monitored by TLC. After completion, the reaction mixture was quenched in saturated aqueous $NH_4Cl$ solution (30 mL) and extracted with EtOAc (3x50 mL). The combined organic layers were washed with brine (20 mL), dried over anhydrous $Na_2SO_4$ and concentrated under reduced pressure to afford trans-4-(methoxymethyl)cyclohexane-1-carbaldehyde (1.2 g, 4.6 mmol, 52% yield) as a colorless semisolid which was carried onto the next step without further purification. LCMS: m/z MM-ES+APCI, positive $[M+H]^+$ Not ionized; $^1H$ NMR (400 MHz, CHLOROFORM-d) δ ppm 9.60-9.66 (m, 1H), 3.35 (s, 3H), 3.22-3.25 (m, 2H) 2.21 (m, 1H), 2.00-2.09 (m, 2H), 1.88-1.97 (m, 2H), 1.49-1.65 (m, 1H), 1.24-1.36 (m, 2H), 0.99-1.12 (m, 2H).

Example 4: Synthesis of Intermediate D, 6-(bromomethyl)-3-(pyridin-2-yl)quinazolin-4(3H)-one

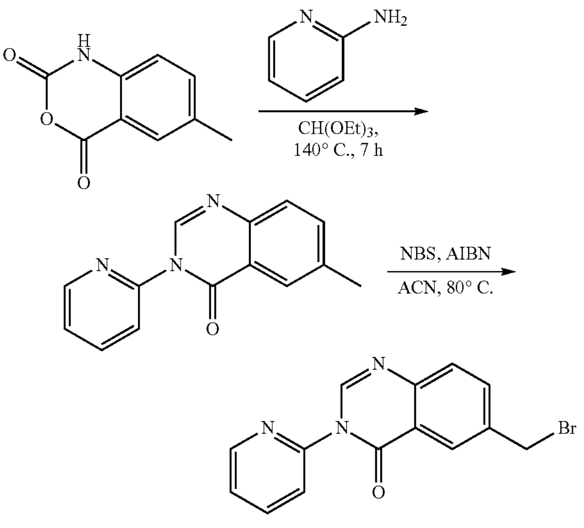

Intermediate D

Step 1: Preparation of 6-methyl-3-(pyridin-2-yl) quinazolin-4(3H)-one

A solution of 6-methyl-2H-benzo[d][1,3]oxazine-2,4(1H)-dione (5.00 g, 28.2 mmol) and pyridin-2-amine (2.92 g, 31.0 mmol) in triethyl orthoformate (30.0 mL, 28.2 mmol) was heated at 140° C. for 16 h. After completion of the reaction, the reaction mixture was concentrated under reduced pressure to get crude product. The crude product was triturated in IPA (50 mL), filtered and dried to get 6-methyl-3-(pyridin-2-yl)quinazolin-4(3H)-one (3.00 g, 12.6 mmol, 44.6% yield) as a light gray solid. LCMS: m/z MM−ES+APCI, positive $[M+H]^+$238.2; $^1$H NMR (400 MHZ, DMSO-$d_6$) δ ppm 8.67 (br d, J=3.63 Hz, 1H) 8.52 (s, 1H) 8.13-8.01 (m, 2H) 7.84 (br d, J=8.00 Hz, 1H) 7.76-7.65 (m, 2H) 7.60-7.53 (m, 1H).

Step 2: Preparation of 6-(bromomethyl)-3-(pyridin-2-yl)quinazolin-4(3H)-one

To a stirred solution of 6-methyl-3-(pyridin-2-yl)quinazolin-4(3H)-one (1.00 g, 4.21 mmol) in acetonitrile (50.0 mL) was added NBS (0.97 g, 5.48 mmol) and AIBN (28.0 mg, 0.169 mmol) at 25° C. The resulting mixture was stirred at 80° C. for 16 h. After completion, the reaction mixture was diluted with brine (10 mL). The aqueous layer was extracted with EtOAc (2×20 mL). The combined organic extracts were dried over anhydrous $Na_2SO_4$ and filtered. The solvent was removed under reduced pressure to afford the crude compound. The crude compound was purified by column chromatography on silica gel using EtOAc in hexane (30-40%) as an eluent. Pure fractions were concentrated to afford 6-(bromomethyl)-3-(pyridin-2-yl)quinazolin-4(3H)-one (0.40 g, 1.0 mmol, 24.4% yield) as an off white solid. LCMS: m/z MM−ES+APCI, positive [M+, M+2]=216.2, 218.2; $^1$H NMR (400 MHZ, DMSO-$d_6$) δ ppm 8.71-8.66 (m, 1H) 8.59 (s, 1H) 8.33 (d, J=2.00 Hz, 1H) 8.12-8.06 (m, 1H) 7.99-7.94 (m, 1H) 7.89-7.82 (m, 1H) 7.77 (d, J=8.38 Hz, 1H) 7.59 (ddd, J=7.44, 4.88, 1.06 Hz, 1H) 4.94 (s, 2H).

Example 5: Synthesis of Compound 84, trans-2-(2,6-dioxopiperidin-3-yl)-5-(4-hydroxy-1-((4-(methoxymethyl)cyclohexyl)methyl)piperidin-4-yl)isoindoline-1,3-dione

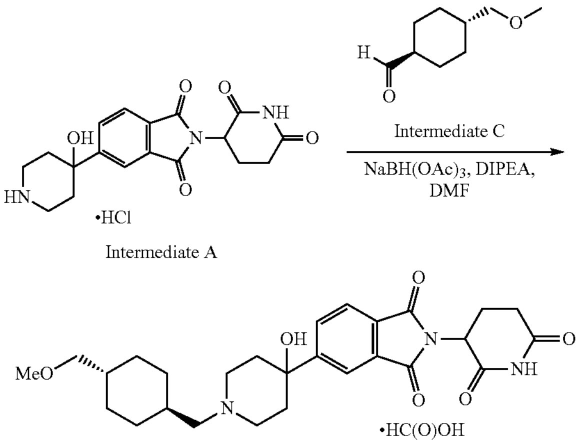

Compound 84

To a stirred solution of 2-(2,6-dioxopiperidin-3-yl)-5-(4-hydroxypiperidin-4-yl)isoindoline-1,3-dione, HCl (30.0 mg, 0.076 mmol) in DMF (2.00 L) was added trans-4-(methoxymethyl)cyclohexane-1-carbaldehyde (17.9 mg, 0.114 mmol) and DIPEA (0.040 L, 0.229 mmol) at RT. To this reaction mixture was added sodium triacetoxyborohydride (81.0 mg, 0.381 mmol) portion wise at 0° C. The resulting mixture was stirred under an atmosphere of nitrogen at 25° C. for 16 h. The reaction was not complete so additional trans-4-(methoxymethyl)cyclohexane-1-carbaldehyde (17.85 mg, 0.114 mmol) and DIPEA (0.040 mL, 0.229 mmol) were added at 0° ° C. After 10 min, sodium triacetoxyborohydride (81.0 mg, 0.381 mmol) was added portion wise at 0° C. and the reaction mixture was stirred under an atmosphere of nitrogen at RT for 16 h. After completion, the reaction mixture was concentrated under reduced pressure. The crude residue was purified by Prep-HPLC [method info: Column: X select C18 (150*19 mm) 5um, Buffer: 0.1% Formic acid in $H_2O$; 100% ACN, Gradient: 0-5, 8-30, Flow rate: 14 mL/min], the collected pure fractions were lyophilized to afford trans-2-(2,6-dioxopiperidin-3-yl)-5-(4-hydroxy-1-((4-(methoxymethyl)cyclohexyl)methyl)piperidin-4-yl)isoindoline-1,3-dione as the formic acid salt (9.00 mg, 0.018 mmol, 23.51% yield) as white solid. LCMS: m/z MM−ES+APCI, positive $[M+H]^+$=498.8; $^1$H NMR (400 MHZ, DMSO-$d_6$) δ ppm 11.19-10.98 (m, 1H), 8.29-8.11 (m, 1H), 8.08-7.94 (m, 2H), 7.90-7.78 (m, 1H), 5.41-5.19 (m, 1H), 5.16-4.97 (m, 1H), 3.24-3.21 (m, 3H), 3.13 (d, J=6.38 Hz, 2H), 2.96-2.83 (m, 1H), 2.74-2.63 (m, 3H), 2.37-2.32 (m, 2H), 2.15 (br d, J=7.13 Hz, 2H), 2.10-1.95 (m, 3H), 1.82 (br d, J=11.51 Hz, 2H), 1.73 (br d, J=12.01 Hz, 2H), 1.61 (br d, J=12.63 Hz, 2H), 1.48 (br s, 2H), 0.99-0.77 (m, 4H).

The following compounds in Table 2 were prepared according to the procedure described in Example 5 using Intermediate A and the appropriate aldehyde.

TABLE 2

| Compound number | Name | [M + H] |
|---|---|---|
| 1 | 2-(2,6-dioxopiperidin-3-yl)-5-[4-hydroxy-1-(4-methoxycyclohexyl)piperidin-4-yl]-2,3-dihydro-1H-isoindole-1,3-dione, formic acid salt | 470.5 |
| 42 | 3-({4-[2-(2,6-dioxopiperidin-3-yl)-1,3-dioxo-2,3-dihydro-1H-isoindol-5-yl]-4-hydroxypiperidin-1-yl}methyl)benzonitrile | 473.1 |
| 57 | 4-({4-[2-(2,6-dioxopiperidin-3-yl)-1,3-dioxo-2,3-dihydro-1H-isoindol-5-yl]-4-hydroxypiperidin-1-yl}methyl)benzonitrile | 473.1 |
| 60 | 5-{1-[(3,4-difluorophenyl)methyl]-4-hydroxypiperidin-4-yl}-2-(2,6-dioxopiperidin-3-yl)-2,3-dihydro-1H-isoindole-1,3-dione, HCl salt | 484.1 |
| 61 | 2-(2,6-dioxopiperidin-3-yl)-5-(4-hydroxy-1-{[4-(methoxymethyl)phenyl]methyl}piperidin-4-yl)-2,3-dihydro-1H-isoindole-1,3-dione, HCl salt | 492.2 |
| 68 | 2-(2,6-dioxopiperidin-3-yl)-5-{4-hydroxy-1-[(pyridin-2-yl)methyl]piperidin-4-yl}-2,3-dihydro-1H-isoindole-1,3-dione, HCl salt | 449.1 |

TABLE 2-continued

| Compound number | Name | [M + H] |
|---|---|---|
| 69 | 2-(2,6-dioxopiperidin-3-yl)-5-{4-hydroxy-1-[(pyridin-3-yl)methyl]piperidin-4-yl}-2,3-dihydro-1H-isoindole-1,3-dione, formic acid salt | 449.1 |
| 70 | 2-(2,6-dioxopiperidin-3-yl)-5-{4-hydroxy-1-[(pyridin-4-yl)methyl]piperidin-4-yl}-2,3-dihydro-1H-isoindole-1,3-dione, HCl salt | 449.5 |
| 72 | 2-(2,6-dioxopiperidin-3-yl)-5-{4-hydroxy-1-[(6-methoxypyridin-3-yl)methyl]piperidin-4-yl}-2,3-dihydro-1H-isoindole-1,3-dione, HCl salt | 479.1 |
| 91 | 2-(2,6-dioxopiperidin-3-yl)-5-{4-hydroxy-1-[(2-phenyl-1,3-oxazol-4-yl)methyl]piperidin-4-yl}-2,3-dihydro-1H-isoindole-1,3-dione, HCl salt | 515.2 |
| 94 | 2-(2,6-dioxopiperidin-3-yl)-5-{4-hydroxy-1-[(1-phenyl-1H-pyrazol-3-yl)methyl]piperidin-4-yl}-2,3-dihydro-1H-isoindole-1,3-dione, HCl salt | 514.3 |
| 96 | 2-(2,6-dioxopiperidin-3-yl)-5-{1-[(1-ethyl-1H-pyrazol-3-yl)methyl]-4-hydroxypiperidin-4-yl}-2,3-dihydro-1H-isoindole-1,3-dione, formic acid salt | 466.3 |
| 99 | 2-(2,6-dioxopiperidin-3-yl)-5-(4-hydroxy-1-{[4-oxo-3-(pyridin-3-yl)-3,4-dihydroquinazolin-6-yl]methyl}piperidin-4-yl)-2,3-dihydro-1H-isoindole-1,3-dione, formic acid salt | 593.2 |
| 111 | 5-{1-[(1,3-benzothiazol-5-yl)methyl]-4-hydroxypiperidin-4-yl}-2-(2,6-dioxopiperidin-3-yl)-2,3-dihydro-1H-isoindole-1,3-dione, HCl salt | 505.1 |
| 140 | 2-(2,6-dioxopiperidin-3-yl)-5-{4-hydroxy-1-[(1-methyl-1H-indazol-6-yl)methyl]piperidin-4-yl}-2,3-dihydro-1H-isoindole-1,3-dione, formic acid salt | 502.0 |
| 141 | 2-(2,6-dioxopiperidin-3-yl)-5-{4-hydroxy-1-[(1-methyl-1H-indol-5-yl)methyl]piperidin-4-yl}-2,3-dihydro-1H-isoindole-1,3-dione, HCl salt | 501.0 |
| 142 | 2-(2,6-dioxopiperidin-3-yl)-5-{4-hydroxy-1-[(1-methyl-1H-indol-2-yl)methyl]piperidin-4-yl}-2,3-dihydro-1H-isoindole-1,3-dione, formic acid salt | 501.3 |
| 144 | 2-(2,6-dioxopiperidin-3-yl)-5-{4-hydroxy-1-[(1H-indol-5-yl)methyl]piperidin-4-yl}-2,3-dihydro-1H-isoindole-1,3-dione, formic acid salt | 486.8 |
| 145 | 2-(2,6-dioxopiperidin-3-yl)-5-{4-hydroxy-1-[(1-methyl-1H-indazol-5-yl)methyl]piperidin-4-yl}-2,3-dihydro-1H-isoindole-1,3-dione, formic acid salt | 502.1 |
| 146 | 2-(2,6-dioxopiperidin-3-yl)-5-(4-hydroxy-1-propylpiperidin-4-yl)-2,3-dihydro-1H-isoindole-1,3-dione, HCl salt | 400.1 |
| 147 | 2-(2,6-dioxopiperidin-3-yl)-5-(4-hydroxy-1-{[4-(1,3-thiazol-2-yl)phenyl]methyl}piperidin-4-yl)-2,3-dihydro-1H-isoindole-1,3-dione, HCl salt | 531.2 |

Example 6: Synthesis of Compound 85, trans-2-(2,6-dioxopiperidin-3-yl)-5-(1-((4-(methoxymethyl)cyclohexyl) methyl)piperidin-4-yl)isoindoline-1,3-dione formic acid

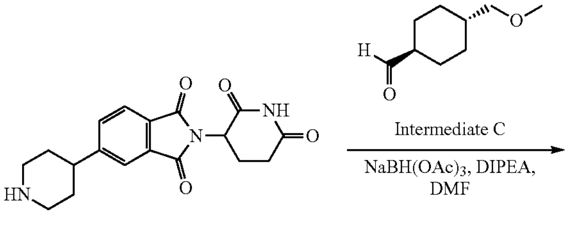

Intermediate B

-continued

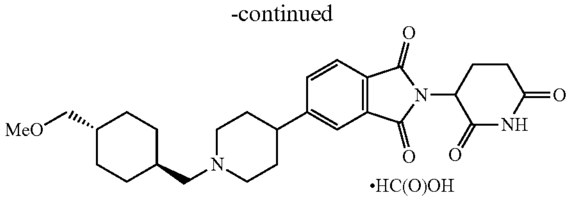

Compound 85

To a stirred solution of 2-(2,6-dioxopiperidin-3-yl)-5-(piperidin-4-yl)isoindoline-1,3-dione (90.0 mg, 0.238 mmol) in DMF (2 mL) was added DIPEA (0.041 mL, 0.238 mmol) at room temperature. After 5 min, AcOH (0.014 mL, 0.238 mmol) and trans-4-(methoxymethyl)cyclohexane-1-carbaldehyde (37.2 mg, 0.238 mmol) were added at room temperature and the resulting mixture was stirred for 15 min. Then sodium triacetoxyborohydride (252 mg, 1.19 mmol) was added and the reaction mixture was stirred at room temperature for 16 h. The reaction mixture was then concentrated to dryness at 27° C. and the crude compound was purified by preparative-HPLC [(Column: X SELECT 150*19.0, Mobile phase A: 0.1% HCOOH in $H_2O$, Mobile phase B: Acetonitrile, flow rate: 15 mL/min)]. Sample was collected in two different fractions and lyophilized separately to afford the title compound, 2-(2,6-dioxopiperidin-3-yl)-5-(1-(((trans-4-(methoxymethyl)cyclohexyl)methyl) piperidin-4-yl)isoindoline-1,3-dione, as the formic acid salt fraction 1 (14 mg, 0.029 mmol, 12.00% yield) as an off white solid; LCMS: m/z MM-ES+APCI, positive $[M+H]^+$ =482.8; $^1$H NMR (400 MHz, DMSO-$d_6$) δ (ppm)=11.25-10.93 (m, 1H), 8.21 (s, 1H), 7.87-7.81 (m, 1H), 7.81-7.75 (m, 2H), 5.14 (dd, J=5.4, 12.9 Hz, 1H), 3.24-3.18 (m, 4H), 3.13 (d, J=6.4 Hz, 2H), 2.99-2.83 (m, 3H), 2.80-2.70 (m, 1H), 2.69-2.65 (m, 1H), 2.65-2.61 (m, 1H), 2.58 (s, 1H), 2.57-2.54 (m, 1H), 2.38-2.30 (m, 1H), 2.16-2.09 (m, 2H), 2.09-1.91 (m, 3H), 1.85-1.63 (m, 8H), 1.56-1.39 (m, 2H), 1.38-1.27 (m, 1H), 1.00-0.77 (1 (m, 4H) & 2-(2,6-dioxopiperidin-3-yl)-5-(1-((trans-4-(methoxymethyl)cyclohexyl) methyl)piperidin-4-yl)isoindoline-1,3-dione as the formic acid salt fraction 2 (3.50 mg, 6.95 μmol, 2.92% yield) as an off white solid. The title compound is a mixture of diastereomers. Absolute stereochemistry was not determined.

Example 7: Synthesis of Compound 98, 2-(2,6-dioxopiperidin-3-yl)-5-(4-hydroxy-1-((4-oxo-3-(pyridin-2-yl)-3,4-dihydroquinazolin-6-yl)methyl)piperidin-4-yl)isoindoline-1,3-dione

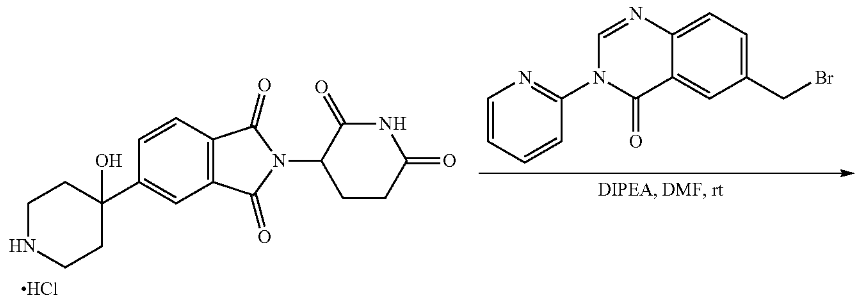

Intermediate A

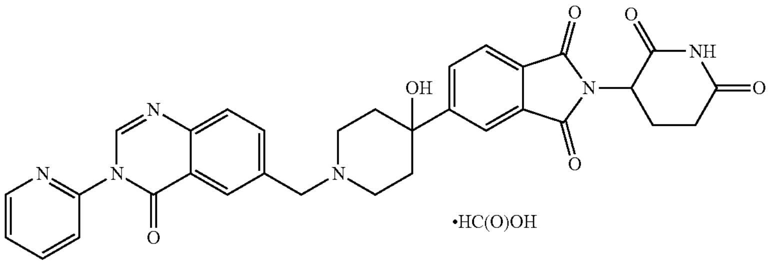

Compound 98

To a stirred solution of 2-(2,6-dioxopiperidin-3-yl)-5-(4-hydroxypiperidin-4-yl)isoindoline-1,3-dione, HCl (0.025 g, 0.063 mmol) in DMF (5.00 mL) was added DIPEA (0.013 mL, 0.076 mmol) and 6-(bromomethyl)-3-(pyridin-2-yl)quinazolin-4(3H)-one (0.020 g, 0.063 mmol) at RT. The resulting mixture was stirred for 10 min at RT. After completion, the reaction mixture was concentrated under reduced pressure. The crude compound was purified by preparative-HPLC [(Column: X select (150 mm*19) 5 μm, Mobile phase A: 0.1% HCOOH in $H_2O$, Mobile phase B: Acetonitrile, flow rate: 15 mL/min)]. ACN/water mixture was removed by lyophilization to get 2-(2,6-dioxopiperidin-3-yl)-5-(4-hydroxy-1-((4-oxo-3-(pyridin-2-yl)-3,4-dihydroquinazolin-6-yl)methyl)piperidin-4-yl)isoindoline-1,3-dione as the formic acid salt (8.00 mg, 0.013 mmol, 20.84% yield) as a white solid. LCMS: m/z MM-ES+APCI, positive $[M+H]^+$ =593.6; $^1$H NMR (400 MHZ, DMSO-$d_6$) δ ppm 11.21-11.10 (m, 1H) 8.74-8.64 (m, 1H) 8.56 (s, 1H) 8.23-8.16 (m, 1H) 8.09 (td, J=7.79, 1.81 Hz, 1H) 8.04-7.99 (m, 2H) 7.95-7.81 (m, 3H) 7.76 (d, J=8.25 Hz, 1H) 7.58 (dd, J=6.63, 5.00 Hz, 1H) 5.29 (s, 1H) 5.15 (dd, J=12.88, 5.38 Hz, 1H) 3.74 (s, 2H) 2.99-2.85 (m, 1H) 2.76-2.68 (m, 2H) 2.61 (br d, J=16.88 Hz, 2H) 2.39-2.28 (m, 1H) 2.12-1.99 (m, 3H) 1.64 (br d, J=12.26 Hz, 2H).

The following compounds in Table 3 were prepared according to the procedure described in Example 7 using Intermediate A and the appropriate alkyl halide.

TABLE 3

| Compound number | Name | [M + H] |
|---|---|---|
| 7 | 5-(1-{5H,6H,7H-cyclopenta[b]pyridin-5-yl}-4-hydroxypiperidin-4-yl)-2-(2,6-dioxopiperidin-3-yl)-2,3-dihydro-1H-isoindole-1,3-dione, HCl salt | 475.2 |
| 34 | 2-(2,6-dioxopiperidin-3-yl)-5-[1-(2-fluoro-1-phenylethyl)-4-hydroxypiperidin-4-yl]-2,3-dihydro-1H-isoindole-1,3-dione, formic acid salt | 480.3 |

TABLE 3-continued

| Compound number | Name | [M + H] |
|---|---|---|
| 35 | 2-(2,6-dioxopiperidin-3-yl)-5-[4-hydroxy-1-(1-phenylethyl)piperidin-4-yl]-2,3-dihydro-1H-isoindole-1,3-dione, HCl salt | 462.0 |
| 143 | 2-(2,6-dioxopiperidin-3-yl)-5-(4-hydroxy-1-{1-[4-(trifluoromethyl)phenyl]ethyl}piperidin-4-yl)-2,3-dihydro-1H-isoindole-1,3-dione, HCl salt | 530.1 |

Example 8: Synthesis of Compound 97, 2-(2,6-dioxopiperidin-3-yl)-5-(1-((4-oxo-3-(pyridin-2-yl)-3,4-dihydroquinazolin-6-yl)methyl)piperidin-4-yl)isoindoline-1,3-dione

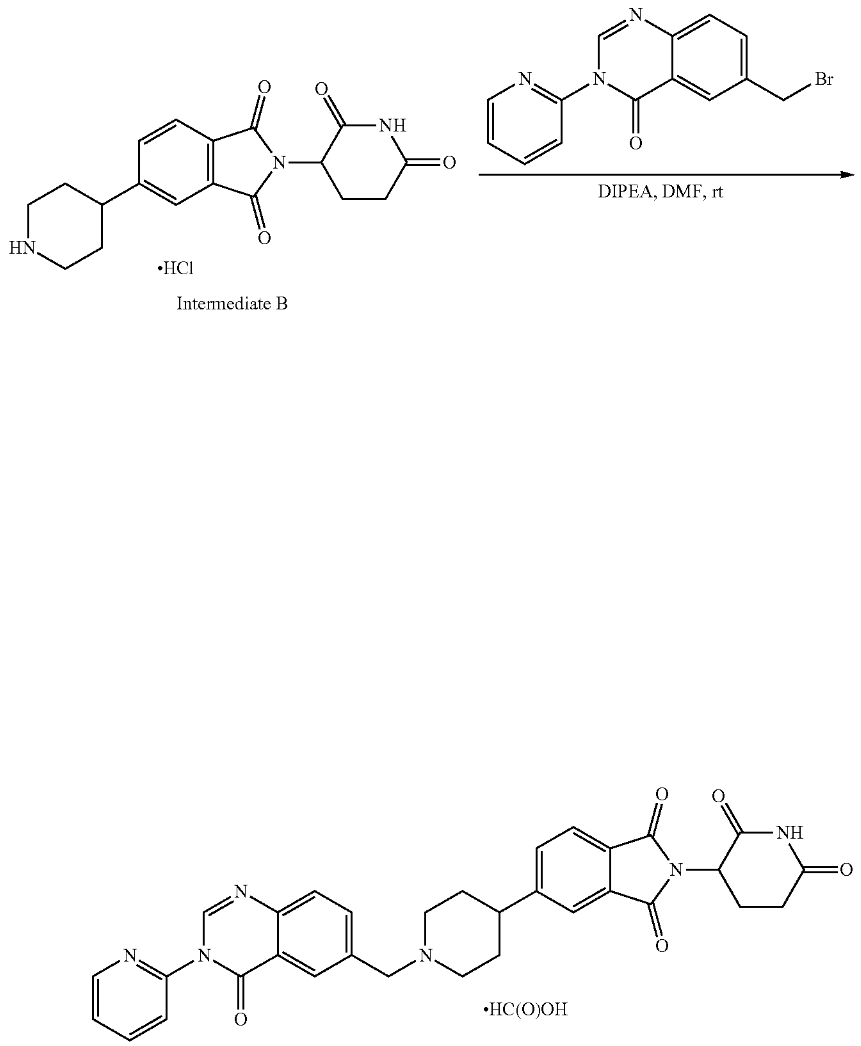

Compound 97

To a stirred solution of 2-(2,6-dioxopiperidin-3-yl)-5-(piperidin-4-yl)isoindoline-1,3-dione (90.0 mg, 0.238 mmol) in DMF (2.00 mL) at 5° ° C. was added DIPEA (0.125 mL, 0.715 mmol) and the resulting mixture was stirred for 5 min. To this mixture was then added 6-(bromomethyl)-3-(pyridin-2-yl)quinazolin-4(3H)-one (75.0 mg, 0.238 mmol) at 5° C. and stirring was continued for 10 min. The reaction mixture was concentrated (at 25° C.) under reduced pressure to get the crude product (120 mg, 0.140 mmol, 58.8% yield) as a brown gum. The crude sample was purified by preparative HPLC [(Column: X select (150 mm*19) 5 μm, Mobile phase A: 0.1% HCOOH in $H_2O$, Mobile phase B: Acetonitrile, flow rate: 15 mL/min)]. ACN/water mixture was removed by lyophilization to afford 2-(2,6-dioxopiperidin-3-yl)-5-(1-((4-oxo-3-(pyridin-2-yl)-3,4-dihydroquinazolin-6-yl)methyl)piperidin-4-yl)isoindoline-1,3-dione as the formic acid salt (28.0 mg, 0.048 mmol, 20.17% yield) as an off-white solid; LCMS: m/z MM-ES+APCI, positive $[M+H]^+$=577.6; $^1$H NMR (400 MHZ, DMSO-$d_6$) δ (ppm)=11.12 (s, 1H), 8.70-8.65 (m, 1H), 8.58-8.53 (m, 1H), 8.23-8.15 (m, 1H), 8.12-8.05 (m, 1H), 7.93-7.73 (m, 6H), 7.62-7.55 (m, 1H), 5.19-5.09 (m, 1H), 3.77-3.66 (m, 2H), 3.06-2.71 (m, 4H), 2.70-2.65 (m, 1H), 2.61 (s, 1H), 2.61-2.55 (m, 3H), 2.47-2.45 (m, 1H), 2.41 (s, 1H), 2.40-2.37 (m, 1H), 2.37-2.28 (m, 1H), 2.23-2.10 (m, 2H), 2.10-2.01 (m, 1H), 1.88-1.70 (m, 4H).

Example 9: Synthesis of Compound 132, 2-(2,6-dioxopiperidin-3-yl)-4-fluoro-5-(1-(4-fluorobenzyl)-4-hydroxypiperidin-4-yl)isoindoline-1,3-dione

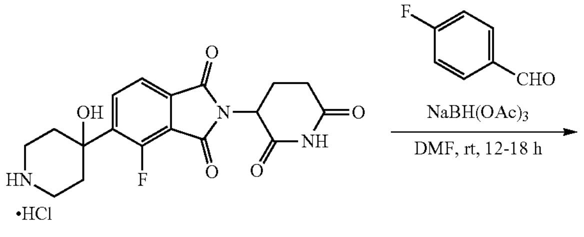

Intermediate A2

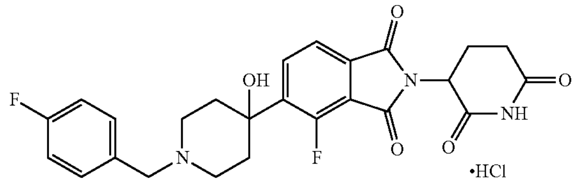

Compound 132

A solution of 2-(2,6-dioxopiperidin-3-yl)-4-fluoro-5-(4-hydroxypiperidin-4-yl)isoindoline-1,3-dione, HCl (0.150 g, 0.364 mmol) and 4-fluorobenzaldehyde (0.050 g, 0.401 mmol) in DMF (5 mL) was stirred at room temperature for 20 min. The resulting mixture was cooled to 0° C. before sodium triacetoxyborohydride (0.232 g, 1.09 mmol) was added in portions. The mixture was then allowed to stir at room temperature for 16 h. The reaction mixture was concentrated under reduced pressure to give the crude product which was purified by prep-HPLC [Method info: Zorbax C18 (50*21.1 mm) 5 μm, 0.1% HCl in $H_2O$: 100% ACN, Flow rate: 15 mL/min, RT: 9.0 min] to give 2-(2,6-dioxopiperidin-3-yl)-4-fluoro-5-(1-(4-fluorobenzyl)-4-hydroxypiperidin-4-yl)isoindoline-1,3-dione, HCl salt (39 mg, 20%) as a white solid. LCMS: m/z MM-ES+APCI, positive $[M+H]^+$=484.1; $^1H$ NMR (400 MHZ, DMSO-$d_6$) δ ppm 11.15 (s, 1H), 10.12 (brs, 1H), 8.20-8.11 (m, 1H), 7.83-7.79 (m, 1H), 7.72-7.61 (m, 2H), 7.40-7.28 (m, 2H), 6.15 (s, 1H), 5.13 (dd, J=5.2, 12.8 Hz, 1H), 4.48-4.35 (m, 2H), 3.32-3.15 (m, 4H), 2.95-2.80 (m, 1H), 2.67-2.52 (m, 3H), 2.12-1.98 (m, 1H), 1.95-1.80 (m, 2H).

The following compounds Table 4 were prepared according to the procedure described in Example 9 using Intermediate A2 and the appropriate aldehyde.

TABLE 4

| Compound number | Name | [M + H] |
|---|---|---|
| 128 | 5-(1-benzyl-4-hydroxypiperidin-4-yl)-2-(2,6-dioxopiperidin-3-yl)-4-fluoro-2,3-dihydro-1H-isoindole-1,3-dione, HCl salt | 466.0 |
| 148 | 2-(2,6-dioxopiperidin-3-yl)-4-fluoro-5-(4-hydroxy-1-propylpiperidin-4-yl)-2,3-dihydro-1H-isoindole-1,3-dione, HCl salt | 418.0 |

Example 10: Synthesis of Compound 149, 2-(2,6-dioxopiperidin-3-yl)-5-(4-hydroxy-1-(2-hydroxy-2-phenylethyl)piperidin-4-yl)isoindoline-1,3-dione

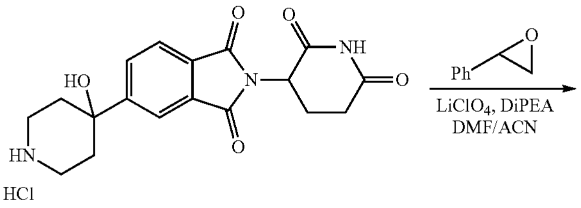

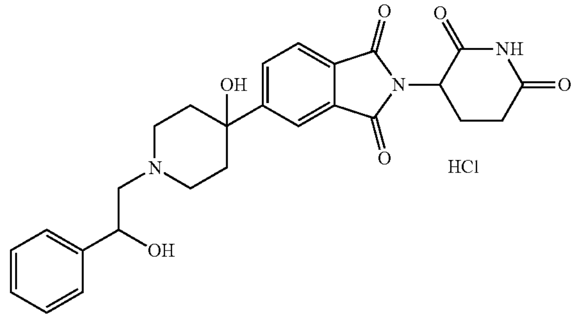

Compound 149

To a stirred solution of 2-(2,6-dioxopiperidin-3-yl)-5-(4-hydroxypiperidin-4-yl)isoindoline-1,3-dione, and HCl (120 mg, 0.305 mmol) in acetonitrile (3 mL)/DMF (1.5 mL) was added DIPEA (0.080 mL, 0.48 mmol), 2-phenyloxirane (73.2 mg, 0.609 mmol) and lithium perchlorate (130 mg, 1.22 mmol) at room temperature. The resulting mixture was stirred at 60° ° C. for 16 h. The reaction mixture was then concentrated under reduced pressure to afford a crude compound (240 mg) which was purified by prep-HPLC [Method info: column: X select (150 mm*19) 5 μm, 0.1% HCl $H_2O$:ACN, Flow rate: 15 mL/min]. The collected fractions were lyophilized to afford 2-(2,6-dioxopiperidin-3-yl)-5-(4-hydroxy-1-(2-hydroxy-2-phenylethyl)piperidin-4-yl)isoindoline-1,3-dione, HCl (45.8 mg, 31%) as an off white solid. LCMS: m/z MM-ES+APCI, positive $[M+H]^+$=478.1; $^1H$ NMR (400 MHZ, DMSO-$d_6$) δ ppm 11.18-11.05 (m, 1H), 9.82-9.63 (m, 1H), 8.10-7.91 (m, 3H), 7.75-7.25 (m, 6H), 6.40-6.28 (m, 1H), 5.95 (s, 1H), 5.26-5.05 (m, 2H), 3.80-3.50 (m, 2H), 3.51-3.33 (m, 3H), 2.98-2.80 (m, 1H), 2.75-2.55 (m, 3H), 2.14-1.98 (m, 1H), 1.95-1.69 (m, 2H).

Example 11: Synthesis of Compound 15, 5-(1-benzyl-4-hydroxy-2-methylpiperidin-4-yl)-2-(2,6-dioxopiperidin-3-yl)-2,3-dihydro-1H-isoindole-1,3-dione

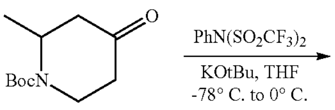

-continued

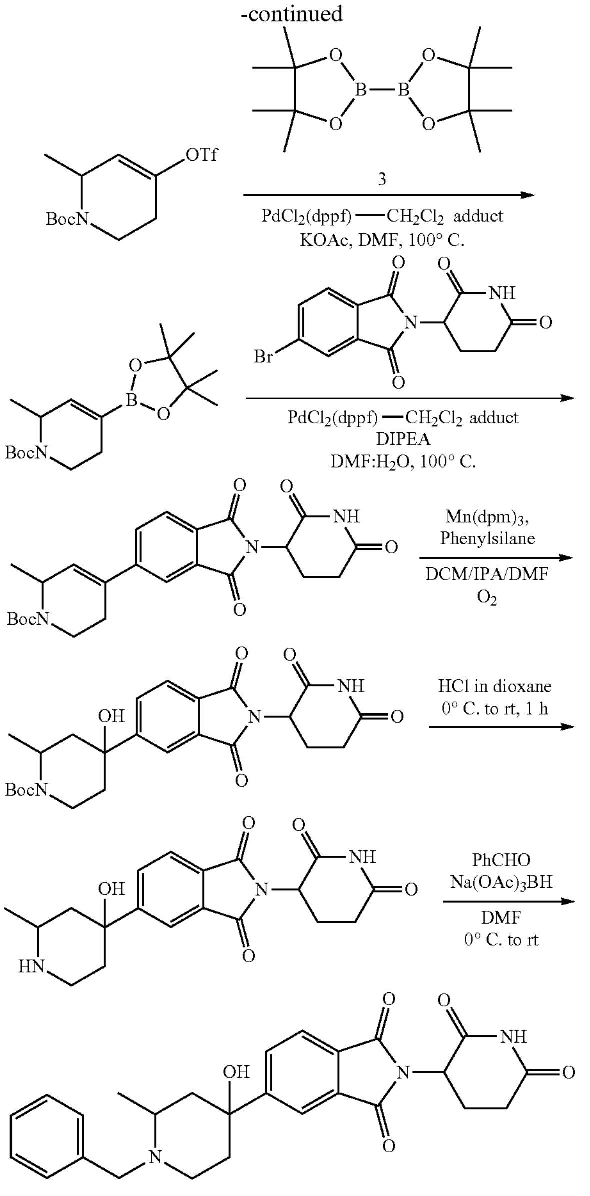

Compound 15

Step 1: Preparation of tert-butyl 6-methyl-4-(((trifluoromethyl)sulfonyl)oxy)-3,6-dihydropyridine-1(2H)-carboxylate To a stirred solution of tert-butyl 2-methyl-4-oxopiperidine-1-carboxylate (2.00 g, 9.38 mmol) in THF (20 mL) was added potassium tert-butoxide solution (1 M in THF) (18.8 mL, 18.8 mmol) dropwise at −78° C. under an atmosphere of $N_2$. The resulting mixture was stirred for 1 h at −78° C. before 1,1,1-trifluoro-N-phenyl-N-((trifluoromethyl)sulfonyl)methanesulfonamide (5.03 g, 14.1 mmol) in THF (5 mL) was added. The mixture was then allowed to stir at 0° C. for 5 h under an atmosphere of $N_2$. The reaction mixture was quenched with aqeuous $NH_4Cl$ and extracted with EtOAc (2×50 mL). The combined organics were dried over $Na_2SO_4$ and concentrated under reduced pressure to give the crude product. The crude product was purified by silica gel chromotography (100-200 mesh silca gel) eluting with (5-10%) EtOAc in hexanes to give tert-butyl 6-methyl-4-(((trifluoromethyl)-sulfonyl)oxy)-3,6-dihydropyridine-1(2H)-carboxylate (2.0 g, 62% yield) as a pale brown liquid. LCMS: m/z MM-ES+APCI, positive $[M+H]^+$ Not ionized; $^1H$ NMR (400 MHz, DMSO-$d_6$) δ ppm 6.14-5.87 (m, 1H) 4.21-3.83 (m, 1H) 3.08-2.85 (m, 2H) 2.34-2.02 (m, 2H) 1.42 (s, 9H) 1.17-1.08 (m, 3H).

Step 2: Preparation of tert-butyl 6-methyl-4-(4,4,5,5-tetramethyl-1,3,2-dioxaborolan-2-yl)-3,6-dihydropyridine-1(2H)-carboxylate To a stirred solution of tert-butyl 6-methyl-4-(((trifluoromethyl)sulfonyl)oxy)-3,6-dihydropyridine-1(2H)-carboxylate (500 mg, 1.45 mmol), bispin (404 mg, 1.59 mmol) in DMF (20 mL) were added potassium acetate (426 mg, 4.34 mmol) and $PdCl_2(dppf)$-$CH_2Cl_2$ adduct (36 mg, 0.043 mmol) at room temperature under an atmosphere of nitrogen. The reaction mixture was stirred at 100° ° C. for 16 h, cooled to room temperature and water (40 mL) was then added before the mixture was extracted with EtOAc (3×50 mL). The combined organics were dried over $Na_2SO_4$ and concentrated under reduced pressure to afford tert-butyl 6-methyl-4-(4,4,5,5-tetramethyl-1,3,2-dioxaborolan-2-yl)-3,6-dihydropyridine-1(2H)-carboxylate (450 mg, 48% yield) as a brown gummy liquid which was carried onto the next step without further purification. LCMS: m/z MM-ES+APCI, positive [M+H]+ Not ionized; $^1H$ NMR (400 MHZ, DMSO-$d_6$) δ ppm 6.55-6.16 (m, 1H) 4.48-4.27 (m, 1H) 4.08-3.85 (m, 2H) 2.90 (s, 2H) 2.74 1.40 (s, 9H) 1.21 (s, 12H) 1.17-1.12 (m, 3H).

Step 3: Preparation of tert-butyl 4-(2-(2,6-dioxopiperidin-3-yl)-1,3-dioxoisoindolin-5-yl)-6-methyl-3,6-dihydropyridine-1(2H)-carboxylate A solution of 5-bromo-2-(2,6-dioxopiperidin-3-yl)isoindoline-1,3-dione (500 mg, 1.48 mmol), tert-butyl 6-methyl-4-(4,4,5,5-tetramethyl-1,3,2-dioxaborolan-2-yl)-3,6-dihydropyridine-1(2H)-carboxylate (479 mg, 1.48 mmol) and DIPEA (0.518 mL, 2.97 mmol) in DMF (18 mL) and water (2 mL) was purged with nitrogen gas for 5 min. To this mixture was added $PdCl_2(dppf)$-$CH_2Cl_2$ adduct (121 mg, 0.148 mmol) at room temperature under an atmosphere of nitrogen. The resulting mixture was stirred at 100° C. for 16 h before it was cooled and concentrated under reduced pressure to give the crude product. The crude product was purified by silica gel chromotography (100-200 mesh silca gel) using 70-100% EtOAc in hexanes as an eluent to afford tert-butyl 4-(2-(2,6-dioxopiperidin-3-yl)-1,3-dioxoisoindolin-5-yl)-6-methyl-3,6-dihydropyridine-1(2H)-carboxylate (425 mg, 41% yield) as a pale brown solid. LCMS: m/z MM-ES+APCI, negative $[M-H]^+$=452.0; $^1H$ NMR (400 MHZ, DMSO-$d_6$) δ ppm 11.13 (s, 1H) 8.06-7.77 (m, 3H) 6.48 (d, J=1.38 Hz, 1H) 5.16 (dd, J=12.94, 5.32 Hz, 1H) 4.57 (d, J=4.13 Hz, 1H) 4.10 (br s, 1H) 2.90 (br s, 2H) 2.76-2.54 (m, 2H) 2.42 (br s, 1H) 2.20-1.93 (m, 2H) 1.44 (s, 9H) 1.31-0.98 (m, 3H).

Step 4: Preparation of tert-butyl 4-(2-(2,6-dioxopiperidin-3-yl)-1,3-dioxoisoindolin-5-yl)-4-hydroxy-2-methylpiperidine-1-carboxylate To a stirred solution of tert-butyl 4-(2-(2,6-dioxopiperidin-3-yl)-1,3-dioxoisoindolin-5-yl)-6-methyl-3,6-dihydropyridine-1(2H)-carboxylate (450 mg, 0.992 mmol) in 2-propanol (10 mL), DMF (2 mL) and DCM (10 mL) was added $Mn(dpm)_3$ (180 mg, 0.298 mmol) followed by phenyl silane (0.245 mL, 1.99 mmol) at 0° C. The reaction mixture was purged with oxygen gas for 30 min before it was allowed to stir at room temperature for 16 h under an atmosphere of oxygen. The reaction mixture was then concentrated under reduced pressure to give the crude product. The crude product was purified by silica gel chromotography (230-400 mesh silca gel) using 70-100% EtOAc in hexanes as an eluent to afford tert-butyl 4-(2-(2,6-dioxopiperidin-3-yl)-1,3-dioxoisoindolin-5-yl)-4-hydroxy-2-methylpiperidine-1-carboxylate (370 mg, 77% yield) as an off-white solid. LCMS: m/z MM-ES+APCI, negative $[M-H]^+$=470.0; $^1H$ NMR (400 MHZ, DMSO-$d_6$) δ ppm 11.13 (s, 1H), 7.98 (m, 2H), 7.89 (d, J=8.5 Hz, 1H), 5.41 (s, 1H), 5.17-5.14 (m, 1H), 4.04 (m, 1H), 3.72 (m, 1H), 3.37 (m, 1H), 2.90-2.88 (m, 1H), 2.59-2.51 (m, 1H), 2.08-1.94 (m, 4H), 1.84-1.78 (m, 2H), 1.43 (s, 9H), 1.10 (d, J=6.5 Hz, 3H).

Step 5: Preparation of 2-(2,6-dioxopiperidin-3-yl)-5-(4-hydroxy-2-methylpiperidin-4-yl)isoindoline-1,3-dione To a stirred solution of tert-butyl 4-(2-(2,6-dioxopiperidin-3-yl)-1,3-dioxoisoindolin-5-yl)-4-hydroxy-2-methylpiperidine-1-carboxylate (350 mg, 0.742 mmol) in 1,4-dioxane (10 mL) was added HCl (4 M in dioxane) (3.71 mL, 14.9 mmol) dropwise at 0° C. The reaction mixture was allowed to stir for 1 h at room temperature before it was concentrated under reduced pressure. The resultant solids were washed with MTBE (15 mL) to afford 2-(2,6-dioxopiperidin-3-yl)-5-(4-hydroxy-2-methylpiperidin-4-yl)isoindoline-1,3-dione, HCl (300 mg, 97% yield) as an off-white solid which was carried onto the next step without further purification. LCMS: m/z MM-ES+APCI, positive $[M+H]^+$=372.2; $^1H$ NMR (400 MHZ, DMSO-$d_6$) δ ppm 11.14 (s, 1H), 8.94 (bs, 1H), 8.76 (bs, 1H), 7.99-7.93 (m, J=8.8 Hz, 3H), 5.90 (s, 1H), 5.18-5.14 (m, 1H), 3.51-3.49 (m, 1H), 3.34-3.24 (m, 2H), 2.94-2.89 (m, 1H), 2.70-2.55 (m, 2H), 2.33-2.21 (m, 1H), 2.05-2.10 (m, 2H), 1.87-1.78 (m, 2H), 1.28 (d, J=6.5 Hz, 3H).

Step 6: Preparation of 5-(1-benzyl-4-hydroxy-2-methylpiperidin-4-yl)-2-(2,6-dioxopiperidin-3-yl)isoindoline-1,3-dione To a stirred solution of 2-(2,6-dioxopiperidin-3-yl)-5-(4-hydroxy-2-methylpiperidin-4-yl)isoindoline-1,3-dione, HCl (150 mg, 0.404 mmol) and benzaldehyde (0.082 mL, 0.81 mmol) in DMF (10 mL) was added sodium triacetoxyborohydride (214 mg, 1.01 mmol) in portions at 0° C. The reaction mixture was allowed to stir at room temperature for 16 h under an atmosphere of $N_2$ before it was concentrated under reduced pressure to give the crude compound as a pale brown semi-solid. The crude material was purified by reverse phase chromatography (C18 cartridge, 40 g) using acetonitrile in water (0.1% HCl acid) (10-20%) as the eluent to give 5-(1-benzyl-4-hydroxy-2-methylpiperidin-4-yl)-2-(2,6-dioxopiperidin-3-yl)isoindoline-1,3-dione, HCl (78 mg, 39%) as a white solid. LCMS: m/z MM-ES+APCI, positive $[M+H]^+$=462.3; $^1H$ NMR (400 MHZ, DMSO-$d_6$) δ ppm 11.13 (s, 1H), 10.45 (bs, 1H), 8.10-7.93 (m, 3H), 7.63 (m, 2H), 7.46-7.53 (m, 3H), 5.88 (s, 1H), 5.18-5.13 (m, 1H), 4.74 (d, J=11.1 Hz, 1H), 4.24-4.19 (m, 1H), 3.33 (m, 1H), 3.24 (m, 1H), 3.08 (d, J=11.9 Hz, 1H), 2.89 (m, 1H), 2.55-2.65 (m, 2H), 2.47-2.33 (m, 2H), 2.08-1.95 (m, 2H), 1.84-1.79 (m, 1H), 1.55 (d, J=6.4 Hz, 3H).

INCORPORATION BY REFERENCE

All of the U.S. patents and U.S. and PCT published patent applications cited herein are hereby incorporated by reference.

EQUIVALENTS

The foregoing written specification is sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of Formula (I):

(I)

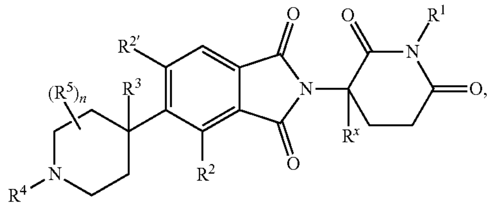

wherein:

$R^1$ is H or —$CH_2OC(O)R^{16}$, —$CH_2OC(O)NHR^{16}$, —$CH_2OC(O)OR^{16}$, —$CH_2OP(O)(OR^{16})_2$, —$CH_2OP(O)(OH)OR^{16}$, or —$CH_2OP(O)(R^{16})_2$;

$R^2$ and $R^{2'}$ are independently selected from H, $(C_1-C_6)$alkyl, $(C_1-C_6)$alkoxy, $(C_1-C_6)$hydroxyalkyl, $(C_1-C_6)$haloalkyl, halogen, —OH, and —CN;

$R^3$ is $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, halogen, —OH, —$NH_2$, —$NHR^{10}$, —$NR^{10}R^{11}$, —$NHC(O)R^{10}$, —$NR^{11}C(O)R^{10}$, —$(CH_2)_{0-2}NH_2$, —$(CH_2)_{0-2}NH(C_1-C_6)$alkyl, —$(CH_2)_{0-2}N((C_1-C_6)$alkyl$)_2$, —$C(O)NH_2$, —C(O)OH, —$C(O)OR^{15}$, —CN, —$OC(O)R^{16}$, —$OCH_2OC(O)R^{16}$, —$OCH_2OC(O)NHR^{16}$, —$OCH_2OC(O)OR^{16}$, —$OP(O)(OR^{15})_2$, —$OCH_2OP(O)(OH)OR^{16}$, or —$OCH_2OP(O)(R^{16})_2$;

$R^4$ is $(C_1-C_6)$alkyl, $(C_6-C_{10})$aryl, 5- or 6-membered heteroaryl comprising 1 to 3 heteroatoms selected from O, N, and S, $(C_3-C_8)$cycloalkyl, or 4- to 7-membered heterocycloalkyl comprising 1 to 3 heteroatoms selected from O, N, and S, wherein the alkyl is optionally substituted with one or more $R^6$; and the aryl, heteroaryl, cycloalkyl, and heterocycloalkyl are optionally substituted with one or more $R^7$;

each $R^5$ is independently H, $(C_1-C_6)$alkyl, $(C_1-C_6)$haloalkyl, $(C_1-C_6)$hydroxyalkyl, $(C_6-C_{10})$aryl, 5- or 6-membered heteroaryl ring comprising 1 to 3 heteroatoms selected from O, N, and S, —CN, or halogen, or two instances of $R^5$ together with the carbon atom or atoms to which they are attached form $(C_3-C_7)$cycloalkyl or a 4- to 7-membered heterocycloalkyl ring comprising 1 to 3 heteroatoms selected from O, N, and S, wherein the cycloalkyl and heterocycloalkyl are optionally substituted with one or more $(C_1-C_6)$alkyl, $(C_1-C_6)$alkoxy, $(C_1-C_6)$hydroxyalkyl, $(C_1-C_6)$haloalkyl, halogen, —OH, or —CN, or two adjacent instances of $R^5$ together with the carbon atoms to which they are attached form a fused $(C_6)$ aryl or 5- to 6-membered heteroaryl, wherein the aryl or heteroaryl are optionally substituted with one or more $(C_1-C_6)$alkyl, $(C_1-C_6)$alkoxy, $(C_1-C_6)$hydroxyalkyl, $(C_1-C_6)$haloalkyl, halogen, —OH, or —CN;

each $R^6$ is independently selected from —C(O)OR$^8$, —C(O)NR$^8$R$^{8'}$, —NR$^8$C(O)R$^{8'}$, halogen, —OH, —NH$_2$, —CN, $(C_6-C_{10})$aryl; monocyclic or bicyclic 5- to 10-membered heteroaryl comprising 1 to 3 heteroatoms selected from O, N, and S; $(C_3-C_8)$ cycloalkyl, and 5- to 7-membered heterocycloalkyl ring comprising 1 to 3 heteroatoms selected from O, N, and S; wherein the aryl, heteroaryl, cycloalkyl, and heterocycloalkyl groups are optionally substituted with one or more $R^9$;

each $R^7$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, $(C_1-C_6)$hydroxyalkyl, halogen, —OH, —NH$_2$, —CN, $(C_3-C_7)$cycloalkyl, 5- to 7-membered heterocycloalkyl comprising 1 to 3 heteroatoms selected from O, N, and S, $(C_6-C_{10})$aryl, and 5- or 6-membered heteroaryl comprising 1 to 3 heteroatoms selected from O, N, and S, or two instances of $R^7$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one or more $R^2$, or two instances of $R^7$ together with the atoms to which they are attached form a $(C_3-C_7)$cycloalkyl ring or a 4- to 7-membered heterocycloalkyl ring comprising 1 to 3 heteroatoms selected from O, N, and S optionally substituted with one or more $R^{12}$;

$R^8$ and $R^{8'}$ are each independently H, $(C_1-C_6)$alkyl, or $(C_6-C_{10})$aryl, or $R^8$ and $R^{8'}$, together with the nitrogen to which they are attached, form a 5- to 7-membered heterocycloalkyl ring comprising 1 to 3 heteroatoms selected from O, N, and S, optionally substituted with one or more $R^{12}$;

each $R^9$ is independently selected from $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, —C(O)R$^{10}$, —$(CH_2)_{0-3}$C(O)OR$^{10}$, —C(O)NR$^{10}$R$^{11}$, —NR$^{10}$C(O)R$^{11}$, —NR$^{10}$C(O)OR$^{11}$, —S(O)$_p$NR$^{10}$R$^{11}$, —S(O)$_p$R$^{14}$, $(C_1-C_6)$hydroxyalkyl, halogen, —OH, —O$(CH_2)_{1-3}$CN, —NH$_2$, —CN, —O$(CH_2)_{0-3}$$(C_6-C_{10})$aryl, adamantyl, —O$(CH_2)_{0-3}$-5- or 6-membered heteroaryl comprising 1 to 3 heteroatoms selected from O, N, and S, $(C_6-C_{10})$aryl, monocyclic or bicyclic 5- to 10-membered heteroaryl comprising 1 to 3 heteroatoms selected from O, N, and S, $(C_3-C_7)$cycloalkyl, and 5- to 7-membered heterocycloalkyl comprising 1 to 3 heteroatoms selected from O, N, and S, wherein the alkyl is optionally substituted with one or more $R^{13}$, and the aryl, heteroaryl, and heterocycloalkyl are optionally substituted with one or more substituents each independently selected from halogen, $(C_1-C_6)$alkyl, $(C_1-C_6)$haloalkyl, and $(C_1-C_6)$alkoxy, or two instances of $R^9$ together with the carbon atom to which they are attached form C═(O), or two instances of $R^9$, when on adjacent atoms, together with the atoms to which they are attached form a $(C_6-C_{10})$aryl ring or a 5- or 6-membered heteroaryl ring comprising 1 to 3 heteroatoms selected from O, N, and S, optionally substituted with one or more $R^{12}$, or two instances of $R^9$ together with the atom or atoms to which they are attached form a $(C_5-C_7)$ cycloalkyl ring or a 5- to 7-membered heterocycloalkyl ring comprising 1 to 3 heteroatoms selected from O, N, and S, optionally substituted with one or more $R^{12}$;

$R^{10}$ and $R^{11}$ are each independently H or $(C_1-C_6)$alkyl, or $R^{10}$ and $R^{11}$, together with the nitrogen to which they are attached, form a 5- to 7-membered heterocycloalkyl ring comprising 1 to 3 heteroatoms selected from O, N, and S, optionally substituted with one or more $R^{12}$;

each $R^{12}$ is independently selected from $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, $(C_6-C_{10})$aryl, 5- to 6-membered heteroaryl, 4- to 7-membered cycloalkyl, 5- to 7-membered heterocycloalkyl, halogen, —OH, —NH$_2$, and —CN, wherein the aryl, heteroaryl, cycloalkyl and heterocycloalkyl are optionally substituted with one or more $(C_1-C_6)$alkyl, $(C_1-C_6)$alkoxy, $(C_1-C_6)$hydroxyalkyl, $(C_1-C_6)$haloalkyl, halogen, —OH, or —CN, or two instances of $R^{12}$ together with the carbon atom to which they are attached form C═(O); each $R^{13}$ is independently selected from —CN, $(C_1-C_6)$alkoxy, $(C_6-C_{10})$aryl, and 5- to 7-membered heterocycloalkyl comprising 1 to 3 heteroatoms selected from O, N, and S, wherein the aryl and heterocycloalkyl are optionally substituted with one or more substituents each independently selected from $(C_1-C_6)$alkyl, $(C_1-C_6)$alkoxy, $(C_1-C_6)$haloalkyl, $(C_1-C_6)$haloalkoxy, $(C_1-C_6)$hydroxyalkyl, halogen, —OH, —NH$_2$, and —CN;

$R^{14}$ is $(C_1-C_6)$alkyl, $(C_1-C_6)$haloalkyl, $(C_6-C_{10})$aryl, $(C_3-C_7)$cycloalkyl, or 5- to 7-membered heterocycloalkyl comprising 1 to 3 heteroatoms selected from O, N, and S;

$R^{15}$ and $R^{16}$ are independently selected for each occurrence H, $(C_1-C_6)$alkyl optionally substituted with one or more substituents independently selected from $(C_6-C_{10})$aryl, $(C_1-C_6)$alkoxy, $(C_1-C_6)$hydroxyalkyl, $(C_1-C_6)$haloalkyl, halogen, —OH, —NH$_2$, and —CN, or $(C_6-C_{10})$aryl optionally substituted with one or more substituents independently selected from $(C_1-C_6)$alkyl, $(C_1-C_6)$alkoxy, $(C_1-C_6)$hydroxyalkyl, $(C_1-C_6)$haloalkyl, halogen, —OH, —NH$_2$, and —CN;

$R^x$ is H or D;

n is 0, 1, 2, 3, or 4; and p is 1 or 2; or a pharmaceutically acceptable salt, hydrate, solvate, prodrug, stereoisomer, or tautomer thereof;

provided that the compound of Formula (I) is not selected from the group consisting of:

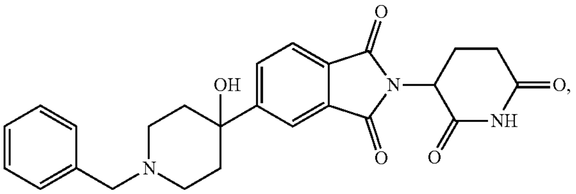

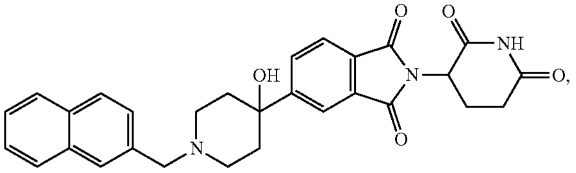

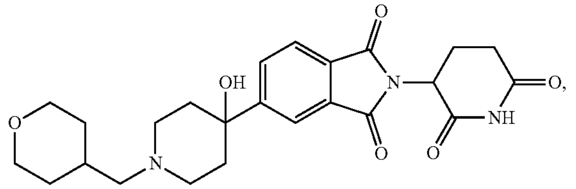

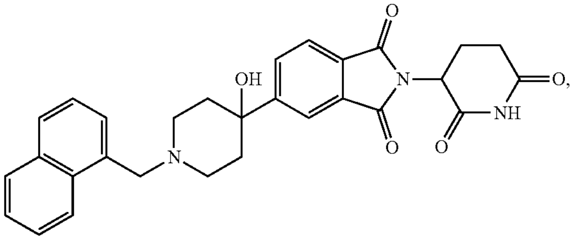

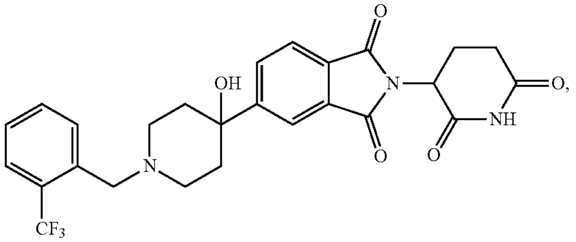

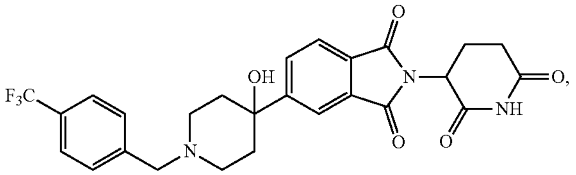

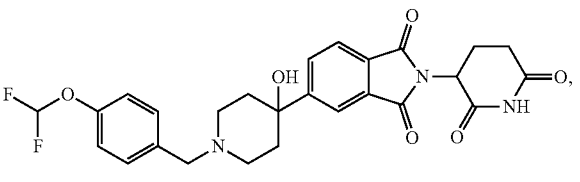

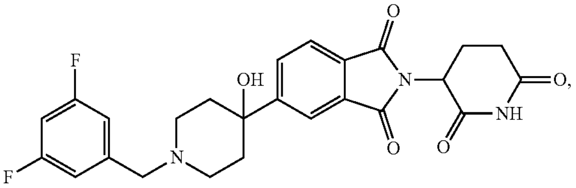

-continued

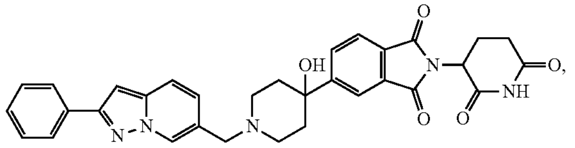

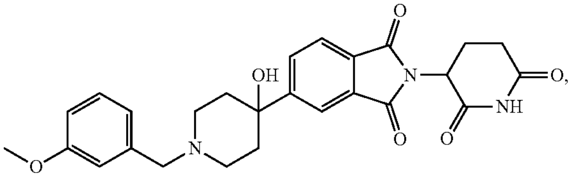

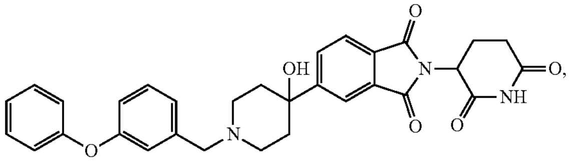

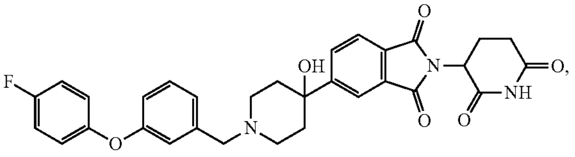

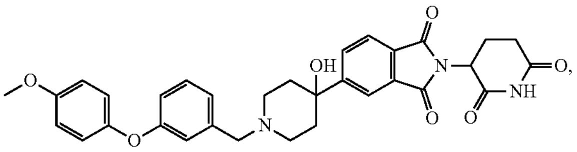

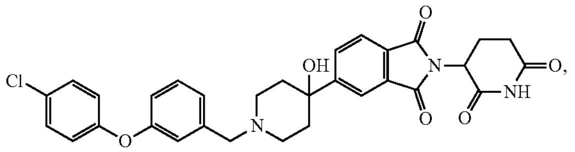

and

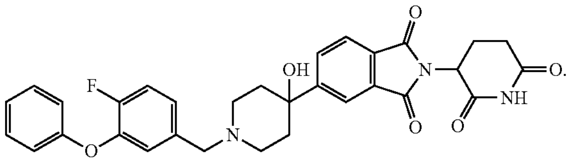

2. The compound of claim 1, wherein $R^x$ is H.

3. The compound of claim 1, wherein $R^1$ is H.

4. The compound of claim 1, wherein $R^2$ is H, $(C_1\text{-}C_6)$alkyl, $(C_1\text{-}C_6)$alkoxy, or halogen.

5. The compound of claim 4, wherein $R^2$ is H, $—CH_3$, F, Cl or $—OCH_3$.

6. The compound of claim 1, wherein $R^{2'}$ is H.

7. The compound of claim 6, wherein $R^2$ is H.

8. The compound of claim 1, wherein $R^3$ is $(C_1\text{-}C_6)$alkyl, $(C_1\text{-}C_6)$alkoxy, $(C_1\text{-}C_6)$hydroxyalkyl, halogen, —OH—, $—(CH_2)_{0\text{-}2}NH_2$, $—C(O)NH_2$, $—C(O)OR^{15}$ or —CN.

9. The compound of claim 8, wherein $R^3$ is —OH.

10. The compound of claim 1, wherein $R^4$ is $(C_1\text{-}C_6)$alkyl optionally substituted with one to three instances of $R^6$.

11. The compound of claim 10, wherein $R^4$ is $(C_1\text{-}C_6)$ alkyl substituted with one to three instances of $R^6$.

12. The compound of claim 1, wherein $R^4$ is $(C_1)$ alkyl, substituted with one or more instances of $R^6$.

13. The compound of claim 1, wherein $R^5$ is $(C_1$-$C_6)$alkyl.

14. The compound of claim 1, wherein $R^6$ is selected from $(C_6$-$C_{10})$aryl and 5- or 6-membered heteroaryl comprising 1 to 4 heteroatoms selected from O, N, and S, wherein the aryl and heteroaryl are optionally substituted with one to three instances of $R^9$.

15. The compound of claim 14, wherein $R^6$ is phenyl optionally substituted with one to three instances of $R^9$.

16. The compound of claim 14, wherein $R^6$ is 5- or 6-membered heteroaryl comprising 1 to 4 heteroatoms selected from O, N, and S, wherein the heteroaryl is optionally substituted with one to three instances of $R^9$.

17. The compound of claim 1, wherein n is 0.

18. A compound selected from the group consisting of:

| Compound number | Structure |
|---|---|
| 1 | 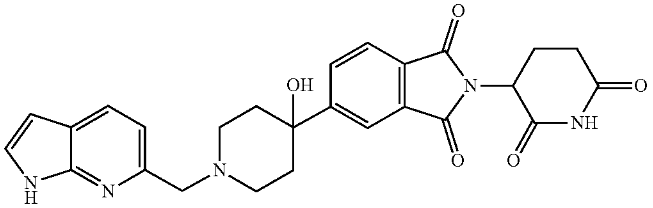 [SMILES: O=C1CCC(N2C(=O)c3ccc(C4(O)CCN(Cc5ccc6cc[nH]c6n5)CC4)cc3C2=O)C(=O)N1] |
| 2 | 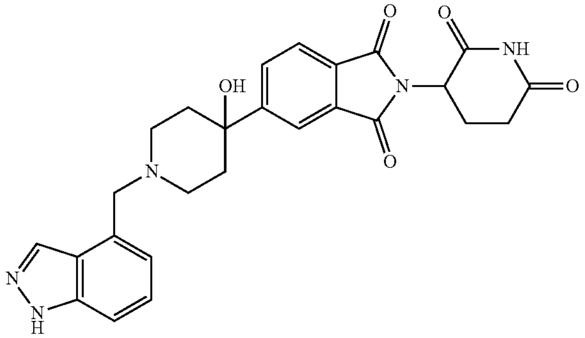 [SMILES: O=C1CCC(N2C(=O)c3ccc(C4(O)CCN(Cc5cccc6[nH]ncc56)CC4)cc3C2=O)C(=O)N1] |
| 3 | 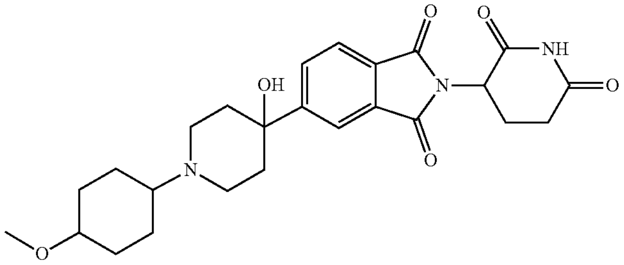 [SMILES: COC1CCC(N2CCC(O)(c3ccc4c(c3)C(=O)N(C3CCC(=O)NC3=O)C4=O)CC2)CC1] |
| 4 | 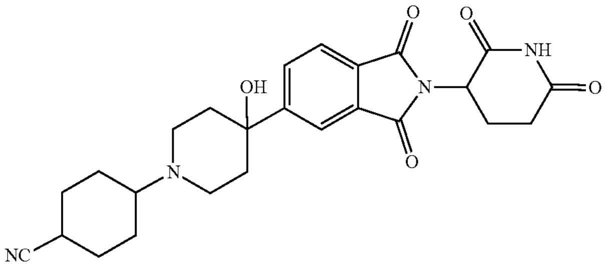 [SMILES: N#CC1CCC(N2CCC(O)(c3ccc4c(c3)C(=O)N(C3CCC(=O)NC3=O)C4=O)CC2)CC1] |
| 5 | 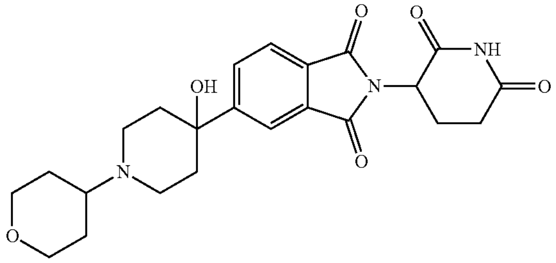 [SMILES: O=C1CCC(N2C(=O)c3ccc(C4(O)CCN(C5CCOCC5)CC4)cc3C2=O)C(=O)N1] |

-continued
| Compound number | Structure |
|---|---|
| 6 | 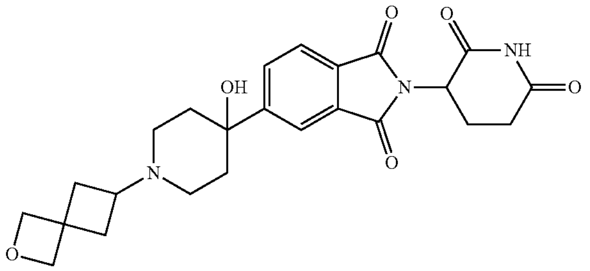 [SMILES: O=C1CCC(N2C(=O)c3ccc(C4(O)CCN(C5CC6(COC6)C5)CC4)cc3C2=O)C(=O)N1] |
| 7 | 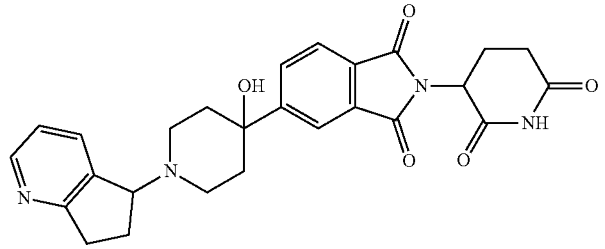 [SMILES: O=C1CCC(N2C(=O)c3ccc(C4(O)CCN(C5CCc6ncccc65)CC4)cc3C2=O)C(=O)N1] |
| 8 | 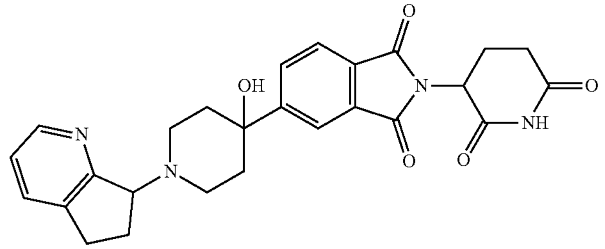 [SMILES: O=C1CCC(N2C(=O)c3ccc(C4(O)CCN(C5CCc6cccnc65)CC4)cc3C2=O)C(=O)N1] |
| 9 | 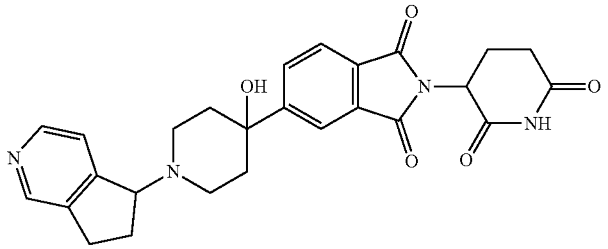 [SMILES: O=C1CCC(N2C(=O)c3ccc(C4(O)CCN(C5CCc6cnccc65)CC4)cc3C2=O)C(=O)N1] |
| 10 | 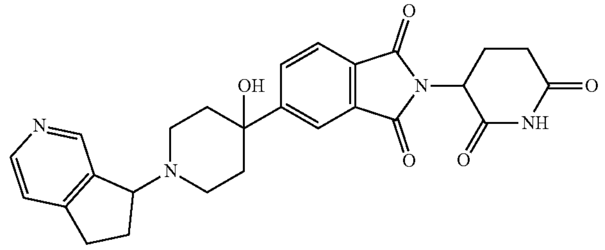 [SMILES: O=C1CCC(N2C(=O)c3ccc(C4(O)CCN(C5CCc6ccncc65)CC4)cc3C2=O)C(=O)N1] |
| 11 | 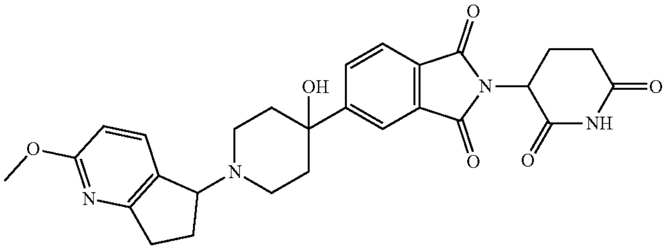 [SMILES: COc1ccc2c(n1)CCC2N1CCC(O)(c2ccc3c(c2)C(=O)N(C2CCC(=O)NC2=O)C3=O)CC1] |

-continued
| Compound number | Structure |
| --- | --- |
| 12 | 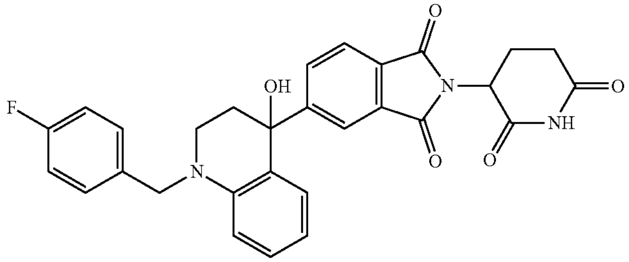 [SMILES: O=C1CCC(N2C(=O)c3ccc(C4(O)CCN(Cc5ccc(F)cc5)c5ccccc54)cc3C2=O)C(=O)N1] |
| 13 | 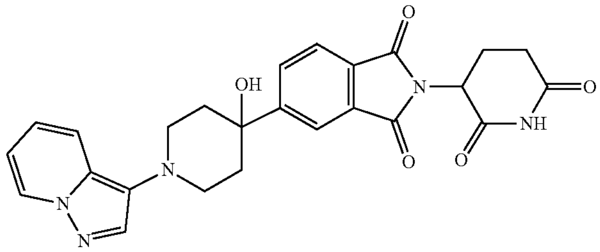 [SMILES: O=C1CCC(N2C(=O)c3ccc(C4(O)CCN(c5cnn6ccccc56)CC4)cc3C2=O)C(=O)N1] |
| 14 | 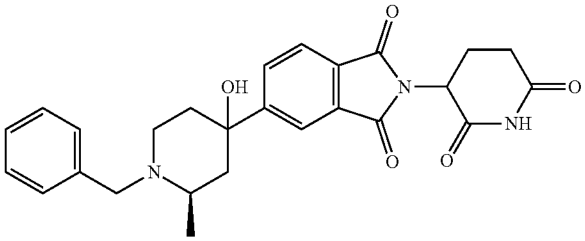 [SMILES: C[C@@H]1CC(O)(c2ccc3c(c2)C(=O)N(C2CCC(=O)NC2=O)C3=O)CCN1Cc1ccccc1] |
| 15 | 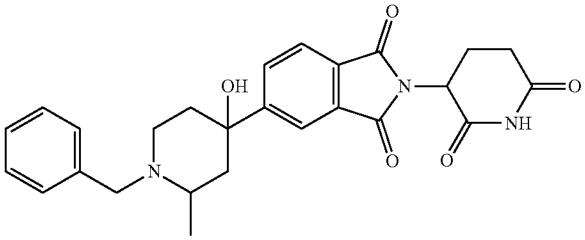 [SMILES: C[C@H]1CC(O)(c2ccc3c(c2)C(=O)N(C2CCC(=O)NC2=O)C3=O)CCN1Cc1ccccc1] |
| 16 | 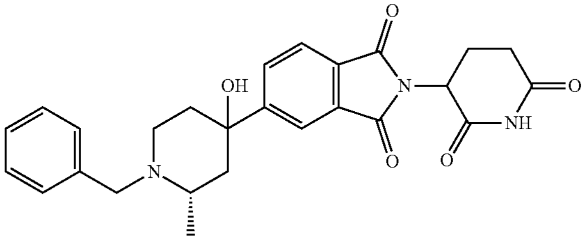 |
| 17 | 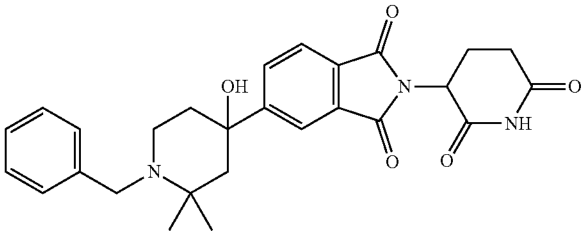 [SMILES: CC1(C)CC(O)(c2ccc3c(c2)C(=O)N(C2CCC(=O)NC2=O)C3=O)CCN1Cc1ccccc1] |

-continued
| Compound number | Structure |
|---|---|
| 18 | 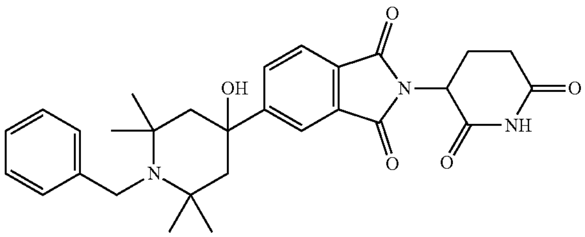 [SMILES: CC1(C)CC(O)(c2ccc3c(c2)C(=O)N(C2CCC(=O)NC2=O)C3=O)CC(C)(C)N1Cc1ccccc1] |
| 19 | 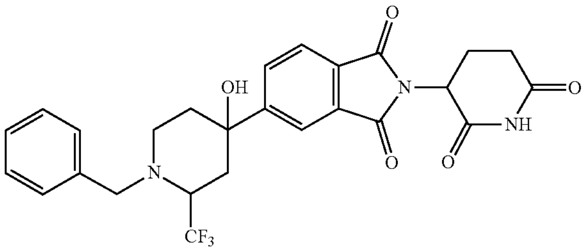 [SMILES: O=C1CCC(N2C(=O)c3ccc(C4(O)CCN(Cc5ccccc5)C(C(F)(F)F)C4)cc3C2=O)C(=O)N1] |
| 20 | 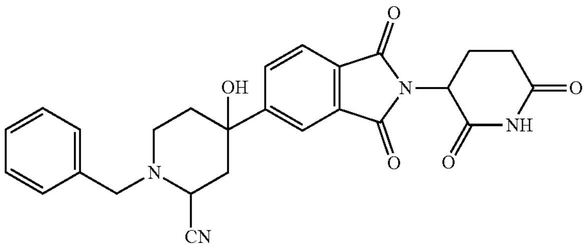 |
| 21 | 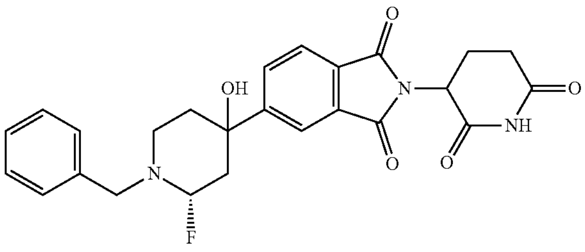 [SMILES: O=C1CCC(N2C(=O)c3ccc(C4(O)CCN(Cc5ccccc5)[C@@H](F)C4)cc3C2=O)C(=O)N1] |
| 22 | 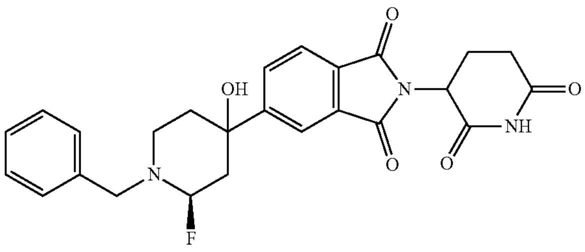 [SMILES: O=C1CCC(N2C(=O)c3ccc(C4(O)CCN(Cc5ccccc5)[C@H](F)C4)cc3C2=O)C(=O)N1] |

-continued
| Compound number | Structure |
|---|---|
| 23 | 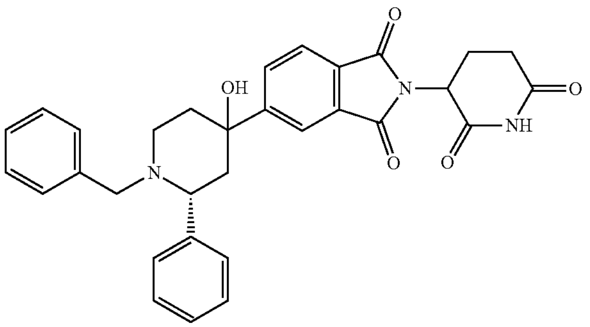 [SMILES: C=C/C=C(\C=C/C)[C@H]1CC(O)(c2ccc3c(c2)C(=O)N(C2CCC(=O)NC2=O)C3=O)CCN1Cc1ccccc1] |
| 24 | 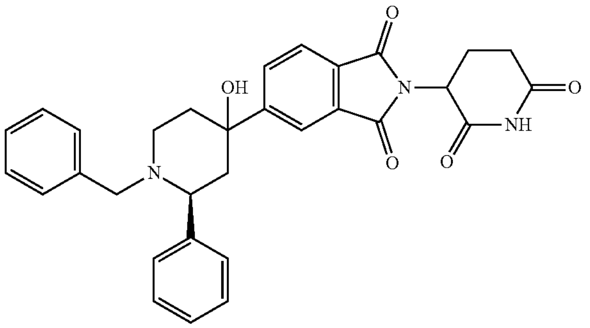 [SMILES: O=C1CCC(N2C(=O)c3ccc(C4(O)CCN(Cc5ccccc5)[C@H](c5ccccc5)C4)cc3C2=O)C(=O)N1] |
| 25 | 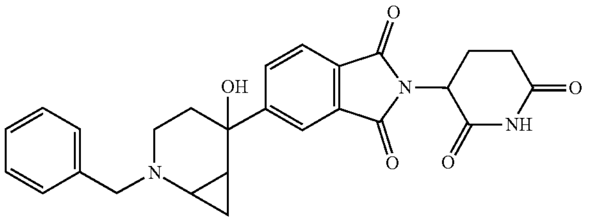 [SMILES: O=C1CCC(N2C(=O)c3ccc(C4(O)CCN(Cc5ccccc5)C5CC54)cc3C2=O)C(=O)N1] |
| 26 | 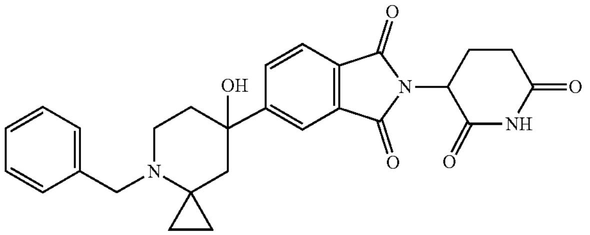 [SMILES: O=C1CCC(N2C(=O)c3ccc(C4(O)CCN(Cc5ccccc5)C5(CC5)C4)cc3C2=O)C(=O)N1] |
| 27 | 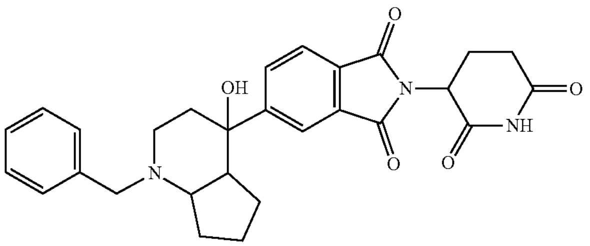 [SMILES: O=C1CCC(N2C(=O)c3ccc(C4(O)CCN(Cc5ccccc5)C5CCCC54)cc3C2=O)C(=O)N1] |

-continued
| Compound number | Structure |
| --- | --- |
| 28 | 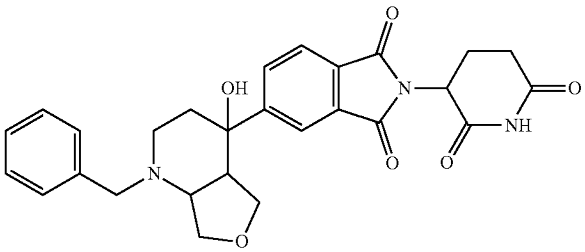 [SMILES: O=C1CCC(N2C(=O)c3ccc(C4(O)CCN(Cc5ccccc5)C5COCC54)cc3C2=O)C(=O)N1] |
| 29 | 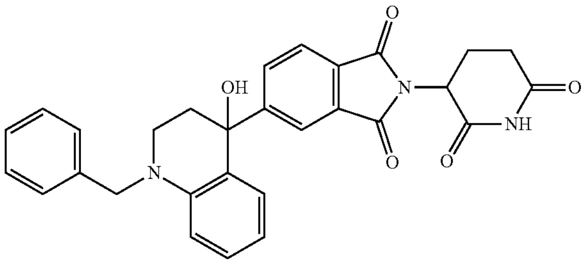 [SMILES: O=C1CCC(N2C(=O)c3ccc(C4(O)CCN(Cc5ccccc5)c5ccccc54)cc3C2=O)C(=O)N1] |
| 30 | 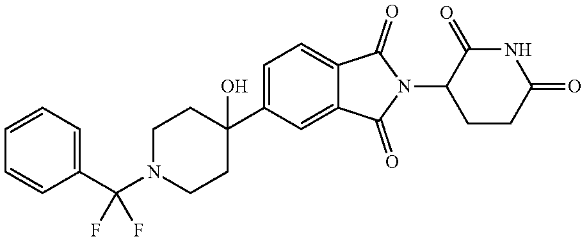 [SMILES: O=C1CCC(N2C(=O)c3ccc(C4(O)CCN(C(F)(F)c5ccccc5)CC4)cc3C2=O)C(=O)N1] |
| 31 | 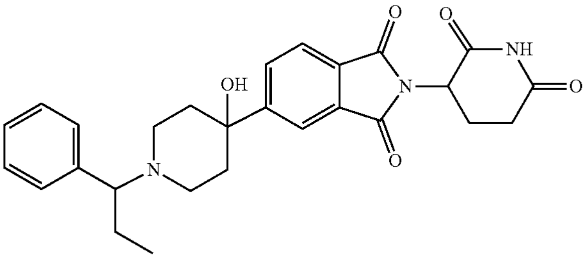 [SMILES: CCC(c1ccccc1)N1CCC(O)(c2ccc3c(c2)C(=O)N(C2CCC(=O)NC2=O)C3=O)CC1] |
| 32 | 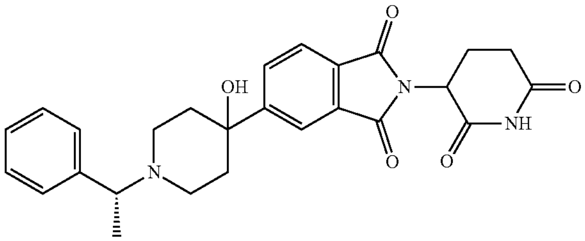 [SMILES: C[C@H](c1ccccc1)N1CCC(O)(c2ccc3c(c2)C(=O)N(C2CCC(=O)NC2=O)C3=O)CC1] |
| 33 | 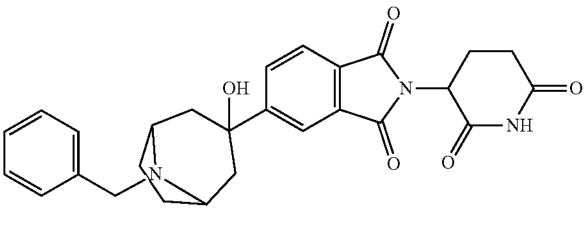 [SMILES: O=C1CCC(N2C(=O)c3ccc(C4(O)CC5CCC(C4)N5Cc4ccccc4)cc3C2=O)C(=O)N1] |

-continued
| Compound number | Structure |
|---|---|
| 34 | 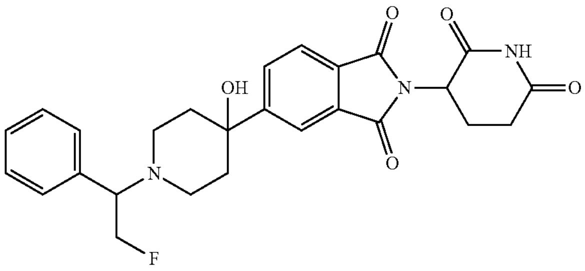 [SMILES: O=C1CCC(N2C(=O)c3ccc(C4(O)CCN(C(CF)c5ccccc5)CC4)cc3C2=O)C(=O)N1] |
| 35 | 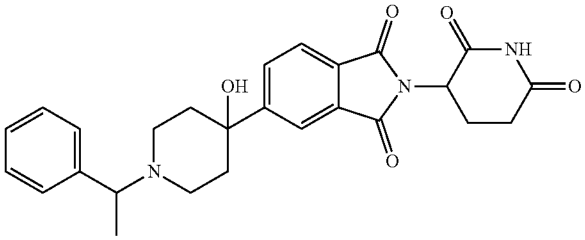 [SMILES: CC(c1ccccc1)N1CCC(O)(c2ccc3c(c2)C(=O)N(C2CCC(=O)NC2=O)C3=O)CC1] |
| 36 | 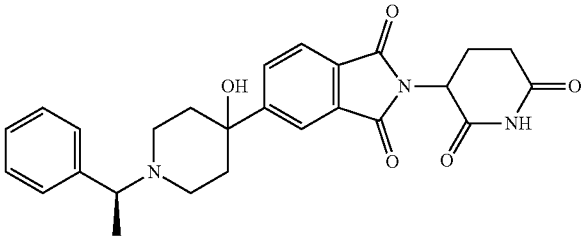 [SMILES: C[C@@H](c1ccccc1)N1CCC(O)(c2ccc3c(c2)C(=O)N(C2CCC(=O)NC2=O)C3=O)CC1] |
| 37 | 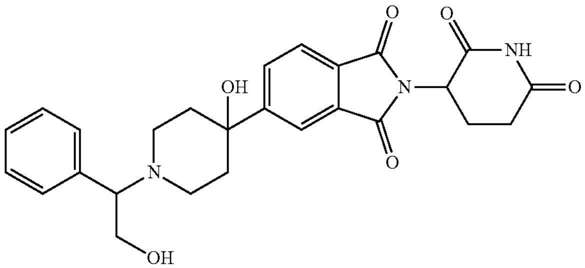 [SMILES: O=C1CCC(N2C(=O)c3ccc(C4(O)CCN(C(CO)c5ccccc5)CC4)cc3C2=O)C(=O)N1] |
| 38 | 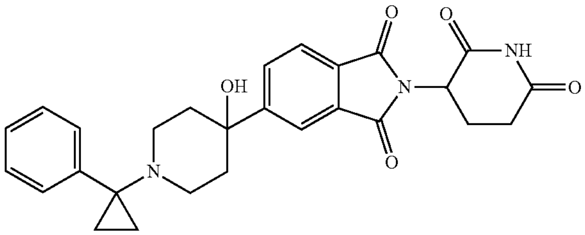 [SMILES: O=C1CCC(N2C(=O)c3ccc(C4(O)CCN(C5(c6ccccc6)CC5)CC4)cc3C2=O)C(=O)N1] |
| 39 | 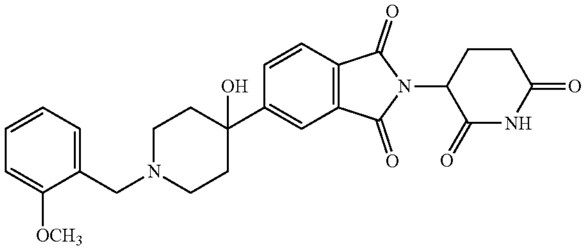 [SMILES: COc1ccccc1CN1CCC(O)(c2ccc3c(c2)C(=O)N(C2CCC(=O)NC2=O)C3=O)CC1] |

-continued
| Compound number | Structure |
| --- | --- |
| 40 | 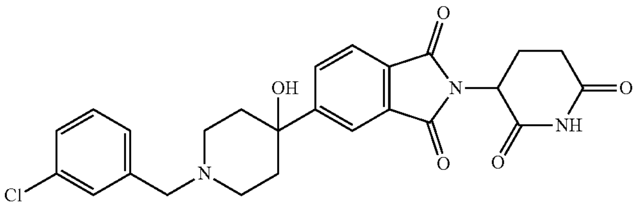 [SMILES: O=C1CCC(N2C(=O)c3ccc(C4(O)CCN(Cc5cccc(Cl)c5)CC4)cc3C2=O)C(=O)N1] |
| 41 | 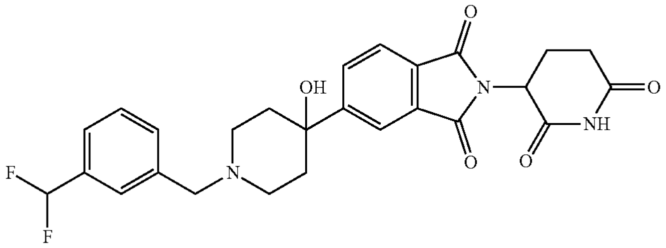 [SMILES: O=C1CCC(N2C(=O)c3ccc(C4(O)CCN(Cc5cccc(C(F)F)c5)CC4)cc3C2=O)C(=O)N1] |
| 42 | 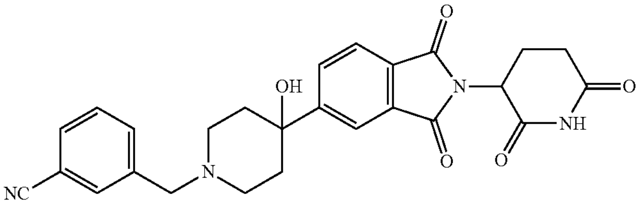 [SMILES: N#Cc1cccc(CN2CCC(O)(c3ccc4c(c3)C(=O)N(C3CCC(=O)NC3=O)C4=O)CC2)c1] |
| 44 | 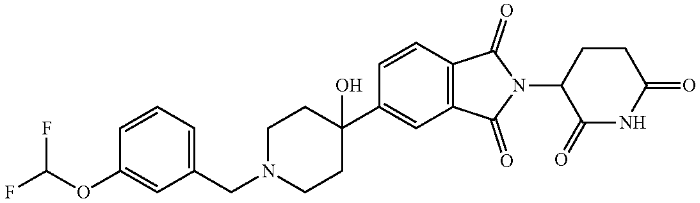 [SMILES: O=C1CCC(N2C(=O)c3ccc(C4(O)CCN(Cc5cccc(OC(F)F)c5)CC4)cc3C2=O)C(=O)N1] |
| 45 | 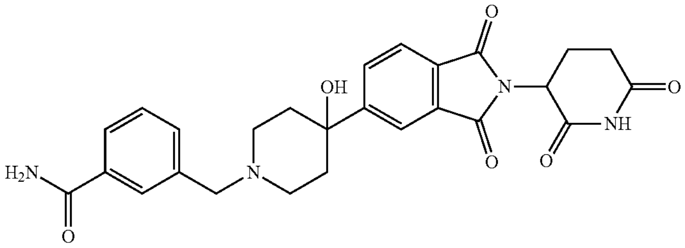 [SMILES: NC(=O)c1cccc(CN2CCC(O)(c3ccc4c(c3)C(=O)N(C3CCC(=O)NC3=O)C4=O)CC2)c1] |
| 46 | 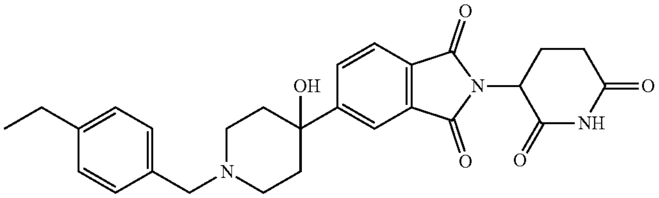 [SMILES: CCc1ccc(CN2CCC(O)(c3ccc4c(c3)C(=O)N(C3CCC(=O)NC3=O)C4=O)CC2)cc1] |
| 47 | 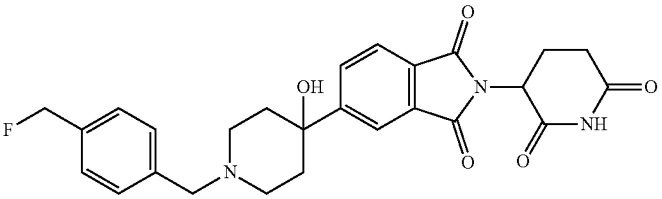 [SMILES: O=C1CCC(N2C(=O)c3ccc(C4(O)CCN(Cc5ccc(CF)cc5)CC4)cc3C2=O)C(=O)N1] |

-continued
| Compound number | Structure |
|---|---|
| 48 | 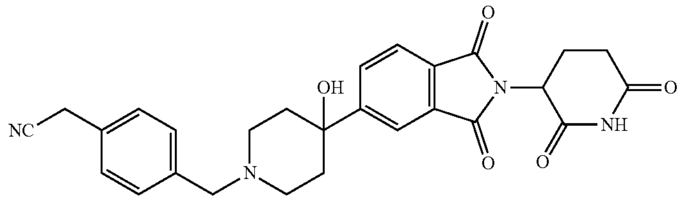 [SMILES: N#CCc1ccc(CN2CCC(O)(c3ccc4c(c3)C(=O)N(C3CCC(=O)NC3=O)C4=O)CC2)cc1] |
| 49 | 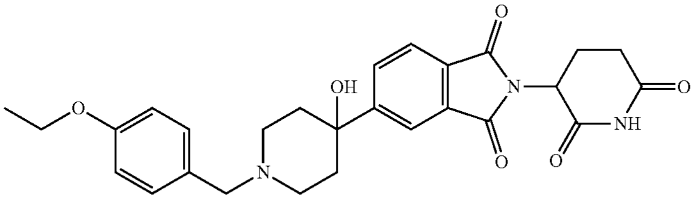 [SMILES: CCOc1ccc(CN2CCC(O)(c3ccc4c(c3)C(=O)N(C3CCC(=O)NC3=O)C4=O)CC2)cc1] |
| 50 | 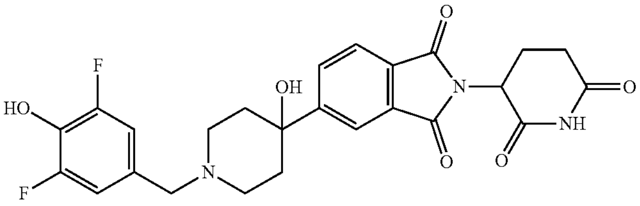 [SMILES: O=C1CCC(N2C(=O)c3ccc(C4(O)CCN(Cc5cc(F)c(O)c(F)c5)CC4)cc3C2=O)C(=O)N1] |
| 51 | 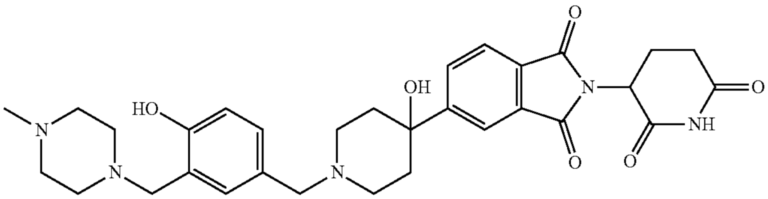 [SMILES: CN1CCN(Cc2cc(CN3CCC(O)(c4ccc5c(c4)C(=O)N(C4CCC(=O)NC4=O)C5=O)CC3)ccc2O)CC1] |
| 52 | 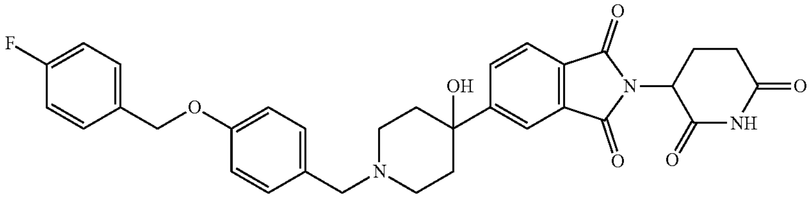 [SMILES: O=C1CCC(N2C(=O)c3ccc(C4(O)CCN(Cc5ccc(OCc6ccc(F)cc6)cc5)CC4)cc3C2=O)C(=O)N1] |
| 53 | 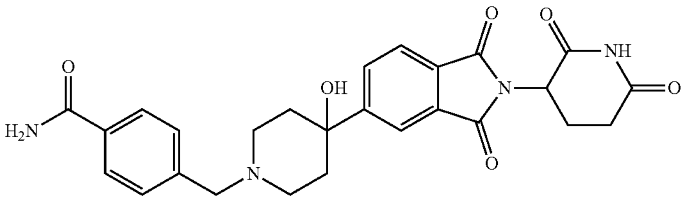 [SMILES: NC(=O)c1ccc(CN2CCC(O)(c3ccc4c(c3)C(=O)N(C3CCC(=O)NC3=O)C4=O)CC2)cc1] |
| 54 | 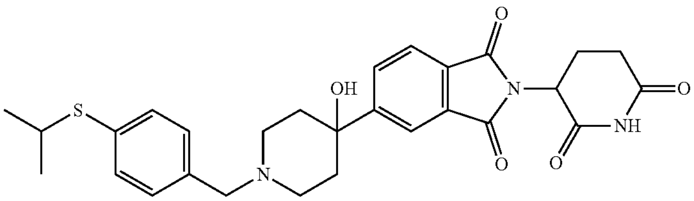 [SMILES: CC(C)Sc1ccc(CN2CCC(O)(c3ccc4c(c3)C(=O)N(C3CCC(=O)NC3=O)C4=O)CC2)cc1] |

-continued
| Compound number | Structure |
|---|---|
| 55 | 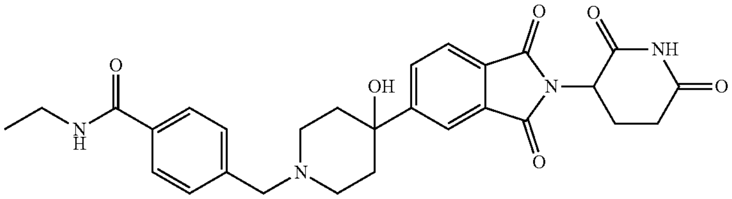 [SMILES: CCNC(=O)c1ccc(CN2CCC(O)(c3ccc4c(c3)C(=O)N(C3CCC(=O)NC3=O)C4=O)CC2)cc1] |
| 56 | 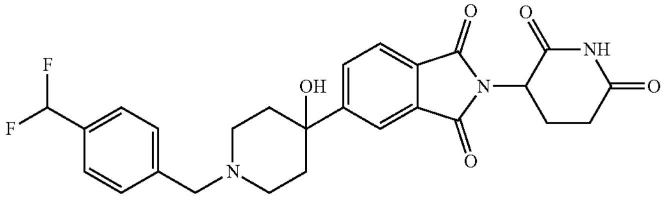 [SMILES: O=C1CCC(N2C(=O)c3ccc(C4(O)CCN(Cc5ccc(C(F)F)cc5)CC4)cc3C2=O)C(=O)N1] |
| 57 | 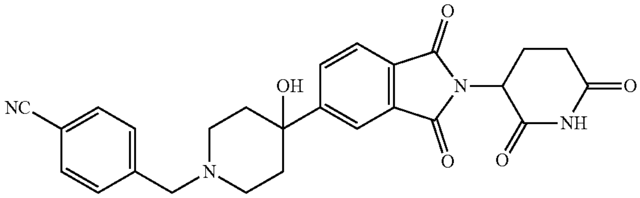 [SMILES: N#Cc1ccc(CN2CCC(O)(c3ccc4c(c3)C(=O)N(C3CCC(=O)NC3=O)C4=O)CC2)cc1] |
| 58 | 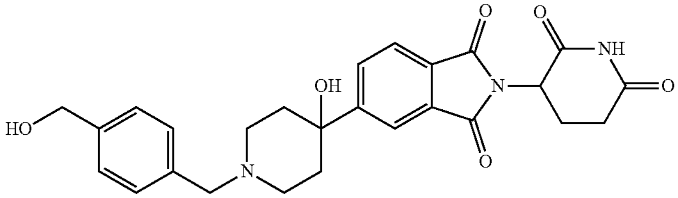 [SMILES: O=C1CCC(N2C(=O)c3ccc(C4(O)CCN(Cc5ccc(CO)cc5)CC4)cc3C2=O)C(=O)N1] |
| 59 | 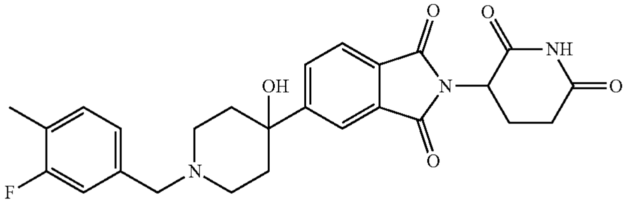 |
| 60 | 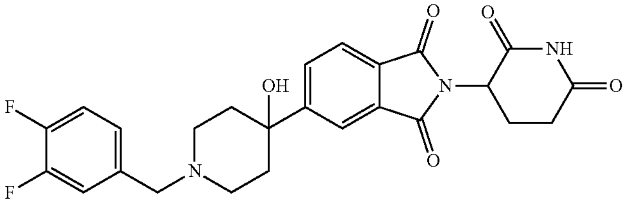 [SMILES: O=C1CCC(N2C(=O)c3ccc(C4(O)CCN(Cc5ccc(F)c(F)c5)CC4)cc3C2=O)C(=O)N1] |
| 61 | 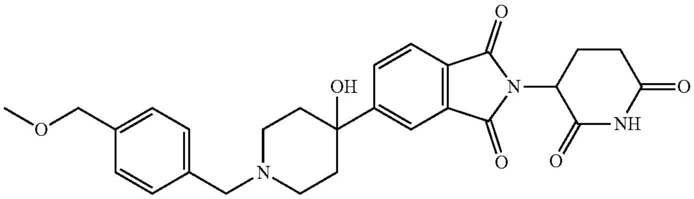 [SMILES: COCc1ccc(CN2CCC(O)(c3ccc4c(c3)C(=O)N(C3CCC(=O)NC3=O)C4=O)CC2)cc1] |

-continued
| Compound number | Structure |
|---|---|
| 62 | 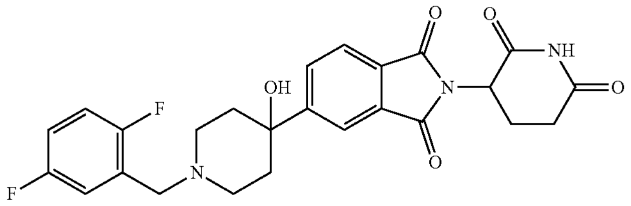 [SMILES: O=C1CCC(N2C(=O)c3ccc(C4(O)CCN(Cc5cc(F)ccc5F)CC4)cc3C2=O)C(=O)N1] |
| 63 | 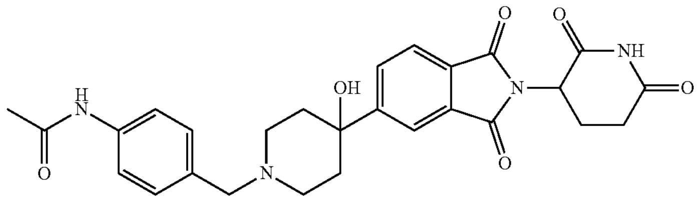 [SMILES: CC(=O)Nc1ccc(CN2CCC(O)(c3ccc4c(c3)C(=O)N(C3CCC(=O)NC3=O)C4=O)CC2)cc1] |
| 64 | 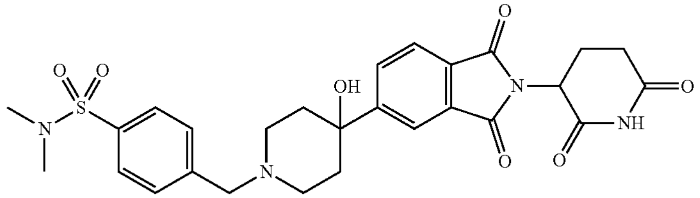 [SMILES: CN(C)S(=O)(=O)c1ccc(CN2CCC(O)(c3ccc4c(c3)C(=O)N(C3CCC(=O)NC3=O)C4=O)CC2)cc1] |
| 65 | 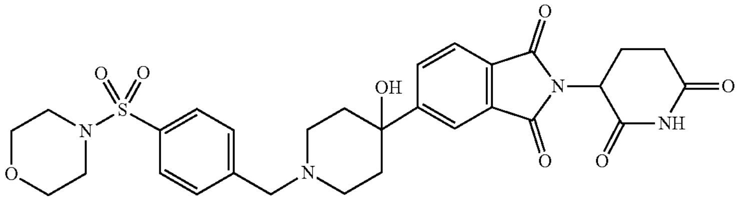 [SMILES: O=C1CCC(N2C(=O)c3ccc(C4(O)CCN(Cc5ccc(S(=O)(=O)N6CCOCC6)cc5)CC4)cc3C2=O)C(=O)N1] |
| 66 | 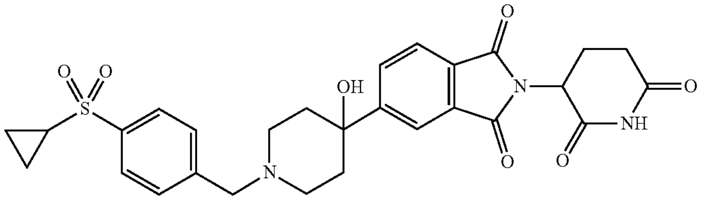 [SMILES: O=C1CCC(N2C(=O)c3ccc(C4(O)CCN(Cc5ccc(S(=O)(=O)C6CC6)cc5)CC4)cc3C2=O)C(=O)N1] |
| 67 | 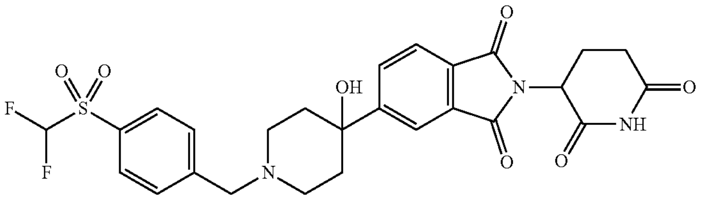 [SMILES: O=C1CCC(N2C(=O)c3ccc(C4(O)CCN(Cc5ccc(S(=O)(=O)C(F)F)cc5)CC4)cc3C2=O)C(=O)N1] |
| 68 | 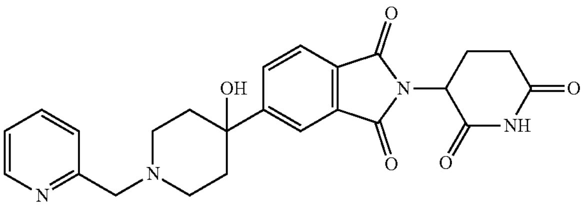 [SMILES: O=C1CCC(N2C(=O)c3ccc(C4(O)CCN(Cc5ccccn5)CC4)cc3C2=O)C(=O)N1] |

-continued
| Compound number | Structure |
| --- | --- |
| 69 | 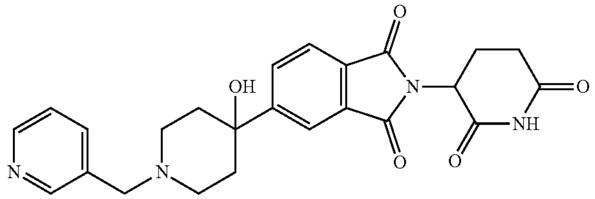 |
| 70 | 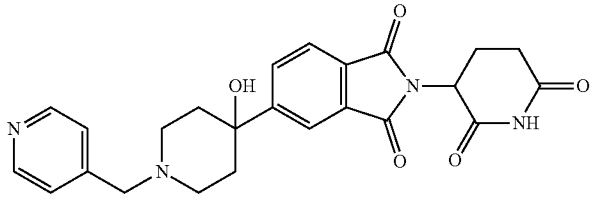 [SMILES: O=C1CCC(N2C(=O)c3ccc(C4(O)CCN(Cc5ccncc5)CC4)cc3C2=O)C(=O)N1] |
| 71 | 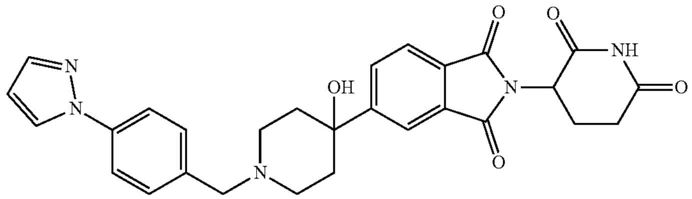 [SMILES: O=C1CCC(N2C(=O)c3ccc(C4(O)CCN(Cc5ccc(-n6cccn6)cc5)CC4)cc3C2=O)C(=O)N1] |
| 72 | 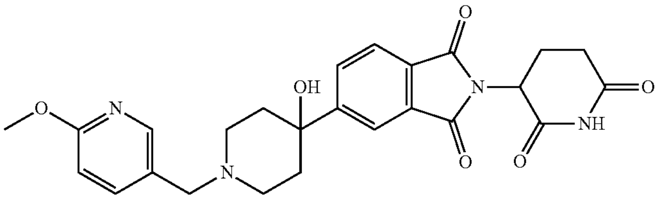 [SMILES: COc1ccc(CN2CCC(O)(c3ccc4c(c3)C(=O)N(C3CCC(=O)NC3=O)C4=O)CC2)cn1] |
| 73 | 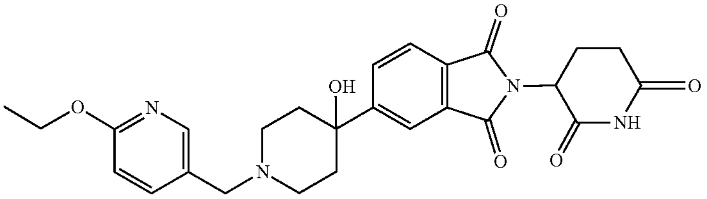 |
| 74 | 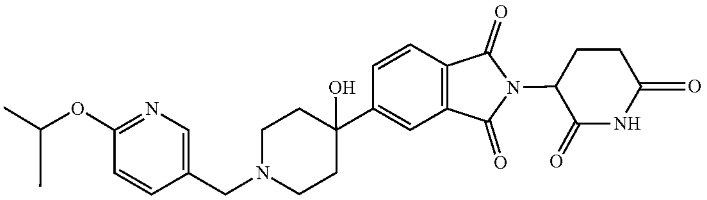 [SMILES: CC(C)Oc1ccc(CN2CCC(O)(c3ccc4c(c3)C(=O)N(C3CCC(=O)NC3=O)C4=O)CC2)cn1] |
| 75 | 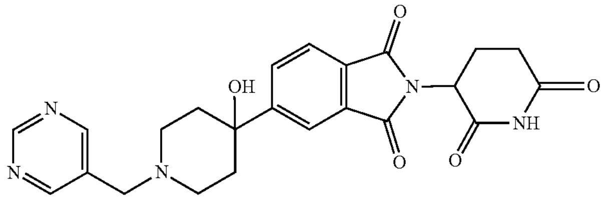 [SMILES: O=C1CCC(N2C(=O)c3ccc(C4(O)CCN(Cc5cncnc5)CC4)cc3C2=O)C(=O)N1] |

-continued
| Compound number | Structure |
|---|---|
| 76 | 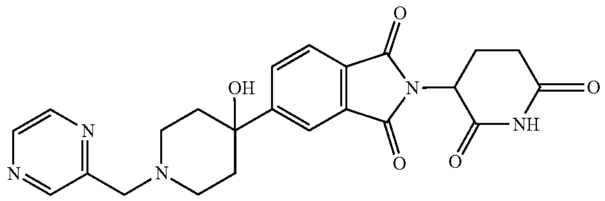 [SMILES: O=C1CCC(N2C(=O)c3ccc(C4(O)CCN(Cc5cnccn5)CC4)cc3C2=O)C(=O)N1] |
| 77 | 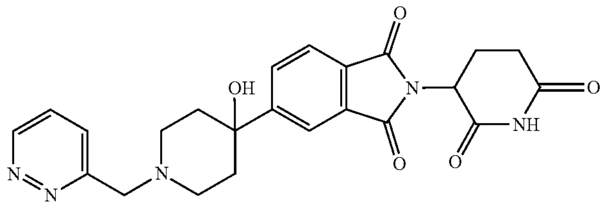 [SMILES: O=C1CCC(N2C(=O)c3ccc(C4(O)CCN(Cc5cccnn5)CC4)cc3C2=O)C(=O)N1] |
| 78 | 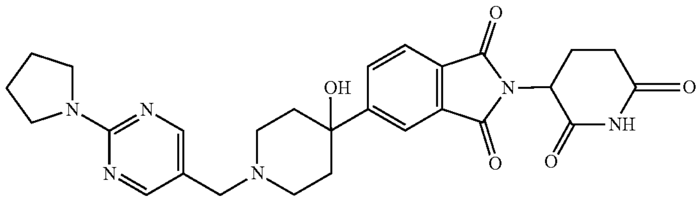 [SMILES: O=C1CCC(N2C(=O)c3ccc(C4(O)CCN(Cc5cnc(N6CCCC6)nc5)CC4)cc3C2=O)C(=O)N1] |
| 79 | 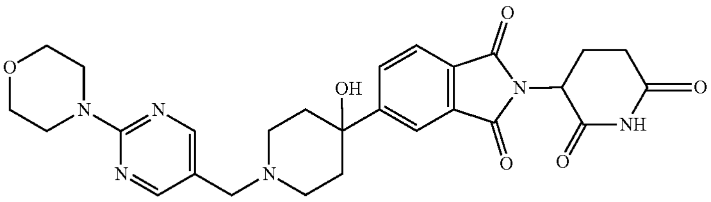 [SMILES: O=C1CCC(N2C(=O)c3ccc(C4(O)CCN(Cc5cnc(N6CCOCC6)nc5)CC4)cc3C2=O)C(=O)N1] |
| 80 | 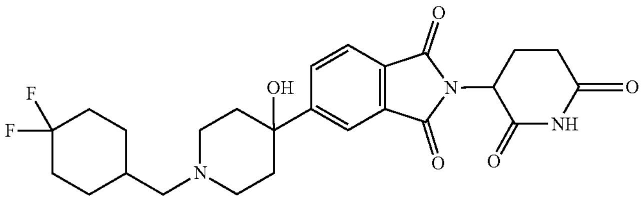 [SMILES: O=C1CCC(N2C(=O)c3ccc(C4(O)CCN(CC5CCC(F)(F)CC5)CC4)cc3C2=O)C(=O)N1] |
| 81 | 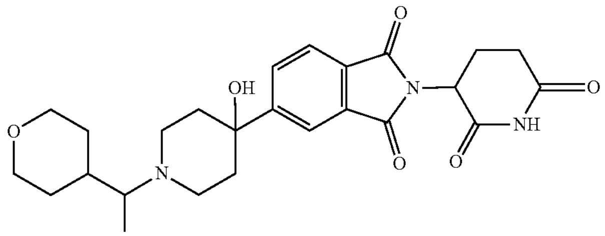 [SMILES: CC(C1CCOCC1)N1CCC(O)(c2ccc3c(c2)C(=O)N(C2CCC(=O)NC2=O)C3=O)CC1] |
| 82 | 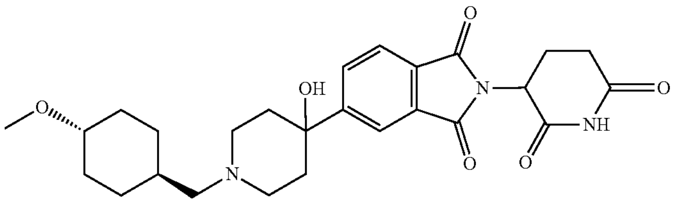 [SMILES: CO[C@H]1CC[C@H](CN2CCC(O)(c3ccc4c(c3)C(=O)N(C3CCC(=O)NC3=O)C4=O)CC2)CC1] |

-continued
| Compound number | Structure |
|---|---|
| 83 | 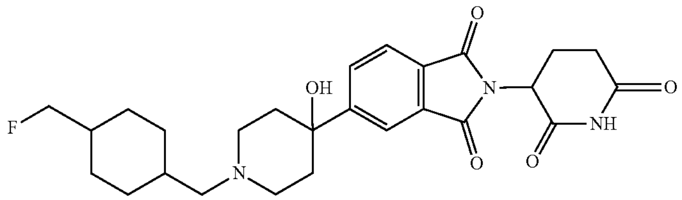 [SMILES: O=C1CCC(N2C(=O)c3ccc(C4(O)CCN(CC5CCC(CF)CC5)CC4)cc3C2=O)C(=O)N1] |
| 84 | 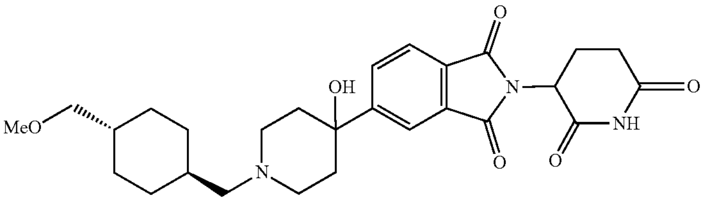 [SMILES: COC[C@H]1CC[C@H](CN2CCC(O)(c3ccc4c(c3)C(=O)N(C3CCC(=O)NC3=O)C4=O)CC2)CC1] |
| 86 | 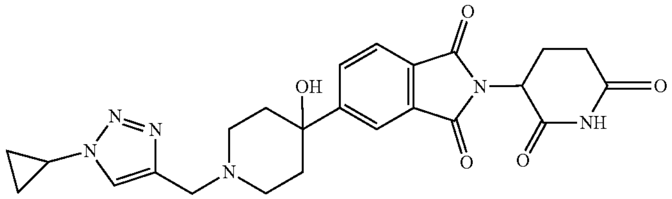 [SMILES: O=C1CCC(N2C(=O)c3ccc(C4(O)CCN(Cc5cn(C6CC6)nn5)CC4)cc3C2=O)C(=O)N1] |
| 87 | 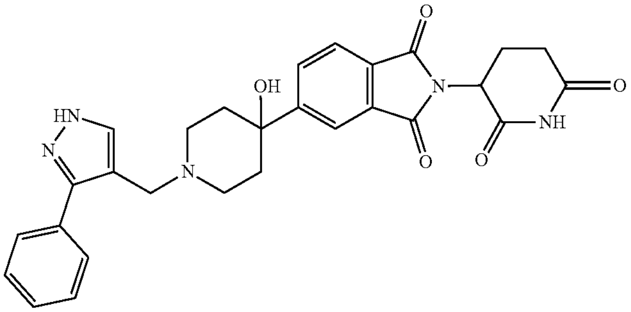 [SMILES: O=C1CCC(N2C(=O)c3ccc(C4(O)CCN(Cc5c[nH]nc5-c5ccccc5)CC4)cc3C2=O)C(=O)N1] |
| 88 | 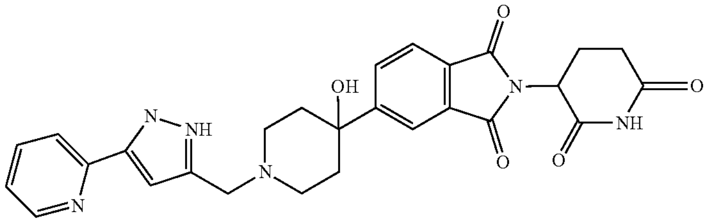 [SMILES: O=C1CCC(N2C(=O)c3ccc(C4(O)CCN(Cc5cc(-c6ccccn6)[nH]n5)CC4)cc3C2=O)C(=O)N1] |
| 89 | 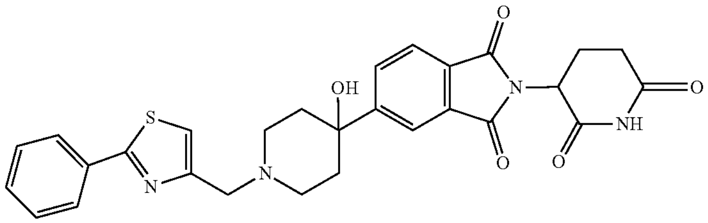 |

-continued
| Compound number | Structure |
|---|---|
| 90 | 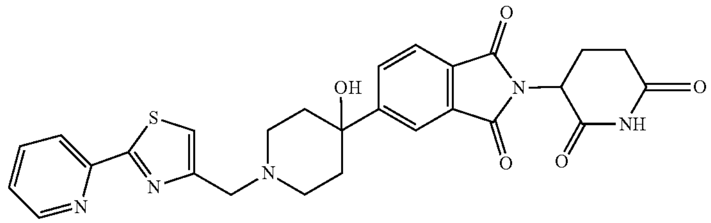 [SMILES: O=C1CCC(N2C(=O)c3ccc(C4(O)CCN(Cc5csc(-c6ccccc6)n5)CC4)cc3C2=O)C(=O)N1] |
| 91 | 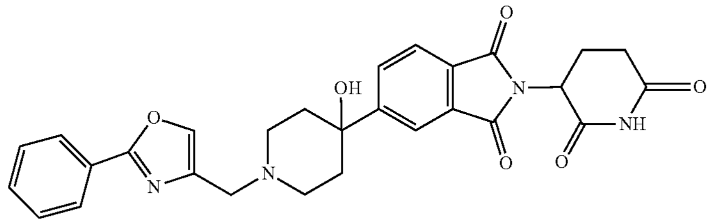 |
| 92 | 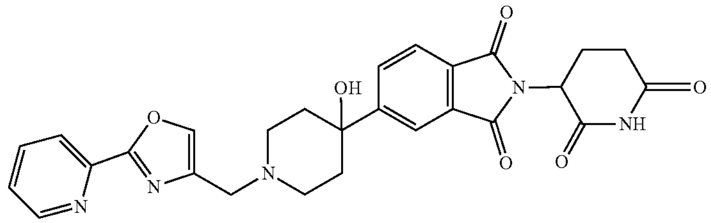 [SMILES: O=C1CCC(N2C(=O)c3ccc(C4(O)CCN(Cc5coc(-c6ccccn6)n5)CC4)cc3C2=O)C(=O)N1] |
| 93 | 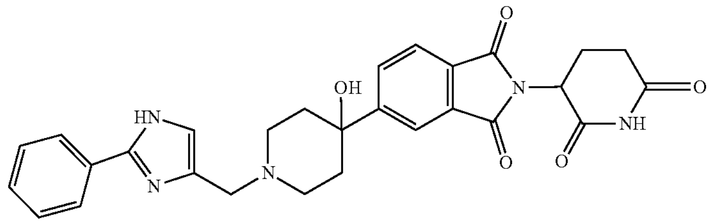 |
| 94 | 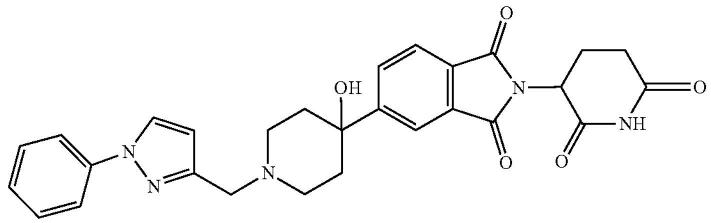 [SMILES: O=C1CCC(N2C(=O)c3ccc(C4(O)CCN(Cc5ccn(-c6ccccc6)n5)CC4)cc3C2=O)C(=O)N1] |
| 95 | 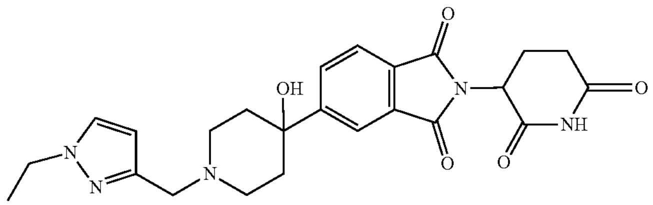 [SMILES: CCn1ccc(CN2CCC(O)(c3ccc4c(c3)C(=O)N(C3CCC(=O)NC3=O)C4=O)CC2)n1] |
| 96 | 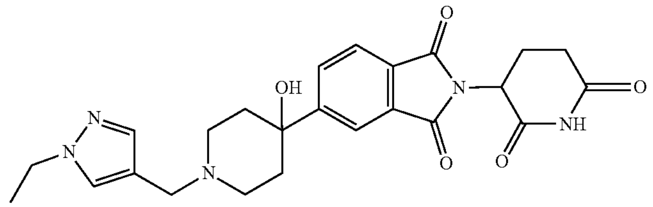 [SMILES: CCn1cc(CN2CCC(O)(c3ccc4c(c3)C(=O)N(C3CCC(=O)NC3=O)C4=O)CC2)cn1] |

-continued
| Compound number | Structure |
|---|---|
| 98 | 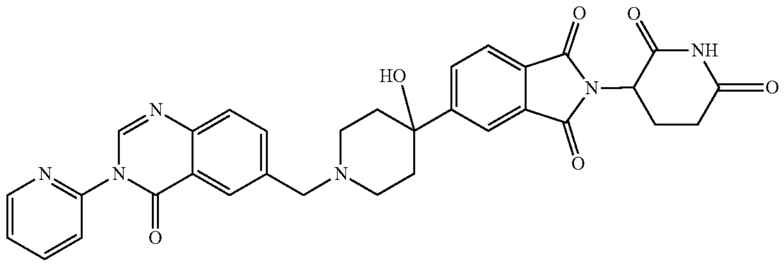 [SMILES: O=C1CCC(N2C(=O)c3ccc(C4(O)CCN(Cc5ccc6ncn(-c7ccccn7)c(=O)c6c5)CC4)cc3C2=O)C(=O)N1] |
| 99 | 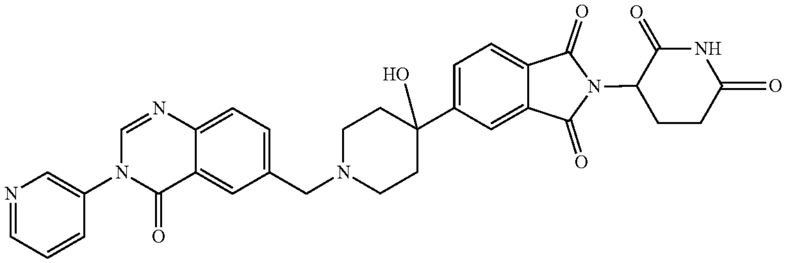 |
| 100 | 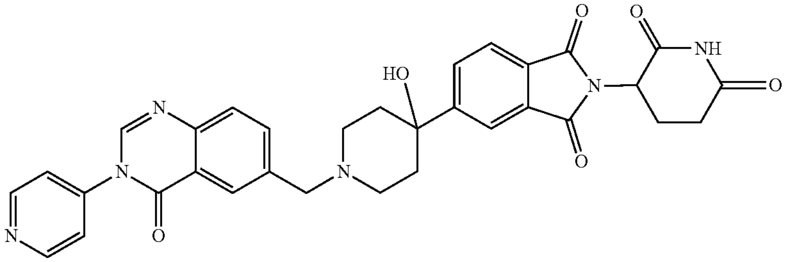 [SMILES: O=C1CCC(N2C(=O)c3ccc(C4(O)CCN(Cc5ccc6ncn(-c7ccncc7)c(=O)c6c5)CC4)cc3C2=O)C(=O)N1] |
| 101 | 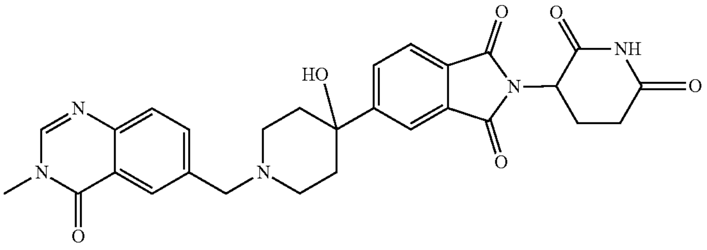 [SMILES: Cn1cnc2ccc(CN3CCC(O)(c4ccc5c(c4)C(=O)N(C4CCC(=O)NC4=O)C5=O)CC3)cc2c1=O] |
| 102 | 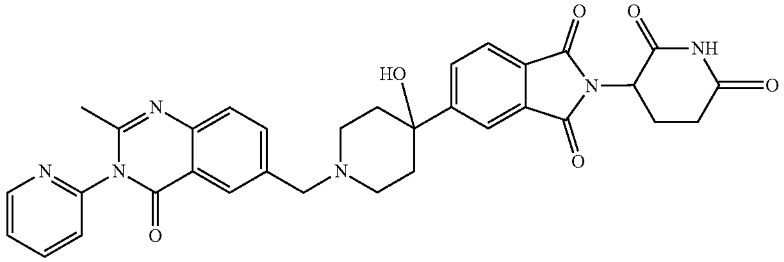 [SMILES: Cc1nc2ccc(CN3CCC(O)(c4ccc5c(c4)C(=O)N(C4CCC(=O)NC4=O)C5=O)CC3)cc2c(=O)n1-c1ccccn1] |

-continued
| Compound number | Structure |
|---|---|
| 103 | 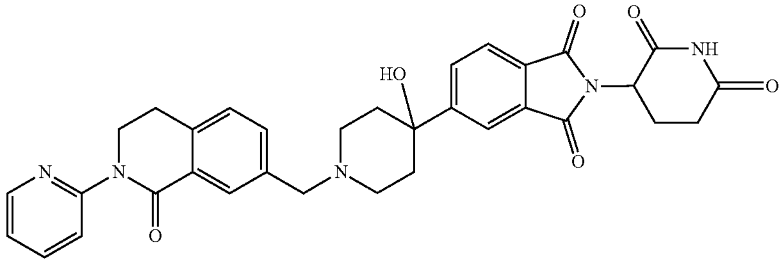 [SMILES: O=C1CCC(N2C(=O)c3ccc(C4(O)CCN(Cc5ccc6c(c5)C(=O)N(c5ccccn5)CC6)CC4)cc3C2=O)C(=O)N1] |
| 104 | 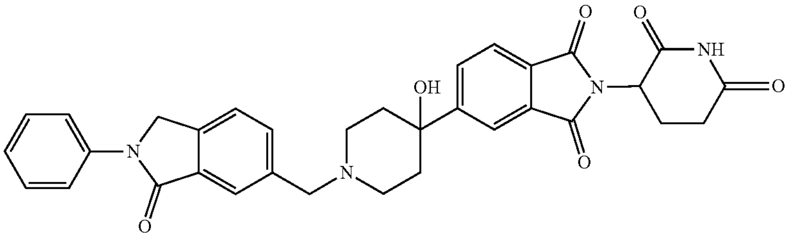 [SMILES: O=C1CCC(N2C(=O)c3ccc(C4(O)CCN(Cc5ccc6c(c5)C(=O)N(c5ccccc5)C6)CC4)cc3C2=O)C(=O)N1] |
| 105 | 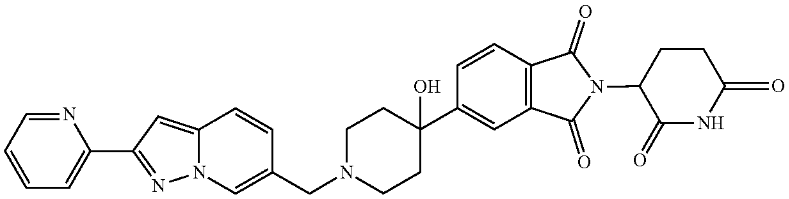 [SMILES: O=C1CCC(N2C(=O)c3ccc(C4(O)CCN(Cc5ccc6cc(-c7ccccn7)nn6c5)CC4)cc3C2=O)C(=O)N1] |
| 106 | 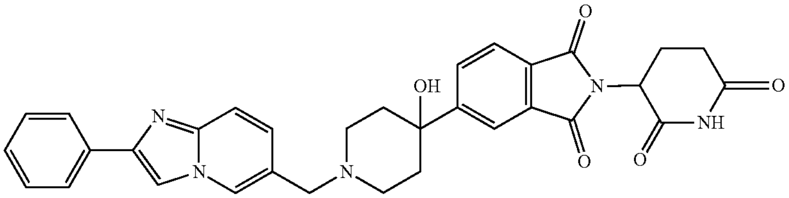 [SMILES: O=C1CCC(N2C(=O)c3ccc(C4(O)CCN(Cc5ccc6nc(-c7ccccc7)cn6c5)CC4)cc3C2=O)C(=O)N1] |
| 107 | 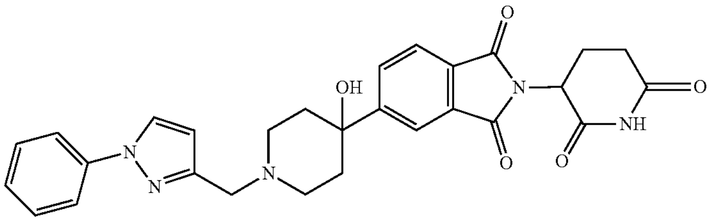 [SMILES: O=C1CCC(N2C(=O)c3ccc(C4(O)CCN(Cc5ccn(-c6ccccc6)n5)CC4)cc3C2=O)C(=O)N1] |
| 108 | 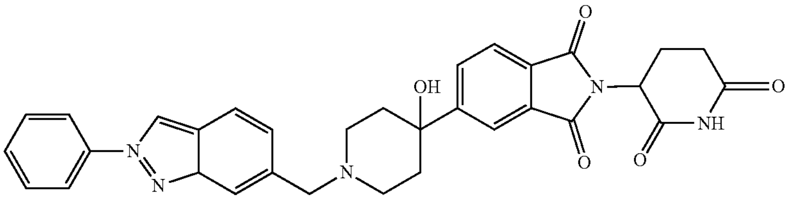 |
| 109 | 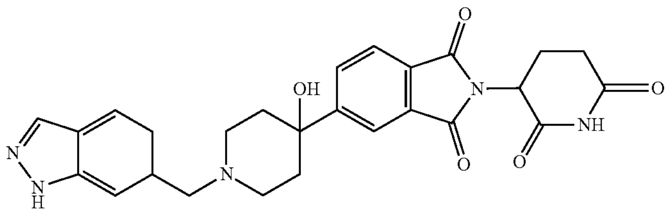 [SMILES: O=C1CCC(N2C(=O)c3ccc(C4(O)CCN(CC5C=c6[nH]ncc6=CC5)CC4)cc3C2=O)C(=O)N1] |

-continued
| Compound number | Structure |
|---|---|
| 110 | 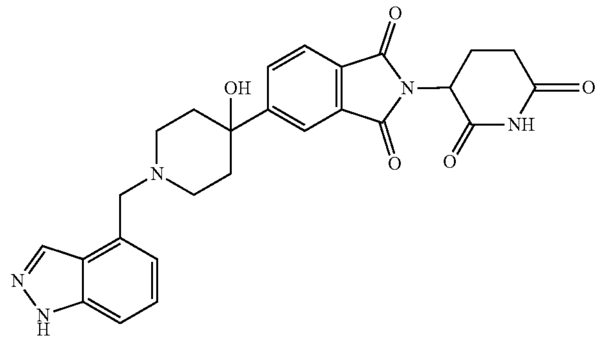 [SMILES: O=C1CCC(N2C(=O)c3ccc(C4(O)CCN(Cc5cccc6[nH]ncc56)CC4)cc3C2=O)C(=O)N1] |
| 111 | 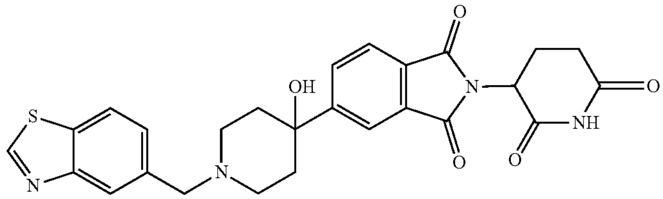 [SMILES: O=C1CCC(N2C(=O)c3ccc(C4(O)CCN(Cc5ccc6scnc6c5)CC4)cc3C2=O)C(=O)N1] |
| 112 | 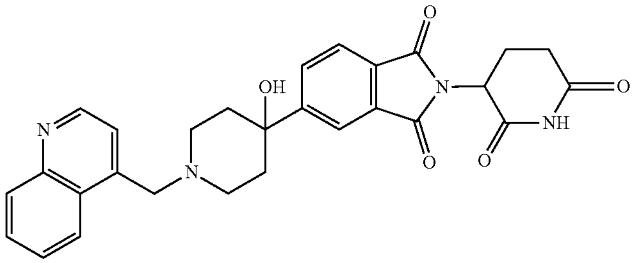 [SMILES: O=C1CCC(N2C(=O)c3ccc(C4(O)CCN(Cc5ccnc6ccccc56)CC4)cc3C2=O)C(=O)N1] |
| 113 | 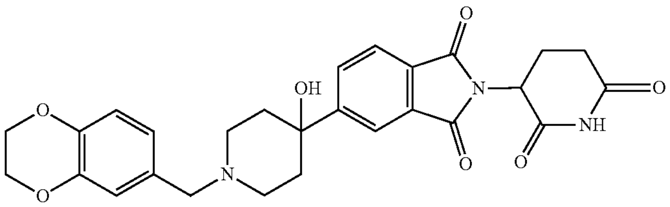 [SMILES: O=C1CCC(N2C(=O)c3ccc(C4(O)CCN(Cc5ccc6c(c5)OCCO6)CC4)cc3C2=O)C(=O)N1] |
| 114 | 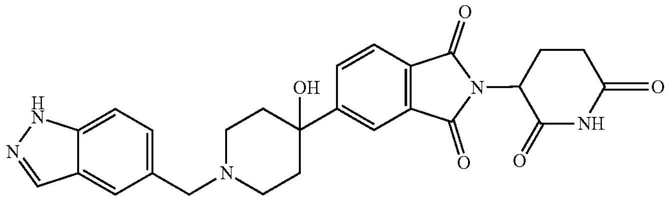 [SMILES: O=C1CCC(N2C(=O)c3ccc(C4(O)CCN(Cc5ccc6[nH]ncc6c5)CC4)cc3C2=O)C(=O)N1] |
| 115 | 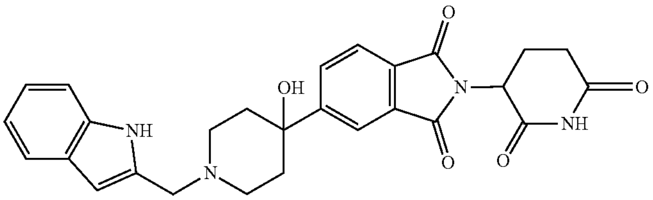 [SMILES: O=C1CCC(N2C(=O)c3ccc(C4(O)CCN(Cc5cc6ccccc6[nH]5)CC4)cc3C2=O)C(=O)N1] |

-continued
| Compound number | Structure |
| --- | --- |
| 116 | 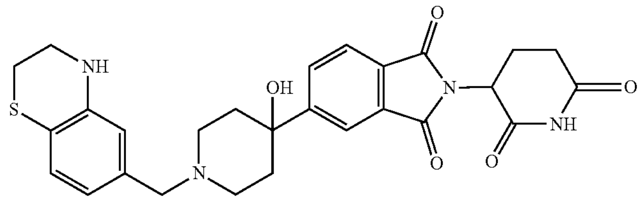 [SMILES: O=C1CCC(N2C(=O)c3ccc(C4(O)CCN(Cc5ccc6c(c5)NCCS6)CC4)cc3C2=O)C(=O)N1] |
| 117 | 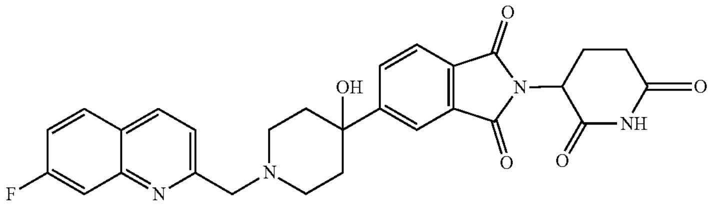 [SMILES: O=C1CCC(N2C(=O)c3ccc(C4(O)CCN(Cc5ccc6ccc(F)cc6n5)CC4)cc3C2=O)C(=O)N1] |
| 118 | 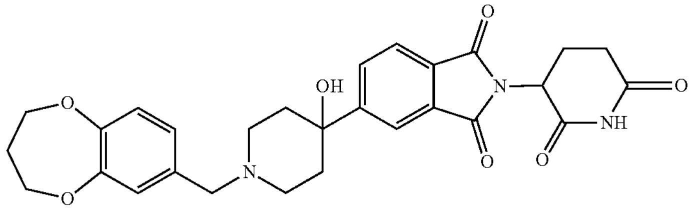 [SMILES: O=C1CCC(N2C(=O)c3ccc(C4(O)CCN(Cc5ccc6c(c5)OCCCO6)CC4)cc3C2=O)C(=O)N1] |
| 119 | 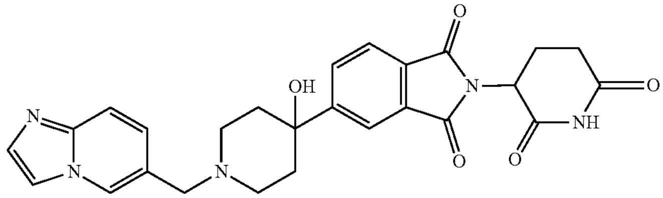 [SMILES: O=C1CCC(N2C(=O)c3ccc(C4(O)CCN(Cc5ccc6nccn6c5)CC4)cc3C2=O)C(=O)N1] |
| 120 | 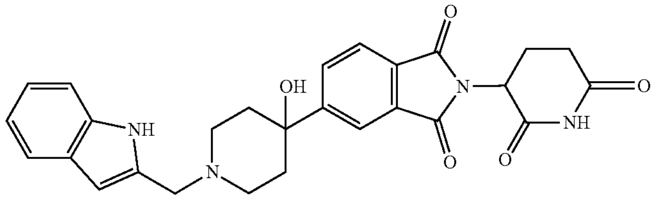 [SMILES: O=C1CCC(N2C(=O)c3ccc(C4(O)CCN(Cc5cc6ccccc6[nH]5)CC4)cc3C2=O)C(=O)N1] |
| 121 | 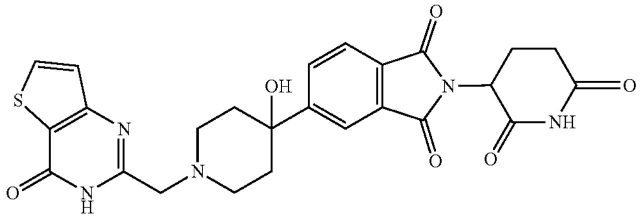 [SMILES: O=C1CCC(N2C(=O)c3ccc(C4(O)CCN(Cc5nc6ccsc6c(=O)[nH]5)CC4)cc3C2=O)C(=O)N1] |
| 122 | 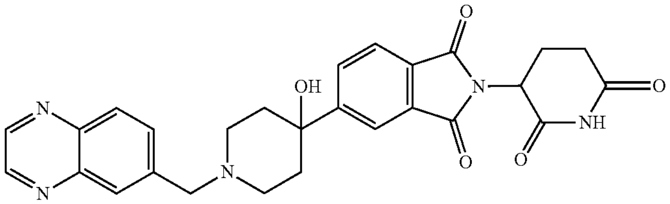 [SMILES: O=C1CCC(N2C(=O)c3ccc(C4(O)CCN(Cc5ccc6nccnc6c5)CC4)cc3C2=O)C(=O)N1] |

-continued
| Compound number | Structure |
|---|---|
| 123 | 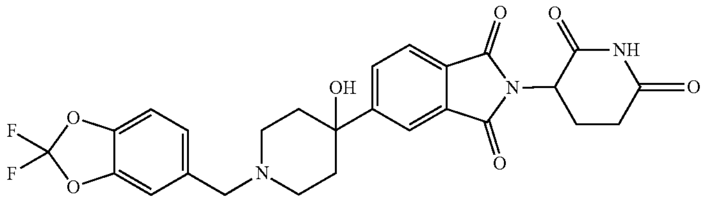 [SMILES: O=C1CCC(N2C(=O)c3ccc(C4(O)CCN(Cc5ccc6c(c5)OC(F)(F)O6)CC4)cc3C2=O)C(=O)N1] |
| 124 | 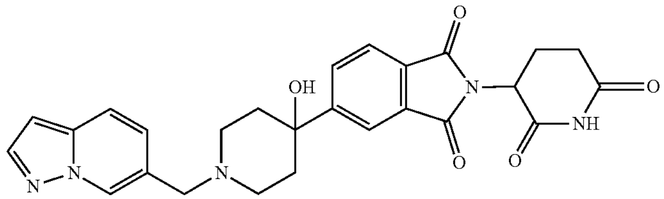 [SMILES: O=C1CCC(N2C(=O)c3ccc(C4(O)CCN(Cc5ccc6ccnn6c5)CC4)cc3C2=O)C(=O)N1] |
| 125 | 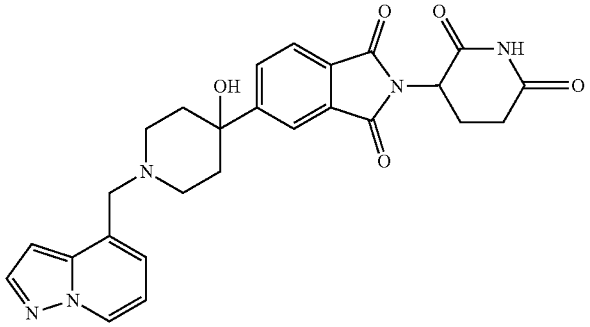 [SMILES: O=C1CCC(N2C(=O)c3ccc(C4(O)CCN(Cc5cccn6nccc56)CC4)cc3C2=O)C(=O)N1] |
| 126 | 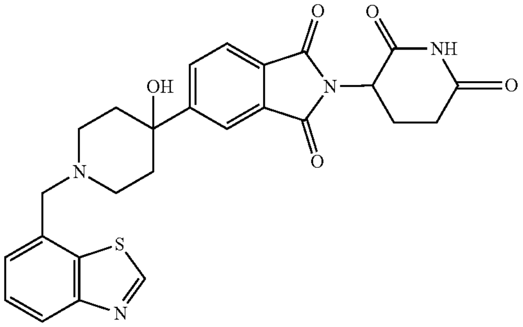 [SMILES: O=C1CCC(N2C(=O)c3ccc(C4(O)CCN(Cc5cccc6ncsc56)CC4)cc3C2=O)C(=O)N1] |
| 127 | 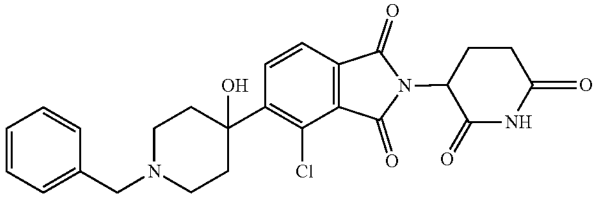 |
| 128 | 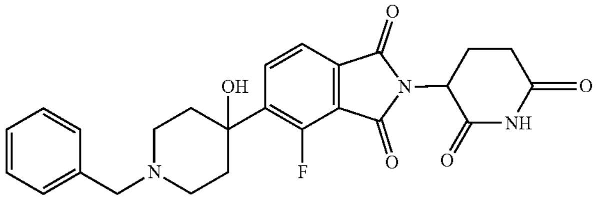 [SMILES: O=C1CCC(N2C(=O)c3ccc(C4(O)CCN(Cc5ccccc5)CC4)c(Cl)c3C2=O)C(=O)N1] |

-continued
| Compound number | Structure |
| --- | --- |
| 129 | 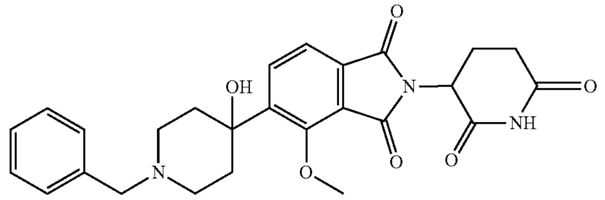 [SMILES: O=C1CCC(N2C(=O)c3ccc(C4(O)CCN(Cc5ccccc5)CC4)c(F)c3C2=O)C(=O)N1] |
| 130 | 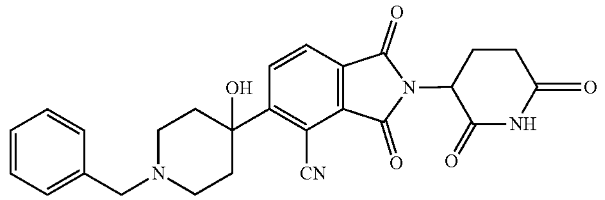 [SMILES: N#Cc1c(C2(O)CCN(Cc3ccccc3)CC2)ccc2c1C(=O)N(C1CCC(=O)NC1=O)C2=O] |
| 131 | 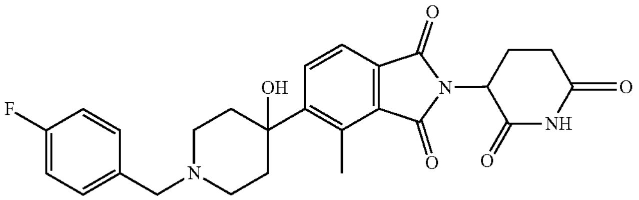 [SMILES: Cc1c(C2(O)CCN(Cc3ccc(F)cc3)CC2)ccc2c1C(=O)N(C1CCC(=O)NC1=O)C2=O] |
| 132 | 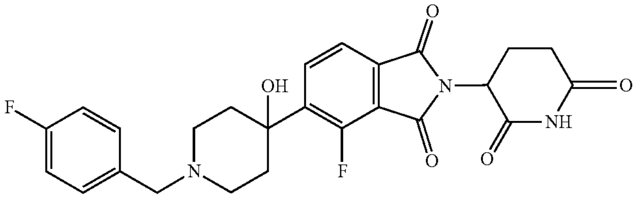 |
| 133 | 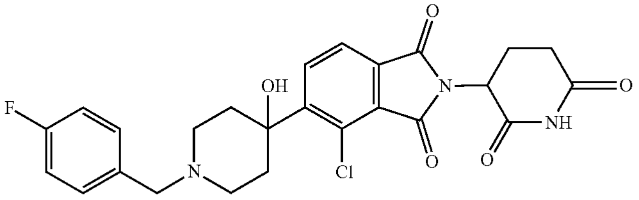 [SMILES: O=C1CCC(N2C(=O)c3ccc(C4(O)CCN(Cc5ccc(F)cc5)CC4)c(F)c3C2=O)C(=O)N1] |
| 134 | 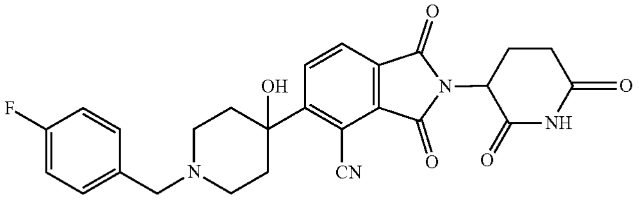 |
| 135 | 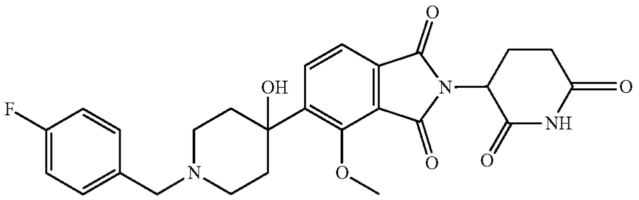 [SMILES: COc1c(C2(O)CCN(Cc3ccc(F)cc3)CC2)ccc2c1C(=O)N(C1CCC(=O)NC1=O)C2=O] |

-continued
| Compound number | Structure |
|---|---|
| 136 | 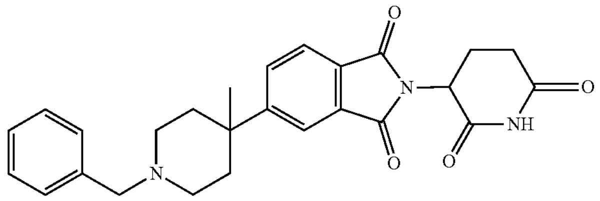 [SMILES: O=C1CCC(N2C(=O)c3ccc(C4(F)CCN(Cc5ccccc5)CC4)cc3C2=O)C(=O)N1] |
| 137 | 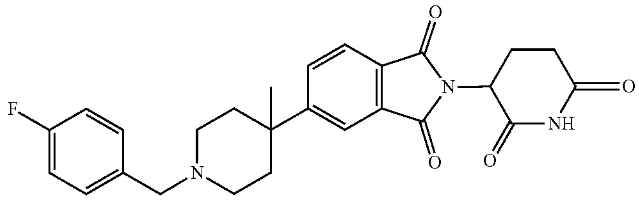 |
| 138 | 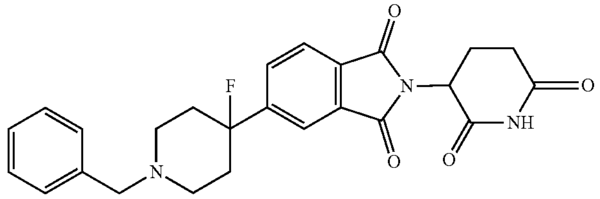 |
| 139 | 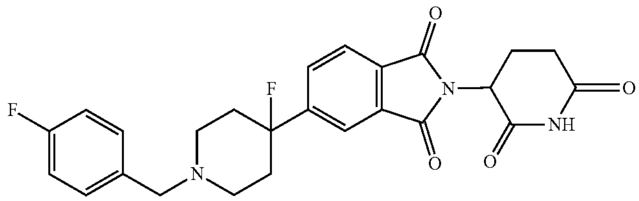 [SMILES: O=C1CCC(N2C(=O)c3ccc(C4(F)CCN(Cc5ccc(F)cc5)CC4)cc3C2=O)C(=O)N1] |
| 140 | 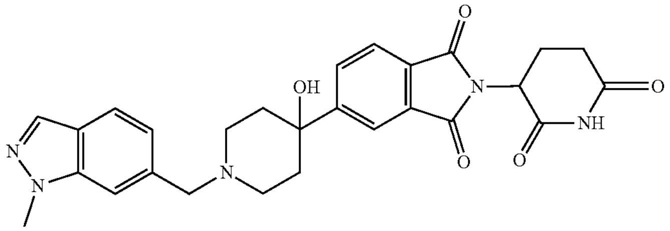 [SMILES: Cn1ncc2ccc(CN3CCC(O)(c4ccc5c(c4)C(=O)N(C4CCC(=O)NC4=O)C5=O)CC3)cc21] |
| 141 | 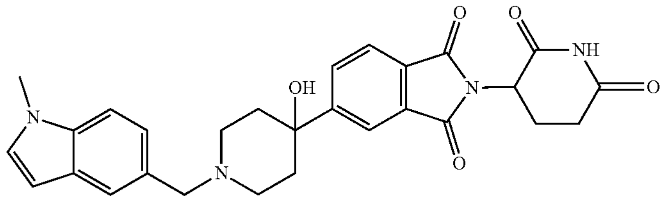 |
| 142 | 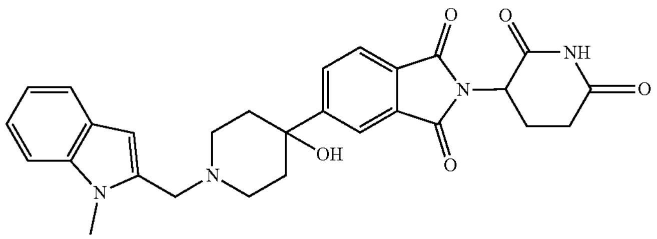 [SMILES: Cn1c(CN2CCC(O)(c3ccc4c(c3)C(=O)N(C3CCC(=O)NC3=O)C4=O)CC2)cc2ccccc21] |

-continued
| Compound number | Structure |
|---|---|
| 143 | 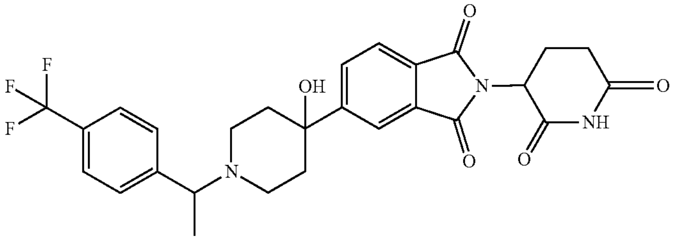 [SMILES: CC(c1ccc(C(F)(F)F)cc1)N1CCC(O)(c2ccc3c(c2)C(=O)N(C2CCC(=O)NC2=O)C3=O)CC1] |
| 144 | 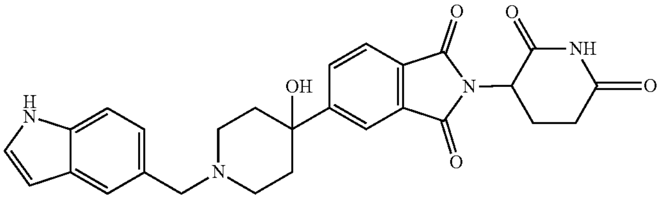 |
| 145 | 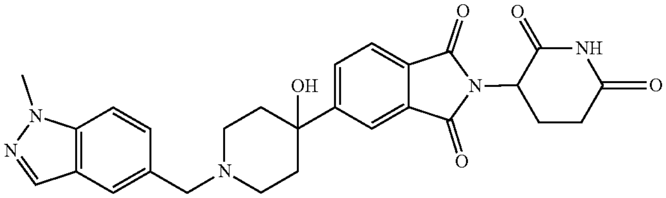 [SMILES: Cn1ncc2cc(CN3CCC(O)(c4ccc5c(c4)C(=O)N(C4CCC(=O)NC4=O)C5=O)CC3)ccc21] |
| 146 | 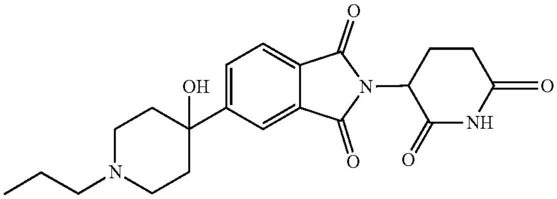 [SMILES: CCCN1CCC(O)(c2ccc3c(c2)C(=O)N(C2CCC(=O)NC2=O)C3=O)CC1] |
| 147 | 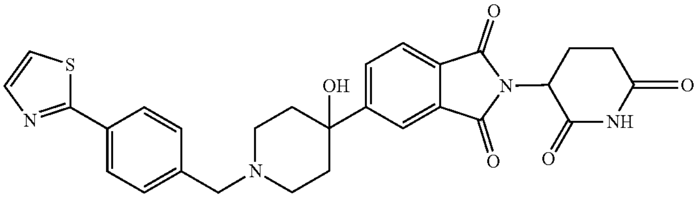 [SMILES: O=C1CCC(N2C(=O)c3ccc(C4(O)CCN(Cc5ccc(-c6nccs6)cc5)CC4)cc3C2=O)C(=O)N1] |
| 148 | 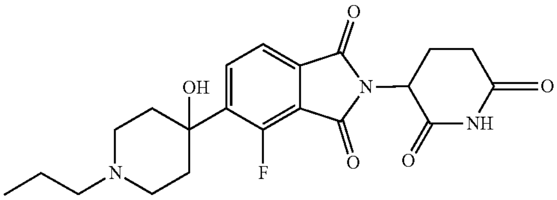 |
| 149 | 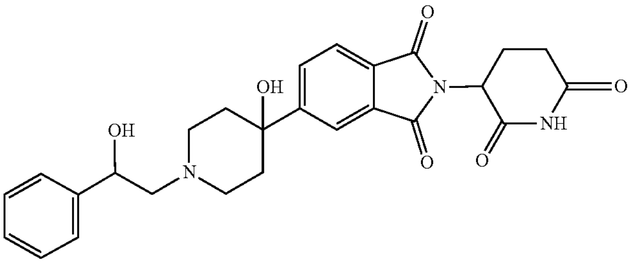 [SMILES: O=C1CCC(N2C(=O)c3ccc(C4(O)CCN(CC(O)c5ccccc5)CC4)cc3C2=O)C(=O)N1] |

or a pharmaceutically acceptable salt, hydrate, solvate, prodrug, stereoisomer, or tautomer thereof.

19. A pharmaceutical composition comprising a compound of claim 1, or a pharmaceutically acceptable salt, hydrate, solvate, prodrug, stereoisomer, or tautomer thereof; and a pharmaceutically acceptable carrier or excipient.

20. The pharmaceutical composition of claim 19, further comprising at least one additional pharmaceutical agent.

21. A method of degrading IKZF2, comprising administering to a patient in need thereof an effective amount of a compound of claim 1, or a pharmaceutically acceptable salt, hydrate, solvate, prodrug, stereoisomer, or tautomer thereof.

22. A method of treating a disease or disorder that is affected by the modulation of IKZF2 protein levels, comprising administering to a patient in need thereof a therapeutically effective amount of a compound of claim 1, or a pharmaceutically acceptable salt, hydrate, solvate, prodrug, stereoisomer, or tautomer thereof.

23. A method of modulating IKZF2 protein levels comprising administering to a patient in need thereof an effective amount of a compound of claim 1, or a pharmaceutically acceptable salt, hydrate, solvate, prodrug, stereoisomer, or tautomer thereof.

24. A method of treating cancer, comprising administering to a patient in need thereof a therapeutically effective amount of a compound of claim 1, or a pharmaceutically acceptable salt, hydrate, solvate, prodrug, stereoisomer, or tautomer thereof.

25. The method of claim 24, wherein the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST).

26. The method of claim 24, wherein the cancer is an immunogenic cancer or a cancer for which the immune response is deficient.

27. A method for reducing IKZF2 protein levels, comprising administering to a subject in need thereof a therapeutically effective amount of a compound of claim 1, or a pharmaceutically acceptable salt thereof.

* * * * *